US008143024B2

(12) United States Patent
Griffais et al.

(10) Patent No.: US 8,143,024 B2
(45) Date of Patent: Mar. 27, 2012

(54) CHLAMYDIA TRACHOMATIS GENOMIC SEQUENCE AND POLYPEPTIDES, FRAGMENTS THEREOF AND USES THEREOF, IN PARTICULAR FOR THE DIAGNOSIS, PREVENTION AND TREATMENT OF INFECTION

(75) Inventors: Rémy Griffais, Montrouge (FR); Susan K. Hoiseth, Fairport, NY (US); Robert J. Zagursky, Victor, NY (US); Benjamin J. Metcalf, Rochester, NY (US); Joel A. Peek, Pittsford, NY (US); Banumathi Sankaran, Penfield, NY (US); Leah D. Fletcher, Geneseo, NY (US)

(73) Assignee: Merck Serono Biodevelopment, Lyons (FR)

( * ) Notice: Subject to any disclaimer, the term of this patent is extended or adjusted under 35 U.S.C. 154(b) by 0 days.

(21) Appl. No.: 13/036,310

(22) Filed: Feb. 28, 2011

(65) Prior Publication Data

US 2011/0159041 A1    Jun. 30, 2011

Related U.S. Application Data

(62) Division of application No. 12/491,474, filed on Jun. 25, 2009, now Pat. No. 7,910,329, which is a division of application No. 11/366,965, filed on Mar. 2, 2006, now Pat. No. 7,575,913, which is a division of application No. 09/201,228, filed on Nov. 30, 1998, now Pat. No. 7,041,490.

(60) Provisional application No. 60/107,077, filed on Nov. 4, 1998.

(30) Foreign Application Priority Data

Nov. 28, 1997   (FR) ....................... 97 15041
Dec. 17, 1997   (FR) ....................... 97 16034

(51) Int. Cl.
C12P 21/06      (2006.01)
C12N 15/09      (2006.01)
C07H 21/04      (2006.01)
A61K 39/118     (2006.01)

(52) U.S. Cl. ................ 435/69.1; 435/69.7; 435/252.3; 435/320.1; 435/325; 536/23.1; 536/23.4; 536/23.7; 424/263.1

(58) Field of Classification Search .................. None
See application file for complete search history.

(56) References Cited

U.S. PATENT DOCUMENTS 5,436,327 A    7/1995  Southern et al.
5,700,637 A   12/1997  Southern
6,207,647 B1   3/2001  Black et al.

FOREIGN PATENT DOCUMENTS

WO    WO 89/10977    11/1989

OTHER PUBLICATIONS

Altschul, S.F. et al. "Basic local alignment search tool," *J. Mol. Biol.*, 1990, pp. 403-410, vol. 215.
Altschul, S.F. et al. "Gapped BLAST and PSI-BLAST: a new generation of protein database search programs," *Nucl. Acids Res.*, 1997, pp. 3389-3402, vol. 25.
Bai, M. et al. "Mutations that alter an Arg-Gly-Asp (RGD) sequence in the adenovirus type 2 penton base protein abolish its cell-rounding activity and delay virus reproduction in flat cells," *Virol.*, 1993, pp. 5198-5205, vol. 67.
Belunis, C.J. et al. "Inhibition of lipopolysaccharide biosynthesis and cell growth following inactivation of the kdtA gene in *Escherichia coli*," *J. Biol. Chem.*, Nov. 1995, pp. 27646-27652, vol. 270, No. 46.
Brade, H. et al. "Chemical and serological investigations on the genus-specific lipopolysaccharide epitope of *Chlamydia*," *Proc. Natl. Acad. Sci USA*, Apr. 1987, pp. 2508-2512, vol. 84, No. 8.
Caldwell, H.D. et al. "Monoclonal antibody against a genus-specific antigen of *Chlamydia* species: location of the epitope on chlamydial lipopolysaccharide," *Infect Immun.*, May 1984, pp. 306-314, vol. 44, No. 2.
Cousineau, B. et al. "The sequence of the gene encoding elongation factor Tu from *Chlamydia trachomatis* compared with those of other organisms," *Gene*, 1992, pp. 33-41, vol. 120, No. 1.
Fox, G. et al. "The cell attachment site on foot-and-mouth disease virus includes the amino acid sequence RGD (Arginine-Glycine-Aspartic Acid)," *J. Gen. Virol.*, 1989, pp. 625-637, vol. 70.
Fu, Y. et al. "A synthetic glycoconjugate representing the genus-specific epitope of chlamydial lipopolysaccharide exhibits the same specificity as its natural counterpart," *Infect Immun*, Apr. 1992, pp. 1314-1321, vol. 60, No. 4.
Girjes, A.A. et al. "Lipopolysaccharide biosynthesis genes in koala type I *Chlamydia*: cloning and characterization," *Res. Microbiol.*, Jun. 1997, pp. 413-425, vol. 148, No. 5.
Gish, W. and States, D.J. "Identification of protein coding regions by database similarity search," *Nature Genetics*, 1993, pp. 266-272, vol. 3.
Gonnet, G.H. et al. "Exhaustive matching of the entire protein sequence database," *Science*, 1992, pp. 1443-1445, vol. 256.

(Continued)

*Primary Examiner* — Padma Baskar
(74) *Attorney, Agent, or Firm* — Saliwanchik, Lloyd & Eisenschenk

(57) ABSTRACT

The subject of the invention is the genomic sequence and the nucleotide sequences encoding polypeptides of *Chlamydia trachomatis*, such as cellular envelope polypeptides, which are secreted or specific, or which are involved in metabolism, in the replication process or in virulence, polypeptides encoded by such sequences, as well as vectors including the said sequences and cells or animals transformed with these vectors. The invention also relates to transcriptional gene products of the *Chlamydia trachomatis* genome, such as, for example, antisense and ribozyme molecules, which can be used to control growth of the microorganism. The invention also relates to methods of detecting these nucleic acids or polypeptides and kits for diagnosing *Chlamydia trachomatis* infection. The invention also relates to a method of selecting compounds capable of modulating bacterial infection and a method for the biosynthesis or biodegradation of molecules of interest using the said nucleotide sequences or the said polypeptides. The invention finally comprises, pharmaceutical, in particular vaccine, compositions for the prevention and/or treatment of bacterial, in particular *Chlamydia trachomatis*, infections.

28 Claims, 3 Drawing Sheets

OTHER PUBLICATIONS

Hackstadt, T. "Origins and functions of the chlamydial inclusion," *Trends in Microbiol.*, 1996, pp. 288-293, vol. 5.

Hayashi, S. et al. "Identification and characterization of lipid-modified proteins in bacteria," in N.M. Hoper and A.J. Turner (ed.), *Lipid Modification of Proteins: A Practical Approach*, 1992, Oxford University Press, New York, pp. 261-285.

Heinkoff et al. "Performance evaluation of amino acid substitution matrices," *Proteins*, 1993, pp. 49-61, vol. 17.

Higgins, D.J. et al. "Using CLUSTAL for multiple sequence alignments," *Meth. Enzymol.*, 1996, pp. 383-402, vol. 266.

Holst, O. et al. "Structure, serological specificity, and synthesis of artificial glycoconjugates representing the genus-specific lipopolysaccharide epitope of *Chlamydia* spp," *J. Bacteriol*, Mar. 1991, pp. 1862-1866, vol. 173, No. 6.

Hueck, C.J. "Type III protein secretion systems in bacterial pathogens of animals and plants," *Molec. Biology Rev.*, 1998, pp. 379-433, vol. 62.

Huovinen, P. et al. "Pharyngitis in adults: the presence and coexistence of viruses and bacterial organisms," *Ann. Intern. Med.*, 1989, pp. 612-616, vol. 110.

Karlin, S. et al. "Methods for assessing the statistical significance of molecular sequence features by using general scoring schemes," *PNAS USA*, 1991, pp. 2264-2268, vol. 87.

Lee, C.A. "Type III secretion systems: machines to deliver bacterial proteins into eukaryotic cells?" *Trends Microbiol.*, 1997, pp. 148-156, vol. 5.

Leininger, E. et al. "Pertactin, an Arg-Gly-Asp-containing *Bordetella pertussis* surface protein that promotes adherence of mammalian cells," *PNAS USA*, 1991, pp. 345-349, vol. 88.

Longbottom, D. et al. "Molecular cloning and characterization of the genes coding for the highly immunogenic cluster of 90-kilodalton envelope proteins from the *Chlamydia psittaci* subtype that causes abortion in sheep," *Infect. Immunol.*, 1998, pp. 1317-1324, vol. 66.

Lukacova, M. et al. "Lipopolysaccharide smooth-rough phase variation in bacteria of the genus *Chlamydia*," *Infect Immunol.*, 1994, pp. 2270-2276, vol. 62, No. 6.

Mamat, U. et al. "The genus-specific lipopolysaccharide epitope of *Chlamydia* is assembled in *C. psittaci* and *C. trachomatis* by glycosyltransferases of low homology," *Mol. Microbiol.*, 1993, pp. 935-941, vol. 10, No. 5.
Morrison, R.P. et al. "Gene knockout mice establish a primary protective role for major histocompatability complex class II-restricted responses in *Chlamydia trachomatis," Infect. Immunol.*, 1995, pp. 4661-4668, vol. 63.
Nakai, K. et al., "Expert system for predicting protein localization sites in gram-negative bacteria," *Proteins*, 1991, pp. 95-110, vol. 11.
Nano, F.E. et al. "Expression of the chlamydial genus-specific lipopolysaccharide epitope in *Escherichia coli," Science*, 1985, pp. 742-744, vol. 228, No. 4700.
Neilsen, H. et al. "Identification of prokaryotic and eukaryotic signal peptides and prediction of their cleavage sites," *Protein Engin.*, 1997, pp. 1-6, vol. 10.
Pearson, W.R., and Lipman, D.J. "Improved tools for biological sequence comparison," *PNAS USA*, 1988, pp. 2444-2448, vol. 85, No. 8.
Peterson, E.M. et al. "Protective role of magnesium in the neutralization by antibodies of *Chlamydia trachomatis* infectivity," *Infect. Immun.*, 1988, pp. 885-891, vol. 56, No. 4.
Pierschbacher, M.D. et al. "Influence of stereochemistry of the sequence Arg-Gly-Asp-Xaa on binding specificity in cell adhesion," *J. Biol. Chem*, 1987, pp. 17294-17298, vol. 262.
Pugsley, A.P. "The complete general secretory pathway in gram-negative bacteria" (abstract), *Microbiol. Rev.*, 1993, pp. 50-108, vol. 57.
Rank, R.G. et al., "Susceptibility to reinfection after a primary chlamydial genital infection," *Infect. Immun.*, 1988, pp. 2243-2249, vol. 56.
Raulston, J.E. "Chlamydial envelope components and pathogen—host cell interactions," *Mol. Microbiol.*, 1995, pp. 607-616, vol. 15.
Reeves, P.R. et al. *Bacterial Polysaccharide Synthesis and Gene Nomenclature*, Elsevier Science Ltd., pp. 10071-10078, from *Trends in Microbiology*, 1996, pp. 495-503, vol. 4, No. 12.
Relman, D. et al. "Recognition of a bacterial adhesin by an integrin: macrophage CR3 ($\alpha_M \beta_2$, CD11b/CD18) binds filamentous hemagglutinin of *Bordetella pertussis," Cell*, 1990, pp. 1375-1382, vol. 61.
Roivainen, M. et al. "Entry of coxsackievrius A9 into host cells: specific interactions with $\alpha v\beta 3$ intergrin, the vitronectin receptor," *Virology*, 1994, pp. 357-365, vol. 203.
Salzberg, S.L. et al. "Microbial gene identification using interpolated Markov models," *Nucl. Acids Res.*, 1988, pp. 544-548, vol. 26.
Schacter J. *Chlamydiae.* In E.H. Lennette (ed.), Manual of clinical microbiology, 3rd ed. American Society for Microbiology, Washington , D.C., 1980, pp. 357-365.
Schnaitman, C.A. et al. "Genetics of lipopolysaccharide biosynthesis in enteric bacteria," *Microbiol. Rev.*, 1993, pp. 655-682, vol. 57.
Schneewind, O. "Structure of the cell wall anchor of surface proteins in *Staphylococcus aureus," Science*, 1995, pp. 103-106, vol. 268.
*Sigma Catalog*, Sigma Chemical Company, Saint Louis, Missouri, 1990, pp. 776-778.
Struyve, M. et al. "Carbox-terminal phenylalanine is essential for the correct assembly of a bacterial outer membrane protein," *J. Mol. Biol*, 1991, pp. 141-148, vol. 218.
Sutcliffe, I.C. et al. "Lipoproteins of gram-positive bacteria," *J. Bacteriol.*, 1995, pp. 1123-1128, vol. 177.
Thompson, J.D. et al. "CLUSTAL W: improving the sensitivity of progressive multiple sequence alignment through sequence weighting, position-specific gap penalties and weight matrix choice," *Nucl. Acids. Res.*, 1994, pp. 4673-4680, vol. 22, No. 2.
Genbank Accession No. X68033 (May 2, 1994).
Genbank Accession No. M74221 (Feb. 16, 1995).
Genbank Accession No. Z11839 (Dec. 6, 1996).
Genbank Accession No. T67502 (Jul. 9, 1997).
Genbank Accession No. Q54841 (Jul. 15, 1994).
Genbank Accession No. X63515 (Feb. 17, 1997).
Genbank Accession No. U76535 (Feb. 1, 1997).
Genbank Accession No. L35530 (Dec. 20, 1994).
Genbank Accession No. X59601 (Dec. 19, 1996).
Genbank Accession No. N70920 (May 7, 1991).

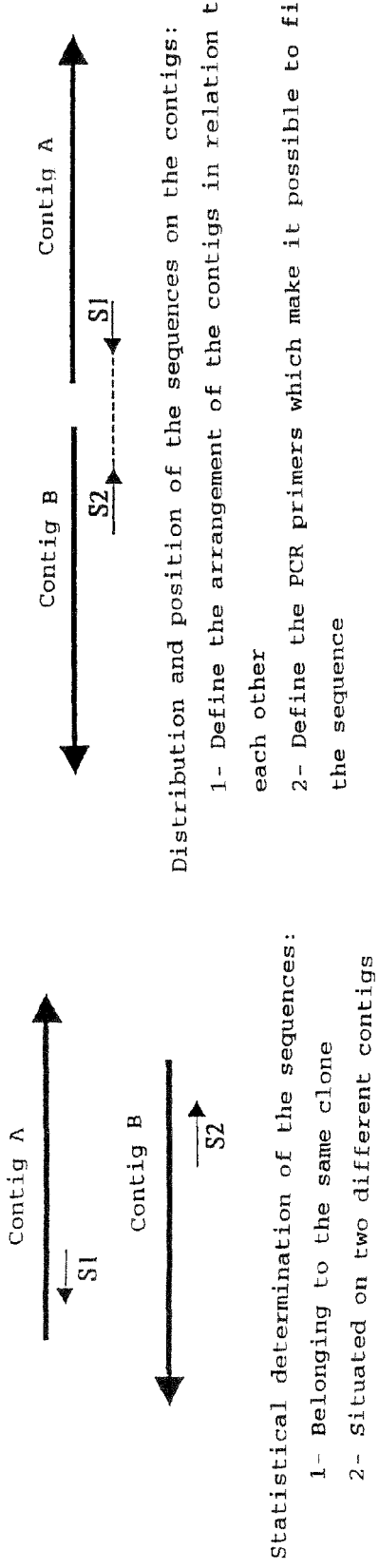
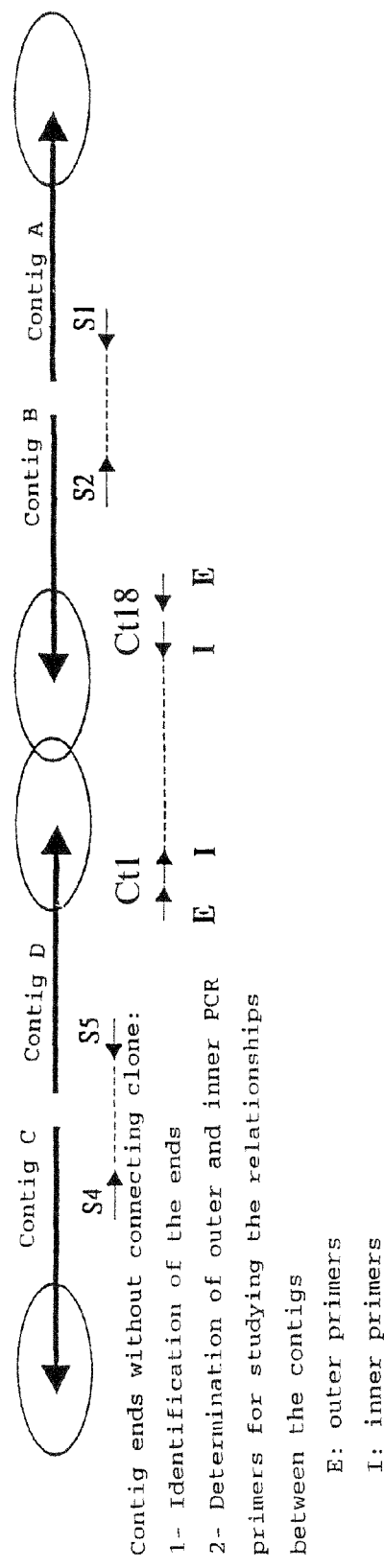
FIG. 3A
FIG. 3B

CHLAMYDIA TRACHOMATIS GENOMIC SEQUENCE AND POLYPEPTIDES, FRAGMENTS THEREOF AND USES THEREOF, IN PARTICULAR FOR THE DIAGNOSIS, PREVENTION AND TREATMENT OF INFECTION

CROSS-REFERENCE TO RELATED APPLICATIONS

This application is a divisional U.S. application Ser. No. 12/491,474, filed on Jun. 25, 2009, now U.S. Pat. No. 7,910,329, which is divisional of U.S. application Ser. No. 11/366,965, filed Mar. 2, 2006, now U.S. Pat. No. 7,575,913, which is a divisional of U.S. application Ser. No. 09/201,228, filed Nov. 30, 1998, now U.S. Pat. No. 7,041,490, which claims priority from U.S. application Ser. No. 60/107,077, filed Nov. 4, 1998, abandoned.

The Sequence Listing for this application is labeled "seqlist.txt", which was created on Feb. 28, 2006, and is 4,771 KB. The entire contents is incorporated herein by reference in its entirety.

The subject of the invention is the genomic sequence and the nucleotide sequences encoding polypeptides of *Chlamydia trachomatis*, such as cellular envelope polypeptides, which are secreted or specific, or which are involved in metabolism, in the replication process or in virulence, polypeptides encoded by such sequences as well as vectors including the said sequences and cells or animals transformed with these vectors. The invention also relates to transcriptional gene products of the *Chlamydia trachomatis* genome, such as, for example, antisense and ribozyme molecules, which can be used to control growth of the microorganism. The invention also relates to methods of detecting these nucleic acids or polypeptides and kits for diagnosing *Chlamydia trachomatis* infection. The invention also relates to a method of selecting compounds capable of modulating bacterial infection and a method for the biosynthesis or biodegradation of molecules of interest using the said nucleotide sequences or the said polypeptides. The invention finally comprises pharmaceutical, in particular vaccine, compositions for the prevention and/or treatment of bacterial, in particular *Chlamydia trachomatis*, infections.

The genus *Chlamydia* is composed of four species: *Chlamydia psittaci, Chlamydia pecorum, Chlamydia pneumoniae* and *Chlamydia trachomatis*.

*Chlamydia psittaci* comprises numerous species, whose hosts are terrestrial vertebrate animals as well as birds and occasionally humans;

*Chlamydia pecorum* is a pathogen of ruminants;

*Chlamydia pneumoniae* is responsible for pneumopathies, for sinusitis and for arterial impairments in humans;

*Chlamydia trachomatis* (Ct) is responsible for a large number of human diseases:

eye diseases: conventional trachoma, nonendemic trachoma, paratrachoma, inclusion conjunctivitis in neonates and in adults;

genital diseases: nongonococcal uretritis, epididymitis, cervicitis, salpingitis, perihepatitis and bartholinitis as well as pneumopathy in breast-feeding infants;

systemic diseases: venereal lymphogranulomatosis (LGV).

These diseases affect a very large number of women and men [more than 600 million individuals are trachoma carriers and there are more than 90 million cases of genital *Chlamydia* infections] worldwide. Accordingly, basic and applied research which makes it possible to understand the physiopathology linked to this bacterium is very important for public health. (Raulston J E., 1995; Hackstadt T. et al., 1996).

Eye impairments due to *Chlamydia trachomatis* cause trachoma and inclusion conjunctivitis. Trachoma is a chronic conjunctivitis. It is the major cause of curable eye diseases leading to blindness. It is estimated that 20 million cases of loss of sight are due to it worldwide. Moreover, inclusion conjunctivitis is an eye inflammation which is caused by *Chlamydia trachomatis* and is transmitted by the venereal route. Inclusion conjunctivitis affects adults and neonates exposed to genital secretions.

Two types of eye disease caused by agents of the species *Chlamydia trachomatis* can be distinguished. The conventional trachomatous disease is found in endemic regions; transmission occurs from eye to eye and through the hands, or it can be passed on by flies. In nonendemic regions, transmission occurs through the genital apparatus; it usually only causes conjunctivitis, most often without associated keratitis; it is rare for a pannus or for scars similar to those in trachoma to develop. This conjunctival impairment is called paratrachoma to differentiate it from the conventional endemic trachoma which is transmitted by the ocular route. The seriousness and the number of cases of trachoma have decreased over the last forty years. This is related to the improvement in hygiene and living conditions. However, trachoma remains the principal cause of avoidable blindness in Africa, in the Middle East and in some regions of Asia. The transmission of the endemic disease occurs in particular through close personal contact, in regions where a secondary exposure exists in a repeated form. Often, the infection is also latent. In some industrialized countries, such as the United States, a mild form of trachoma still exists in some ethnic groups. Sometimes, a tardive trachoma may be found following an immunosuppressive treatment. The eye impairments caused by *Chlamydia trachomatis*, such as inclusion conjunctivitis and paratrachoma, are also a complication due to a common venereal infection. These infections are not very frequent; they occur most often in young adults. The eye impairments in neonates are produced during the passage through the maternal genital routes during childbirth. Theoretically, endemic trachoma and inclusion conjunctivitis in adults appear in the form of conjunctivitis, the latter being characterized by the presence of lymphoid follicles. In regions where the endemic disease is serious, the disease often starts before the age of 2 years and reinfection is frequent. Superficial neovascularization is added, in this case, to leukocytic infiltration. The conjunctival scars will then cause trichiasis and entropion. The eroded cornea will become a carrier of a corneal ulcer of bacterial origin. The scar on the cornea causes blindness. Impairment of the lachrymal glands gives a picture of dryness of the cornea. Xerosis becomes complicated with secondary bacterial ulcer. In regions where trachoma is endemic, the infectious process disappears towards the age of fifteen. The scars then progress to blindness, which affects almost exclusively adults. In regions where exposure is lower, the infectious process is, in this case, less rapid and adults are carriers of a chronic disease.

Positive diagnosis of trachoma can be most often established by clinical observation: lymphoid follicles are visible on the upper tarsal conjuctiva; conjunctival scar is typical. Vascular pannus exists. In endemic regions, clinical diagnosis is often sufficient. However, isolated cases of inclusion conjunctivitis must be the subject of a differential diagnosis, in particular to distinguish viral conjunctivitis.

Public health measures against the endemic form of the disease provide for mass treatments with tetracycline or erythromycin collyria of all children. The treatment may also provide for surgical correction of the lesions. The other conjunctival impairments respond well to general treatments with tetracyclines or erythromycin. The prevention of trachomatous disease by health measures and by improving living standards is sufficient. Furthermore, to avoid the spread of trachoma, antibiotic collyria may be used.

The role of *Chlamydia trachomatis* in a number of genital impairments has been demonstrated over the last three decades. *Chlamydia trachomatis* is responsible in this case for a pathology which may be superposed on the impairments observed with *Neisseria gonorrhoeae*. The pathologies for which *Chlamydia trachomatis* may be responsible at the genital level are acquired by the venereal route and are a major source of sexually transmitted diseases.

The epidemiology of *Chlamydia trachomatis* genital infections shows each year more than 4 million new cases in the United States, and more than 3 million new cases in Europe. Like the other venereal infections, *Chlamydia trachomatis* affects young subjects. There is a direct relationship between the number of sexual partners and the frequency of the disease. For example, the frequency of *Chlamydia trachomatis* appears to be five to ten times higher than that of *Neisseria gonorrhoea* in pregnant women. The *Chlamydia trachomatis* infection is probably more discreet than its *Neisseria gonorrhoea* homologue. This relative clinical silence, estimated in women at 50% or even 70% of infections, explains why the total morbidity of *Chlamydia trachomatis* conditions is high. Diagnosis must therefore be requested in patients who are sometimes asymptomatic carriers of infection.

*Chlamydia trachomatis* is responsible for nearly 30% of nongonococcal urethritis, or NGU. *Chlamydia trachomatis* urethritis may be discreet, the disease then progresses to a certain form of chronicity. The diagnosis will, like for the other clinical forms of the disease, be called into play later.

*Chlamydia trachomatis* is a cause of epididymitis in humans during a period of sexual activity. The bacterium may be found in the urethra, urine, sperm or even a sample collected by aspiration from the epididymis. It is in particular found in humans under 35 years of age. A discharge from the urethra which is associated with the disease suggests the diagnosis of a *Chlamydia* condition or sometimes a gonococcal condition.

Untreated Reiter's syndrome, if accompanied by urethritis, evokes a *Chlamydia trachomatis* condition.

*Chlamydia trachomatis* affects 30% to 40% of women who are clinically carriers of a gonorrhoea (or have had contact), 10% to 20% of women having a venereal origin, and 5% of women consulting having no particular origin.

The cervix is often normal during a *Chlamydia trachomatis* infection. However, a hypertrophic cervical erythema will cause such an infection to be suspected. *Chlamydia trachomatis* is responsible for an endocervicitis whereas viral impairments result in exocervicitis. A nongonococcal endocervicitis requires treating the patient and partners with tetracyclines.

*Chlamydia trachomatis* is responsible for a large number of acute salpingites. The picture is often complicated by an acute peritonitis or even a perihepatitis.

In case of pregnancy, the risk is first that of infection of the neonate at birth. However, the risk of postpartum complications exists (endometritis or salpingitis).

The reference method for the diagnosis of *Chlamydia trachomatis* is the isolation of the bacterium on cell culture. For all infections, the sample collection should make it possible to obtain a suitable sample with the aid of a swab. This sample should be transported to a laboratory under excellent conditions; in particular, the cold chain must absolutely be maintained. The placing in cell culture on mouse fibroblasts will be carried out by people having specific skills. The distinction of *Chlamydia trachomatis* with labelled antibodies and the observation of cell cultures under a microscope will take place two days after placing in culture. Provided these imperatives are observed, cell culture is a reliable technique. However, the constraints linked to this technique are many: not only must the laboratory be equipped for the cell culture, but, furthermore, highly competent staff must take care of this type of diagnosis.

Techniques for identifying genetic material can obviously be used for the detection of *Chlamydia trachomatis*. Among these techniques, enzymatic gene amplification or PCR is favoured by those skilled in the art. The technique indeed makes it possible to identify *Chlamydia trachomatis* with a very high sensitivity and complete specificity. Initially used in specialist laboratories, PCR is now performed in numerous medical laboratories. This diagnostic approach is important because it allows detection of the bacteria even in samples which have been transported under poor conditions.

The treatment of *Chlamydia* urethritis with antibiotics such as tetracycline or quinolones is very effective. The duration of treatment varies between 7 and 14 days. The treatment of pregnant women poses the problem of contraindications to tetracycline.

Neonatal infections caused by *Chlamydia trachomatis* are explained by the frequency of these bacteria in the cervix. In some studies, 5% to 13% of impairments are observed in the cervix in asymptomatic pregnant women. The neonates risk, in this case, developing an inclusion conjunctivitis. Not only can *Chlamydia trachomatis* be isolated from the children's eyes, but also persistently from the rhinopharynx and also from the rectum. Pneumopathies and otitis media are also found, a result of contamination at childbirth.

Differential diagnosis of inclusion conjunctivitis in neonates is required with gonococcal ophthalmia; while the duration of incubation is from one to three days in the case of a gonococcal ophthalmia, neonatal inclusion conjunctivitis has an acute beginning with discharge and formation of membranes or even of conjunctival scars.

Treatment consists of oral erythromycin at the dose of 40 to 50 mg per kg of weight, for two to three weeks. In a nonendemic trachoma region, this disease never progresses to chronicity.

Finally, mention should be made of infantile pneumopathy. The syndrome is well defined; it is found in children affected by *Chlamydia trachomatis*. Less than ten children are affected by *Chlamydia trachomatis* pneumopathies per thousand births. The syndrome is, in this case, always found at an early age (less than four months).

Venereal lymphogranulomatosis is an infection which is transmitted through sexual contact and is due to *Chlamydia trachomatis* strains L1, L2 and L3. In humans, a passing primary genital lesion is followed by an often suppurative and multiple regional lymphadenopathy. This disease is a general disease which is accompanied by fever and a rise in the number of white blood cells. If it progresses to chronicity, the disease then becomes complicated with genital elephantiasis, stricture or even fistula of the genital apparatus, of the penis, of the urethra and of the rectum.

The three *Chlamydia trachomatis* strains L1, L2 and L3 are responsible for venereal lymphogranulomatosis. These *Chlamydia* strains are more virulent than the strains responsible for trachoma and STD. It is very important to note that venereal lymphogranulomatosis is a systemic disease which affects primarily the lymphatic tissue. Generally transmitted by the sexual route, *Chlamydia trachomatis* L may also cause contamination through direct contact or even during poor laboratory handling. In spite of these variable modes of transmission, the age for the highest incidence of these diseases corresponds to that for greater sexual activity. Venereal lymphogranulomatosis is still endemic in South America, in Africa and sometimes in Asia. For a long time, the prevalence of venereal lymphogranulomatosis was difficult to establish because of the difficulty of performing diagnosis with certitude. It should also be noted that men are affected more often than women. In low endemic regions, it is difficult to recognize the reservoir of microbes. This situation is explained by the fact that the isolation of the strains causing venereal lymphogranulomatoses from asymptomatic subjects is rarely successful.

Clinical impairment by venereal lymphogranulomatosis manifests itself by the appearance of a small ulcer 3 to 21 days after the exposure of small nonpainful vesicles. In both men and women, the lesion is most often silent. Since this impairment disappears within a few days and causes no functional discomfort and leaves no visible scar, the disease is often recognized late. The venereal lymphogranulomatosis strains may be found in the urethra or the endocervix in patients with inguinal adenopathies; these regions are then considered as the initial site of infection. The characteristic feature of the venereal lymphogranulomatosis strains is that from the initial site of infection, *Chlamydia* exhibits a diffusion drained by the lymphatic ducts. The disease is then complicated by a ganglionic impairment of the region draining the site of inoculation. By way of example, anorectal infection causes deep adenopathies. These adenopathies are marked by the appearance of a periadenitis which forms a fluctuating and suppurative ganglionic mass. Fistulae will appear during the decline of the disease. As general signs are present at this stage of the disease, it is often confused with a malignant lymphoma. The other general complications are rarely observed. Clinical examinations have been able to lead biologists to isolate *Chlamydia* from the cerebrospinal fluid or from the blood. It should also be noted that in a number of cases (5%), venereal lymphogranulomatosis is complicated by a chronic oedema: this is genital elephantiasis.

The diagnosis of venereal lymphogranulomatosis requires the isolation of the *Chlamydia* strains involved in the disease. However, isolation on cell cultures is rarely used, but immunological reactions may be used.

The treatment of venereal lymphogranulomatosis in its initial phase is identical to the treatment of other *Chlamydia* infections. In the chronic phases, antibiotics have little effect on the progress of the disease, but they are however useful in case of superinfection. Although the recommended therapeutic arsenal is identical, it is advisable to prolong the treatment for a period of at least four weeks. In addition to this treatment, reconstructive surgery may be useful in cases of urethral, penile or rectal strictures, as well as for the treatment of fistulae.

In conclusion, a short and effective treatment, without recurrences, and a well-tolerated treatment of *Chlamydia trachomatis* infections therefore remains desirable.

An even greater need up until now relates to a diagnosis which is specific to each of the strains, which is sensitive, which can be carried out conveniently and rapidly, and which allows early detection of the infection.

No vaccine is currently available against *Chlamydia trachomatis*. The role of the immune defense in the physiology and pathology of the disease should probably be understood in order to develop satisfactory vaccines.

More detailed information relating to the biology of these strains, their interactions with their hosts, the associated phenomena of infectivity and those of escaping the immune defenses of the host in particular, and finally their involvement in the development of the these associated pathologies, will allow a better understanding of these mechanisms. In the light of the preceding text which shows in particular the limitations of the means of controlling *Chlamydia trachomatis* infection, it is therefore at present essential, on the one hand, to develop molecular tools, in particular from a better genetic knowledge of *Chlamydia trachomatis*, but also to develop new preventive and therapeutic treatments, new diagnostic methods and new vaccine strategies which are specific, effective and tolerated. This is precisely the object of the present invention.

The subject of the present invention is the nucleotide sequence having the sequence SEQ ID No. 1 of the *Chlamydia trachomatis* LGV2 genome. However, the invention is not limited to SEQ ID No. 1, but encompasses genomes and nucleotides encoding polypeptides of strain variants, polymorphisms, allelic variants, and mutants.

Thus, the subject of the present invention encompasses nucleotide sequences characterized in that they are chosen from:

a) the nucleotide sequence of SEQ ID No. 1, a nucleotide sequence exhibiting at least 99.9% identity with the sequence SEQ ID No. 1, the nucleotide sequence of the genomic DNA contained within ECACC Deposit No. 98112618, the nucleotide sequence of a clone insert within ECACC Deposit No. 98112617 (these being provisional deposit numbers);

b) a nucleotide sequence homologous to the sequence SEQ ID No. 1;

c) a polynucleotide sequence that hybridizes to the nucleotide sequence of a) under conditions of high or intermediate stringency as described below:

(i) By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C., the preferred hybridization temperature, in prehybridization mixture containing 100 μg/ml denatured salmon sperm DNA and 5-20×$10^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

(ii) By way of example and not limitation, procedures using conditions of intermediate stringency are as follows: Filters containing DNA are prehybridized, and then hybridized at a temperature of 60° C. in the presence of a 5×SSC buffer and labeled probe. Subsequently, filter washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

d) a nucleotide sequence complementary to the sequence SEQ ID No. 1 or complementary to a nucleotide sequence as defined in a), b) or c), and a nucleotide sequence of their corresponding RNA;

e) a nucleotide sequence of a representative fragment of the sequence SEQ ID No. 1, or of a representative fragment of the nucleotide sequence as defined in a), b), c) or d);

f) a nucleotide sequence comprising a sequence as defined in a), b), c), d) or e);

g) a nucleotide sequence capable of being obtained from a nucleotide sequence as defined in a), b), c), d), e) or f); and h) a modified nucleotide sequence of a nucleotide sequence as defined in a), b), c), d), e), f) or g).

Sequence of the genome, or genomic sequence of *Chlamydia trachomatis* is understood to mean the sequence of the chromosome of *Chlamydia trachomatis*, in contrast with the plasmid sequence of *Chlamydia trachomatis*.

Nucleotide sequence, polynucleotide or nucleic acid are understood to mean, according to the present invention, either a double-stranded DNA, a single-stranded DNA or products of transcription of the said DNAs.

It should be understood that the present invention does not relate to the genomic nucleotide sequences of *Chlamydia trachomatis* taken in their natural environment, that is to say in the natural state. They are sequences which may have been isolated, purified or partially purified, by separation methods such as, for example, ion-exchange chromatography, molecular size exclusion chromatography or affinity chromatography, or alternatively fractionation techniques based on solubility in various solvents, or by genetic engineering methods such as amplification, cloning or subcloning, it being possible for the sequences of the invention to be carried by vectors.

The nucleotide sequence SEQ ID No. 1 was obtained by sequencing the *Chlamydia trachomatis* LGV2 genome by the method of directed sequencing after fluorescent automated sequencing of the inserts of clones and assembling of these sequences of nucleotide fragments (inserts) by means of softwares (cf. Examples). In spite of the high precision of the sequence SEQ ID No. 1, it is possible that it does not perfectly, 100% represent the nucleotide sequence of the *Chlamydia trachomatis* LGV2 genome and that a few rare sequencing errors or uncertainties still remain in the sequence SEQ ID No. 1. In the present invention, the presence of an uncertainty for an amino acid is designated by "Xaa" and that for a nucleotide is designated by "N" in the sequence listing below. These few rare errors or uncertainties could be easily detected and corrected by persons skilled in the art using the entire chromosome and/or its representative fragments according to the invention and standard amplification, cloning and sequencing methods, it being possible for the sequences obtained to be easily compared, in particular by means of a computer software and using computer-readable media for recording the sequences according to the invention as described, for example, below. After correcting these possible rare errors or uncertainties, the corrected nucleotide sequence obtained would still exhibit at least 99.9% identity with the sequence SEQ ID No. 1. Such rare sequencing uncertainties are not present within the DNA contained within ECACC Deposit No. 98112617 or 98112618 (provisional numbers), and whatever rare sequence uncertainties that exist within SEQ ID No. 1 can routinely be corrected utilizing the DNA of the ECACC Deposits.

Homologous nucleotide sequence for the purposes of the present invention is understood to mean a nucleotide sequence having a percentage identity with the bases of the nucleotide sequence SEQ ID No. 1 of at least 80%, preferably 90% and 95%, this percentage being purely statistical and it being possible for the differences between the two nucleotide sequences to be distributed randomly and over their entire length. The said homologous sequences exhibiting a percentage identity with the bases of the nucleotide sequence SEQ ID No. 1 of at least 80%, preferably 90% and 95%, may comprise, for example, the sequences corresponding to the genomic sequence or to the sequences of its representative fragments of a bacterium belonging to the *Chlamydia* family, including the species Chlamydia *pneumoniae, Chlamydia psittaci* and *Chlamydia pecorum* mentioned above, as well as the sequences corresponding to the genomic sequence or to the sequences of its representative fragments of a bacterium belonging to the variants of the species *Chlamydia trachomatis*. In the present invention, the terms family and genus are mutually interchangeable, the terms variant, serotype, strain and subspecies *are* also mutually interchangeable. These homologous sequences may thus correspond to variations linked to mutations within the same species or between species and may correspond in particular to truncations, substitutions, deletions and/or additions of at least one nucleotide. The said homologous sequences may also correspond to variations linked to the degeneracy of the genetic code or to a bias in the genetic code which is specific to the family, to the species or to the variant and which are likely to be present in *Chlamydia*.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3): 403-410; Thompson et al., 1994, *Nucleic Acids Res.* 22(2): 4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272).

In a particularly preferred embodiment, protein and nucleic acid sequence homologies are evaluated using the Basic Local Alignment Search Tool ("BLAST") which is well known in the art (see, e.g., Karlin and Altschul, 1990, *Proc. Natl. Acad. Sci. USA* 87:2267-2268; Altschul et al., 1990, *J. Mol. Biol.* 2/5:403-410; Altschul et al., 1993, *Nature Genetics* 3:266-272; Altschul et al., 1997, *Nuc. Acids Res.* 25:3389-3402). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, *Science* 256:1443-1445; Henikoff and Henikoff, 1993, *Proteins* 17:49-61). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation)

The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, *Proc. Natl. Acad. Sci. USA* 87:2267-2268).

Nucleotide sequence complementary to a sequence of the invention is understood to mean any DNA whose nucleotides are complementary to those of the sequence of the invention, and whose orientation is reversed (antiparallel sequence).

The present invention further comprises fragments of the sequences of a) through h) above. Representative fragments of the sequences according to the invention will be understood to mean any nucleotide fragment having at least 8 successive nucleotides, preferably at least 12 successive nucleotides, and still more preferably at least 15 or at least 20 successive nucleotides of the sequence from which it is derived. It is understood that such fragments refer only to portions of SEQ ID No. 1 that are not currently listed in a publicly available database.

Among these representative fragments, those capable of hybridizing under stringent conditions with a nucleotide sequence according to the invention are preferred. Hybridization under stringent conditions means that the temperature and ionic strength conditions are chosen such that they allow hybridization to be maintained between two complementary DNA fragments.

By way of illustration, high stringency conditions for the hybridization step for the purposes of defining the nucleotide fragments described above, are advantageously the following.

The hybridization is carried out at a preferred temperature of 65° C. in the presence of SSC buffer, 1×SSC corresponding to 0.15 M NaCl and 0.05 M Na citrate. The washing steps may be, for example, the following: 2×SSC, 0.1% SDS at room temperature followed by three washes with 1×SSC, 0.1% SDS; 0.5×SSC, 0.1% SDS; 0.1×SSC, 0.1% SDS at 68° C. for 15 minutes.

Intermediate stringency conditions, using, for example, a temperature of 60° C. in the presence of a 5×SSC buffer, or of low stringency, for example a temperature of 50° C. in the presence of a 5×SSC buffer, respectively require a lower overall complementarity for the hybridization between the two sequences.

The stringent hybridization conditions described above for a polynucleotide of about 300 bases in size will be adapted by persons skilled in the art for larger- or smaller-sized oligonucleotides, according to the teaching of Sambrook et al., 1989.

Among the representative fragments according to the invention, those which can be used as primer or probe in methods which make it possible to obtain homologous sequences or their representative fragments according to the invention, or to reconstitute a genomic fragment found to be incomplete in the sequence SEQ ID No. 1 or carrying an error or an uncertainty, are also preferred, these methods, such as the polymerase chain reaction (PCR), cloning and sequencing of nucleic acid being well known to persons skilled in the art. These homologous nucleotide sequences corresponding to mutations or to inter- or intra-species variations, as well as the complete genomic sequence or one of its representative fragments capable of being reconstituted, of course form part of the invention.

Among the said representative fragments, those which can be used as primer or probe in methods allowing diagnosis of the presence of *Chlamydia trachomatis* or one of its associated microorganisms as defined below are also preferred.

The representative fragments capable of modulating, regulating, inhibiting or inducing the expression of a gene of *Chlamydia trachomatis* or one of its associated microorganisms, and/or capable of modulating the replication cycle of *Chlamydia trachomatis* or one of its associated microorganisms in the host cell and/or organism, are also preferred. Replication cycle is intended to designate invasion, multiplication, intracellular localization, in particular retention in the vacuole and inhibition of the process of fusion to the lysosome, and propagation of *Chlamydia trachomatis* or one of its associated microorganisms from host cells to host cells.

Among the said representative fragments, those corresponding to nucleotide sequences corresponding to open reading frames, called ORF sequences (ORF for open reading frame), and encoding polypeptides, such as for example, but without being limited thereto, the ORF sequences which will be later described, are finally preferred.

The representative fragments according to the invention may be obtained, for example, by specific amplification, such as PCR, or after digestion, with appropriate restriction enzymes, of nucleotide sequences according to the invention; these methods are in particular described in the manual by Sambrook et al., 1989. The said representative fragments may also be obtained by chemical synthesis when they are not too large in size and according to methods well known to persons skilled in the art. For example, such fragments can be obtained by isolating fragments of the genomic DNA of ECACC Deposit No. 98112618 or a clone insert present at this ECACC Deposit No. 98112617 (provisional numbers).

The representative fragments according to the invention may be used, for example, as primer, to reconstitute some of the said representative fragments, in particular those in which a portion of the sequence is likely to be missing or imperfect, by methods well known to persons skilled in the art such as amplification, cloning or sequencing techniques.

Modified nucleotide sequence will be understood to mean any nucleotide sequence obtained by mutagenesis according to techniques well known to persons skilled in the art, and exhibiting modifications in relation to the normal sequences, for example mutations in the regulatory and/or promoter sequences for the expression of a polypeptide, in particular leading to a modification of the level of expression of the said polypeptide or to a modulation of the replicative cycle.

Modified nucleotide sequence will also be understood to mean any nucleotide sequence encoding a modified polypeptide as defined below.

The subject of the present invention also includes *Chlamydia trachomatis* nucleotide sequences characterized in that they are chosen from a nucleotide sequence of an open reading frame (ORF), that is, the ORF2 to ORF1197 sequences.

The ORF2 to ORF1197 nucleotide sequences are defined in Tables 1 and 2, infra, represented below by their position on the sequence SEQ ID No. 1. For example, the ORF10 sequence is defined by the nucleotide sequence between the nucleotides at position 9828 and 10430 on the sequence SEQ ID No. 1, ends included. ORF2 to ORF1197 have been identified via homology analyses as well as via analyses of potential ORF start sites, as discussed in the examples below. It is to be understood that each identified ORF of the invention comprises a nucleotide sequence that spans the contiguous nucleotide sequence from the codon immediately 3' to the stop codon of the preceding ORF and through the 5' codon to the next stop codon of SEQ ID No.:1 in-frame to the ORF nucleotide sequence. Table 2, infra, lists the beginning, end and potential start site of each of ORFs 2-1197. In one embodiment, the ORF comprises the contiguous nucleotide sequence spanning from the potential OR start site downstream (that is, 3') to the ORF stop codon (or the ORF codon immediately adjacent to and upstream of the ORF stop codon). ORF2 to ORF1197 encode the polypeptides of SEQ ID No. 2 to SEQ ID No. 1197.

Upon introduction of minor frameshifts, certain individual ORFs can comprise larger "combined" ORFs. A list of such putative "combined" ORFs is shown in Table 3, below. For example, a combined ORF can comprise ORF 1076 and ORF 1073, including intervening in-frame, nucleotide sequences. The order of ORFs (5' to 3'), within each "combined" ORF is as listed. It is to be understood that when ORF2 to ORF 1197 are referred to herein, such reference is also meant to include "combined" ORFs. Polypeptide sequences encoded by such "combined" ORFs are also part of the present invention.

TABLE 3

ORF 1076, ORF 1073;
ORF 3, ORF 2;
ORF 23, ORF 22, ORF 21;
ORF 1141, ORF 477, ORF 478, ORF 479;
ORF 487, ORF 486, ORF 485, ORF 484, ORF 483, ORF 482, ORF 481;
ORF 488, ORF 489;
ORF 573, ORF 572, ORF 571;
ORF 817, ORF 818;
ORF 819, ORF 820;
ORF 1037, ORF 1038;
ORF 1071, ORF 1070;
ORF 17, ORF 1077;
ORF 1185, ORF 933, ORF 934;
ORF 1060, ORF 1059;
ORF 155, ORF 156;
ORF 679, ORF 680;
ORF 879, ORF 878;
ORF 1028; ORF 1029,
and representative fragments.

Table 1 also depicts the results of homology searches that compared the sequences of the polypeptides encoded by each of the ORFs to sequences present in public published databases. It is understood that in one embodiment, those polypeptides listed in Table 1 as exhibiting greater than about 95% identity to a polypeptide present in a publicly disclosed database are not considered part of the present invention; likewise in this embodiment, those nucleotide sequences encoding such polypeptides are not considered part of the invention. In another embodiment, it is understood that those polypeptides listed in Table 1 as exhibiting greater than about 99% identity to a polypeptide present in a publicly disclosed database are not considered part of the invention; likewise, in this embodiment, those nucleotide sequences encoding such polypeptides are not considered part of the invention.

The invention also relates to the nucleotide sequences characterized in that they comprise a nucleotide sequence chosen from:

a) an ORF2 to ORF1197, a "combined" ORF nucleotide sequence, the nucleotide sequence of the genomic DNA contained within ECACC Deposit No. 98112618 or the nucleotide sequence of a clone insert in ECACC Deposit No. 98112617 according to the invention;

b) a homologous nucleotide sequence exhibiting at least 80% identity across an entire ORF2 to ORF1197 nucleotide sequence according to the invention or as defined in a);

c) a polynucleotide sequence that hybridizes to ORF2 to ORF1197 under conditions of high or intermediate stringency as described below:

(i) By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in prehybridization mixture containing 100 µg/ml denatured salmon sperm DNA and 5–20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety. Preferably, such sequences encode a homolog of a polypeptide encoded by one of ORF2 to ORF1197. In one embodiment, such sequences encode a *Chlamydia trachomatis* polypeptide.

(ii) By way of example and not limitation, procedures using conditions of intermediate stringency are as follows: Filters containing DNA are prehybridized, and then hybridized at a temperature of 60° C. in the presence of a 5×SSC buffer and labeled probe. Subsequently, filter washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety. Preferably, such sequences encode a homolog of a polypeptide encoded by one of ORF2 to ORF1197. In one embodiment, such sequences encode a *Chlamydia trachomatis* polypeptide.

d) a complementary or RNA nucleotide sequence corresponding to an ORF2 to ORF1197 sequence according to the invention or as defined in a), b) or c);

e) a nucleotide sequence of a representative fragment of an ORF2 to ORF1197 sequence according to the invention or of a sequence as defined in a), b), c) or d);

f) a nucleotide sequence capable of being obtained from an ORF2 to ORF1197 sequence according to the invention or as defined in a), b), c), d) or e); and g) a modified nucleotide sequence of an ORF2 to ORF1197 sequence according to the invention or as defined in a), b), c), d), e) or f).

As regards the homology with the ORF2 to ORF1197 nucleotide sequences, the homologous sequences exhibiting a percentage identity with the bases of one of the ORF2 to ORF1197 nucleotide sequences of at least 80%, preferably 90% and 95%, are preferred. Such homologous sequences are identified routinely via, for example, the algorithms described above and in the examples below. The said homologous sequences correspond to the homologous sequences as defined above and may comprise, for example, the sequences corresponding to the ORF sequences of a bacterium belonging to the Chlamydia family, including the species *Chlamydia pneumoniae, Chlamydia psittaci* and *Chlamydia pecorum* mentioned above, as well as the sequences corresponding to the ORF sequences of a bacterium belonging to the variants of the species *Chlamydia trachomatis*. These homologous sequences may likewise correspond to variations linked to mutations within the same species or between species and may correspond in particular to truncations, substitutions, deletions and/or additions of at least one nucleotide. The said homologous sequences may also correspond to variations linked to the degeneracy of the genetic code or to a bias in the genetic code which is specific to the family, to the species or to the variant and which are likely to be present in *Chlamydia*.

The invention comprises the polypeptides encoded by a nucleotide sequence according to the invention, preferably by a representative fragment of the sequence SEQ ID No. 1 and corresponding to an ORF sequence, in particular the *Chlamydia trachomatis* polypeptides, characterized in that they are chosen from the sequences SEQ ID No. 2 to SEQ ID No. 1197, and representative fragments thereof. However, the invention is not limited to polypeptides encoded by ORFs in SEQ ID No. 1 and its corresponding ORF sequences, but encompasses polypeptides of strain variants, polymorphisms, allelic variants, and mutants.

Thus, the invention also comprises the polypeptides characterized in that they comprise a polypeptide chosen from:

a) a polypeptide encoded by a polynucleotide sequence in SEQ ID No. 1 (e.g., any polypeptide encoded by a polynucleotide sequence corresponding to ORF2 to ORF1197) and/or representative fragments thereof according to the invention;

b) a polypeptide homologous to a polypeptide according to the invention, or as defined in a);

c) a polypeptide encoded by a polynucleotide sequence that hybridizes to SEQ ID No. 1 or ORF2 to ORF1197 under high or intermediate stringency as described below:

(i) By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C., the preferred hybridization temperature, in prehybridization mixture containing 100 μg/ml denatured salmon sperm DNA and 5–20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety. Preferably, such sequences encode a homolog of a polypeptide encoded by one of ORF2 to ORF1197. In one embodiment, such sequences encode a *Chlamydia trachomatis* polypeptide.

(ii) By way of example and not limitation, procedures using conditions of intermediate stringency are as follows: Filters containing DNA are prehybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety. Preferably, such sequences encode a homolog of a polypeptide encoded by one of ORF2 to ORF1197. In one embodiment, such sequences encode a *Chlamydia trachomatis* polypeptide.

d) a fragment of at least 5 amino acids of a polypeptide according to the invention, or as defined in a), b) or c);

e) a biologically active fragment of a polypeptide according to the invention, or as defined in a), b), c) or d); and f) a modified polypeptide of a polypeptide according to the invention, as defined in a), b), c), d) or e).

In the present description, the terms polypeptide, peptide and protein are interchangeable.

It should be understood that the invention does not relate to the polypeptides in natural form, that is to say that they are not taken in their natural environment but that they may have been isolated or obtained by purification from natural sources, or alternatively obtained by genetic recombination, or else by chemical synthesis and that they may, in this case, comprise normatural amino acids, as will be described below.

Homologous polypeptide will be understood to designate the polypeptides exhibiting, in relation to the natural polypeptide, certain modifications such as in particular a deletion, addition or substitution of at least one amino acid, a truncation, an extension, a chimeric fusion, and/or a mutation, or polypeptides exhibiting post-translational modifications. Among the homologous polypeptides, those whose amino acid sequence exhibits at least 80%, preferably 90%, homology or identity with the amino acid sequences of the polypeptides according to the invention are preferred. In the case of a substitution, one or more consecutive or nonconsecutive amino acids are replaced by "equivalent" amino acids. The expression "equivalent" amino acid is intended here to designate any amino acid capable of being substituted for one of the amino acids in the basic structure without, however, essentially modifying the biological activities of the corresponding peptides and as will be defined later.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3): 403-410; Thompson et al., 1994, *Nucleic Acids Res.* 22(2): 4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272).

In a particularly preferred embodiment, protein and nucleic acid sequence homologies are evaluated using the Basic Local Alignment Search Tool ("BLAST") which is well known in the art (see, e.g., Karlin and Altschul, 1990, *Proc. Natl. Acad. Sci. USA* 87:2267-2268; Altschul et al. 1990, *J. Mol. Biol.* 215:403-410; Altschul et al., 1993, *Nature Genetics* 3:266-272; Altschul et al., 1997, *Nuc. Acids Res.* 25:3389-3402). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, *Science* 256:1443-1445; Henikoff and Henikoff, 1993, *Proteins* 17:49-61). Less preferably, the PAM or PAM250 matrices may also be used (see, e.g., Schwartz and Dayhoff, eds., 1978, *Matrices, for Detecting Distance Relationships: Atlas of Protein Sequence and Structure*, Washington: National Biomedical Research Foundation).

The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, *Proc. Natl. Acad. Sci. USA* 87:2267-2268).

Equivalent amino acids may be determined either based on their structural homology with the amino acids for which they are substituted, or on results of comparative tests of biological activity between the various polypeptides which may be carried out.

By way of example, there may be mentioned the possibilities of substitutions which may be carried out without resulting in a substantial modification of the biological activity of the corresponding modified polypeptides; the replacements, for example, of leucine with valine or isoleucine, of aspartic acid with glutamic acid, of glutamine with asparagine, of arginine with lysine, and the like, the reverse substitutions naturally being feasible under the same conditions.

The homologous polypeptides also correspond to the polypeptides encoded by the homologous nucleotide sequences as defined above and thus comprise in the present definition the mutated polypeptides or polypeptides corresponding to inter- or intra-species variations which may exist in *Chlamydia*, and which correspond in particular to truncations, substitutions, deletions and/or additions of at least one amino acid residue.

Biologically active fragment of a polypeptide according to the invention will be understood to designate in particular a polypeptide fragment, as defined below, exhibiting at least one of the characteristics of the polypeptides according to the invention, in particular in that it is:

capable of eliciting an immune response directed against *Chlamydia trachomatis*; and/or capable of being recognized by an antibody specific for a polypeptide according to the invention; and/or capable of binding to a polypeptide or to a nucleotide sequence of *Chlamydia trachomatis*; and/or capable of modulating, regulating, inducing or inhibiting the expression of a gene of *Chlamydia trachomatis* or one of its associated microorganisms, and/or capable of modulating the replication cycle of *Chlamydia trachomatis* or one of its associated microorganisms in the host cell and/or organism; and/or capable of generally exerting an even partial physiological activity, such as for example a structural activity (cellular envelope, ribosome), an enzymatic (metabolic) activity, a transport activity, an activity in the secretion or in the virulence.

A representative polypeptide fragment according to the invention is understood to designate a polypeptide comprising a minimum of 5 amino acids, preferably 10 amino acids or preferably 15 amino acids. It is to be understood that such fragments refer only to portions of polypeptides encoded by ORF2 or ORF1197 that are not currently listed in a publicly available database.

The polypeptide fragments according to the invention may correspond to isolated or purified fragments which are naturally present in *Chlamydia trachomatis* or which are secreted by *Chlamydia trachomatis*, or may correspond to fragments capable of being obtained by cleaving the said polypeptide with a proteolytic enzyme, such as trypsin or chymotrypsin or collagenase, or with a chemical reagent, such as cyanogen bromide (CNBr) or alternatively by placing the said polypeptide in a highly acidic environment, for example at pH 2.5. Such polypeptide fragments may be equally well prepared by chemical synthesis, using hosts transformed with an expression vector according to the invention containing a nucleic acid allowing the expression of the said fragments, placed under the control of appropriate elements for regulation and/or expression.

"Modified polypeptide" of a polypeptide according to the invention is understood to designate a polypeptide obtained by genetic recombination or by chemical synthesis as will be described below, exhibiting at least one modification in relation to the normal sequence. These modifications may in particular affect amino acids responsible for a specificity or for the efficiency of the activity, or responsible for the structural conformation, for the charge or for the hydrophobicity, and for the capacity for multimerization and for membrane insertion of the polypeptide according to the invention. It is thus possible to create polypeptides with an equivalent, an increased or a reduced activity, and with an equivalent, a narrower or a broader specificity. Among the modified polypeptides, there may be mentioned the polypeptides in which up to 5 amino acids may be modified, truncated at the N- or C-terminal end, or alternatively deleted, or else added.

As is indicated, the modifications of the polypeptide may have in particular the objective:

- of making it capable of modulating, regulating, inhibiting or inducing the expression of a gene of *Chlamydia*, in particular of *Chlamydia trachomatis* and its variants, or one of its associated micro-organisms, and/or capable of modulating the replication cycle of *Chlamydia*, in particular of *Chlamydia trachomatis* and its variants, or one of its associated microorganisms, in the host cell and/or organism,
- of allowing its use in methods of biosynthesis or of biodegradation, or its incorporation into vaccine compositions,
- of modifying its bioavailability as a compound for therapeutic use.

The said modified polypeptides may also be used on any cell or microorganism for which the said modified polypeptides will be capable of modulating, regulating, inhibiting or inducing gene expression, or of modulating the growth or the replication cycle of the said cell or of the said microorganism. The methods allowing demonstration of the said modulations on eukaryotic or prokaryotic cells are well known to persons skilled in the art. The said cells or microorganisms will be chosen, in particular, from tumour cells or infectious microorganisms and the said modified polypeptides may be used for the prevention or treatment of pathologies linked to the presence of the said cells or of the said microorganisms. It is also clearly understood that the nucleotide sequences encoding the said modified polypeptides may be used for the said modulations, for example by the intermediacy of vectors according to the invention and which are described below, so as to prevent or to treat the said pathologies.

The above modified polypeptides may be obtained using combinatory chemistry, in which it is possible to systematically vary portions of the polypeptide before testing them on models, cell cultures or microorganisms for example, so as to select the compounds which are the most active or which exhibit the desired properties.

Chemical synthesis also has the advantage of being able to use:

normatural amino acids, or
nonpeptide bonds.

Accordingly, in order to extend the life of the polypeptides according to the invention, it may be advantageous to use normatural amino acids, for example in the D form, or alternatively amino acid analogues, in particular sulphur-containing forms for example.

Finally, the structure of the polypeptides according to the invention, its homologous or modified forms, as well as the corresponding fragments may be integrated into chemical structures of the polypeptide type and the like. Accordingly, it may be advantageous to provide at the N- and C-terminal ends compounds which are not recognized by proteases.

Also forming part of the invention are the nucleotide sequences encoding a polypeptide according to the invention. Described below are ORF nucleotide sequences encoding polypeptides exhibiting particularly preferable characteristics. For each group of preferred ORFs described below, it is to be understood that in addition to the individual ORFs listed, in instances wherein such ORFs are present as part of "combined" ORFs, the "combined" ORFs are also to be included within the preferred group.

More particularly, the subject of the invention is nucleotide sequences, characterized in that they encode a polypeptide of the cellular envelope, preferably of the outer cellular envelope of *Chlamydia trachomatis* or one of its representative fragments, such as for example the predominant proteins of the outer membrane, the adhesion proteins or the proteins entering into the composition of the *Chlamydia* wall. Among these sequences, the sequences comprising a nucleotide sequence chosen from the following sequences are most preferred:
ORF3; ORF19; ORF51; ORF189; ORF212; ORF213; ORF324; ORF477; ORF478; ORF479; ORF481; ORF482; ORF483; ORF484; ORF486; ORF488; ORF489; ORF490; ORF572; ORF573; ORF742; ORF817; ORF818; ORF820; ORF1035; ORF1036; ORF1037; ORF1038; ORF1070; ORF1071; ORF1073 and one of their representative fragments.

The structure of the cytoplasmic membranes and of the wall of bacteria is dependent on the associated proteins. The structure of the cytoplasmic membrane makes it impermeable to water, to water-soluble substances and to small-sized molecules (ions, small inorganic molecules, peptides or proteins). To enter into or to interfere with a cell or a bacterium, a ligand must establish a special relationship with a protein anchored in the cytoplasmic membrane (the receptor). These proteins which are anchored on the membrane play an important role in metabolism since they control the exchanges in the bacterium. These exchanges apply to molecules of interest for the bacterium (small molecules such as sugars and small peptides) as well as undesirable molecules for the bacterium such as antibiotics or heavy metals.

The double lipid layer structure of the membrane requires the proteins which are inserted therein to have hydrophobic domains of about twenty amino acids forming an alpha helix. Predominantly hydrophobic and potentially transmembrane regions may be predicted from the primary sequence of the proteins, itself deduced from the nucleotide sequence. The presence of one or more putative transmembrane domains raises the possibility for a protein to be associated with the cytoplasmic membrane and to be able to play an important metabolic role therein or alternatively for the protein thus exposed to be able to exhibit potentially protective epitopes.

If the proteins inserted into the membrane exhibit several transmembrane domains capable of interacting with one another via electrostatic bonds, it then becomes possible for these proteins to form pores which go across the membrane which becomes permeable for a number of substances. It should be noted that proteins which do not have transmembrane domains may also be anchored by the intermediacy of fatty acids in the cytoplasmic membrane, it being possible for the breaking of the bond between the protein and its anchor in some cases to be responsible for the release of the peptide outside the bacterium.

Preferably, the invention relates to the nucleotide sequences according to the invention, characterized in that they encode a *Chlamydia trachomatis* transmembrane polypeptide or one of its representative fragments, having between 1 and 3 transmembrane domains and in that they comprise a nucleotide sequence chosen from the following sequences:
ORF2; ORF3; ORF5; ORF8; ORF9; ORF10; ORF11; ORF12; ORF17; ORF21; ORF26; ORF27; ORF28; ORF29; ORF30; ORF31; ORF33; ORF35; ORF37; ORF39; ORF40; ORF41; ORF42; ORF43; ORF44; ORF45; ORF46; ORF47; ORF48; ORF49; ORF52; ORF53; ORF55; ORF56; ORF58;

ORF65; ORF66; ORF68; ORF70; ORF74; ORF75; ORF76; ORF78; ORF79; ORF81; ORF82; ORF83; ORF86; ORF91; ORF92; ORF94; ORF97; ORF100; ORF102; ORF103; ORF105; ORF106; ORF107; ORF109; ORF110; ORF111; ORF112; ORF113; ORF114; ORF115; ORF116; ORF117; ORF120; ORF122; ORF123; ORF130; ORF134; ORF135; ORF137; ORF140; ORF141; ORF143; ORF144; ORF145; ORF147; ORF148; ORF149; ORF150; ORF151; ORF155; ORF156; ORF162; ORF163; ORF164; ORF165; ORF166; ORF167; ORF168; ORF169; ORF170; ORF171; ORF173; ORF175; ORF176; ORF177; ORF181; ORF183; ORF184; ORF186; ORF187; ORF188; ORF190; ORF191; ORF192; ORF194; ORF195; ORF196; ORF197; ORF198; ORF199; ORF201; ORF202; ORF204; ORF206; ORF207; ORF209; ORF212; ORF213; ORF217; ORF219; ORF220; ORF221; ORF222; ORF223; ORF224; ORF225; ORF227; ORF228; ORF231; ORF232; ORF234; ORF236; ORF237; ORF243; ORF244; ORF245; ORF247; ORF248; ORF249; ORF252; ORF254; ORF257; ORF260; ORF261; ORF263; ORF265; ORF266; ORF267; ORF270; ORF271; ORF272; ORF274; ORF276; ORF277; ORF278; ORF279; ORF282; ORF283; ORF284; ORF285; ORF287; ORF289; ORF290; ORF291; ORF294; ORF298; ORF305; ORF306; ORF310; ORF311; ORF313; ORF315; ORF316; ORF319; ORF320; ORF322; ORF323; ORF325; ORF326; ORF327; ORF328; ORF330; ORF331; ORF332; ORF333; ORF334; ORF335; ORF336; ORF338; ORF339; ORF340; ORF341; ORF344; ORF345; ORF348; ORF349; ORF350; ORF351; ORF352; ORF353; ORF356; ORF357; ORF358; ORF361; ORF362; ORF366; ORF367; ORF368; ORF370; ORF372; ORF373; ORF375; ORF377; ORF378; ORF379; ORF380; ORF382; ORF383; ORF384; ORF385; ORF387; ORF389; ORF390; ORF391; ORF393; ORF396; ORF398; ORF399; ORF403; ORF404; ORF406; ORF407; ORF413; ORF414; ORF417; ORF418; ORF420; ORF421; ORF424; ORF426; ORF427; ORF428; ORF430; ORF433; ORF434; ORF435; ORF436; ORF437; ORF440; ORF443; ORF446; ORF448; ORF450; ORF451; ORF454; ORF455; ORF457; ORF458; ORF459; ORF463; ORF464; ORF466; ORF467; ORF468; ORF469; ORF470; ORF473; ORF474; ORF475; ORF476; ORF477; ORF479; ORF480; ORF481; ORF483; ORF484; ORF485; ORF486; ORF487; ORF488; ORF491; ORF493; ORF496; ORF497; ORF498; ORF500; ORF501; ORF503; ORF504; ORF508; ORF512; ORF513; ORF514; ORF519; ORF521; ORF523; ORF524; ORF526; ORF527; ORF529; ORF530; ORF531; ORF532; ORF534; ORF536; ORF537; ORF538; ORF540; ORF541; ORF542; ORF543; ORF544; ORF545; ORF546; ORF547; ORF551; ORF552; ORF553; ORF555; ORF558; ORF559; ORF560; ORF561; ORF562; ORF566; ORF567; ORF568; ORF569; ORF571; ORF572; ORF574; ORF575; ORF576; ORF580; ORF582; ORF585; ORF587; ORF589; ORF592; ORF593; ORF595; ORF596; ORF597; ORF599; ORF601; ORF602; ORF603; ORF604; ORF608; ORF609; ORF610; ORF611; ORF615; ORF616; ORF617; ORF618; ORF621; ORF622; ORF623; ORF624; ORF625; ORF628; ORF632; ORF633; ORF634; ORF635; ORF637; ORF638; ORF640; ORF641; ORF643; ORF646; ORF648; ORF649; ORF651; ORF652; ORF653; ORF654; ORF655; ORF658; ORF664; ORF665; ORF666; ORF668; ORF669; ORF670; ORF671; ORF672; ORF673; ORF674; ORF676; ORF677; ORF678; ORF680; ORF682; ORF683; ORF684; ORF686; ORF688; ORF689; ORF690; ORF691; ORF692; ORF693; ORF695; ORF696; ORF698; ORF701; ORF703; ORF704; ORF705; ORF706; ORF707; ORF709; ORF710; ORF711; ORF712; ORF713; ORF714; ORF715; ORF717; ORF718; ORF720; ORF721; ORF722; ORF724; ORF726; ORF728; ORF729; ORF730; ORF731; ORF732; ORF733; ORF734; ORF737; ORF738; ORF739; ORF740; ORF742; ORF743; ORF744; ORF745; ORF746; ORF748; ORF750; ORF751; ORF752; ORF753; ORF754; ORF755; ORF757; ORF758; ORF759; ORF760; ORF764; ORF766; ORF768; ORF769; ORF771; ORF772; ORF773; ORF774; ORF775; ORF776; ORF777; ORF778; ORF779; ORF780; ORF781; ORF782; ORF783; ORF786; ORF787; ORF788; ORF789; ORF790; ORF793; ORF798; ORF800; ORF802; ORF803; ORF806; ORF808; ORF809; ORF810; ORF811; ORF813; ORF814; ORF817; ORF820; ORF822; ORF824; ORF825; ORF827; ORF828; ORF829; ORF830; ORF833; ORF834; ORF835; ORF837; ORF838; ORF839; ORF840; ORF841; ORF842; ORF843; ORF845; ORF848; ORF849; ORF850; ORF851; ORF852; ORF854; ORF855; ORF856; ORF857; ORF859; ORF860; ORF862; ORF863; ORF864; ORF866; ORF869; ORF872; ORF873; ORF874; ORF878; ORF879; ORF880; ORF881; ORF883; ORF884; ORF885; ORF886; ORF887; ORF892; ORF893; ORF894; ORF895; ORF897; ORF899; ORF900; ORF901; ORF904; ORF906; ORF909; ORF910; ORF912; ORF914; ORF917; ORF920; ORF921; ORF922; ORF923; ORF924; ORF925; ORF926; ORF927; ORF930; ORF933; ORF934; ORF935; ORF936; ORF937; ORF940; ORF941; ORF942; ORF943; ORF944; ORF945; ORF947; ORF948; ORF951; ORF952; ORF953; ORF954; ORF955; ORF956; ORF957; ORF958; ORF960; ORF961; ORF962; ORF963; ORF964; ORF966; ORF967; ORF969; ORF970; ORF971; ORF973; ORF974; ORF979; ORF980; ORF981; ORF982; ORF984; ORF988; ORF989; ORF990; ORF991; ORF995; ORF996; ORF999; ORF1001; ORF1003; ORF1004; ORF1005; ORF1006; ORF1007; ORF1009; ORF1010; ORF1011; ORF1012; ORF1013; ORF1014; ORF1016; ORF1017; ORF1018; ORF1020; ORF1021; ORF1025; ORF1026; ORF1027; ORF1029; ORF1030; ORF1031; ORF1035; ORF1036; ORF1037; ORF1038; ORF1039; ORF1040; ORF1044; ORF1045; ORF1047; ORF1048; ORF1050; ORF1051; ORF1052; ORF1053; ORF1055; ORF1056; ORF1057; ORF1058; ORF1061; ORF1062; ORF1063; ORF1064; ORF1065; ORF1066; ORF1068; ORF1069; ORF1072; ORF1074; ORF1076 and one of their representative fragments.

Preferably, the invention relates to the nucleotide sequences according to the invention, characterized in that they encode a *Chlamydia trachomatis* transmembrane polypeptide or one of its representative fragments, having between 4 and 6 transmembrane domains and in that they comprise a nucleotide sequence chosen from the following sequences:

ORF7; ORF14; ORF16; ORF32; ORF34; ORF36; ORF38; ORF50; ORF57; ORF59; ORF61; ORF62; ORF63; ORF64; ORF67; ORF69; ORF72; ORF77; ORF80; ORF84; ORF87; ORF93; ORF95; ORF99; ORF108; ORF119; ORF125; ORF126; ORF129; ORF131; ORF136; ORF139; ORF146; ORF152; ORF154; ORF160; ORF161; ORF172; ORF179; ORF182; ORF185; ORF200; ORF203; ORF205; ORF239; ORF242; ORF250; ORF1253; ORF256; ORF259; ORF262; ORF268; ORF275; ORF281; ORF286; ORF288; ORF292; ORF295; ORF296; ORF297; ORF299; ORF300; ORF308; ORF314; ORF317; ORF318; ORF324; ORF342; ORF343; ORF355; ORF360; ORF374; ORF376; ORF386; ORF388; ORF392; ORF394; ORF395; ORF402; ORF405; ORF411; ORF415; ORF416; ORF422; ORF423; ORF429; ORF432; ORF441; ORF442; ORF444; ORF449; ORF452; ORF456; ORF460; ORF461; ORF465; ORF471; ORF472; ORF482; ORF489; ORF492; ORF494; ORF495; ORF502; ORF505; ORF506; ORF509; ORF516; ORF517; ORF520; ORF525; ORF533; ORF539; ORF549; ORF554; ORF557; ORF563; ORF570; ORF573; ORF581; ORF590; ORF591; ORF600;

ORF607; ORF612; ORF613; ORF620; ORF626; ORF629; ORF630; ORF639; ORF644; ORF647; ORF656; ORF659; ORF661; ORF685; ORF687; ORF699; ORF700; ORF708; ORF716; ORF719; ORF725; ORF747; ORF749; ORF756; ORF765; ORF767; ORF794; ORF796; ORF797; ORF799; ORF801; ORF807; ORF821; ORF823; ORF826; ORF847; ORF853; ORF861; ORF870; ORF871; ORF875; ORF882; ORF888; ORF889; ORF898; ORF902; ORF903; ORF911; ORF916; ORF931; ORF939; ORF975; ORF976; ORF978; ORF983; ORF986; ORF987; ORF992; ORF993; ORF1000; ORF1002; ORF1008; ORF1019; ORF1022; ORF1032; ORF1034; ORF1046; ORF1054; ORF1060; ORF1071 and one of their representative fragments.

Preferably, the invention also relates to the nucleotide sequences according to the invention, characterized in that they encode a *Chlamydia trachomatis* transmembrane polypeptide or one of its representative fragments, having at least 7 transmembrane domains and in that they comprise a nucleotide sequence chosen from the following sequences: ORF4; ORF6; ORF13; ORF20; ORF51; ORF71; ORF88; ORF118; ORF128; ORF132; ORF133; ORF158; ORF159; ORF174; ORF180; ORF189; ORF210; ORF211; ORF214; ORF215; ORF226; ORF229; ORF233; ORF235; ORF240; ORF246; ORF251; ORF255; ORF273; ORF354; ORF364; ORF369; ORF371; ORF397; ORF401; ORF409; ORF412; ORF419; ORF439; ORF453; ORF462; ORF490; ORF510; ORF51; ORF518; ORF535; ORF548; ORF550; ORF564; ORF565; ORF578; ORF579; ORF614; ORF631; ORF636; ORF650; ORF662; ORF667; ORF679; ORF681; ORF702; ORF727; ORF741; ORF763; ORF791; ORF792; ORF815; ORF816; ORF832; ORF846; ORF858; ORF865; ORF867; ORF868; ORF877; ORF891; ORF896; ORF907; ORF908; ORF918; ORF919; ORF932; ORF959; ORF977; ORF994; ORF998; ORF1024; ORF1028; ORF1042; ORF1067; ORF1070; ORF1073 and one of their representative fragments.

Preferably, the invention relates to the nucleotide sequences according to the invention, characterized in that they encode a *Chlamydia trachomatis* surface exposed polypeptide (e.g., an outer membrane protein) or one of its representative fragments, said nucleotide sequences comprising a nucleotide sequence chosen from the following sequences:
ORF 2, ORF 3, ORF 21, ORF 22, ORF 23, ORF 53, ORF 77, ORF 187, ORF 203, ORF 383, ORF 477, ORF 478, ORF 479, ORF 481, ORF 482, ORF 483, ORF 484, ORF 485, ORF 486, ORF 487, ORF 488, ORF 489, ORF 490, ORF 571, ORF 572, ORF 573, ORF 593, ORF 670, ORF 693, ORF 742, ORF 749, ORF 801, ORF 817, ORF 818, ORF 819, ORF 820, ORF 851, ORF 902, ORF 923, ORF 1035, ORF 1036, ORF 1037, ORF 1038, ORF 1069, ORF 1070, ORF 1071, ORF 1073, ORF 1076, ORF 1095, ORF 1096, ORF 1141, ORF 1181, and their representative fragments.

Preferably, the invention relates to the nucleotide sequences according to the invention, characterized in that they encode a *Chlamydia trachomatis* lipoprotein or one of its representative fragments, said nucleotide sequences comprising a nucleotide sequence chosen from the following sequences:
ORF 29, ORF 42, ORF 66, ORF 72, ORF 76, ORF 78, ORF 148, ORF 154, ORF 180, ORF 182, ORF 184, ORF 187, ORF 200, ORF 242, ORF 245, ORF 250, ORF 253, ORF 272, ORF 274, ORF 275, ORF 308, ORF 350, ORF 362, ORF 383, ORF 394, ORF 396, ORF 399,
ORF 422, ORF 488, ORF 535, ORF 568, ORF 573, ORF 578, ORF 593, ORF 607, ORF 625, ORF 662, ORF 669, ORF 688, ORF 690, ORF 716, ORF 773, ORF 778, ORF 781, ORF 783, ORF 788, ORF 817, ORF 848, ORF 851, ORF 853, ORF 857, ORF 875, ORF 877, ORF 886, ORF 898, ORF 902, ORF 923, ORF 938, ORF 976, ORF 978, ORF 990, ORF 1005, ORF 1021, ORF 1035, ORF 1069, ORF 1083, ORF 1088, ORF 1089, ORF 1091, ORF 1092, ORF 1095, ORF 1096, ORF 1100, ORF 1105, ORF 1108, ORF 1117, ORF 1120, ORF 1121, ORF 1124, ORF 1128, ORF 1133, ORF 1135, ORF 1139, ORF 1140, ORF 1157, ORF 1159, ORF 1163, ORF 1165, ORF 1167, ORF 1168, ORF 1169, ORF 1171, ORF 1173, ORF 1174, ORF 1177, ORF 1180, ORF 1181, ORF 1186, ORF 1194, ORF 1197, and their representative fragments.

Preferably, the invention relates to the nucleotide sequences according to the invention, characterized in that they encode a *Chlamydia trachomatis* polypeptide involved in lipopolysaccharide (LPS) biosynthesis, said nucleotide sequences comprising a nucleotide sequence chosen from the following sequences: ORF 17, ORF 201, ORF 691, ORF 807, ORF 936, ORF 983, ORF 1019, ORF 1077 and one of their representative fragments.

Preferably the invention relates to additional LPS-related nucleotide sequences according to the invention, characterized in that they encode:

(a) a *Chlamydia trachomatis* KDO (3-deoxy-D-manno-octulosonic acid)-related polypeptide or one of its representative fragments, said nucleotide sequences comprising a nucleotide sequence chosen from the following sequences: ORF 41, ORF 242, ORF 269, ORF 772, and one of their representative fragments;

(b) a *Chlamydia trachomatis* phosphomannomutase-related polypeptide or one of its representative fragments, said nucleotide sequences comprising a nucleotide sequence chosen from the following sequence: ORF 139, and one of its representative fragments;

(c) a *Chlamydia trachomatis* phosphoglucomutase-related polypeptide or one of its representative fragments, said nucleotide sequences comprising a nucleotide sequence chosen from the following sequence: ORF 567, and one of its representative fragments; and (d) a *Chlamydia trachomatis* lipid A component-related polypeptide or one of its representative fragments, said nucleotide sequences comprising a nucleotide sequence chosen from the following sequences: ORF 4, ORF 933, ORF 934, ORF 935, ORF 1185, and one of their representative fragments.

Preferably, the invention relates to the nucleotide sequences according to the invention, characterized in that they encode a *Chlamydia trachomatis* Type III or other, non-Type III secreted polypeptides or one of its representative fragments, said nucleotide sequences comprising a nucleotide sequence chosen from the following sequences: ORF 180, ORF 181, ORF 207, ORF 208, ORF 372, ORF 391, ORF 399, ORF 477, ORF 486, ORF 749, ORF 758, ORF 819, ORF 878, ORF 888, ORF 896, ORF 897, ORF 900, ORF 902, ORF 923, ORF 1015, ORF 1018, ORF 1059, ORF 1060, ORF 1069, ORF 1071, ORF 1073, ORF 1076, ORF 1189, and their representative fragments.

Preferably, the invention relates to the nucleotide sequences according to the invention, characterized in that they encode a *Chlamydia trachomatis* polypeptide containing RGD (Arg-Gly-Asp) attachment sites or one of its representative fragments:

(a) RGD-containing proteins that are outer membrane proteins, are more likely to play a role in cell attachment. ORFs that encoded a protein containing an RGD sequence and also were classified as outer membrane proteins are ORF 488, ORF 489, ORF 571, ORF 572, ORF 573 or ORF 716, and its representative fragments.

(b) The outer membrane of *Chlamydia* is made of cysteine-rich proteins that form a network of both intra and inter molecular disulfide links. This contributes to the integrity of the membrane since *Chlamydia* lacks the peptidoglycan layer that other gram-negative bacteria have Cysteine-rich proteins that have the RGD sequence are also considered to be potential vaccine candidates. Cysteine-rich proteins were defined as proteins that had more than 3.0% cysteine in their primary amino acid sequence, above the mean genomic ORF cysteine content. The corresponding ORF is: ORF 1144 and one of its representative fragments.

(c) The outer membrane of *Chlamydia* may also contain small proteins that have cysteines in their N- and C-terminus that may contribute to the network formed by disulfide linkages. These proteins may be anchored in the outer membrane via their N-terminus and may have their C-terminus exposed, which then can interact with the host cells. Alternatively, these proteins may be anchored in the outer membrane via both N- and C-terminus and may have regions in the middle that may be exposed which can in turn interact with the host cells. ORFs encoding polypeptides that contain cysteines in their first 30 amino acids and also contain an RGD sequence are: ORF 101, ORF 122, ORF 308, ORF 488, ORF 489, ORF 571, ORF 572, ORF 573, ORF 651, ORF 679, ORF 680, ORF 705, ORF 716, ORF 763, ORF 870, ORF 878, ORF 879, ORF 995, ORF 1028, ORF 1029, ORF 1176, and one of their representative fragments.

(d) RGD-containing ORFs homologous to RGD-containing ORFs from *Chlamydia pneumoniae* are:
ORF 28, ORF 101, ORF 125, ORF 155, ORF 156, ORF 286, ORF 571, ORF 572, ORF 573, ORF 763, ORF 870, and one of their representative fragments.

Preferably, the invention relates to the nucleotide sequences according to the invention, characterized in that they encode a *Chlamydia trachomatis* cell wall anchored surface polypeptide or one of its representative fragments, said nucleotide sequences comprising a nucleotide sequence chosen from the following sequences: ORF 662, ORF 681, ORF 1182, ORF 1192, and their representative fragments.

Preferably, the invention relates to the nucleotide sequences according to the invention, characterized in that they encode *Chlamydia trachomatis* polypeptides not found in *Chlamydia pneumoniae* (Blastp P>$e^{-10}$), said nucleotide sequences comprising a nucleotide sequence chosen from the following sequences: ORF 2, ORF 18, ORF 60, ORF 66, ORF 67, ORF 68, ORF 69, ORF 70, ORF 81, ORF 89, ORF 107, ORF 108, ORF 109, ORF 134, ORF 147, ORF 191, ORF 194, ORF, 216, ORF 217, ORF 218, ORF 219, ORF 220, ORF 221, ORF 222, ORF 223, ORF 224, ORF 225, ORF 228, ORF 235, ORF 257, ORF 276, ORF 277, ORF 278, ORF 279, ORF 280, ORF 281, ORF 282, ORF 283, ORF 284, ORF 285, ORF 289, ORF 291, ORF 298, ORF 313, ORF 314, ORF 315, ORF 316, ORF 334, ORF 335, ORF 336, ORF 337, ORF 338, ORF 339, ORF 340, ORF 381, ORF 393, ORF 413, ORF 418, ORF 419, ORF 420, ORF 421, ORF 422, ORF 423, ORF 436, ORF 460, ORF 475, ORF 476, ORF 480, ORF 485, ORF 487, ORF 491, ORF 492, ORF 493, ORF 494, ORF 496, ORF 500, ORF 504, ORF 514, ORF 527, ORF 559, ORF 569, ORF 570, ORF 575, ORF 580, ORF 582, ORF 593, ORF 598, ORF 632, ORF 640, ORF 651, ORF 671, ORF 690, ORF 694, ORF 698, ORF 710, ORF 722, ORF 723, ORF 724, ORF 770, ORF 771, ORF 782, ORF 783, ORF 784, ORF 790, ORF 795, ORF 798, ORF 805, ORF 810, ORF 817, ORF 829, ORF 830, ORF 864, ORF 866, ORF 876, ORF 887, ORF 892, ORF 899, ORF 913, ORF 921, ORF 933, ORF 938, ORF 949, ORF 956, ORF 1010, ORF 1017, ORF 1018, ORF 1027, ORF 1030, ORF 1037, ORF 1038, ORF 1047, ORF 1072, ORF 1074, ORF 1075, ORF 1078, ORF 1079, ORF 1081, ORF 1083, ORF 1084, ORF 1087, ORF 1088, ORF 1089, ORF 1091, ORF 1092, ORF 1094, ORF 1095, ORF 1096, ORF 1098, ORF 1104, ORF 1105, ORF 1106, ORF 1108, ORF 1110, ORF 1114, ORF 1115, ORF 1116, ORF 1117, ORF 1119, ORF 1128, ORF 1132, ORF 1133, ORF 1135, ORF 1136, ORF 1139, ORF 1140, ORF 1141, ORF 1142, ORF 1144, ORF 1148, ORF 1151, ORF 1155, ORF 1157, ORF 1159, ORF 1161, ORF 1162, ORF 1165, ORF 1166, ORF 1167, ORF 1168, ORF 1169, ORF 1171, ORF 1172, ORF 1173, ORF 1174, ORF 1175, ORF 1176, ORF 1177, ORF 1178, ORF 1180, ORF 1181, ORF 1183, ORF 1184, ORF 1186, ORF 1187, ORF 1188, ORF 1192, ORF 1194, ORF 1197, and their representative fragments.

Preferably, the invention also relates to the nucleotide sequences according to the invention, characterized in that they encode a *Chlamydia trachomatis* polypeptide or one of its representative fragments which is involved in the intermediate metabolism, in particular in the metabolism of sugars and/or of cofactors, such as for example triose phosphate isomerase or pyruvate kinase, and in that they comprise a nucleotide sequence chosen from the following sequences:
ORF10; ORF44; ORF45; ORF46; ORF47; ORF93; ORF101; ORF102; ORF103; ORF106; ORF107; ORF120; ORF121; ORF130; ORF135; ORF140; ORF143; ORF144; ORF145; ORF158; ORF159; ORF160; ORF161; ORF192; ORF193; ORF196; ORF197; ORF198; ORF199; ORF227; ORF229; ORF236; ORF236; ORF239; ORF243; ORF245; ORF264; ORF265; ORF297; ORF331; ORF333; ORF359; ORF360; ORF374; ORF404; ORF405; ORF405; ORF410; ORF415; ORF415; ORF416; ORF417; ORF432; ORF460; ORF461; ORF462; ORF495; ORF513; ORF515; ORF566; ORF566; ORF566; ORF589; ORF613; ORF645; ORF646; ORF647; ORF652; ORF653; ORF654; ORF672; ORF673; ORF674; ORF682; ORF684; ORF692; ORF700; ORF725; ORF801; ORF802; ORF835; ORF836; ORF837; ORF860; ORF861; ORF862; ORF863; ORF869; ORF869; ORF925; ORF964; ORF983 and one of their representative fragments.

Preferably, the invention also relates to the nucleotide sequences according to the invention, characterized in that they encode a *Chlamydia trachomatis* polypeptide or one of its representative fragments which is involved in the intermediate metabolism of nucleotides or nucleic acids, such as for example CTP synthetase or GMP synthetase, and in that they comprise a nucleotide sequence chosen from the following sequences:
ORF142; ORF142; ORF169; ORF256; ORF268; ORF325; ORF352; ORF366; ORF435; ORF444; ORF528; ORF529; ORF530; ORF548; ORF549; ORF601; ORF602; ORF617; ORF619; ORF644; ORF745; ORF971; ORF972; ORF1023 and one of their representative fragments.

Preferably, the invention also relates to the nucleotide sequences according to the invention, characterized in that they encode a *Chlamydia trachomatis* polypeptide or one of its representative fragments which is involved in the metabolism of nucleic acids, such as for example DNA polymerases or DNA topoisomerases, and in that they comprise a nucleotide sequence chosen from the following sequences:
ORF5; ORF12; 0182; ORF96; ORF97; ORF98; ORF99; ORF100; ORF105; ORF118; ORF136; ORF137; ORF163; ORF190; ORF204; ORF259; ORF260; ORF262; ORF290; ORF300; ORF301; ORF302; ORF387; ORF427; ORF434; ORF441; ORF444; ORF471; ORF595; ORF596; ORF597; ORF599; ORF600; ORF605; ORF612; ORF624; ORF625;

ORF650; ORF657; ORF658; ORF702; ORF703; ORF704; ORF708; ORF719; ORF766; ORF767; ORF775; ORF779; ORF787; ORF, 788; ORF794; ORF841; ORF842; ORF883; ORF884; ORF907; ORF918; ORF924; ORF928; ORF929; ORF962; ORF962; ORF963; ORF969; ORF970; ORF975; ORF979; ORF995; ORF1031; ORF1032 and one of their representative fragments.

Preferably, the invention also relates to the nucleotide sequences according to the invention, characterized in that they encode a *Chlamydia trachomatis* polypeptide or one of its representative fragments which is involved in the metabolism of amino acids or polypeptides, such as for example serine hydroxymethyl transferase or the proteins which load amino acids onto transfer RNAs, and in that they comprise a nucleotide sequence chosen from the following sequences:
ORF27; ORF41; ORF55; ORF56; ORF57; ORF59; ORF62; ORF63; ORF64; ORF65; ORF119; ORF132; ORF240; ORF241; ORF277; ORF278; ORF279; ORF382; ORF406; ORF428; ORF442; ORF446; ORF447; ORF453; ORF454; ORF541; ORF542; ORF591; ORF608; ORF609; ORF610; ORF618; ORF648; ORF649; ORF660; ORF661; ORF677; ORF717; ORF765; ORF797; ORF871; ORF875; ORF920; ORF922; ORF937; ORF998; ORF1020; ORF1021; ORF1034; ORF1044; ORF1046; ORF1049 and one of their representative fragments.

Preferably, the invention also relates to the nucleotide sequences according to the invention, characterized in that they encode a *Chlamydia trachomatis* polypeptide or one of its representative fragments which is involved in the metabolism of polypeptides, such as for example protein kinases or proteases, and in that they comprise a nucleotide sequence chosen from the following sequences:
ORF21; ORF22; ORF23; ORF24; ORF25; ORF26; ORF75; ORF84; ORF86; ORF92; ORF133; ORF151; ORF152; ORF157; ORF179; ORF209; ORF307; ORF326; ORF343; ORF344; ORF345; ORF371; ORF429; ORF519; ORF557; ORF586; ORF587; ORF630; ORF656; ORF706; ORF707; ORF730; ORF751; ORF752; ORF786; ORF847; ORF885; ORF923; ORF978; ORF1039; ORF1048 and one of their representative fragments.

Preferably, the invention also relates to the nucleotide sequences according to the invention, characterized in that they encode a *Chlamydia trachomatis* polypeptide or one of its representative fragments which is involved in the metabolism of fatty acids, such as for example succinyl-CoA-synthesizing proteins or phosphatidylserine synthetase, and in that they comprise a nucleotide sequence chosen from the following sequences:
ORF4; ORF15; ORF16; ORF141; ORF173; ORF205; ORF205; ORF206; ORF207; ORF208; ORF312; ORF355; ORF415; ORF550; ORF558; ORF560; ORF561; ORF574; ORF574; ORF577; ORF578; ORF590; ORF614; ORF772; ORF808; ORF809; ORF904; ORF905; ORF905; ORF933; ORF934; ORF934; ORF936 and one of their representative fragments.

Preferably, the invention also relates to the nucleotide sequences according to the invention, characterized in that they encode a *Chlamydia trachomatis* polypeptide or one of its representative fragments which is involved in the synthesis of the wall, such as for example KDO transferase, and the proteins responsible for the attachment of certain sugars onto the exposed proteins, and in that they comprise a nucleotide sequence chosen from the following sequences:
ORF87; ORF196; ORF242; ORF269; ORF628; ORF629; ORF634; ORF635; ORF637; ORF638; ORF1019 and one of their representative fragments.

Preferably, the invention also relates to the nucleotide sequences according to the invention, characterized in that they encode a *Chlamydia trachomatis* polypeptide or one of its representative fragments which is involved in the transcription, translation and/or maturation process, such as for example initiation factors, RNA polymerases or certain chaperone proteins, and in that they comprise a nucleotide sequence chosen from the following sequences:
ORF112; ORF113; ORF332; ORF212; ORF213; ORF350; ORF362; ORF363; ORF364; ORF407; ORF451; ORF546; ORF643; ORF744; ORF746; ORF833; ORF868; ORF981; ORF982; ORF1003; ORF1011; ORF1042 and one of their representative fragments.

Preferably, the invention also relates to the nucleotide sequences according to the invention, characterized in that they encode a *Chlamydia trachomatis* ribosomal polypeptide or one of its representative fragments, such as for example the ribosomal proteins L21, L27 and S10, and in that they comprise a nucleotide sequence chosen from the following sequences:
ORF114; ORF115; ORF116; ORF328; ORF361; ORF375; ORF445; ORF543; ORF584; ORF585; ORF743; ORF813; ORF941; ORF942; ORF944; ORF946; ORF947; ORF948; ORF950; ORF951; ORF952; ORF953; ORF954; ORF955; ORF955; ORF957; ORF958; ORF960; ORF961; ORF1040; ORF1041; ORF1043; ORF1063; ORF1064 and one of their representative fragments.

Preferably, the invention also relates to the nucleotide sequences according to the invention, characterized in that they encode a *Chlamydia trachomatis* transport polypeptide or one of its representative fragments, such as for example the proteins for transporting amino acids, sugars and certain oligopeptides, and in that they comprise a nucleotide sequence chosen from the following sequences:
ORF6; ORF50; ORF51; ORF80; ORF125; ORF126; ORF128; ORF129; ORF215; ORF246; ORF248; ORF249; ORF251; ORF252; ORF253; ORF255; ORF271; ORF275; ORF293; ORF309; ORF323; ORF324; ORF398; ORF401; ORF449; ORF511; ORF512; ORF564; ORF565; ORF667; ORF679; ORF680; ORF711; ORF712; ORF713; ORF714; ORF715; ORF730; ORF731; ORF736; ORF737; ORF738; ORF870; ORF908; ORF919; ORF977; ORF987; ORF988; ORF992; ORF993; ORF994; ORF1028; ORF1029 and one of their representative fragments.

Preferably, the invention also relates to the nucleotide sequences according to the invention, characterized in that they encode a *Chlamydia trachomatis* polypeptide or one of its representative fragments which is involved in the virulence process, such as for example the proteins analogous to the *Escherichia coli* vacB protein, and in that they comprise a nucleotide sequence chosen from the following sequences:
ORF20; ORF815; ORF816; ORF898; ORF1059; ORF1060 and one of their representative fragments.

Preferably, the invention also relates to the nucleotide sequences according to the invention, characterized in that they encode a *Chlamydia trachomatis* polypeptide or one of its representative fragments which is involved in the secretory system and/or which is secreted, such as for example proteins homologous to proteins in the secretory system of certain bacteria such as the Salmonellae or the Yersiniae, and in that they comprise a nucleotide sequence chosen from the following sequences:
ORF758; ORF888; ORF889; ORF890; ORF891; ORF896; ORF897; ORF898 and one of their representative fragments.

Preferably, the invention also relates to nucleotide sequences according to the invention, characterized in that they encode a polypeptide specific to Chlamydiae or one of its representative fragments, and in that they comprise a nucleotide sequence chosen from the following sequences:
ORF22; ORF29; ORF31; ORF32; ORF34; ORF35; ORF39; ORF40; ORF43; ORF48; ORF49; ORF50; ORF52; ORF53; ORF54; ORF72; ORF77; ORF78; ORF87; ORF90; ORF95; ORF108; ORF1101; ORF111; ORF122; ORF123; ORF124; ORF127; ORF138; ORF144; ORF146; ORF153; ORF155; ORF164; ORF166; ORF175; ORF182; ORF184; ORF186; ORF187; ORF188; ORF202; ORF210; ORF247; ORF258; ORF266; ORF267; ORF270; ORF273; ORF274; ORF295; ORF296; ORF305; ORF306; ORF309; ORF318; ORF319; ORF322; ORF326; ORF342; ORF357; ORF376; ORF379; ORF380; ORF388; ORF390; ORF400; ORF431; ORF433; ORF438; ORF443; ORF456; ORF457; ORF458; ORF464; ORF468; ORF470; ORF473; ORF486; ORF489; ORF497; ORF501; ORF503; ORF504; ORF508; ORF512; ORF521; ORF522; ORF523; ORF524; ORF533; ORF535; ORF536; ORF537; ORF538; ORF539; ORF540; ORF554; ORF563; ORF572; ORF579; ORF595; ORF603; ORF604; ORF606; ORF607; ORF615; ORF616; ORF622; ORF641; ORF642; ORF659; ORF668; ORF670; ORF693; ORF695; ORF696; ORF699; ORF703; ORF704; ORF716; ORF726; ORF728; ORF739; ORF742; ORF747; ORF750; ORF751; ORF755; ORF757; ORF759; ORF761; ORF762; ORF763; ORF764; ORF773; ORF780; ORF781; ORF789; ORF800; ORF803; ORF804; ORF818; ORF820; ORF822; ORF823; ORF824; ORF827; ORF828; ORF839; ORF849; ORF850; ORF851; ORF852; ORF855; ORF856; ORF857; ORF858; ORF859; ORF860; ORF861; ORF862; ORF863; ORF865; ORF868; ORF869; ORF870; ORF871; ORF872; ORF873; ORF874; ORF875; ORF877; ORF878; ORF880; ORF882; ORF884; ORF886; ORF893; ORF901; ORF906; ORF910; ORF912; ORF915; ORF916; ORF917; ORF926; ORF929; ORF933; ORF965; ORF967; ORF968; ORF984; ORF986; ORF989; ORF990; ORF996; ORF997; ORF1001; ORF1002; ORF1013; ORF1016; ORF1031; ORF1033; ORF1035; ORF1049; ORF1051; ORF1052; ORF1054; ORF1056; ORF1057; ORF1058; ORF1062; ORF1070; ORF1071; ORF1073 and one of their representative fragments.

Also forming part of the invention are polypeptides encoded by the polynucleotides of the invention, as well as fusion polypeptides comprising such polypeptides. In one embodiment, the polypeptides and fusion polypeptides immunoreact with seropositive serum of an individual infected with *Chlamydia trachomatis*. For example, described below, are polypeptide sequences exhibiting particularly preferable characteristics. For each group of preferred polypeptides described below, it is to be understood that in addition to the individual polypeptides listed, in instances wherein such polypeptides are encoded as part of "combined" ORFs, such "combined" polypeptides are also to be included within the preferred group.

The subject of the invention is also a polypeptide according to the invention, characterized in that it is a polypeptide of the cellular envelope, preferably of the outer cellular envelope, of *Chlamydia trachomatis* or one of its representative fragments. According to the invention, the said polypeptide is preferably chosen from the polypeptides having the following sequences:
SEQ ID No. 3; SEQ ID No. 19; SEQ ID No. 51; SEQ ID No. 189; SEQ ID No. 212; SEQ ID No. 213; SEQ ID No. 324; SEQ ID No. 477; SEQ II) No. 478; SEQ ID No. 479; SEQ ID No. 481; SEQ ID No. 482; SEQ ID No. 483; SEQ ID No. 484; SEQ ID No. 486; SEQ ID No. 488; SEQ ID No. 489; SEQ ID No. 490; SEQ ID No. 572; SEQ ID No. 573; SEQ ID No. 742; SEQ ID No. 817; SEQ ID No. 818; SEQ ID No. 820; SEQ ID No. 1035; SEQ ID No. 1036; SEQ ID No. 1037; SEQ ID No. 1038; SEQ ID No. 1070; SEQ ID No. 1071; SEQ ID No. 1073 and one of their representative fragments.

Preferably, the invention relates to a polypeptide according to the invention, characterized in that it is a *Chlamydia trachomatis* transmembrane polypeptide or one of its representative fragments, having between 1 and 3 transmembrane domains, and in that it is chosen from the polypeptides having the following sequences:
SEQ ID No. 2; SEQ ID No. 3; SEQ ID No. 5; SEQ ID No. 8; SEQ ID No. 9; SEQ ID No. 10; SEQ ID No. 1; SEQ ID No. 12; SEQ ID No. 17; SEQ ID No. 21; SEQ ID No. 26; SEQ ID No. 27; SEQ ID No. 28; SEQ ID No. 29; SEQ ID No. 30; SEQ ID No. 31; SEQ ID No. 33; SEQ ID No. 35; SEQ ID No. 37; SEQ ID No. 39; SEQ ID No. 40; SEQ ID No. 41; SEQ ID No. 42; SEQ ID No. 43; SEQ ID No. 44; SEQ ID No. 45; SEQ ID No. 46; SEQ ID No. 47; SEQ ID No. 48; SEQ ID No. 49; SEQ ID No. 52; SEQ ID No. 53; SEQ ID No. 55; SEQ ID No. 56; SEQ ID No. 58; SEQ ID No. 65; SEQ ID No. 66; SEQ ID No. 68; SEQ ID No. 70; SEQ ID No. 74; SEQ ID No. 75; SEQ ID No. 76; SEQ ID No. 78; SEQ ID No. 79; SEQ ID No. 81; SEQ ID No. 82; SEQ ID No. 83; SEQ ID No. 86; SEQ ID No. 91; SEQ ID No. 92; SEQ ID No. 94; SEQ ID No. 97; SEQ ID No. 100; SEQ ID No. 102; SEQ ID No. 103; SEQ ID No. 105; SEQ ID No. 106; SEQ ID No. 107; SEQ ID No. 109; SEQ ID No. 110; SEQ ID No. 111; SEQ ID No. 112; SEQ ID No. 113; SEQ ID No. 114; SEQ ID No. 115; SEQ ID No. 116; SEQ ID No. 117; SEQ ID No. 120; SEQ ID No. 122; SEQ ID No. 123; SEQ ID No. 130; SEQ ID No. 134; SEQ ID No. 135; SEQ ID No. 137; SEQ ID No. 140; SEQ ID No. 141; SEQ ID No. 143; SEQ ID No. 144; SEQ ID No. 145; SEQ ID No. 147; SEQ ID No. 148; SEQ ID No. 149; SEQ ID No. 150; SEQ ID No. 151; SEQ ID No. 155; SEQ ID No. 156; SEQ ID No. 162; SEQ ID No. 163; SEQ ID No. 164; SEQ ID No. 165; SEQ ID No. 166; SEQ ID No. 167; SEQ ID No. 168; SEQ ID No. 169; SEQ ID No. 170; SEQ ID No. 171; SEQ ID No. 173; SEQ ID No. 175; SEQ ID No. 176; SEQ ID No. 177; SEQ ID No. 181; SEQ ID No. 183; SEQ ID No. 184; SEQ ID No. 186; SEQ ID No. 187; SEQ ID No. 188; SEQ ID No. 190; SEQ ID No. 191; SEQ ID No. 192; SEQ ID No. 194; SEQ ID No. 195; SEQ ID No. 196; SEQ ID No. 197; SEQ ID No. 198; SEQ ID No. 199; SEQ ID No. 201; SEQ ID No. 202; SEQ ID No. 204; SEQ ID No. 206; SEQ ID No. 207; SEQ ID No. 209; SEQ ID No. 212; SEQ ID No. 213; SEQ ID No. 217; SEQ ID No. 219; SEQ ID No. 220; SEQ ID No. 221; SEQ ID No. 222; SEQ ID No. 223; SEQ ID No. 224; SEQ ID No. 225; SEQ ID No. 227; SEQ ID No. 228; SEQ ID No. 231; SEQ ID No. 232; SEQ ID No. 234; SEQ ID No. 236; SEQ ID No. 237; SEQ ID No. 243; SEQ ID No. 244; SEQ ID No. 245; SEQ ID No. 247; SEQ ID No. 248; SEQ ID No. 249; SEQ ID No. 252; SEQ ID No. 254; SEQ ID No. 257; SEQ ID No. 260; SEQ ID No. 261; SEQ ID No. 263; SEQ ID No. 265; SEQ ID No. 266; SEQ ID No. 267; SEQ ID No. 270; SEQ ID No. 271; SEQ ID No. 272; SEQ ID No. 274; SEQ ID No. 276; SEQ ID No. 277; SEQ ID No. 278; SEQ ID No. 279; SEQ ID No. 282; SEQ ID No. 283; SEQ ID No. 284; SEQ ID No. 285; SEQ ID No. 287; SEQ ID No. 289; SEQ ID No. 290; SEQ ID No. 291; SEQ ID No. 294; SEQ ID No. 298; SEQ ID No. 305; SEQ ID No. 306; SEQ ID No. 310; SEQ ID No. 311; SEQ ID No. 313; SEQ ID No. 315; SEQ ID No. 316; SEQ ID No. 319; SEQ ID No. 320; SEQ ID No. 322; SEQ ID No. 323; SEQ ID No. 325; SEQ ID No. 326; SEQ ID No. 327; SEQ ID No. 328; SEQ ID No. 330; SEQ ID No. 331; SEQ ID No. 332; SEQ ID No. 333; SEQ ID No. 334; SEQ ID No. 335; SEQ ID No. 336; SEQ ID No. 338; SEQ ID No. 339; SEQ ID No. 340; SEQ ID No. 341; SEQ ID No. 344; SEQ ID No. 345; SEQ ID No. 348; SEQ ID No. 349; SEQ ID No. 350; SEQ ID No. 351; SEQ ID No. 352; SEQ ID No. 353; SEQ ID No. 356; SEQ ID No. 357; SEQ ID No. 358; SEQ ID No. 361; SEQ ID No. 362;

SEQ ID No. 366; SEQ ID No. 367; SEQ ID No. 368; SEQ ID No. 370; SEQ ID No. 372; SEQ ID No. 373; SEQ ID No. 375; SEQ ID No. 377; SEQ ID No. 378; SEQ ID No. 379; SEQ ID No. 380; SEQ ID No. 382; SEQ ID No. 383; SEQ ID No. 384; SEQ ID No. 385; SEQ ID No. 387; SEQ ID No. 389; SEQ ID No. 390; SEQ ID No. 391; SEQ ID No. 393; SEQ ID No. 396; SEQ ID No. 398; SEQ ID No. 399; SEQ ID No. 403; SEQ ID No. 404; SEQ ID No. 406; SEQ ID No. 407; SEQ ID No. 413; SEQ ID No. 414; SEQ ID No. 417; SEQ ID No. 418; SEQ ID No. 420; SEQ ID No. 421; SEQ ID No. 424; SEQ ID No. 426; SEQ ID No. 427; SEQ ID No. 428; SEQ ID No. 430; SEQ ID No. 433; SEQ ID No. 434; SEQ ID No. 435; SEQ ID No. 436; SEQ ID No. 437; SEQ ID No. 440; SEQ ID No. 443; SEQ ID No. 446; SEQ ID No. 448; SEQ ID No. 450; SEQ ID No. 451; SEQ ID No. 454; SEQ ID No. 455; SEQ ID No. 457; SEQ ID No. 458; SEQ ID No. 459; SEQ ID No. 463; SEQ ID No. 464; SEQ ID No. 466; SEQ ID No. 467; SEQ ID No. 468; SEQ ID No. 469; SEQ ID No. 470; SEQ ID No. 473; SEQ ID No. 474; SEQ ID No. 475; SEQ ID No. 476; SEQ ID No. 477; SEQ ID No. 479; SEQ ID No. 480; SEQ ID No. 481; SEQ ID No. 483; SEQ ID No. 484; SEQ ID No. 485; SEQ ID No. 486; SEQ ID No. 487; SEQ ID No. 488; SEQ ID No. 491; SEQ ID No. 493; SEQ ID No. 496; SEQ ID No. 497; SEQ ID No. 498; SEQ ID No. 500; SEQ ID No. 501; SEQ ID No. 503; SEQ ID No. 504; SEQ ID No. 508; SEQ ID No. 512; SEQ ID No. 513; SEQ ID No. 514; SEQ ID No. 519; SEQ ID No. 521; SEQ ID No. 523; SEQ ID No. 524; SEQ ID No. 526; SEQ ID No. 527; SEQ ID No. 529; SEQ ID No. 530; SEQ ID No. 531; SEQ ID No. 532; SEQ ID No. 534; SEQ ID No. 536; SEQ ID No. 537; SEQ ID No. 538; SEQ ID No. 540; SEQ ID No. 541; SEQ ID No. 542; SEQ ID No. 543; SEQ ID No. 544; SEQ ID No. 545; SEQ ID No. 546; SEQ ID No. 547; SEQ ID No. 551; SEQ ID No. 552; SEQ ID No. 553; SEQ ID No. 555; SEQ ID No. 558; SEQ ID No. 559; SEQ ID No. 560; SEQ ID No. 561; SEQ ID No. 562; SEQ ID No. 566; SEQ ID No. 567; SEQ ID No. 568; SEQ ID No. 569; SEQ ID No. 571; SEQ ID No. 572; SEQ ID No. 574; SEQ ID No. 575; SEQ ID No. 576; SEQ ID No. 580; SEQ ID No. 582; SEQ ID No. 585; SEQ ID No. 587; SEQ ID No. 589; SEQ ID No. 592; SEQ ID No. 593; SEQ ID No. 595; SEQ ID No. 596; SEQ ID No. 597; SEQ ID No. 599; SEQ ID No. 601; SEQ ID No. 602; SEQ ID No. 603; SEQ ID No. 604; SEQ ID No. 608; SEQ D No. 609; SEQ ID No. 610; SEQ ID No. 611; SEQ ID No. 615; SEQ ID No. 616; SEQ ID No. 617; SEQ ID No. 618; SEQ ID No. 621; SEQ ID No. 622; SEQ ID No. 623; SEQ ID No. 624; SEQ ID No. 625; SEQ ID No. 628; SEQ ID No. 632; SEQ ID No. 633; SEQ ID No. 634; SEQ ID No. 635; SEQ ID No. 637; SEQ ID No. 638; SEQ ID No. 640; SEQ ID No. 641; SEQ ID No. 643; SEQ ID No. 646; SEQ ID No. 648; SEQ ID No. 649; SEQ ID No. 651; SEQ ID No. 652; SEQ ID No. 653; SEQ ID No. 654; SEQ ID No. 655; SEQ ID No. 658; SEQ ID No. 664; SEQ ID No. 665; SEQ ID No. 666; SEQ ID No. 668; SEQ ID No. 669; SEQ ID No. 670; SEQ ID No. 671; SEQ ID No. 672; SEQ ID No. 673; SEQ ID No. 674; SEQ ID No. 676; SEQ ID No. 677; SEQ ID No. 678; SEQ ID No. 680; SEQ ID No. 682; SEQ ID No. 683; SEQ ID No. 684; SEQ ID No. 686; SEQ ID No. 688; SEQ ID No. 689; SEQ ID No. 690; SEQ ID No. 691; SEQ ID No. 692; SEQ ID No. 693; SEQ ID No. 695; SEQ ID No. 696; SEQ ID No. 698; SEQ ID No. 701; SEQ ID No. 703; SEQ ID No. 704; SEQ ID No. 705; SEQ ID No. 706; SEQ ID No. 707; SEQ ID No. 709; SEQ ID No. 710; SEQ ID No. 711; SEQ ID No. 712; SEQ ID No. 713; SEQ ID No. 714; SEQ ID No. 715; SEQ ID No. 717; SEQ ID No. 718; SEQ ID No. 720; SEQ ID No. 721; SEQ ID No. 722; SEQ ID No. 724; SEQ ID No. 726; SEQ ID No. 728; SEQ ID No. 729; SEQ ID No. 730; SEQ ID No. 731; SEQ ID No. 732; SEQ ID No. 733; SEQ ID No. 734; SEQ ID No. 737; SEQ ID No. 738; SEQ ID No. 739; SEQ ID No. 740; SEQ ID No. 742; SEQ ID No. 743; SEQ ID No. 744; SEQ ID No. 745; SEQ ID No. 746; SEQ ID No. 748; SEQ ID No. 750; SEQ ID No. 751; SEQ ID No. 752; SEQ ID No. 753; SEQ ID No. 754; SEQ ID No. 755; SEQ ID No. 757; SEQ ID No. 758; SEQ ID No. 759; SEQ ID No. 760; SEQ ID No. 764; SEQ ID No. 766; SEQ ID No. 768; SEQ ID No. 769; SEQ ID No. 771; SEQ ID No. 772; SEQ ID No. 773; SEQ ID No. 774; SEQ ID No. 775; SEQ ID No. 776; SEQ ID No. 777; SEQ ID No. 778; SEQ ID No. 779; SEQ ID No. 780; SEQ ID No. 781; SEQ ID No. 782; SEQ ID No. 783; SEQ ID No. 786; SEQ ID No. 787; SEQ ID No. 788; SEQ ID No. 789; SEQ ID No. 790; SEQ ID No. 793; SEQ ID No. 798; SEQ ID No. 800; SEQ ID No. 802; SEQ ID No. 803; SEQ ID No. 806; SEQ ID No. 808; SEQ ID No. 809; SEQ ID No. 810; SEQ ID No. 811; SEQ ID No. 813; SEQ ID No. 814; SEQ ID No. 817; SEQ ID No. 820; SEQ ID No. 822; SEQ ID No. 824; SEQ ID No. 825; SEQ ID No. 827; SEQ ID No. 828; SEQ ID No. 829; SEQ ID No. 830; SEQ ID No. 833; SEQ ID No. 834; SEQ ID No. 835; SEQ ID No. 837; SEQ ID No. 838; SEQ ID No. 839; SEQ ID No. 840; SEQ ID No. 841; SEQ ID No. 842; SEQ ID No. 843; SEQ ID No. 845; SEQ ID No. 848; SEQ ID No. 849; SEQ ID No. 850; SEQ ID No. 851; SEQ ID No. 852; SEQ ID No. 854; SEQ ID No. 855; SEQ ID No. 856; SEQ ID No. 857; SEQ ID No. 859; SEQ ID No. 860; SEQ ID No. 862; SEQ ID No. 863; SEQ ID No. 864; SEQ ID No. 866; SEQ ID No. 869; SEQ ID No. 872; SEQ ID No. 873; SEQ ID No. 874; SEQ ID No. 878; SEQ ID No. 879; SEQ ID No. 880; SEQ ID No. 881; SEQ ID No. 883; SEQ ID No. 884; SEQ ID No. 885; SEQ ID No. 886; SEQ ID No. 887; SEQ ID No. 892; SEQ ID No. 893; SEQ ID No. 894; SEQ ID No. 895; SEQ ID No. 897; SEQ ID No. 899; SEQ H) No. 900; SEQ ID No. 901; SEQ ID No. 904; SEQ ID No. 906; SEQ ID No. 909; SEQ ID No. 910; SEQ ID No. 912; SEQ ID No. 914; SEQ ID No. 917; SEQ ID No. 920; SEQ ID No. 921; SEQ ID No. 922; SEQ ID No. 923; SEQ ID No. 924; SEQ ID No. 925; SEQ ID No. 926; SEQ ID No. 927; SEQ ID No. 930; SEQ ID No. 933; SEQ ID No. 934; SEQ ID No. 935; SEQ ID No. 936; SEQ ID No. 937; SEQ ID No. 940; SEQ ID No. 941; SEQ ID No. 942; SEQ ID No. 943; SEQ ID No. 944; SEQ ID No. 945; SEQ ID No. 947; SEQ ID No. 948; SEQ ID No. 951; SEQ ID No. 952; SEQ ID No. 953; SEQ ID No. 954; SEQ ID No. 955; SEQ ID No. 956; SEQ ID No. 957; SEQ ID No. 958; SEQ ID No. 960; SEQ ID No. 961; SEQ ID No. 962; SEQ ID No. 963; SEQ ID No. 964; SEQ ID No. 966; SEQ ID No. 967; SEQ ID No. 969; SEQ ID No. 970; SEQ ID No. 971; SEQ ID No. 973; SEQ ID No. 974; SEQ ID No. 979; SEQ ID No. 980; SEQ ID No. 981; SEQ ID No. 982; SEQ ID No. 984; SEQ ID No. 988; SEQ ID No. 989; SEQ ID No. 990; SEQ ID No. 991; SEQ ID No. 995; SEQ ID No. 996; SEQ ID No. 999; SEQ ID No. 1001; SEQ ID No. 1003; SEQ ID No. 1004; SEQ ID No. 1005; SEQ ID No. 1006; SEQ ID No. 1007; SEQ ID No. 1009; SEQ ID No. 1010; SEQ ID No. 1011; SEQ ID No. 1012; SEQ ID No. 1013; SEQ ID No. 1014; SEQ ID No. 1016; SEQ ID No. 1017; SEQ ID No. 1018; SEQ ID No. 1020; SEQ ID No. 1021; SEQ ID No. 1025; SEQ ID No. 1026; SEQ ID No. 1027; SEQ ID No. 1029; SEQ ID No. 1030; SEQ ID No. 1031; SEQ ID No. 1035; SEQ ID No. 1036; SEQ ID No. 1037; SEQ ID No. 1038; SEQ ID No. 1039; SEQ ID No. 1040; SEQ ID No. 1044; SEQ ID No. 1045; SEQ ID No. 1047; SEQ ID No. 1048; SEQ ID No. 1050; SEQ ID No. 1051; SEQ ID No. 1052; SEQ ID No. 1053; SEQ ID No. 1055; SEQ ID No. 1056; SEQ ID No. 1057; SEQ ID No. 1058; SEQ ID No. 1061; SEQ ID No. 1062; SEQ ID No. 1063; SEQ ID No. 1064; SEQ ID No. 1065; SEQ ID No. 1066; SEQ ID No. 1068; SEQ ID No. 1069; SEQ ID No. 1072; SEQ ID No. 1074; SEQ ID No. 1076 and one of their representative fragments.

Preferably, the invention relates to a polypeptide according to the invention, characterized in that it is a *Chlamydia trachomatis* transmembrane polypeptide or one of its representative fragments, having between 4 and 6 transmembrane domains, and in that it is chosen from the polypeptides having the following sequences:
SEQ ID No. 7; SEQ ID No. 14; SEQ ID No. 16; SEQ ID No. 32; SEQ ID No. 34; SEQ ID No. 36; SEQ ID No. 38; SEQ ID No. 50; SEQ ID No. 57; SEQ ID No. 59; SEQ ID No. 61; SEQ ID No. 62; SEQ ID No. 63; SEQ ID No. 64; SEQ ID No. 67; SEQ ID No. 69; SEQ ID No. 72; SEQ ID No. 77; SEQ ID No. 80; SEQ ID No. 84; SEQ ID No. 87; SEQ ID No. 93; SEQ ID No. 95; SEQ ID No. 99; SEQ ID No. 108; SEQ ID No. 119; SEQ ID No. 125; SEQ ID No. 126; SEQ ID No. 129; SEQ ID No. 131; SEQ ID No. 136; SEQ ID No. 139; SEQ ID No. 146; SEQ ID No. 152; SEQ ID No. 154; SEQ ID No. 160; SEQ ID No. 161; SEQ ID No. 172; SEQ ID No. 179; SEQ ID No. 182; SEQ ID No. 185; SEQ ID No. 200; SEQ ID No. 203; SEQ ID No. 205; SEQ ID No. 239; SEQ ID No. 242; SEQ ID No. 250; SEQ ID No. 253; SEQ ID No. 256; SEQ ID No. 259; SEQ ID No. 262; SEQ ID No. 268; SEQ ID No. 275; SEQ ID No. 281; SEQ ID No. 286; SEQ ID No. 288; SEQ ID No. 292; SEQ ID No. 295; SEQ ID No. 296; SEQ ID No. 297; SEQ ID No. 299; SEQ ID No. 300; SEQ ID No. 308; SEQ ID No. 314; SEQ ID No. 317; SEQ ID No. 318; SEQ ID No. 324; SEQ ID No. 342; SEQ ID No. 343; SEQ ID No. 355; SEQ ID No. 360; SEQ ID No. 374; SEQ ID No. 376; SEQ ID No. 386; SEQ ID No. 388; SEQ ID No. 392; SEQ ID No. 394; SEQ ID No. 395; SEQ ID No. 402; SEQ ID No. 405; SEQ ID No. 411; SEQ ID No. 415; SEQ ID No. 416; SEQ ID No. 422; SEQ ID No. 423; SEQ ID No. 429; SEQ ID No. 432; SEQ ID No. 441; SEQ ID No. 442; SEQ ID No. 444; SEQ ID No. 449; SEQ ID No. 452; SEQ ID No. 456; SEQ ID No. 460; SEQ ID No. 461; SEQ ID No. 465; SEQ ID No. 471; SEQ ID No. 472; SEQ ID No. 482; SEQ ID No. 489; SEQ ID No. 492; SEQ ID No. 494; SEQ ID No. 495; SEQ ID No. 502; SEQ ID No. 505; SEQ ID No. 506; SEQ ID No. 509; SEQ ID No. 516; SEQ ID No. 517; SEQ ID No. 520; SEQ ID No. 525; SEQ ID No. 533; SEQ ID No. 539; SEQ ID No. 549; SEQ ID No. 554; SEQ ID No. 557; SEQ ID No. 563; SEQ ID No. 570; SEQ ID No. 573; SEQ ID No. 581; SEQ ID No. 590; SEQ ID No. 591; SEQ ID No. 600; SEQ ID No. 607; SEQ ID No. 612; SEQ ID No. 613; SEQ ID No. 620; SEQ ID No. 626; SEQ ID No. 629; SEQ ID No. 630; SEQ ID No. 639; SEQ ID No. 644; SEQ ID No. 647; SEQ ID No. 656; SEQ ID No. 659; SEQ ID No. 661; SEQ ID No. 685; SEQ ID No. 687; SEQ ID No. 699; SEQ ID No. 700; SEQ ID No. 708; SEQ ID No. 716; SEQ ID No. 719; SEQ ID No. 725; SEQ ID No. 747; SEQ ID No. 749; SEQ ID No. 756; SEQ ID No. 765; SEQ ID No. 767; SEQ ID No. 794; SEQ ID No. 796; SEQ ID No. 797; SEQ ID No. 799; SEQ ID No. 801; SEQ ID No. 807; SEQ ID No. 821; SEQ ID No. 823; SEQ ID No. 826; SEQ ID No. 847; SEQ ID No. 853; SEQ ID No. 861; SEQ ID No. 870; SEQ ID No. 871; SEQ ID No. 875; SEQ ID No. 882; SEQ ID No. 888; SEQ ID No. 889; SEQ ID No. 898; SEQ ID No. 902; SEQ ID No. 903; SEQ ID No. 911; SEQ ID No. 916; SEQ ID No. 931; SEQ ID No. 939; SEQ ID No. 975; SEQ ID No. 976; SEQ ID No. 978; SEQ ID No. 983; SEQ ID No. 986; SEQ ID No. 987; SEQ ID No. 992; SEQ ID No. 993; SEQ ID No. 1000; SEQ ID No. 1002; SEQ ID No. 1008; SEQ ID No. 1019; SEQ ID No. 1022; SEQ ID No. 1032; SEQ ID No. 1034; SEQ ID No. 1046; SEQ ID No. 1054; SEQ ID No. 1060; SEQ ID No. 1071 and one of their representative fragments.

Preferably, the invention relates to a polypeptide according to the invention, characterized in that it is a *Chlamydia trachomatis* transmembrane polypeptide or one of its representative fragments, having at least 7 transmembrane domains, and in that it is chosen from the polypeptides having the following sequences: SEQ ID No. 4; SEQ ID No. 6; SEQ ID No. 13; SEQ ID No. 20; SEQ ID No. 51; SEQ ID No. 71; SEQ ID No. 88; SEQ ID No. 118; SEQ ID No. 128; SEQ ID No. 132; SEQ ID No. 133; SEQ ID No. 158; SEQ ID No. 159; SEQ ID No. 174; SEQ ID No. 180; SEQ ID No. 189; SEQ ID No. 210; SEQ ID No. 211; SEQ ID No. 214; SEQ ID No. 215; SEQ ID No. 226; SEQ ID No. 229; SEQ ID No. 233; SEQ ID No. 235; SEQ ID No. 240; SEQ ID No. 246; SEQ ID No. 251; SEQ ID No. 255; SEQ ID No. 273; SEQ ID No. 354; SEQ ID No. 364; SEQ ID No. 369; SEQ ID No. 371; SEQ ID No. 397; SEQ ID No. 401; SEQ ID No. 409; SEQ ID No. 412; SEQ ID No. 419; SEQ ID No. 439; SEQ ID No. 453; SEQ ID No. 462; SEQ ID No. 490; SEQ ID No. 510; SEQ ID No. 511; SEQ ID No. 518; SEQ ID No. 535; SEQ ID No. 548; SEQ ID No. 550; SEQ ID No. 564; SEQ ID No. 565; SEQ ID No. 578; SEQ ID No. 579; SEQ ID No. 614; SEQ ID No. 631; SEQ ID No. 636; SEQ ID No. 650; SEQ ID No. 662; SEQ ID No. 667; SEQ ID No. 679; SEQ ID No. 681; SEQ ID No. 702; SEQ ID No. 727; SEQ ID No. 741; SEQ ID No. 763; SEQ ID No. 791; SEQ ID No. 792; SEQ ID No. 815; SEQ ID No. 816; SEQ ID No. 832; SEQ ID No. 846; SEQ ID No. 858; SEQ ID No. 865; SEQ ID No. 867; SEQ ID No. 868; SEQ ID No. 877; SEQ ID No. 891; SEQ ID No. 896; SEQ ID No. 907; SEQ ID No. 908; SEQ ID No. 918; SEQ ID No. 919; SEQ ID No. 932; SEQ ID No. 959; SEQ ID No. 977; SEQ ID No. 994; SEQ ID No. 998; SEQ ID No. 1024; SEQ ID No. 1028; SEQ ID No. 1042; SEQ ID No. 1067; SEQ ID No. 1070; SEQ ID No. 1073 and one of their representative fragments.

Preferably, the invention relates to a polypeptide according to the invention, in that it is a *Chlamydia trachomatis* surface exposed polypeptide or one of its representative fragments, and in that it is chosen from the polypeptides having the following sequences:
SEQ ID No. 2, SEQ ID No. 3, SEQ ID No. 21, SEQ ID No. 22, SEQ ID No. 23, SEQ ID No. 53, SEQ ID No. 77, SEQ ID No. 187, SEQ ID No. 203, SEQ ID No. 383, SEQ ID No. 477, SEQ ID No. 478, SEQ ID No. 479, SEQ ID No. 481, SEQ ID No. 482, SEQ ID No. 483, SEQ ID No. 484, SEQ ID No. 485, SEQ ID No. 486, SEQ ID No. 487, SEQ ID No. 488, SEQ ID No. 489, SEQ ID No. 490, SEQ ID No. 571, SEQ ID No. 572, SEQ ID No. 573, SEQ ID No. 593, SEQ ID No. 670, SEQ ID No. 693, SEQ ID No. 742, SEQ ID No. 749, SEQ ID No. 801, SEQ ID No. 817, SEQ ID No. 818, SEQ ID No. 819, SEQ ID No. 820, SEQ ID No. 851, SEQ ID No. 902, SEQ ID No. 923, SEQ ID No. 1035, SEQ ID No. 1036, SEQ ID No. 1037, SEQ ID No. 1038, SEQ ID No. 1069, SEQ ID No. 1070, SEQ ID No. 1071, SEQ ID No. 1073, SEQ ID No. 1076, SEQ ID No. 1095, SEQ ID No. 1096, SEQ ID No. 1141, SEQ ID No. 1181, and their representative fragments.

Preferably, the invention relates to a polypeptide according to the invention, characterized in that it is a *Chlamydia trachomatis* lipoprotein or one of its representative fragments, and in that it is chosen from the polypeptides having the following sequences:
SEQ ID No. 29, SEQ ID No. 42, SEQ ID No. 66, SEQ ID No. 72, SEQ ID No. 76, SEQ ID No. 78, SEQ ID No. 148, SEQ ID No. 154, SEQ ID No. 180, SEQ ID No. 182, SEQ ID No. 184, SEQ ID No. 187, SEQ ID No. 200, SEQ ID No. 242, SEQ ID No. 245, SEQ ID No. 250, SEQ ID No. 253, SEQ ID No. 272, SEQ ID No. 274, SEQ ID No. 275, SEQ ID No. 308, SEQ ID No. 350, SEQ ID No. 362, SEQ ID No. 383, SEQ ID No. 394, SEQ ID No. 396, SEQ ID No. 399, SEQ ID No. 422, SEQ ID No. 488, SEQ ID No. 535, SEQ ID No. 568, SEQ ID No. 573, SEQ ID No. 578, SEQ ID No. 593, SEQ ID No. 607, SEQ ID No. 625, SEQ ID No. 662, SEQ ID No. 669, SEQ ID No. 688, SEQ ID No. 690, SEQ ID No. 716, SEQ ID No. 773, SEQ ID No. 778, SEQ ID No. 781, SEQ ID No. 783, SEQ ID No. 788, SEQ ID No. 817, SEQ ID No. 848, SEQ ID No. 851, SEQ ID No. 853, SEQ ID No. 857, SEQ ID No. 875, SEQ ID No. 877, SEQ ID No. 886, SEQ ID No. 898, SEQ ID No. 902, SEQ ID No. 923, SEQ ID No. 938, SEQ ID No. 976, SEQ ID No. 978, SEQ ID No. 990, SEQ ID No. 1005, SEQ ID No. 1021, SEQ ID No. 1035, SEQ ID No. 1069, SEQ ID No. 1083, SEQ ID No. 1088, SEQ ID No. 1089, SEQ ID No. 1091, SEQ ID No. 1092, SEQ ID No. 1095, SEQ ID No. 1096, SEQ ID No. 1100, SEQ ID No. 1105, SEQ ID No. 1108, SEQ ID No. 1117, SEQ ID No. 1120, SEQ ID No. 1121, SEQ ID No. 1124, SEQ ID No. 1128, SEQ ID No. 1133, SEQ ID No. 1135, SEQ ID No. 1139, SEQ ID No. 1140, SEQ ID No. 1157, SEQ ID No. 1159, SEQ ID No. 1163, SEQ ID No. 1165, SEQ ID No. 1167, SEQ ID No. 1168, SEQ ID No. 1169, SEQ ID No. 1171, SEQ ID No. 1173, SEQ ID No. 1174, SEQ ID No. 1177, SEQ ID No. 1180, SEQ ID No. 1181, SEQ ID No. 1186, SEQ ID No. 1194, SEQ ID No. 1197, and their representative fragments.

Preferably, the invention relates to a polypeptide according to the invention, in that it is a *Chlamydia trachomatis* polypeptide involved in lipopolysaccharide (LPS) biosynthesis, and in that it is chosen from the polypeptides having the following sequences: SEQ ID No. 17, SEQ ID No. 201, SEQ ID No. 691, SEQ ID No. 807, SEQ ID No. 936, SEQ ID No. 983, SEQ ID No. 1019, SEQ ID No. 1077, and their representative fragments.

Preferably, the invention relates to additional LPS-related polypeptides according to the invention, in that it is:

(a) a *Chlamydia trachomatis* KDO (3-deoxy-D-manno-octylosonic acid)-related polypeptide or one of its representative fragments, and in that it is chosen from the polypeptides having the following sequences: SEQ ID No. 41, SEQ ID No. 242, SEQ ID No. 269, SEQ ID No. 772, and one of their representative fragments;

(b) a *Chlamydia trachomatis* phosphomannomutase-related polypeptide or one of its representative fragments, and in that it is chosen from the polypeptides having the following sequence: SEQ ID No. 139, and its representative fragments;

(c) a *Chlamydia trachomatis* phosphoglucomutase-related polypeptide or one of its representative fragments, and in that it is chosen from the polypeptides having the following sequence: SEQ ID No. 567 and its representative fragments; and (d) a *Chlamydia trachomatis* lipid A component-related polypeptide or one of its representative fragments, and in that it is chosen from the polypeptides having the following sequences: SEQ ID No. 4, SEQ ID No. 933, SEQ ID No. 934, SEQ ID No. 935, SEQ ID No. 1185, and one of their representative fragments.

Preferably, the invention relates to a polypeptide according to the invention, in that it is a *Chlamydia trachomatis* polypeptide or one of its representative fragments that contains an RGD sequence and is also an outer membrane protein, and in that it is chosen from the polypeptides having the following sequences: SEQ ID No. 488, SEQ ID No. 489, SEQ ID No. 571, SEQ ID No. 572, SEQ No. 573, SEQ ID No. 716 and one of their representative fragments.

Preferably, the invention relates to a polypeptide according to the invention, in that it is a *Chlamydia trachomatis* polypeptide or one of its representative fragments that is cysteine-rich and contains RGD sequence, and in that it is chosen from the polypeptides having the following sequence: SEQ ID No. 144 and one of its representative fragments.

Preferably, the invention relates to a polypeptide according to the invention, in that it is a *Chlamydia trachomatis* outer membrane polypeptide that contains cysteines in their first 30 amino acids and also contain an RGD sequence, and in that it is chosen from the polypeptides having the following sequences: SEQ ID No. 101, SEQ ID No. 122, SEQ ID No. 308, SEQ ID No. 488, SEQ ID No. 489, SEQ ID No. 571, SEQ ID No. 572, SEQ ID No. 573, SEQ ID No. 651, SEQ ID No. 679, SEQ ID No. 680, SEQ ID No. 705, SEQ ID No. 716, SEQ ID No. 763, SEQ ID No. 870, SEQ ID No. 878, SEQ ID No. 879, SEQ ID No. 995, SEQ ID No. 1028, SEQ ID No. 1029, SEQ ID No. 1176, and one of their representative fragments.

Preferably, the invention relates to a polypeptide according to the invention, in that it is a *Chlamydia trachomatis* polypeptide or one of its representative fragments that contains RGD sequences homologous to *Chlamydia pneumoniae* polypeptides containing RGD sequences, and in that it is chosen from the polypeptides having the following sequences: SEQ ID No. 28, SEQ ID No. 101, SEQ ID No. 125, SEQ ID No. 155, SEQ ID No. 156, SEQ ID No. 286, SEQ ID No. 571, SEQ ID No. 572, SEQ ID No. 573, SEQ ID No. 763, SEQ ID No. 870, and one of their representative fragments.

Preferably, the invention relates to a polypeptide according to the invention, in that it is a *Chlamydia trachomatis* Type III or non-Type III secreted polypeptide or one of its representative fragments, and in that it is chosen from the polypeptides having the following sequences:
SEQ ID No. 180, SEQ ID No. 181, SEQ ID No. 207, SEQ ID No. 208, SEQ ID No. 372, SEQ ID No. 391, SEQ ID No. 399, SEQ ID No. 477, SEQ ID No. 486, SEQ ID No. 749, SEQ ID No. 758, SEQ ID No. 819, SEQ ID No. 878, SEQ ID No. 888, SEQ ID No. 896, SEQ ID No. 897, SEQ ID No. 900, SEQ ID No. 902, SEQ ID No. 923, SEQ ID No. 1015, SEQ ID No. 1018, SEQ ID No. 1059, SEQ ID No. 1060, SEQ ID No. 1069, SEQ ID No. 1071, SEQ ID No. 1073, SEQ ID No. 1076, SEQ ID No. 1189, and their representative fragments.

Preferably, the invention relates to a polypeptide according to the invention, in that it is a *Chlamydia trachomatis* cell wall anchored surface polypeptide or one of its representative fragments, and in that it is chosen from the polypeptides having the following sequences:
SEQ ID No. 662, SEQ ID No. 681, SEQ ID No. 1182, SEQ ID No. 1192, and their representative fragments.

Preferably, the invention relates to a polypeptide according to the invention, in that it is a *Chlamydia trachomatis* polypeptide or one of its representative fragments not found in *Chlamydia pneumoniae* (Blastp P>e$^{-10}$) and in that it is chosen from the polypeptides having the following sequences: SEQ ID No. 2, SEQ ID No. 18, SEQ ID No. 60, SEQ ID No. 66, SEQ ID No. 67, SEQ ID No. 68, SEQ ID No. 69, SEQ ID No. 70, SEQ ID No. 81, SEQ ID No. 89, SEQ ID No. 107, SEQ ID No. 108, SEQ ID No. 109, SEQ ID No. 134, SEQ ID No. 147, SEQ ID No. 191, SEQ ID No. 194, SEQ ID No. 216, SEQ ID No. 217, SEQ ID No. 218, SEQ ID No. 219, SEQ ID No. 220, SEQ ID No. 221, SEQ ID No. 222, SEQ ID No. 222, SEQ ID No. 223, SEQ ID No. 224, SEQ ID No. 225, SEQ ID No. 228, SEQ ID No. 235, SEQ ID No. 257, SEQ ID No. 276, SEQ ID No. 277, SEQ ID No. 278, SEQ ID No. 279, SEQ ID No. 280, SEQ ID No. 281, SEQ ID No. 282, SEQ ID No. 283, SEQ ID No. 284, SEQ ID No. 285, SEQ ID No. 289, SEQ ID No. 291, SEQ ID No. 298, SEQ ID No. 284, SEQ ID No. 313, SEQ ID No. 314, SEQ ID No. 315, SEQ ID No. 316, SEQ ID No. 334, SEQ ID No. 335, SEQ ID No. 336, SEQ ID No. 337, SEQ ID No. 338, SEQ ID No. 339, SEQ ID No. 340, SEQ ID No. 381, SEQ ID No. 393, SEQ ID No. 413, SEQ ID No. 418, SEQ ID No. 419, SEQ ID No. 419, SEQ ID No. 420, SEQ ID No. 421, SEQ ID No. 422, SEQ ID No. 423, SEQ ID No. 436, SEQ ID No. 460, SEQ ID No. 475, SEQ ID No. 476, SEQ ID No. 480, SEQ ID No. 485, SEQ ID No. 487, SEQ ID No. 491, SEQ ID No. 492, SEQ ID No. 493, SEQ ID No. 494, SEQ ID No. 496, SEQ ID No. 500, SEQ ID No. 504, SEQ ID No. 514, SEQ ID No. 527, SEQ ID No. 559, SEQ ID No. 569, SEQ ID No. 570, SEQ ID No. 575, SEQ ID No. 580, SEQ ID No. 582, SEQ ID No. 593, SEQ ID No. 598, SEQ ID No. 632, SEQ ID No. 640, SEQ ID No. 651, SEQ ID No. 671, SEQ ID No. 690, SEQ ID No. 694, ID No. 698, SEQ ID No. 710, SEQ ID No. 722, SEQ ID No. 723, SEQ ID No. 724, SEQ ID No. 770, SEQ ID No. 771, SEQ ID No. 782, SEQ ID No. 783, SEQ ID No. 784, SEQ ID No. 790, SEQ ID No. 795, SEQ ID No. 798, SEQ ID No. 805, SEQ ID No. 810, SEQ ID No. 817, SEQ ID No. 829, SEQ ID No. 830, SEQ ID No. 864, SEQ ID No. 866, SEQ ID No. 876, SEQ ID No. 887, SEQ ID No. 892, SEQ ID No. 899, SEQ ID No. 913, SEQ ID No. 921, SEQ ID No. 933, SEQ ID No. 938, SEQ ID No. 949, SEQ ID No. 956, SEQ ID No. 1010, SEQ ID No. 1017, SEQ ID No. 1018, SEQ ID No. 1027, SEQ ID No. 1030, SEQ ID No. 1037, SEQ ID No. 1038, SEQ ID No. 1047, SEQ ID No. 1072, SEQ ID No. 1074, SEQ ID No. 1075, SEQ ID No. 1078, SEQ ID No. 1079, SEQ ID No. 1081, SEQ ID No. 1083, SEQ ID No. 1084, SEQ ID No. 1087, SEQ ID No. 1088, SEQ ID No. 1089, SEQ ID No. 1091, SEQ ID No. 1092, SEQ ID No. 1094, SEQ ID No. 1095, SEQ ID No. 1096, SEQ ID No. 1098, SEQ ID No. 1104, SEQ ID No. 1105, SEQ ID No. 1106, SEQ ID No. 1108, SEQ ID No. 110, SEQ ID No. 1114, SEQ ID No. 1115, SEQ ID No. 1116, SEQ ID No. 1117, SEQ ID No. 1119, SEQ D No. 1128, SEQ ID No. 1132, SEQ ID No. 1133, SEQ ID No. 1135, SEQ ID No. 1136, SEQ ID No. 1139, SEQ ID No. 1140, SEQ ID No. 1141, SEQ ID No. 1142, SEQ ID No. 1144, SEQ ID No. 1148, SEQ ID No. 1151, SEQ ID No. 1155, SEQ ID No. 1157, SEQ ID No. 1159, SEQ ID No. 1161, SEQ ID No. 1162, SEQ ID No. 1165, SEQ ID No. 1166, SEQ ID No. 1167, SEQ ID No. 1168, SEQ ID No. 1169, SEQ ID No. 1171, SEQ ID No. 1172, SEQ ID No. 1173, SEQ ID No. 1174, SEQ ID No. 1175, SEQ ID No. 1176, SEQ ID No. 1177, SEQ ID No. 1178, SEQ ID No. 1180, SEQ ID No. 1181, SEQ ID No. 1183, SEQ ID No. 1184, SEQ ID No. 1186, SEQ ID No. 1187, SEQ ID No. 1188, SEQ ID No. 1192, SEQ ID No. 1194, SEQ ID No. 1197, and their representative fragments.

Preferably, the invention relates to a polypeptide according to the invention, characterized in that it is a *Chlamydia trachomatis* polypeptide or one of its representative fragments which is involved in the intermediate metabolism, in particular in the metabolism of sugars and/or of cofactors, and in that it is chosen from the polypeptides having the following sequences:
SEQ ID No. 10; SEQ ID No. 44; SEQ ID No. 45; SEQ ID No. 46; SEQ ID No. 47; SEQ ID No. 93; SEQ D No. 101; SEQ ID No. 102; SEQ ID No. 103; SEQ ID No. 106; SEQ ID No. 107; SEQ ID No. 120; SEQ ID No. 121; SEQ ID No. 130; SEQ ID No. 135; SEQ ID No. 140; SEQ ID No. 143; SEQ ID No. 144; SEQ ID No. 145; SEQ ID No. 158; SEQ ID No. 159; SEQ ID No. 160; SEQ ID No. 161; SEQ ID No. 192; SEQ ID No. 193; SEQ ID No. 196; SEQ ID No. 197; SEQ ID No. 198; SEQ ID No. 199; SEQ ID No. 227; SEQ ID No. 229; SEQ ID No. 236; SEQ ID No. 236; SEQ ID No. 239; SEQ ID No. 243; SEQ ID No. 245; SEQ ID No. 264; SEQ ID No. 265; SEQ ID No. 297; SEQ ID No. 331; SEQ ID No. 333; SEQ ID No. 359; SEQ ID No. 360; SEQ ID No. 374; SEQ ID No. 404; SEQ ID No. 405; SEQ ID No. 405; SEQ ID No. 410; SEQ ID No. 415; SEQ ID No. 415; SEQ ID No. 416; SEQ ID No. 417; SEQ ID No. 432; SEQ ID No. 460; SEQ ID No. 461; SEQ ID No. 462; SEQ ID No. 495; SEQ ID No. 513; SEQ ID No. 515; SEQ ID No. 566; SEQ ID No. 566; SEQ ID No. 566; SEQ ID No. 589; SEQ ID No. 613; SEQ ID No. 645; SEQ ID No. 646; SEQ ID No. 647; SEQ ID No. 652; SEQ ID No. 653; SEQ ID No. 654; SEQ ID No. 672; SEQ ID No. 673; SEQ ID No. 674; SEQ ID No. 682; SEQ ID No. 684; SEQ ID No. 692; SEQ ID No. 700; SEQ ID No. 725; SEQ ID No. 801; SEQ ID No. 802; SEQ ID No. 835; SEQ ID No. 836; SEQ ID No. 837; SEQ ID No. 860; SEQ ID No. 861; SEQ ID No. 862; SEQ ID No. 863; SEQ ID No. 869; SEQ ID No. 869; SEQ ID No. 925; SEQ ID No. 964; SEQ ID No. 983 and one of their representative fragments.

Preferably, the invention relates to a polypeptide according to the invention, characterized in that it is a *Chlamydia trachomatis* polypeptide or one of its representative fragments which is involved in the intermediate metabolism of nucleotides or nucleic acids, and in that it is chosen from the polypeptides having the following sequences:
SEQ ID No. 142; SEQ ID No. 142; SEQ ID No. 169; SEQ ID No. 256; SEQ ID No. 268; SEQ ID No. 325; SEQ ID No. 352; SEQ ID No. 366; SEQ ID No. 435; SEQ ID No. 444; SEQ ID No. 528; SEQ ID No. 529; SEQ ID No. 530; SEQ ID No. 548; SEQ ID No. 549; SEQ ID No. 601; SEQ ID No. 602; SEQ ID No. 617; SEQ ID No. 619; SEQ ID No. 644; SEQ ID No. 745; SEQ ID No. 971; SEQ ID No. 972; SEQ ID No. 1023 and one of their representative fragments.

Preferably, the invention relates to a polypeptide according to the invention, characterized in that it is a *Chlamydia trachomatis* polypeptide or one of its representative fragments which is involved in the metabolism of nucleic acids, and in that it is chosen from the polypeptides having the following sequences:
SEQ ID No. 5; SEQ ID No. 12; SEQ ID No. 82; SEQ ID No. 96; SEQ ID No. 97; SEQ ID No. 98; SEQ ID No. 99; SEQ ID No. 100; SEQ ID No. 105; SEQ ID No. 118; SEQ ID No. 136; SEQ ID No. 137; SEQ ID No. 163; SEQ ID No. 190; SEQ ID No. 204; SEQ ID No. 259; SEQ ID No. 260; SEQ ID No. 262; SEQ ID No. 290; SEQ H) No. 300; SEQ ID No. 301; SEQ ID No. 302; SEQ ID No. 387; SEQ ID No. 427; SEQ ID No. 434; SEQ ID No. 441; SEQ ID No. 444; SEQ ID No. 471; SEQ ID No. 595; SEQ ID No. 596; SEQ ID No. 597; SEQ ID No. 599; SEQ ID No. 600; SEQ ID No. 605; SEQ ID No. 612; SEQ ID No. 624; SEQ ID No. 625; SEQ ID No. 650; SEQ ID No. 657; SEQ ID No. 658; SEQ ID No. 702; SEQ ID No. 703; SEQ ID No. 704; SEQ ID No. 708; SEQ ID No. 719; SEQ ID No. 766; SEQ ID No. 767; SEQ ID No. 775; SEQ ID No. 779; SEQ ID No. 787; SEQ ID No. 788; SEQ ID No. 794; SEQ ID No. 841; SEQ ID No. 842; SEQ ID No. 883; SEQ ID No. 884; SEQ ID No. 907; SEQ ID No. 918; SEQ ID No. 924; SEQ ID No. 928; SEQ ID No. 929; SEQ ID No. 962; SEQ ID No. 962; SEQ ID No. 963; SEQ ID No. 969; SEQ ID No. 970; SEQ ID No. 975; SEQ ID No. 979; SEQ ID No. 995; SEQ ID No. 1031; SEQ ID No. 1032 and one of their representative fragments.

Preferably, the invention relates to a polypeptide according to the invention, characterized in that it is a *Chlamydia trachomatis* polypeptide or one of its representative fragments which is involved in the metabolism of amino acids or polypeptides, and in that it is chosen from the polypeptides having the following sequences:
SEQ ID No. 27; SEQ ID No. 41; SEQ ID No. 55; SEQ ID No. 56; SEQ ID No, 57; SEQ ID No. 59; SEQ ID No. 62; SEQ ID No. 63; SEQ ID No. 64; SEQ ID No. 65; SEQ ID No. 119; SEQ ID No. 132; SEQ ID No. 240; SEQ ID No. 241; SEQ ID No. 277; SEQ ID No. 278; SEQ ID No. 279; SEQ ID No. 382; SEQ ID No. 406; SEQ ID No. 428; SEQ ID No. 442; SEQ ID No. 446; SEQ ID No. 447; SEQ ID No. 453; SEQ ID No. 454; SEQ ID No. 541; SEQ ID No. 542; SEQ ID No. 591; SEQ ID No. 608; SEQ ID No. 609; SEQ ID No. 610; SEQ ID No. 618; SEQ ID No. 648; SEQ ID No. 649; SEQ ID No. 660; SEQ ID No. 661; SEQ ID No. 677; SEQ ID No. 717; SEQ ID No. 765; SEQ ID No. 797; SEQ ID No. 871; SEQ ID No. 875; SEQ ID No. 920; SEQ ID No. 922; SEQ ID No. 937; SEQ ID No. 998;

SEQ ID No. 1020; SEQ ID NO. 1021; SEQ ID No. 1034; SEQ ID No. 1044; SEQ ID No. 1046; SEQ D No. 1049 and one of their representative fragments.

Preferably, the invention relates to a polypeptide according to the invention, characterized in that it is a *Chlamydia trachomatis* polypeptide or one of its representative fragments which is involved in the metabolism of polypeptides, and in that it is chosen from the polypeptides having the following sequences:
SEQ ID No. 21; SEQ ID No. 22; SEQ ID No. 23; SEQ ID No. 24; SEQ ID No. 25; SEQ ID No. 26; SEQ ID NO. 75; SEQ ID No. 84; SEQ ID No. 86; SEQ ID NO. 92; SEQ ID NO. 133; SEQ ID No. 151; SEQ ID No. 152; SEQ ID No. 157; SEQ ID No. 179; SEQ ID No. 209; SEQ ID No. 307; SEQ ID No. 326; SEQ ID No. 343; SEQ ID No. 344; SEQ ID No. 345; SEQ ID No. 371; SEQ ID No. 429; SEQ ID No. 519; SEQ ID No. 557; SEQ ID No. 586; SEQ ID No. 587; SEQ ID No. 630; SEQ ID No. 656; SEQ ID No. 706; SEQ ID No. 707; SEQ ID No. 730; SEQ ID No. 751; SEQ ID No. 752; SEQ ID No. 786; SEQ ID No. 847; SEQ ID No. 885; SEQ ID No. 923; SEQ ID No. 978; SEQ ID No. 1039; SEQ ID No. 1048 and one of their representative fragments.

Preferably, the invention relates to a polypeptide according to the invention, characterized in that it is a *Chlamydia trachomatis* polypeptide or one of its representative fragments which is involved in the metabolism of fatty acids, and in that it is chosen from the polypeptides having the following sequences:
SEQ ID No. 4; SEQ ID No. 15; SEQ ID No. 16; SEQ ID No. 141; SEQ ID No. 173; SEQ ID No. 205; SEQ ID No. 205; SEQ ID No. 206; SEQ ID No. 207; SEQ ID No. 208; SEQ ID No. 312; SEQ ID No. 355; SEQ ID No. 415; SEQ ID No. 550; SEQ ID No. 558; SEQ ID No. 560; SEQ ID No. 561; SEQ ID No. 574; SEQ ID No. 574; SEQ ID No. 577; SEQ ID No. 578; SEQ ID No. 590; SEQ ID No. 614; SEQ ID No. 772; SEQ ID No. 808; SEQ ID No. 809; SEQ ID No. 904; SEQ ID No. 905; SEQ ID No. 905; SEQ ID No. 933; SEQ ID No. 934; SEQ ID No. 934; SEQ ID No. 936 and one of their representative fragments.

Preferably, the invention relates to a polypeptide according to the invention, characterized in that it is a *Chlamydia trachomatis* polypeptide or one of its representative fragments which is involved in the synthesis of the wall, and in that it is chosen from the polypeptides having the following sequences:
SEQ ID No. 87; SEQ ID No. 196; SEQ ID No. 242; SEQ ID No. 269; SEQ ID No. 628; SEQ ID No. 629; SEQ ID No. 634; SEQ ID No. 635; SEQ ID No. 637; SEQ ID No. 638; SEQ ID No. 1019 and one of their representative fragments.

Preferably, the invention relates to a polypeptide according to the invention, characterized in that it is a *Chlamydia trachomatis* polypeptide or one of its representative fragments which is involved in the transcription, translation and/or maturation process, and in that it is chosen from the polypeptides having the following sequences:
SEQ ID No. 112; SEQ ID No. 113; SEQ ID No. 332; SEQ ID No. 212; SEQ ID No. 213; SEQ ID No. 350; SEQ ID No. 362; SEQ ID No. 363; SEQ ID No. 364; SEQ ID No. 407; SEQ ID No. 451; SEQ ID No. 546; SEQ ID No. 643; SEQ ID No. 744; SEQ ID No. 746; SEQ ID No. 833; SEQ ID No. 868; SEQ ID No. 981; SEQ ID No. 982; SEQ ID No. 1003; SEQ ID No. 1011; SEQ ID No. 1042 and one of their representative fragments.

Preferably, the invention relates to a polypeptide according to the invention, characterized in that it is a *Chlamydia trachomatis* ribosomal polypeptide or one of its representative fragments, and in that it is chosen from the polypeptides having the following sequences:
SEQ ID No. 114; SEQ ID No. 115; SEQ ID No. 116; SEQ ID No. 328; SEQ ID No. 361; SEQ ID No. 375; SEQ ID No. 445; SEQ ID No. 543; SEQ ID No. 584; SEQ ID No. 585; SEQ ID No. 743; SEQ ID No. 813; SEQ ID No. 941; SEQ ID No. 942; SEQ ID No. 944; SEQ ID No. 946; SEQ ID No. 947; SEQ ID No. 948; SEQ ID No. 950; SEQ ID No. 951; SEQ ID No. 952; SEQ ID No. 953; SEQ ID No. 954; SEQ ID No. 955; SEQ ID No. 955; SEQ ID No. 957; SEQ ID No. 958; SEQ ID No. 960; SEQ ID No. 961; SEQ ID No. 1040; SEQ ID No. 1041; SEQ ID No. 1043; SEQ ID No. 1063; SEQ ID No. 1064 and one of their fragments.

Preferably, the invention also relates to a polypeptide according to the invention, characterized in that it is a *Chlamydia trachomatis* transport polypeptide or one of its representative fragments, and in that it is chosen from the polypeptides having the following sequences:
SEQ ID No. 6; SEQ ID No. 50; SEQ ID No. 51; SEQ ID No. 80; SEQ ID No. 125; SEQ ID No. 126; SEQ ID No. 128; SEQ ID No. 129; SEQ ID No. 215; SEQ ID No. 246; SEQ ID No. 248; SEQ ID No. 249; SEQ ID No. 251; SEQ ID No. 252; SEQ ID No. 253; SEQ ID No. 255; SEQ ID No. 271; SEQ ID No. 275; SEQ ID No. 293; SEQ ID No. 309; SEQ ID No. 323; SEQ ID No. 324; SEQ ID No. 398; SEQ ID No. 401; SEQ ID No. 449; SEQ ID No. 511; SEQ ID No. 512; SEQ ID No. 564; SEQ ID No. 565; SEQ ID No. 667; SEQ ID No. 679; SEQ ID No. 680; SEQ ID No. 711; SEQ ID No. 712; SEQ ID No. 713; SEQ ID No. 714; SEQ ID No. 715; SEQ ID No. 730; SEQ ID No. 731; SEQ ID No. 736; SEQ ID No. 737; SEQ ID No. 738; SEQ ID No. 870; SEQ ID No. 908; SEQ ID No. 919; SEQ ID No. 977; SEQ ID No. 987; SEQ ID No. 988; SEQ ID No. 992; SEQ ID No. 993; SEQ ID No. 994; SEQ ID No. 1028; SEQ ID No. 1029 and one of their representative fragments.

Preferably, the invention relates to a polypeptide according to the invention, characterized in that it is a *Chlamydia trachomatis* polypeptide or one of its representative fragments which is involved in the virulence process, and in that it is chosen from the polypeptides having the following sequences:
SEQ ID No. 20; SEQ ID No. 815; SEQ ID No. 816; SEQ ID No. 898; SEQ ID No. 1059; SEQ ID No. 1060 and one of their representative fragments.

Preferably, the invention relates to a polypeptide according to the invention, characterized in that it is a *Chlamydia trachomatis* polypeptide or one of its representative fragments which is involved in the secretory system and/or which is secreted, and in that it is chosen from the polypeptides having the following sequences:
SEQ ID No. 758; SEQ ID No. 888; SEQ ID No. 889; SEQ ID No. 890; SEQ ID No. 891; SEQ ID No. 896; SEQ ID No. 897; SEQ ID No. 898 and one of their representative fragments.

The secreted polypeptides, including the Type III and other, non-Type III secreted polypeptides, of the present invention, as well as the corresponding nucleotide sequences, may be detected by techniques known to persons skilled in the art, such as for example the techniques using cloning combined with vectors allowing the expression of the said polypeptides fused to export markers such as the luc gene for luciferase or the PhoA gene for alkaline phosphatase.

Preferably, the invention relates to a polypeptide according to the invention, characterized in that it is a polypeptide specific to Chlamydiae or one of its representative fragments, and in that it is chosen from the polypeptides having the following sequences:
SEQ ID No. 22; SEQ ID No. 29; SEQ ID No. 31; SEQ ID No. 32; SEQ ID No. 34; SEQ ID No. 35; SEQ ID No. 39; SEQ ID No. 40; SEQ ID No. 43; SEQ ID No. 48; SEQ ID No. 49; SEQ ID No. 50; SEQ ID No. 52; SEQ ID No. 53; SEQ ID No. 54; SEQ ID No. 72; SEQ ID No. 77; SEQ ID No. 78; SEQ ID No. 87; SEQ ID No. 90; SEQ ID No. 95; SEQ ID No. 108; SEQ ID No. 110; SEQ ID No. 111; SEQ ID No. 122; SEQ ID No. 123; SEQ ID No. 124; SEQ ID No. 127; SEQ ID No. 138; SEQ ID No. 144; SEQ ID No. 146; SEQ ID No. 153; SEQ ID No. 155; SEQ ID No. 164; SEQ ID No. 166; SEQ H No. 175; SEQ ID No. 182; SEQ ID No. 184; SEQ ID No. 186; SEQ ID No. 187; SEQ ID No. 188; SEQ ID No. 202; SEQ ID No. 210; SEQ ID No. 247; SEQ ID No. 258; SEQ ID No. 266; SEQ ID No. 267; SEQ ID No. 270; SEQ ID No. 273; SEQ ID No. 274; SEQ ID No. 295; SEQ ID No. 296; SEQ ID No. 305; SEQ ID No. 306; SEQ ID No. 309; SEQ ID No. 318; SEQ ID No. 319; SEQ ID No. 322; SEQ ID No. 326; SEQ ID No. 342; SEQ ID No. 357; SEQ ID No. 376; SEQ ID No. 379; SEQ ID No. 380; SEQ ID No. 388; SEQ ID No. 390; SEQ ID No. 400; SEQ ID No. 431; SEQ ID No. 433; SEQ ID No. 438; SEQ ID No. 443; SEQ ID No. 456; SEQ ID No. 457; SEQ ID No. 458; SEQ ID No. 464; SEQ ID No. 468; SEQ ID No. 470; SEQ ID No. 473; SEQ ID No. 486; SEQ ID No. 489; SEQ ID No. 497; SEQ ID No. 501; SEQ ID No. 503; SEQ ID No. 504; SEQ ID No. 508; SEQ ID No. 512; SEQ ID No. 521; SEQ ID No. 522; SEQ ID No. 523; SEQ ID No. 524; SEQ ID No. 533; SEQ ID No. 535; SEQ ID No. 536; SEQ ID No. 537; SEQ ID No. 538; SEQ ID No. 539; SEQ ID No. 540; SEQ ID No. 554; SEQ ID No. 563; SEQ ID No. 572; SEQ ID No. 579; SEQ ID No. 595; SEQ ID No. 603; SEQ ID No. 604; SEQ ID No. 606; SEQ ID No. 607; SEQ ID No. 615; SEQ ID No. 616; SEQ ID No. 622; SEQ ID No. 641; SEQ ID No. 642; SEQ ID No. 659; SEQ ID No. 668; SEQ ID No. 670; SEQ ID No. 693; SEQ ID No. 695; SEQ ID No. 696; SEQ ID No. 699; SEQ ID No. 703; SEQ ID No. 704; SEQ ID No. 716; SEQ ID No. 726; SEQ ID No. 728; SEQ ID No. 739; SEQ ID No. 742; SEQ ID No. 747; SEQ ID No. 750; SEQ ID No. 751; SEQ ID No. 755; SEQ ID No. 757; SEQ ID No. 759; SEQ ID No. 761; SEQ ID No. 762; SEQ ID No. 763; SEQ ID No. 764; SEQ ID No. 773; SEQ ID No. 780; SEQ ID No. 781; SEQ ID No. 789; SEQ ID No. 800; SEQ ID No. 803; SEQ ID No. 804; SEQ ID No. 818; SEQ ID No. 820; SEQ ID No. 822; SEQ ID No. 823; SEQ ID No. 824; SEQ ID No. 827; SEQ ID No. 828; SEQ ID No. 839; SEQ ID No. 849; SEQ ID No. 850; SEQ ID No. 851; SEQ ID No. 852; SEQ ID No. 855; SEQ ID No. 856; SEQ ID No. 857; SEQ ID No. 858; SEQ ID No. 859; SEQ ID No. 860; SEQ ID No. 861; SEQ ID No. 862; SEQ ID No. 863; SEQ ID No. 865; SEQ ID No. 868; SEQ ID No. 869; SEQ ID No. 870; SEQ ID No. 871; SEQ ID No. 872; SEQ ID No. 873; SEQ ID No. 874; SEQ ID No. 875; SEQ ID No. 877; SEQ ID No. 878; SEQ ID No. 880; SEQ ID No. 882; SEQ ID No. 884; SEQ ID No. 886; SEQ ID No. 893; SEQ ID No. 901; SEQ ID No. 906; SEQ ID No. 910; SEQ ID No. 912; SEQ ID No. 915; SEQ ID No. 916; SEQ ID No. 917; SEQ ID No. 926; SEQ ID No. 929; SEQ ID No. 933; SEQ ID No. 965; SEQ ID No. 967; SEQ ID No. 968; SEQ ID No. 984; SEQ ID No. 986; SEQ ID No. 989; SEQ ID No. 990; SEQ ID No. 996; SEQ ID No. 997; SEQ ID No. 1001; SEQ ID No. 1002; SEQ ID No. 1013; SEQ ID No. 016; SEQ ID No. 1031; SEQ ID No. 1033; SEQ ID No. 1035; SEQ ID No. 1049; SEQ ID No. 1051; SEQ ID No. 1052; SEQ ID No. 1054; SEQ ID No. 1056; SEQ ID No. 1057; SEQ ID No. 1058; SEQ ID No. 1062; SEQ ID No. 1070; SEQ ID No. 1071; SEQ ID No. 1073 and one of their representative fragments.

In general, in the present invention, the functional group to which a polypeptide of the invention belongs, as well as its corresponding nucleotide sequence, may be determined either by comparative analogy with sequences already known, or by the use of standard techniques of biochemistry, of cytology combined with the techniques of genetic engineering such as immunoaffinity, localization by immunolabelling, differential extraction, measurement of enzymatic activity, study of the activity inducing or repressing expression or the study of expression in *E. coli*.

It is clearly understood, on the one hand, that, in the present invention, the nucleotide sequences (ORF) and the amino acid sequences (SEQ ID No. 2 to SEQ ID No. 1197) which are listed by functional group, are not exhaustive within the group considered. Moreover, it is also clearly understood that, in the present invention, a nucleotide sequence (ORF) or an amino acid sequence mentioned within a given functional group may also be part of another group taking into account, for example, the interrelationship between the groups listed. Accordingly, and as an example of this interrelationship, an exported and/or secreted polypeptide as well as its coding nucleotide sequence may also be involved in the *Chlamydia trachomatis* virulence process by modifying the defense mechanism of the infected host cell, or a transmembrane polypeptide or its coding nucleotide sequence is also part of the polypeptides or coding nucleotide sequences of the cellular envelope.

The subject of the present invention is also the nucleotide and/or polypeptide sequences according to the invention, characterized in that the said sequences are recorded on a medium, called recording medium, whose type and nature facilitate the reading, the analysis and the exploitation of the said sequences. These media may of course also contain other information extracted from the present invention, such as in particular the analogies with already known sequences, such as those mentioned in Table 1 of the present description, and/or may contain, in addition, information relating to the nucleotide and/or polypeptide sequences of other microorganisms so as to facilitate the comparative analysis and the exploitation of the results obtained.

Among these recording media, computer-readable media, such as magnetic, optical, electrical and hybrid media such as, for example, floppy disks, CD-ROMs or recording cassettes, are preferred in particular.

The invention also relates to nucleotide sequences which can be used as primer or probe, characterized in that the said sequences are chosen from the nucleotide sequences according to the invention.

The invention relates, in addition, to the use of a nucleotide sequence according to the invention, as primer or probe, for the detection and/or amplification of nucleic acid sequences.

The nucleotide sequences according to the invention may thus be used to amplify nucleotide sequences, in particular by the PCR technique (polymerase chain reaction) (Erlich, 1989; Innis et al., 1990; Rolfs et al., 1991, and White et al., 1997).

These oligodeoxyribonucleotide or oligoribonucleotide primers correspond to representative nucleotide fragments, and are advantageously at least 8 nucleotides, preferably at least 12 nucleotides, 15 nucleotides and still more preferably at least 20 nucleotides long.

Other techniques for amplifying the target nucleic acid may be advantageously used as alternatives to PCR.

The nucleotide sequences of the invention, in particular the primers according to the invention, may also be used in other methods for amplifying a target nucleic acid, such as:

the TAS (Transcription-based Amplification System) technique described by Kwoh et al. in 1989;
the 3SR (Self-Sustained Sequence Replication) technique described by Guatelli et al. in 1990;
the NASBA (Nucleic Acid Sequence Based Amplification) technique described by Kievitis et al. in 1991;

the SDA (Strand Displacement Amplification) technique (Walker et al., 1992);

the TMA (Transcription Mediated Amplification) technique.

The polynucleotides of the invention may also be used in techniques for amplifying or for modifying the nucleic acid serving as probe, such as:

the LCR (Ligase Chain Reaction) technique described by Landegren et al. in 1988 and perfected by Barany et al. in 1991, which uses a thermostable ligase;

the RCR (Repair Chain Reaction) technique described by Segev in 1992;

the CPR (Cycling Probe Reaction) technique described by Duck et al. in 1990;

the Q-beta-replicase amplification technique described by Miele et al. in 1983 and perfected in particular by Chu et al. in 1986, Lizardi et al. in 1988, and then by Burg et al. as well as by Stone et al. in 1996.

The invention also relates to the nucleotide sequences of fragments which can be obtained by amplification with the aid of at least one primer according to the invention. The present invention encompasses both hybridization probes and primers. In general, the complementary probes should be of the length sufficient to form a stable hybrid complex with the target sequences. Primers, while complementary to the target sequences need not form stable hybridization complexes with the target sequences alone. Rather, primers form stable complexes with the target sequences in the presence of polymerase to permit extension of the primer.

In the case where the target polynucleotide to be detected is possibly an RNA, for example an mRNA, it will be possible to use, prior to the use of an amplification reaction with the aid of at least one primer according to the invention or to the use of a method of detection with the aid of at least one probe of the invention, a reverse transcriptase-type enzyme so as to obtain a cDNA from the RNA contained in the biological sample. The cDNA obtained will then serve as target for the primer(s) or the probe(s) used in the amplification or detection method according to the invention.

The detection probe will be chosen so that it hybridizes with the target sequence or the amplicon generated from the target sequence. Such a detection probe will advantageously have as sequence a sequence of at least 12 nucleotides, 15 nucleotides, in particular of at least 20 nucleotides, and preferably at least 100 nucleotides.

The invention also comprises the nucleotide sequences which can be used as probe or primer according to the invention, characterized in that they are labelled with a radioactive compound or with a nonradioactive compound.

The nonlabelled nucleotide sequences may be used directly as probes or primers; however, the sequences are generally labelled with a radioactive element ($^{32}$P, $^{35}$S, $^{3}$H, $^{125}$I) or with a nonradioactive molecule (biotin, acetylaminofluorene, digoxigenin, 5-bromo-deoxyuridine, fluorescein) so as to obtain probes which can be used in numerous applications.

Examples of nonradioactive labelling of nucleotide sequences are described, for example, in French patent No. 78,10975 or by Urdea et al. or by Sanchez-Pescador et al. in 1988.

In the latter case, one of the labelling methods described in patents FR-2 422 956 and FR-2 518 755 may also be used.

The invention also relates to the nucleotide sequences of fragments which can be obtained by hybridization with the aid of at least one probe according to the invention.

The hybridization technique may be performed in various ways (Matthews et al., 1988). The most common method consists in immobilizing the nucleic acid extracted from *C. trachomatis* cells on a support (such as nitrocellulose, nylon, polystyrene) and in incubating, under well-defined conditions, the target nucleic acid immobilized with the probe. After hybridization, the excess probe is removed and the hybrid molecules formed are detected by the appropriate method (measurement of the radioactivity, of the fluorescence or of the enzymatic activity linked to the probe).

The invention also comprises the nucleotide sequences according to the invention, characterized in that they are covalently or noncovalently immobilized on a support.

According to another advantageous embodiment of the nucleic sequences according to the invention, the latter may be used immobilized on a support and may thus serve to capture, through specific hybridization, the target nucleic acid obtained from the biological sample to be tested. If necessary, the solid support is separated from the sample and the hybridization complex formed between the so-called capture probe and the target nucleic acid is then detected by means of a second probe, called detection probe, labelled with an easily detectable element.

The nucleotide sequences according to the invention may also be used in new analytical systems, DNA chips, which allow sequencing, the study of mutations and of the expression of genes, and which are currently of interest given their very small size and their high capacity in terms of number of analyses.

The principle of the operation of these chips is based on molecular probes, most often oligo-nucleotides, which are attached onto a miniaturized surface, generally of the order of a few square centimetres. During an analysis, a sample containing fragments of a target nucleic acid to be analysed, for example DNA or RNA labelled, for example, after amplification, is deposited onto the DNA chip in which the support has been coated beforehand with probes. Bringing the labelled target sequences into contact with the probes leads to the formation, through hybridization, of a duplex according to the rule of pairing defined by J. D. Watson and F. Crick. After a washing step, analysis of the surface of the chip allows the effective hybridizations to be located by means of the signals emitted by the labels tagging the target. A hybridization fingerprint results from this analysis which, by appropriate computer processing, will make it possible to determine information such as the presence of specific fragments in the sample, the determination of sequences and the presence of mutations.

The chip consists of a multitude of molecular probes, precisely organized or arrayed on a solid support whose surface is miniaturized. It is at the centre of a system where other elements (imaging system, microcomputer) allow the acquisition and interpretation of a hybridization fingerprint.

The hybridization supports are provided in the form of flat or porous surfaces (pierced with wells) composed of various materials. The choice of a support is determined by its physicochemical properties, or more precisely, by the relationship between the latter and the conditions under which the support will be placed during the synthesis or the attachment of the probes or during the use of the chip. It is therefore necessary, before considering the use of a particular support (R. S. Matson et al., 1994), to consider characteristics such as its stability to pH, its physical strength, its reactivity and its chemical stability as well as its capacity to nonspecifically bind nucleic acids. Materials such as glass, silicon and polymers are commonly used. Their surface is, in a first step, called "functionalization", made reactive towards the groups which it is desired to attach thereon. After the functionalization, so-called spacer molecules are grafted onto the activated surface. Used as intermediates between the surface and the probe, these molecules of variable size render unimportant the surface properties of the supports, which often prove to be problematic for the synthesis or the attachment of the probes and for the hybridization.

Among the hybridization supports, there may be mentioned glass which is used, for example, in the method of in situ synthesis of oligonucleotides by photochemical addressing developed by the company Affymetrix (E. L. Sheldon, 1993), the glass surface being activated by silane. Genosensor Consortium (P. Mérel, 1994) also uses glass slides carrying wells 3 mm apart, this support being activated with epoxysilane.

Polymers or silicon may also be mentioned among these hybridization supports. For example, the Andrein Mirzabekov team has developed a chip consisting of polyacrylamide squares polymerized on a silanized glass surface (G. Yershov et al., 1996). Several teams use silicon, in particular the IFOS laboratory of Ecole Centrale of Lyon which uses a silicon semiconductor substrate which is p-doped by introducing it into its crystalline structure atoms whose valency is different from that of silicon. Various types of metals, in particular gold and platinum, may also be used as support (Genosensor Consortium (K. Beattie et al., 1993)).

The probes according to the invention may be synthesized directly in situ on the supports of the DNA chips. This in situ synthesis may be carried out by photochemical addressing (developed by the company Affymax (Amsterdam, Holland) and exploited industrially by its subsidiary Affymetrix (United States)) or based on the VLSIPS (very large scale immobilized polymer synthesis) technology (S. P. A. Fodor et al., 1991) which is based on a method of photochemically directed combinatory synthesis and the principle of which combines solid-phase chemistry, the use of photolabile protecting groups and photolithography.

The probes according to the invention may be attached to the DNA chips in various ways such as electrochemical addressing, automated addressing or the use of probe printers (T. Livache et al., 1994; G. Yershov et al., 1996; J. Derisi et al., 1996, and S. Borman, 1996).

The revealing of the hybridization between the probes of the invention, deposited or synthesized in situ on the supports of the DNA chips, and the sample to be analysed, may be determined, for example, by measurement of fluorescent signals, by radioactive counting or by electronic detection.

The use of fluorescent molecules such as fluorescein constitutes the most common method of labelling the samples. It allows direct or indirect revealing of the hybridization and allows the use of various fluorochromes.

Affymetrix currently provides an apparatus or a scanner designed to read its "Gene Chip" chips. It makes it possible to detect the hybridizations by scanning the surface of the chip in confocal microscopy (R. J. Lipshutz et al., 1995). Other methods of detecting fluorescent signals have been tested: coupling of an epifluorescence microscope and a CCD camera (G. Yershov et al., 1996), the use of an optical fibre collecting system (E. L. Sheldon, 1993). A conventional method consists in carrying out an end labelling, with phosphorus 32, of the target sequences, by means of an appropriate apparatus, the Phosphorimager (marketed by Molecular Dynamics). The electronic detection is based on the principle that the hybridization of two nucleic acid molecules is accompanied by physical phenomena which can be quantified under certain conditions (system developed by Ecole Centrale of Lyon and called GEN-FET (GEN field effect transistor)). Genosensor Consortium and the company Beckman Instruments who are developing an electronic chip "Permittivity Chips" may also be mentioned (K. Beattie et al., 1993).

The nucleotide sequences according to the invention may thus be used in DNA chips to carry out the analysis of mutations. This analysis is based on the production of chips capable of analysing each base of a nucleotide sequence according to the invention. It is possible, in particular to this end, to use the microsequencing techniques on a DNA chip. The mutations are detected by extending immobilized primers which hybridize to the template of sequences analysed, just at the position adjacent to that of the mutated nucleotide to be detected. A single-stranded template, RNA or DNA, of the sequences to be analysed will be advantageously prepared according to conventional methods, from products amplified according to PCR-type techniques. The templates of single-stranded DNA, or of RNA thus obtained are then deposited on the DNA chip, under conditions allowing their specific hybridization to the immobilized primers. A thermostable polymerase, for example Tth or T7 DNA polymerase, specifically extends the 3' end of the immobilized primer with a labelled nucleotide analogue complementary to the nucleotide at the position of the variable site. For example a thermal cycling is performed in the presence of fluorescent dideoxyribonucleotides. The experimental conditions will be adapted in particular to the chips used, to the immobilized primers, to the polymerases used and to the labelling system chosen. One advantage of microsequencing, compared with techniques based on the hybridization of probes, is that it makes it possible to identify all the variable nucleotides with optimal discrimination under homogeneous reaction conditions; used on DNA chips, it allows optimal resolution and specificity for the routine and industrial detection of mutations in multiplex.

The nucleotide sequences according to the invention may also be used in DNA chips to carry out the analysis of the expression of the *Chlamydia trachomatis* genes. This analysis of the expression of *Chlamydia trachomatis* genes is based on the use of chips where probes of the invention, chosen for their specificity to characterize a given gene, are present (D. J. Lockhart et al., 1996; D. D. Shoemaker et al., 1996). For the methods of analysis of gene expression using the DNA chips, reference may, for example, be made to the methods described by D. J. Lockhart et al. (1996) and Sosnowsky et al. (1997) for the synthesis of probes in situ or for the addressing and the attachment of previously synthesized probes. The target sequences to be analysed are labelled and in general fragmented into sequences of about 50 to 100 nucleotides before being hybridized onto the chip. After washing as described, for example, by D. J. Lockhart et al. (1996) and application of different electric fields (Sosnowsky et al., 1997), the labelled compounds are detected and quantified, the hybridizations being carried out at least in duplicate. Comparative analyses of the signal intensities obtained with respect to the same probe for different samples and/or for different probes with the same sample, determine the differential expression of RNA or of DNA derived from the sample.

The nucleotide sequences according to the invention may, in addition, be used in DNA chips where other nucleotide probes specific for other microorganisms are also present, and may allow the carrying out of a serial test allowing rapid identification of the presence of a microorganism in a sample.

Accordingly, the subject of the invention is also the nucleotide sequences according to the invention, characterized in that they are immobilized on a support of a DNA chip.

The DNA chips, characterized in that they contain at least one nucleotide sequence according to the invention, immobilized on the support of the said chip, also form part of the invention.

The said chips will preferably contain several probes or nucleotide sequences of the invention of different length and/or corresponding to different genes so as to identify, with greater certainty, the specificity of the target sequences or the desired mutation in the sample to be analysed.

Accordingly, the analyses carried out by means of primers and/or probes according to the invention, immobilized on supports such as DNA chips, will make it possible, for example, to identify, in samples, mutations linked to variations such as intraspecies variations. These variations may be correlated or associated with pathologies specific to the variant identified and will make it possible to select the appropriate treatment.

The invention thus comprises a DNA chip according to the invention, characterized in that it contains, in addition, at least one nucleotide sequence of a microorganism different from Chlamydia trachomatis, immobilized on the support of the said chip; preferably, the different microorganism will be chosen from an associated microorganism, a bacterium of the Chlamydia family, and a variant of the species Chlamydia trachomatis.

Another subject of the present invention is a vector for the cloning and/or the expression of a sequence, characterized in that it contains a nucleotide sequence according to the invention.

Among the said vectors according to the invention, the vectors containing a nucleotide sequence encoding a polypeptide of the cellular, preferably outer, envelope of Chlamydia trachomatis or one of its representative fragments, are preferred.

In a specific embodiment, the vectors contain a nucleotide sequence encoding a Chlamydia trachomatis secreted polypeptide or one of its representative fragments or encoding a transport polypeptide, a surface exposed polypeptide, a lipoprotein or one of its representative fragments, a polypeptide involved in lipopolysaccharide (LPS) biosynthesis, a Type III or non-Type III secreted polypeptide, a polypeptide containing RGD attachment sites, a cell wall anchored surface polypeptide, a polypeptide not found in Chlamydia pneumoniae, a ribosomal polypeptide or a polypeptide involved in secretion, transcription, translation, maturation of proteins, a polypeptide involved in the synthesis of the wall, a polypeptide involved in the virulence, a polypeptide involved in the intermediate metabolism, in particular in the metabolism of sugars and/or of cofactors, a polypeptide involved in the metabolism of nucleotides, of amino acids, of nucleic acids or of fatty acids of Chlamydia trachomatis or one of their representative fragments, or a polypeptide specific to Chlamydiae, are also preferred.

According to the invention, the vectors comprise the elements necessary to allow the expression and/or the secretion of the said nucleotide sequences in a given host cell, and also form part of the invention.

The vector should, in this case, comprise a promoter, signals for initiation and for termination of translation, as well as appropriate regions for regulation of transcription. It should be capable of being stably maintained in the host cell and may optionally possess particular signals specifying the secretion of the translated protein. These different elements are chosen according to the host cell used. To this effect, the nucleotide sequences according to the invention may be inserted into autonomously-replicating vectors within the chosen host, or integrative vectors in the chosen host.

Any of the standard methods known to those skilled in the art for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of a polypeptide, peptide or derivative, or analogs thereof encoded by a polynucleotide sequence in SEQ ID No. 1 or ORFs contained within SEQ ID No. 1 may be regulated by a second nucleic acid sequence so that the protein or peptide is expressed in a host transformed with the recombinant DNA molecule. For example, expression of a protein or peptide may be controlled by any promoter/enhancer element known in the art. Promoters which may be used to control expression include, but are not limited to, the CMV promoter, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (VIIIa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., 1983, Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

The vectors according to the invention are, for example, vectors of plasmid or viral origin. In a specific embodiment, a vector is used that comprises a promoter operably linked to a protein or peptide-encoding nucleic acid sequence in SEQ ID No. 1, or ORFs contained within SEQ ID No. 1, one or more origins of replication, and, optionally, one or more selectable markers (e.g., an antibiotic resistance gene). Expression vectors comprise regulatory sequences that control gene expression, including gene expression in a desired host cell. Preferred vectors for the expression of the polypeptides of the invention include the pET-type plasmid vectors (Promega) or pBAD plasmid vectors (Invitrogen). Furthermore, the vectors according to the invention are useful for transforming host cells so as to clone or express the nucleotide sequences of the invention.

Expression can also be achieved using targeted homologous recombination to activate *Chlamydia trachomatis* genes present in the cloned genomic DNA. A heterologous regulatory element may be inserted into a stable cell line or cloned microorganism, such that it is operatively linked with an endogenous *Chlamydia trachomatis* gene present in the cloned genome, using techniques, such as targeted homologous recombination, which are well known to those of skill in the art (See, e.g., Chappel, U.S. Pat. No. 4,215,051 and Skoultchi, WO 91/06667 each of which is incorporated herein in its entirety).

Expression vector/host cell systems containing inserts of polynucleotide sequences in SEQ ID No. 1 or ORFs within SEQ ID No. 1, which encode polypeptides, peptides or derivatives, or analogs thereof; can be identified by three general approaches: (a) nucleic acid hybridization, (b) presence or absence of "marker" gene functions, and (c) expression of inserted sequences. In the first approach, the presence of a polynucleotide sequence inserted in an expression vector can be detected by nucleic acid hybridization using probes comprising sequences that are homologous to an inserted polynucleotide sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a polynucleotide sequence in the vector. For example, if the polynucleotide sequence in SEQ ID No. 1 or ORFs within SEQ ID No. 1 is inserted within the marker gene sequence of the vector, recombinants containing the insert can be identified by the absence of the marker gene function. In the third approach, recombinant expression vectors can be identified by assaying the product of the polynucleotide sequence expressed by the recombinant. Such assays can be based, for example, on the physical or functional properties of the expressed polypeptide in in vitro assay systems, e.g., binding with antibody, promotion of cell proliferation.

Once a particular recombinant DNA molecule is identified and isolated, several methods known in the art may be used to propagate it. The clones identified may be introduced into an appropriate host cell by standard methods, such as for example lipofection, electroporation, and heat shock. Once a suitable host system and growth conditions are established, recombinant expression vectors can be propagated and prepared in quantity.

The invention also encompasses the host cells transformed by a vector according to the invention. These cells may be obtained by introducing into host cells a nucleotide sequence inserted into a vector as defined above, and then culturing the said cells under conditions allowing the replication and/or the expression of the transfected nucleotide sequence.

The host cell may be chosen from eukaryotic or prokaryotic systems, such as for example bacterial cells (Olins and Lee, 1993), but also yeast cells (Buckholz, 1993), as well as animal cells, in particular cultures of mammalian cells (Edwards and Aruffo, 1993), and in particular Chinese hamster ovary (CHO) cells, but also insect cells in which methods using baculoviruses for example may be used (Luckow, 1993).

Furthermore, a host cell strain may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

A preferred host cell for the expression of the proteins of the invention consists of prokaryotic cells, such as Gram negative bacteria.

A further preferred host cell according to the invention is a bacterium belonging to the Chlamydia family, more preferably belonging to the species *Chlamydia trachomatis* or chosen from a microorganism associated with the species *Chlamydia trachomatis*.

In other specific embodiments, the polypeptides, peptides or derivatives, or analogs thereof may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Genomic sequences can be cloned and expressed as translational gene products (i.e., peptides, polypeptides, and proteins) or transcriptional gene products (i.e., antisense and ribozymes).

The invention further relates to the intracellular production of an antisense nucleic acid sequence of SEQ ID No. 1 by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding an antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include but are not limited to: the CMV promoter, the SV40 early promoter region (Bemoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al, 1981, Proc. Natl. Acad. Sci. U.S.A. 78:1441-1445), the regulatory sequences of the metallothionein gene (Brinster et al., 1982, Nature 296:39-42), etc.

In a specific embodiment, the antisense oligonucleotide comprises catalytic RNA, or a ribozyme (see, e.g., PCT International Publication WO 90/11364, published Oct. 4, 1990; Sarver et al., 1990, Science 247:1222-1225). In another embodiment, the oligonucleotide is a 2'-β-methylribonucleotide (Inoue et al., 1987, Nucl. Acids Res. 15:6131-6148), or a chimeric RNA-DNA analog (Inoue et al., 1987, FEBS Lett. 215:327-330).

In another embodiment, the antisense nucleic acids of the invention comprise a sequence complementary to at least a portion of an RNA transcript of a polynucleotide sequence in SEQ ID No. 1. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acid sequence, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA transcribed from SEQ ID No. 1 may contain and still form a stable duplex (or triplex, as the case may be). One skilled in the art can ascertain a tolerable degree of mismatch by use of standard procedures to determine the melting point of the hybridized complex.

The invention also relates to the animals, except humans, comprising one of the above-described transformed cells according to the invention.

The production of transgenic animals according to the invention overexpressing one or more of the *Chlamydia trachomatis* genes will be preferably carried out on rats, mice or rabbits according to methods well known to persons skilled in the art such as viral or nonviral transfections. The transgenic animals overexpressing one or more of the said genes may be obtained by transfection of multiple copies of the said genes under the control of a powerful promoter of a ubiquitous nature, or which is selective for one type of tissue. The transgenic animals may also be obtained by homologous recombination on embryonic stem cells, transfer of these stem cells to embryos, selection of the chimeras affected at the level of the reproductive lines, and growth of the said chimeras.

The transformed cells as well as the transgenic animals according to the invention can be used in methods of preparing the recombinant polypeptide.

It is now possible to produce recombinant polypeptides in a relatively large quantity by genetic engineering using the cells transformed with expression vectors according to the invention or using transgenic animals according to the invention.

The methods of preparing a polypeptide of the invention in recombinant form, characterized in that they use a vector and/or a cell transformed with a vector according to the invention and/or a transgenic animal comprising one of the said transformed cells according to the invention, are themselves included in the present invention.

Among the said methods of preparing a polypeptide of the invention in recombinant form, the methods of preparation using a vector, and/or a cell transformed with the said vector and/or a transgenic animal comprising one of the said transformed cells, containing a nucleotide sequence encoding a polypeptide of the cellular envelope of *Chlamydia trachomatis* or one of its representative fragments, more preferably encoding a polypeptide of the outer cellular envelope of *Chlamydia trachomatis* or one of its fragment, are preferred.

Among the said methods of preparing a polypeptide of the invention in recombinant form, the methods of preparation using a vector, and/or a cell transformed with the said vector and/or a transgenic animal comprising one of the said transformed cells, containing a nucleotide sequence encoding a *Chlamydia trachomatis* secreted polypeptide or one of its representative fragments, or encoding a transport polypeptide, a surface exposed polypeptide, a lipoprotein or one of its representative fragments, a polypeptide involved in lipopolysaccharide biosynthesis, a Type III or other secreted polypeptide, a polypeptide containing RGD attachment sites, a cell wall anchored surface polypeptide, a polypeptide not found in *Chlamydia pneumoniae*, a ribosomal polypeptide or a polypeptide involved in secretion, transcription, translation, maturation of proteins, a polypeptide involved in the synthesis of the wall, a polypeptide involved in the virulence, a polypeptide involved in the intermediate metabolism, in particular in the metabolism of sugars and/or of cofactors, a polypeptide involved in the metabolism of nucleotides, of amino acids, of nucleic acids or of fatty acids of *Chlamydia trachomatis* or one of their representative fragments, or a polypeptide specific to Chlamydiae, are also preferred.

The recombinant polypeptides obtained as indicated above may be provided either in glycosylated or nonglycosylated form and may or may not have the natural tertiary structure.

A preferred variant consists in producing a recombinant polypeptide fused to a "carrier" protein (chimeric protein). The advantage of this system is that it allows a stabilization and a reduction in proteolysis of the recombinant product, an increase in solubility during renaturation in vitro and/or a simplification of purification when the fusion partner has affinity for a specific ligand.

More particularly, the invention relates to a method of preparing a polypeptide of the invention comprising the following steps:

a) culture of the transformed cells under conditions allowing the expression of a recombinant polypeptide having a nucleic acid sequence according to the invention;

b) where appropriate, recovery of the said recombinant polypeptide.

When the method of preparing a polypeptide of the invention uses a transgenic animal according to the invention, the recombinant polypeptide is then extracted from the said animal.

The subject of the invention is also a polypeptide capable of being obtained by a method of the invention as described above.

The invention also comprises a method of preparing a synthetic polypeptide, characterized in that it uses an amino acid sequence of polypeptides according to the invention.

The invention also relates to a synthetic polypeptide obtained by a method according to the invention.

Polypeptides according to the invention may also be prepared by conventional techniques in the field of peptide synthesis under conditions suitable to produce the polypeptides encoded by the polynucleotide of the invention. This synthesis may be carried out in and recovered from a homogeneous solution or on a solid phase.

For example, the synthesis technique in a homogeneous solution described by Houbenweyl in 1974 may be used.

This method of synthesis consists in successively condensing, in pairs, the successive amino acids in the required order, or in condensing amino acids and fragments previously formed and already containing several amino acids in the appropriate order, or alternatively several fragments thus previously prepared, it being understood that care will have been taken to protect beforehand all the reactive functional groups carried by these amino acids or fragments, with the exception of the amine functional groups of one and the carboxyl functional groups of the other or vice versa, which should normally take part in the formation of the peptide bonds, in particular after activation of the carboxyl functional group, according to methods well known in peptide synthesis.

According to another preferred technique of the invention, the one described by Merrifield is used.

To manufacture a peptide chain according to the Merrifield method, a highly porous polymer resin is used, onto which the first C-terminal amino acid of the chain is attached. This amino acid is attached onto a resin via its carboxyl group and its amine functional group is protected. The amino acids which will constitute the peptide chain are thus attached, one after another, onto the amine group, each time deprotected beforehand, of the portion of the peptide chain already formed, and which is attached to the resin. When the entire peptide chain desired is formed, the protecting groups are removed from the various amino acids constituting the peptide chain and the peptide is detached from the resin with the aid of an acid.

The invention relates, in addition, to hybrid (fusion) polypeptides having at least one polypeptide or one of its representative fragments according to the invention, and a sequence of a polypeptide capable of eliciting an immune response in humans or animals.

Advantageously, the antigenic determinant is such that it is capable of eliciting a humoral and/or cellular response.

An antigenic determinant may be identified by screening expression libraries of the *Chlamydia trachomatis* genome with antibodies contained in the serum of patients infected with a bacterium belonging to the species *Chlamydia trachomatis*. An antigenic determinant may comprise a polypeptide or one of its fragments according to the invention, in glycosylated form, used in order to obtain immunogenic compositions capable of inducing the synthesis of antibodies directed against multiple epitopes. The said polypeptides or their glycosylated fragments also form part of the invention.

These hybrid molecules may consist, in part, of a carrier molecule for polypeptides or for their representative fragments according to the invention, combined with a portion which may be immunogenic, in particular an epitope of the diphtheria toxin, the tetanus toxin, a hepatitis B virus surface antigen (patent FR7921811), the poliomyelitis virus VP1 antigen or any other viral or bacterial toxin or antigen.

The methods of synthesizing the hybrid molecules include the methods used in genetic engineering to construct hybrid nucleotide sequences encoding the desired polypeptide sequences. Reference may be advantageously made, for example, to the technique for producing genes encoding fusion proteins described by Minton in 1984.

The said hybrid nucleotide sequences encoding a hybrid polypeptide as well as the hybrid polypeptides according to the invention, characterized in that they are recombinant polypeptides obtained by the expression of the said hybrid nucleotide sequences, also form part of the invention.

The invention also comprises the vectors characterized in that they contain one of the said hybrid nucleotide sequences. The host cells transformed by the said vectors, the transgenic animals comprising one of the said transformed cells as well as the methods of preparing recombinant polypeptides using the said vectors, the said transformed cells and/or the said transgenic animals of course also form part of the invention.

The polypeptides according to the invention, the antibodies according to the invention described below and the nucleotide sequences according to the invention may advantageously be used in in vitro and/or in vivo methods for the detection and/or the identification of bacteria belonging to the species *Chlamydia trachomatis*, in a biological sample (biological tissue or fluid) which is likely to contain them. These methods, depending on the specificity of the polypeptides, of the antibodies and of the nucleotide sequences according to the invention which will be used, may in particular detect and/or identify the bacterial variants belonging to the species *Chlamydia trachomatis* as well as the associated microorganisms capable of being detected by the polypeptides, the antibodies and the nucleotide sequences according to the invention which will be chosen. It may, for example, be advantageous to choose a polypeptide, an antibody or a nucleotide sequence according to the invention, which is capable of detecting any bacterium of the *Chlamydia* family by choosing a polypeptide, an antibody and/or a nucleotide sequence according to the invention which is specific to the family or, on the contrary, it will be most particularly advantageous to target a variant of the species *Chlamydia trachomatis*, which is responsible, for example, for the induction or the worsening of pathologies specific to the targeted variant, by choosing a polypeptide, an antibody and/or a nucleotide sequence according to the invention which is specific to the said variant.

The polypeptides according to the invention may advantageously be used in a method for the detection and/or the identification of bacteria belonging to the species *Chlamydia trachomatis* or to an associated microorganism, in a biological sample (biological tissue or fluid) which is likely to contain them, characterized in that it comprises the following steps:

a) bringing this biological sample into contact with a polypeptide or one of its representative fragments according to the invention (under conditions allowing an immunological reaction between the said polypeptide and the antibodies which may be present in the biological sample);

b) detecting the antigen-antibody complexes which may be formed.

Preferably, the biological sample consists of a fluid, for example a human or animal serum, blood or biopsies.

Any conventional procedure may be used to carry out such a detection of the antigen-antibody complexes which may be formed.

By way of example, a preferred method uses immunoenzymatic procedures based on the ELISA technique, immunofluorescence procedures or radioimmunological procedures (RIA), and the like.

Accordingly, the invention also relates to the polypeptides according to the invention, labelled with the aid of a suitable label such as a label of the enzymatic, fluorescent or radioactive type.

Such methods comprise, for example, the following steps:

deposition of defined quantities of a polypeptide composition according to the invention into the wells of a microtitre plate, introduction, into the said wells, of increasing dilutions of serum, or of a different biological sample as defined above, which has to be analysed, incubation of the microplate, introduction, into the wells of the microtitre plate, of labelled antibodies directed against human or animal immunoglobulins, these antibodies having been labelled with the aid of an enzyme selected from those which are capable of hydrolyzing a substrate, thereby modifying the absorption of the radiation of the latter, at least at a defined wavelength, for example at 550 nm, detection, by comparison with a control, of the quantity of substrate hydrolyzed.

The invention also relates to a kit or set for the detection and/or the identification of bacteria belonging to the species *Chlamydia trachomatis* or to an associated microorganism, characterized in that it comprises the following components:

a polypeptide according to the invention, where appropriate, the reagents for constituting the medium appropriate for the immunological or specific reaction, the reagents allowing the detection of the antigen-antibody complexes produced by the immunological reaction between the polypeptide(s) of the invention and the antibodies which may be present in the biological sample, it being possible for these reagents also to carry a label, or to be capable of being recognized in turn by a labelled reagent, more particularly in the case where the polypeptide according to the invention is not labelled, where appropriate, a reference biological sample (negative control) free of antibodies recognized by a polypeptide according to the invention, where appropriate, a reference biological sample (positive control) containing a predetermined quantity of antibodies recognized by a polypeptide according to the invention.

According to the invention, the polypeptides, peptides, fusion proteins or other derivatives, or analogs thereof encoded by a polynucleotide sequence in SEQ ID No. 1, may be used as an immunogen to generate antibodies which immunospecifically bind such an immunogen. Such antibodies may include, but are not limited to, polyclonal and monoclonal antibodies, humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. In a specific embodiment, the antibody to a polypeptide, peptide or other derivative, or analog thereof encoded by a polynucleotide sequence in SEQ ID No. 1 is a bispecific antibody (see generally, e.g. Fanger and Drakeman, 1995, *Drug News and Perspectives* 8: 133-137). Such a bispecific antibody is genetically engineered to recognize both (1) an epitope and (2) one of a variety of "trigger" molecules, e.g. Fc receptors on myeloid cells, and CD3 and CD2 on T cells, that have been identified as being able to cause a cytotoxic T-cell to destroy a particular target. Such bispecific antibodies can be prepared either by chemical conjugation, hybridoma, or recombinant molecular biology techniques known to the skilled artisan.

Various procedures known in the art may be used for the production of polyclonal antibodies to a polypeptide, peptide or other derivative, or analog thereof encoded by a polynucleotide sequence in SEQ ID No. 1. For the production of antibody, various host animals can be immunized by injection with a polypeptide, or peptide or other derivative, or analog thereof, including but not limited to rabbits, mice, rats, etc. Various adjuvants, depending on the host species, may be used to increase the immunological response, including but not limited to Stimulon™ QS-21 (Aquila Biopharmaceuticals, Inc., Framingham, Mass.), MPL™ (3-O-deacylated monophosphoryl lipid A; RIBI ImmunoChem Research, Inc., Hamilton, Mont.), aluminum phosphate, IL-12 (Genetics Institute, Cambridge, Mass.), Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, BCG (bacille Calmette-Guerin), and *Corynebacterium parvum*. Alternatively, polyclonal antibodies may be prepared by purifying, on an affinity column onto which a polypeptide according to the invention has been previously attached, the antibodies contained in the serum of patients infected with a bacterium belonging to the species *Chlamydia trachomatis*.

For preparation of monoclonal antibodies directed toward a polypeptide, peptide or other derivative, or analog, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing technology described in PCT/US90/02545. In another embodiment of the invention, transgenic non-human animals can be used for the production of human antibodies utilizing technology described in WO 98/24893 and WO 96/33735. According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies", (Morrison et al., 1984, PROC. NATL. ACAD. SCI. U.S.A. 81:6851-6855; Neuberger et al., 1984, Nature 312:604-608; Takeda et al., 1985, Nature 314:452-454) by splicing the genes from a mouse antibody molecule specific for a polypeptide, peptide or other derivative, or analog together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce polypeptide or peptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for polypeptides, derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent, and Fv fragments.

In addition, techniques have been developed for the production of chimerized (See, e.g., Boss, M. et al., U.S. Pat. No. 4,816,397; and Cabilly, S. et al., U.S. Pat. No. 5,585,089 each of which is incorporated herein by reference in its entirety) humanized antibodies (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (See, "Sequences of Proteins of Immunological Interest", Kabat, E. et al., U.S. Department of Health and Human Services (1983)). Briefly, humanized antibodies are antibody molecules from non-human species having one or more CDRs from the non-human species and a framework from a human immunoglobulin molecule.

The antibodies of the invention may also be labelled in the same manner as described above for the nucleic probes of the invention such as an enzymatic, fluorescent or radioactive type labelling.

The invention relates, in addition, to a method for the detection and/or the identification of bacteria belonging to the species *Chlamydia trachomatis* or to an associated microorganism in a biological sample, characterized in that it comprises the following steps:
a) bringing the biological sample (biological tissue or fluid) into contact with a mono- or polyclonal antibody according to the invention (under conditions allowing an immunological reaction between the said antibodies and the polypeptides of the bacterium belonging to the species *Chlamydia trachomatis* or to an associated microorganism which may be present in the biological sample, that is, under conditions suitable for the formation of immune complexes);
b) detecting the antigen-antibody complex which may be formed.

Also falling within the scope of the invention is a kit or set for the detection and/or the identification of bacteria belonging to the species *Chlamydia trachomatis* or to an associated microorganism, characterized in that it comprises the following components:
  a polyclonal or monoclonal antibody according to the invention, labelled where appropriate;
  where appropriate, a reagent for constituting the medium appropriate for carrying out the immunological reaction;
  a reagent allowing the detection of the antigen-antibody complexes produced by the immunological reaction, it being possible for this reagent also to carry a label, or to be capable of being recognized in turn by a labelled reagent, more particularly in the case where the said monoclonal or polyclonal antibody is not labelled;
  where appropriate, reagents for carrying out the lysis of the cells in the sample tested.

The principle of the DNA chip which was explained above may also be used to produce protein "chips" on which the support has been coated with a polypeptide or an antibody according to the invention, or arrays thereof, in place of the DNA. These protein "chips" make it possible, for example, to analyse the biomolecular interactions (BIA) induced by the affinity capture of target analytes onto a support coated, for example, with proteins, by surface plasma resonance (SPR). Reference may be made, for example, to the techniques for coupling proteins onto a solid support which are described in EP 524 800 or to the methods describing the use of biosensor-type protein chips such as the BLAcore-type technique (Pharmacia) (Arlinghaus et al., 1997, Krone et al., 1997, Chatelier et al., 1995). These polypeptides or antibodies according to the invention, capable of specifically binding antibodies or polypeptides derived from the sample to be analysed, may thus be used in protein chips for the detection and/or the identification of proteins in samples. The said protein chips may in particular be used for infectious diagnosis and may preferably contain, per chip, several polypeptides and/or antibodies of the invention of different specificity, and/or polypeptides and/or antibodies capable of recognizing microorganisms different from *Chlamydia trachomatis*.

Accordingly, the subject of the present invention is also the polypeptides and the antibodies according to the invention, characterized in that they are immobilized on a support, in particular of a protein chip.

The protein chips, characterized in that they contain at least one polypeptide or one antibody according to the invention immobilized on the support of the said chip, also form part of the invention.

The invention comprises, in addition, a protein chip according to the invention, characterized in that it contains, in addition, at least one polypeptide of a microorganism different from *Chlamydia trachomatis* or at least one antibody directed against a compound of a microorganism different from *Chlamydia trachomatis*, immobilized on the support of the said chip.

The invention also relates to a kit or set for the detection and/or the identification of bacteria belonging to the species *Chlamydia trachomatis* or to an associated microorganism, or for the detection and/or the identification of a microorganism characterized in that it comprises a protein chip according to the invention.

The subject of the present invention is also a method for the detection and/or the identification of bacteria belonging to the species *Chlamydia trachomatis* or to an associated microorganism in a biological sample, characterized in that it uses a nucleotide sequence according to the invention.

More particularly, the invention relates to a method for the detection and/or the identification of bacteria belonging to the species *Chlamydia trachomatis* or to an associated microorganism in a biological sample, characterized in that it comprises the following steps:
a) where appropriate, isolation of the DNA from the biological sample to be analysed, or optionally production of a cDNA from the RNA in the biological sample;
b) specific amplification of the DNA of bacteria belonging to the species *Chlamydia trachomatis* or to an associated microorganism with the aid of at least one primer according to the invention;
c) detection of the amplification products.

These may be detected, for example, by the molecular hybridization technique using a nucleic probe according to the invention. This probe will be advantageously labelled with a nonradioactive (cold probe) or radioactive element.

For the purposes of the present invention, "DNA in the biological sample" or "DNA contained in the biological sample" will be understood to mean either the DNA present in the biological sample considered, or optionally the cDNA obtained after the action of a reverse transcriptase-type enzyme on the RNA present in the said biological sample.

Another aim of the present invention consists in a method according to the invention, characterized in that it comprises the following steps:
a) bringing a nucleotide probe according to the invention into contact with a biological sample, the DNA contained in the biological sample having, where appropriate, been previously made accessible to hybridization, under conditions allowing the hybridization of the probe to complementary base pairs of the DNA of a bacterium belonging to the species *Chlamydia trachomatis* or to an associated microorganism;
b) detecting the hybridization complex formed between the nucleotide probe and the DNA in the biological sample.

The present invention also relates to a method according to the invention, characterized in that it comprises the following steps:
a) bringing a nucleotide probe immobilized on a support according to the invention into contact with a biological sample, the DNA in the sample having, where appropriate, been previously made accessible to hybridization, under conditions allowing the hybridization of the probe to the DNA of a bacterium belonging to the species *Chlamydia trachomatis* or to an associated microorganism;
b) bringing the hybrid formed between the nucleotide probe immobilized on a support and the DNA contained in the biological sample, where appropriate after removal of the DNA in the biological sample which has not hybridized with the probe, into contact with a labelled nucleotide probe according to the invention;
c) detecting the new hybrid formed in step b).

According to an advantageous embodiment of the method for the detection and/or the identification defined above, it is characterized in that, prior to step a), the DNA in the biological sample is primer-extended and/or amplified beforehand with the aid of at least one primer according to the invention.

The invention relates, in addition, to a kit or set for the detection and/or the identification of bacteria belonging to the species *Chlamydia trachomatis* or to an associated microorganism, characterized in that it comprises the following components:
a) a nucleotide probe according to the invention;
b) where appropriate, the reagents necessary for carrying out a hybridization reaction;
c) where appropriate, at least one primer according to the invention as well as the reagents (e.g., polymerase and/or deoxynucleotide triphosphates) necessary for a DNA amplification reaction.

The invention also relates to a kit or set for the detection and/or the identification of bacteria belonging to the species *Chlamydia trachomatis* or to an associated microorganism, characterized in that it comprises the following components:
a) a nucleotide probe, called capture probe, according to the invention;
b) an oligonucleotide probe, called detection probe, according to the invention;
c) where appropriate, at least one primer according to the invention as well as the reagents (e.g., polymerase and/or deoxynucleotide triphosphates) necessary for a DNA amplification reaction.

The invention also relates to a kit or set for the detection and/or the identification of bacteria belonging to the species *Chlamydia trachomatis* or to an associated microorganism, characterized in that it comprises the following components:
a) at least one primer according to the invention;
b) where appropriate, the reagents necessary for carrying out a DNA amplification reaction;
c) where appropriate, a component which makes it possible to check the sequence of the amplified fragment, more particularly an oligonucleotide probe according to the invention.

The invention relates, in addition, to a kit or set for the detection and/or the identification of bacteria belonging to the species *Chlamydia trachomatis* or to an associated microorganism, or for the detection and/or the identification of a microorganism characterized in that it comprises a DNA chip according to the invention.

The invention also relates to a method or to a kit or set according to the invention for the detection and/or the identification of bacteria belonging to the species *Chlamydia trachomatis*, characterized in that the said primer and/or the said probe according to the invention are chosen from the nucleotide sequences specific to the species *Chlamydia trachomatis*, in that the said polypeptides according to the invention are chosen from the polypeptides specific to the species *Chlamydia trachomatis* and in that the said antibodies according to the invention are chosen from the antibodies directed against the polypeptides according to the invention chosen from the polypeptides specific to the species *Chlamydia trachomatis*.

Preferably, the said method or the said kit or set above according to the invention, for the detection and/or the identification of bacteria belonging to the species *Chlamydia trachomatis* is characterized in that the said primer and/or the said probe or the said polypeptides are chosen from the nucleotide sequences or polypeptides according to the invention which have been identified as being specific to the species *Chlamydia trachomatis* and in that the said antibodies according to the invention are chosen from the antibodies directed against the polypeptides according to the invention chosen from the polypeptides identified as being specific to the species *Chlamydia trachomatis*.

The invention relates, in addition, to a method or a kit or set according to the invention for the diagnosis of predispositions to, or of a condition caused by, genital diseases which are induced or worsened by a *Chlamydia trachomatis* infection.

The invention also relates to a method or a kit or set according to the invention for the diagnosis of predispositions to, or of conditions caused by, eye diseases induced or worsened by a *Chlamydia trachomatis* infection.

The invention also relates to a method or a kit or set according to the invention for the diagnosis of predispositions to, or of conditions caused by, systemic diseases, in particular of the lymphatic system, which are induced or worsened by a *Chlamydia trachomatis* infection.

According to another aspect, the subject of the invention is the use of polypeptides according to the invention, of cells transformed with a vector according to the invention and/or of transformed animals according to the invention, for the biosynthesis or the biodegradation of organic or inorganic compounds.

As has been mentioned above, the nucleotide sequences of the invention were identified by homology with sequences known to encode, for example, polypeptides or fragments of enzymatic polypeptides involved in the biosynthesis or the biodegradation of organic or inorganic molecules.

It is thus possible to use the said polypeptides of the invention in a similar manner for the biosynthesis or the biodegradation of organic or inorganic compounds of industrial or therapeutic interest (called compounds of interest).

Among these polypeptides, there may be mentioned in particular the enzymes involved in metabolism, such as the proteolytic enzymes, amino transferases, glucose metabolism, or the enzymes which may be used in the biosynthesis of sugars, amino acids, fatty acids, polypeptides, nucleotides, nucleic acids or any other organic or inorganic compound or in the biodegradation of organic or inorganic compounds.

Among these polypeptides, there may be mentioned, in addition, the mutated or modified enzymes corresponding to mutated or modified polypeptides according to the invention which may also be used for the biosynthesis or the biodegradation of organic or inorganic compounds at the industrial level, such as, for example, the production of compounds of interest, the reprocessing of manufacturing residues applied to the food industries, to the papermaking industry or to the chemical and pharmaceutical industries.

The methods of biosynthesis or biodegradation of organic or inorganic compounds, characterized in that they use a polypeptide or one of its representative fragments according to the invention, transformed cells according to the invention and/or a transformed animal according to the invention, also form part of the invention.

The invention relates, in addition, to the use of a nucleotide sequence according to the invention, of a polypeptide according to the invention, of an antibody according to the invention, of a cell according to the invention, and/or of a transformed animal according to the invention, for the selection of an organic or inorganic compound capable of modulating, regulating, inducing or inhibiting the expression of genes, and/or of modifying the cellular replication of eukaryotic or prokaryotic cells or capable of inducing, inhibiting or worsening the pathologies linked to an infection by *Chlamydia trachomatis* or one of its associated microorganisms.

The invention also comprises screening assays that comprise methods of selecting compounds capable of binding to a polypeptide, fusion polypeptide, or one of its representative fragments according to the invention, capable of binding to a nucleotide sequence according to the invention, or capable of recognizing an antibody according to the invention, and/or capable of modulating, regulating, inducing or inhibiting the expression of genes, and/or of modifying the growth or the cellular replication of eukaryotic or prokaryotic cells, or capable of inducing, inhibiting or worsening, in an animal or human organism, the pathologies linked to an infection by *Chlamydia trachomatis* or one of its associated microorganisms, characterized in that it comprises the following steps:

a) bringing the said compound into contact with the said polypeptide, the said nucleotide sequence, with a transformed cell according to the invention and/or administering the said compound to a transformed animal according to the invention;

b) determining the capacity of the said compound to bind with the said polypeptide or the said nucleotide sequence, or to modulate, regulate, induce or inhibit the expression of genes, or to modulate growth or cellular replication, or to induce, inhibit or worsen in the said transformed animal, the pathologies linked to an infection by *Chlamydia trachomatis* or one of its associated microorganisms.

The transformed cells and/or animals according to the invention may advantageously serve as a model and may be used in methods for studying, identifying and/or selecting compounds capable of being responsible for pathologies induced or worsened by *Chlamydia trachomatis*, or capable of preventing and/or of treating these pathologies such as, for example, genital, eye or systemic diseases, especially of the lymphatic system. In particular, the transformed host cells, in particular bacteria of the *Chlamydia* family whose transformation with a vector according to the invention may, for example, increase or inhibit its infectivity, or modulate the pathologies usually induced or worsened by the infection, may be used to infect animals in which the onset of pathologies will be monitored. These nontransformed animals, infected for example with transformed *Chlamydia* bacteria, may serve as a study model. In the same manner, the transformed animals according to the invention may, for example, exhibit predispositions to genital and/or eye and/or systemic diseases, especially of the lymphatic system, and thus be used in methods for selecting compounds capable of preventing and/or of treating the said diseases. The said methods using the said transformed cells and/or transformed animals form part of the invention.

The compounds capable of being selected may be organic compounds such as polypeptides or carbohydrates or any other organic or inorganic compounds already known, or new organic compounds produced using molecular modelling techniques and obtained by chemical or biochemical synthesis, these techniques being known to persons skilled in the art.

The said selected compounds may be used to modulate the growth and/or the cellular replication of *Chlamydia trachomatis* or any other associated microorganism and thus to control infection by these microorganisms. The said compounds according to the invention may also be used to modulate the growth and/or the cellular replication of all eukaryotic or prokaryotic cells, in particular tumour cells and infectious microorganisms, for which the said compounds will prove active, the methods which make it possible to determine the said modulations being well known to persons skilled in the art.

Compound capable of modulating the growth of a microorganism is understood to designate any compound which makes it possible to act, to modify, to limit and/or to reduce the development, the growth, the rate of proliferation and/or the viability of the said microorganism.

This modulation may be achieved, for example, by an agent capable of binding to a protein and thus of inhibiting or of potentiating its biological activity, or capable of binding to a membrane protein of the outer surface of a microorganism and of blocking the penetration of the said microorganism into the host cell or of promoting the action of the immune system of the infected organism directed against the said microorganism. This modulation may also be achieved by an agent capable of binding to a nucleotide sequence of a DNA or RNA of a microorganism and of blocking, for example, the expression of a polypeptide whose biological or structural activity is necessary for the growth or for the reproduction of the said microorganism.

Associated microorganism is understood to designate in the present invention any microorganism whose gene expression may be modulated, regulated, induced or inhibited, or whose growth or cellular replication may also be modulated by a compound of the invention. Associated microorganism is also understood to designate in the present invention any microorganism containing nucleotide sequences or polypeptides according to the invention. These microorganisms may, in some cases, contain polypeptides or nucleotide sequences identical or homologous to those of the invention may also be detected and/or identified by the detection and/or identification methods or kit according to the invention and may also serve as a target for the compounds of the invention.

The invention relates to the compounds capable of being selected by a method of selection according to the invention.

The invention also relates to a pharmaceutical composition comprising a compound chosen from the following compounds: a nucleotide sequence according to the invention; a polypeptide or fusion polypeptide according to the invention; a vector according to the invention; an antibody according to the invention; and a compound capable of being selected by a method of selection according to the invention, optionally in combination with a pharmaceutically acceptable vehicle or carrier.

An effective quantity is understood to designate a sufficient quantity of the said compound or antibody, or of a polypeptide of the invention, which makes it possible to modulate the growth of *Chlamydia trachomatis* or of an associated microorganism.

The invention also relates to a pharmaceutical composition according to the invention for the prevention or the treatment of an infection by a bacterium belonging to the species *Chlamydia trachomatis* or by an associated microorganism.

The invention relates, in addition, to an immunogenic and/or vaccine composition, characterized in that it comprises one or more polypeptides according to the invention and/or one or more hybrid polypeptides according to the invention.

The invention also comprises the use of a transformed cell according to the invention, for the preparation of a vaccine composition.

The invention also relates to a vaccine composition, characterized in that it contains a nucleo-tide sequence according to the invention, a vector according to the invention and/or a transformed cell according to the invention.

The invention also relates to the vaccine compositions according to the invention, for the prevention or the treatment of an infection by a bacterium belonging to the species *Chlamydia trachomatis* or by an associated microorganism.

The invention also relates to the use of DNA encoding polypeptides of *Chlamydia trachomatis*, in particular antigenic determinants, to be formulated as vaccine compositions. In accordance with this aspect of the invention, the DNA of interest is engineered into an expression vector under the control of regulatory elements, which will promote expression of the DNA, i.e., promoter or enhancer elements. In one preferred embodiment, the promoter element may be cell-specific and permit substantial transcription of the DNA only in predetermined cells. The DNA may be introduced directly into the host either as naked DNA (U.S. Pat. No. 5,679,647 incorporated herein by reference in their entirety) or formulated in compositions with other agents which may facilitate uptake of the DNA including viral vectors, i.e., adenovirus vectors, or agents which facilitate immunization, such as bupivacaine and other local anesthetics (U.S. Pat. No. 5,593,972 incorporated herein by reference in their entirety), saponins (U.S. Pat. No. 5,739,118 incorporated herein by reference in their entirety) and cationic polyamines (published international application WO 96/10038 incorporated herein by reference in their entirety).

The DNA sequence encoding the antigenic polypeptide and regulatory element may be inserted into a stable cell line or cloned microorganism, using techniques, such as targeted homologous recombination, which are well known to those of skill in the art, and described e.g., in Chappel, U.S. Pat. No. 4,215,051; Skoultehi, WO 91/06667 each of which is incorporated herein by reference in its entirety.

Such cell lines and microorganisms may be formulated for vaccine purposes. In yet another embodiment, the DNA sequence encoding the antigenic polypeptide and regulatory element may be delivered to a mammalian host and introduced into the host genome via homologous recombination (See, Chappel, U.S. Pat. No. 4,215,051; Skoultchi, WO 91/06667 each of which is incorporated herein by reference in its entirety.

Preferably, the immunogenic and/or vaccine compositions according to the invention intended for the prevention and/or the treatment of an infection by *Chlamydia trachomatis* or by an associated microorganism will be chosen from the immunogenic and/or vaccine compositions comprising a polypeptide or one of its representative fragments corresponding to a protein, or one of its representative fragments, of the cellular envelope of *Chlamydia trachomatis*. The vaccine compositions comprising nucleotide sequences will also preferably comprise nucleotide sequences encoding a polypeptide or one of its fragments corresponding to a protein, or one of its representative fragments, of the cellular envelope of *Chlamydia trachomatis*.

Among these preferred immunogenic and/or vaccine compositions, the most preferred are those comprising a polypeptide or one of its representative fragments, or a nucleotide sequence or one of its representative fragments whose sequences are chosen from the nucleotide or amino acid sequences identified in this functional group and listed above.

The polypeptides of the invention or their representative fragments entering into the immunogenic compositions according to the invention may be selected by techniques known to persons skilled in the art, such as for example on the capacity of the said polypeptides to stimulate T cells, which results, for example, in their proliferation or the secretion of interleukins, and which leads to the production of antibodies directed against the said polypeptides.

In mice, in which a weight dose of the vaccine composition comparable to the dose used in humans is administered, the antibody reaction is tested by collecting serum followed by a study of the formation of a complex between the antibodies present in the serum and the antigen of the vaccine composition, according to the customary techniques.

According to the invention, the said vaccine compositions will be preferably in combination with a pharmaceutically acceptable vehicle and, where appropriate, with one or more appropriate immunity adjuvants.

Various types of vaccines are currently available for protecting humans against infectious diseases: attenuated live microorganisms (*M. bovis*—BCG for tuberculosis), inactivated microorganisms (influenza virus), acellular extracts (*Bordetella pertussis* for whooping cough), recombinant proteins (hepatitis B virus surface antigen), polysaccharides (pneumococci). Experiments are underway on vaccines prepared from synthetic peptides or from genetically modified microorganisms expressing heterologous antigens. Even more recently, recombinant plasmid DNAs carrying genes encoding protective antigens were proposed as an alternative vaccine strategy. This type of vaccination is carried out with a particular plasmid derived from an *E. coli* plasmid which does not replicate in vivo and which encodes only the vaccinal protein. Animals were immunized by simply injecting the naked plasmid DNA into the muscle. This technique leads to the expression of the vaccine protein in situ and to a cell-type (CTL) and a humoral type (antibody) immune response. This double induction of the immune response is one of the main advantages of the technique of vaccination with naked DNA.

The vaccine compositions of the present invention can be evaluated in in vitro and in vivo animal models prior to host, e.g., human, administration. For example, in vitro neutralization assays such as those described by Peterson et al. (1988) can be utilized. The assay described by Peterson et al. (1988) is suitable for testing vaccine compositions directed toward either *Chlamydia trachomatis* or *Chlamydia pneumoniae*.

Briefly, hyper-immune antisera is diluted in PBS containing 5% guinea pig serum, as a complement source. Chlamydiae ($10^4$ IFU; inclusion forming units) are added to the antisera dilutions. The antigen-antibody mixtures are incubated at 37° C. for 45 minutes and inoculated into duplicate confluent Hep-2 or HeLa cell monolayers contained in glass vials (e.g., 15 by 45 mm), which have been washed twice with PBS prior to inoculation. The monolayer cells are infected by centrifugation at 1000×g for 1 hour followed by stationary incubation at 37° C. for 1 hour. Infected monolayers are incubated for 48 or 72 hours, fixed and stained with a Chlamydiae specific antibody, such as anti-MOMP for *C. trachomatis*, etc. Inclusion-bearing cells are counted in ten fields at a magnification of 200×. Neutralization titer is assigned based on the dilution that gives 50% inhibition as compared to control monolayers/IFU.

The efficacy of vaccine compositions can be determined in vivo by challenging animal models of *Chlamydia trachomatis* infection, e.g., guinea pigs or mice, with the vaccine compositions. For example, in vivo vaccine composition challenge studies in the guinea pig model of *Chlamydia trachomatis* infection can be performed. Briefly, female guinea pigs weighing 450 to 500 g are housed in an environmentally controlled room with a 12 hour light-dark cycle and immunized with vaccine compositions via a variety of immunization routes. Post-vaccination, guinea pigs are infected in the genital tract with the agent of guinea pig inclusion conjunctivitis (GPIC), which has been grown in HeLa or McCoy cells (Rank et al. (1988)). Each animal receives approximately $1.4\times10^7$ inclusion forming units (IFU) contained in 0.05 ml of sucrose-phosphate-glutamate buffer, pH 7.4 (Schacter, J. (1980)). The course of infection monitored by determining the percentage of inclusion-bearing cells by indirect immunofluorescence with GPIC specific antisera, or by Giemsa-stained smear from a scraping from the genital tract (Rank et al. (1988)). Antibody titers in the serum is determined by an enzyme-linked immunosorbent assay.

Alternatively, in vivo vaccine composition challenge studies can be performed in the murine model of *Chlamydia trachomatis* (Morrison et al., 1995). Briefly, female mice 7 to 12 weeks of age receive 2.5 mg of depoprovera subcutaneously at 10 and 3 days before vaginal infection. Post-vaccination, mice are infected in the genital tract with 1,500 inclusion-forming units of *Chlamydia trachomatis* contained in 5 ml of sucrose-phosphate-glutamate buffer, pH. 7.4. The course of infection is monitored by determining the percentage of inclusion-bearing cells by indirect immunofluorence with *Chlamydia trachomatis* specific antisera, or by a Giemsa-stained smear from a scraping from the genital tract of an infected mouse. The presence of antibody titers in the serum of a mouse is determined by an enzyme-linked immunosorbent assay.

The vaccine compositions comprising nucleotide sequences or vectors into which the said sequences are inserted are in particular described in International Application No. WO 90/11092 and also in International Application No. WO 95/11307.

The nucleotide sequence constituting the vaccine composition according to the invention may be injected into the host after having been coupled to compounds which promote the penetration of this polynucleotide inside the cell or its transport up to the cell nucleus. The resulting conjugates may be encapsulated into polymeric microparticles, as described in International Application No. WO 94/27238 (Medisorb Technologies International).

According to another embodiment of the vaccine composition according to the invention, the nucleotide sequence, preferably a DNA, is complexed with the DEAE-dextran (Pagano et al., 1967) or with nuclear proteins (Kaneda et al., 1989), with lipids (Felgner et al., 1987) or encapsulated into liposomes (Fraley et al., 1980) or alternatively introduced in the form of a gel facilitating its transfection into the cells (Midoux et al., 1993, Pastore et al., 1994). The polynucleotide or the vector according to the invention may also be in suspension in a buffer solution or may be combined with liposomes.

Advantageously, such a vaccine will be prepared in accordance with the technique described by Tacson et al. or Huygen et al. in 1996 or alternatively in accordance with the technique described by Davis et al. in International Application No. WO 95/11307.

Such a vaccine may also be prepared in the form of a composition containing a vector according to the invention, placed under the control of regulatory elements allowing its expression in humans or animals. It is possible, for example, to use, as vector for the in vivo expression of the polypeptide antigen of interest, the plasmid pcDNA3 or the plasmid pcDNA1/neo, both marketed by Invitrogen (R & D Systems, Abingdon, United Kingdom). It is also possible to use the plasmid V1Jns.tPA, described by Shiver et al. in 1995. Such a vaccine will advantageously comprise, in addition to the recombinant vector, a saline solution, for example a sodium chloride solution.

The immunogenic compositions of the invention can be utilized as part of methods of immunization, wherein such methods comprise administering to a host, e.g., a human host, an immunizing amount of the immunogenic compositions of the invention. In a preferred embodiment, the method of immunizing is a method of immunizing against *Chlamydia trachomatis.*

A pharmaceutically acceptable vehicle is understood to designate a compound or a combination of compounds entering into a pharmaceutical or vaccine composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen.

As regards the vaccine formulations, these may comprise appropriate immunity adjuvants which are known to persons skilled in the art, such as, for example, aluminum hydroxide, a representative of the family of muramyl peptides such as one of the peptide derivatives of N-acetyl-muramyl, a bacterial lysate, or alternatively incomplete Freund's adjuvant, Stimulon™ QS-21 (Aquila Biopharmaceuticals, Inc., Framingham, Mass.), MPL™ (3-O-deacylated monophosphoryl lipid A; RIBI ImmunoChem Research, Inc., Hamilton, Mont.), aluminum phosphate, IL-12 (Genetics Institute, Cambridge, Mass.).

Preferably, these compounds will be administered by the systemic route, in particular by the intravenous route, by the intranasal, intramuscular, intradermal or subcutaneous route, or by the oral route. More preferably, the vaccine composition comprising polypeptides according to the invention will be administered several times, spread out over time, by the intradermal or subcutaneous route.

Their optimum modes of administration, dosages and galenic forms may be determined according to criteria which are generally taken into account in establishing a treatment adapted to a patient, such as for example the patient's age or body weight, the seriousness of his general condition, tolerance of the treatment and the side effects observed.

The invention comprises the use of a composition according to the invention for the treatment or the prevention of genital diseases which are induced or worsened by *Chlamydia trachomatis.*

Finally, the invention comprises the use of a composition according to the invention for the treatment or the prevention of eye diseases which are induced or worsened by the presence of *Chlamydia trachomatis.*

Finally, the invention comprises the use of a composition according to the invention for the treatment or the prevention of systemic diseases, especially of the lymphatic system, which are induced or worsened by the presence of *Chlamydia trachomatis.*

Other characteristics and advantages of the invention appear in the following examples and figures:

Figure 1:
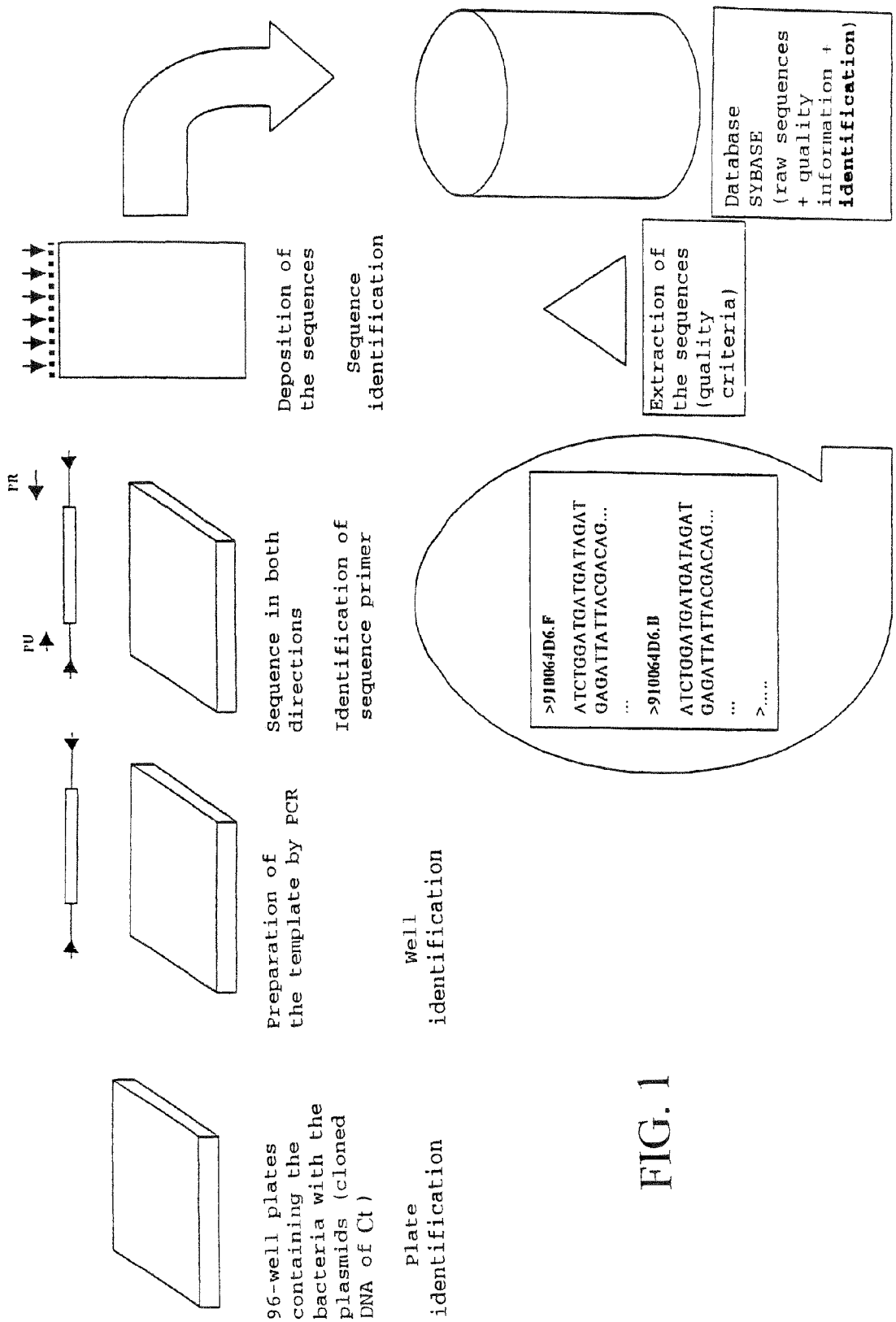
FIG. 1: Line for the production of *Chlamydia trachomatis* sequences (SEQ ID NO: 5182)

Cloning of the DNA. After precipitation, the DNA is quantified by measuring the optical density at 260 nm. Thirty µg of *Chlamydia* DNA are distributed into 10 tubes of 1.5 ml and diluted in 300 µl of water. Each of the tubes is subjected to 10 applications of ultrasound lasting for 0.5 sec in a sonicator (Unisonix XL2020). The contents of the 10 tubes are then grouped and concentrated by successive extractions with butanol (Sigma B1888) in the following manner: two volumes of butanol are added to the dilute DNA mixture. After stirring, the whole is centrifuged for five minutes at 2500 rpm and the butanol is removed. This operation is repeated until the volume of the aqueous phase is less than 1 ml. The DNA is then precipitated in the presence of ethanol and of 0.5 M sodium acetate pH 5.4, and then centrifuged for thirty minutes at 15,000 rpm at cold temperature (4° C.). The pellet is washed with 75% ethanol, centrifuged for five minutes at 15,000 rpm and dried at room temperature. A tenth of the preparation is analysed on a 0.8% agarose gel. Typically, the size of the DNA fragments thus prepared is between 200 and 8000 base pairs.

To allow the cloning of the DNA obtained, the ends are repaired. The DNA is distributed in an amount of 10 µg/tube, in the following reaction medium: 100 µl final volume, 1× buffer (Biolabs 201L), 0.5 µl BSA 0.05 mg/ml, 0.1 mM dATP, 0.1 mM each of dGTP, dCTP or dTTP, 60,000 IU T4 DNA polymerase. The reaction is incubated for thirty minutes at 16° C. The contents of each of the tubes are then grouped before carrying out an extraction with phenol-chloroform and then precipitating the aqueous phase as described above. After this step, the DNA thus prepared is phosphorylated. For that, the DNA is distributed into tubes in an amount of 10 µg per tube, and then in a final volume of 50 µl, the reaction is prepared in the following manner: 1 mM ATP, 1× kinase buffer, 10 IU T4 polynucleotide kinase (Biolabs 201L). The preparation is incubated for thirty minutes at 37° C. The contents of the tubes are combined and a phenol-chloroform extraction and a precipitation are carried out in order to precipitate the DNA. The latter is then suspended in 1 µl of water and then the DNA fragments are separated according to their size on a 0.8% agarose gel (1×TAE). The DNA is subjected to an electric field of 5 V/cm and then visualized on a UV table. The fragments whose size varies between 1200 and 2000 base pairs are selected by cutting out the gel. The gel fragment thus isolated is placed in a tube and then the DNA is purified with the Qiaex kit (20021 Qiagen), according to the procedure provided by the manufacturer.

Preparation of the vector. 14 µg of the cloning vector pGEM-5Zf (Proméga P2241) are diluted in a final volume of 150 µl and are subjected to digestion with the restriction enzyme EcoRV 300 IU (Biolabs 195 S) according to the protocol and with the reagents provided by the manufacturer. The whole is placed at 37° C. for 150 min and then distributed in the wells of a 0.8% agarose gel subjected to an electric field of 5 V/cm. The linearized vector is visualized on a UV table, isolated by cutting out the gel and then purified by the Qiaex kit (Qiagen 20021) according to the manufacturer's recommendations. The purification products are grouped in a tube, the volume is measured and then half the volume of phenol is added and the whole is vigorously stirred for 1 min. Half the volume of chloroform-isoamyl alcohol 24:1 is added and vigorously stirred for 1 min. The whole is centrifuged at 15,000 rpm for 5 min at 4° C., the aqueous phase is recovered and transferred into a tube. The DNA is precipitated in the presence of 0.3 M sodium acetate, pH 5.4 and 3 volumes of ethanol and placed at −20° C. for 1 hour. The DNA is then centrifuged at 15,000 rpm for 30 min at 4° C., the supernatant is removed while preserving the pellet, washed twice with 70% ethanol. After drying at room temperature, the DNA is suspended in 25 µl of water.

Phosphorylation of the vector. 25 µl of the vector prepared in the preceding step are diluted in a final volume of 500 µl of the following reaction mixture:

After repair, the DNA is subjected to a phenol-chloroform extraction and a precipitation, the pellet is then taken up in 10 µl of water, the DNA is quantified by measuring the optical density at 260 nm. The quantified DNA is ligated into the vector PGEm-5Zf(+) prepared by the restriction enzyme EcoRV and dephosphorylated (see preparation of the vector). The ligation is carried out under three conditions which vary in the ratio between the number of vector molecules and the number of insert molecules. Typically, an equimolar ratio, a ratio of 1:3 and a ratio of 3:1 are used for the ligations which are, moreover, carried out under the following conditions: vector PGEm-5Zf(+) 25 ng, cut DNA, ligation buffer in a final volume of 20 µl with T4 DNA ligase (Amersham E70042X); the whole is then placed in a refrigerator overnight and then a phenol-chloroform extraction and a precipitation are carried out in a conventional manner. The pellet is taken up in 5 µl of water.

Transformation of the Bacteria. Plating of the Bacteria

Petri dishes containing LB Agar medium containing ampicillin (50 µg/ml), Xgal (280 µg/ml) [5-bromo-4-chloro-indolyl-beta-D-galactopyranoside (Sigma B-4252)], IPTG (140 µg/ml) [isopropyl-beta-D-thiogalactoside (Sigma I-6758)] are used, 50 and 100 µl of bacteria are plated for each of the ligations. The Petri dishes are placed upside down at 37° C. for 15 to 16 hours in an oven. The number of "recombinant" positive clones is evaluated by counting the white colonies and the blue colonies which are thought to contain the vector alone.

Evaluation of the "recombinant" positive clones. Ninety-four white colonies and two blue colonies are collected with the aid of sterile cones and are deposited at the bottom of the wells of plates designed for carrying out the amplification techniques. 30 µl of the following reaction mixture are added to each well: 1.7 mM MgCl$_2$, 0.2 mM each of dATP, dCTP, dGTP and dTTP, two synthetic oligonucleotides corresponding to sequences flanking the cloning site on either side and orienting the synthesis of the DNA in a convergent manner (0.5 mM RP and PU primers, 1 U TAQ polymerase (Gibco-BRL 18038-026)).

The colonies thus prepared are subjected to a temperature of 94° C. for 5 min and then to 30 thermal cycles composed of the following steps: 94° C. for 40 s, 50° C. for 30 s, 72° C. for 180 s. The reaction is then kept for 7 min at 72° C. and then kept at 4° C.

The amplification products are deposited on an agarose gel (0.8%), stained with ethidium bromide, subjected to electrophoresis, and then analysed on an ultraviolet table. The presence of an amplification fragment having a size greater than 500 base pairs indicates the presence of an insert. The bacterial clones are then prepared so as to study the sequence of their insert.

Sequencing. To sequence the inserts of the clones obtained as above, these were amplified by PCR on bacteria cultures carried out overnight using the primers for the vectors flanking the inserts. The sequence of the ends of these inserts (on average 500 bases on each side) was determined by automated fluorescent sequencing on an ABI 377 sequencer, equipped with the ABI Prism DNA Sequencing Analysis software (version 2.1.2).

Analysis of the sequences. The sequences obtained by sequencing in a high-yield line (FIG. 1) are stored in a database; this part of the production is independent of any treatment of the sequences. The sequences are extracted from the database, avoiding all the regions of inadequate quality, that is to say the regions for which uncertainties are observed on the sequence at more than 95%. After extraction, the sequences are introduced into a processing line, the diagram of which is described in FIG. 2. In a first path of this processing line, the sequences are assembled by the Gap4 software from R. Staden (Bonfield et al., 1995) (OS UNIX/SUN Solaris); the results obtained by this software are kept in the form of two files which will be used for a subsequent processing. The first of these files provides information on the sequence of each of the contigs obtained. The second file represents all the clones participating in the composition of all the contigs as well as their positions on the respective contigs.

The second processing path uses a sequence assembler (TIGR-Asmg assembler UNIX/SUN Solaris); the results of this second processing path are kept in the form of a file in the TIGR-Asmg format which provides information on the relationship existing between the sequences selected for the assembly. This assembler is sometimes incapable of linking contigs whose ends overlap over several hundreds of base pairs.

The results obtained from these two assemblers are compared with the aid of the BLAST program, each of the contigs derived from one assembly path being compared with the contigs derived from the other path.

For the two processing paths, the strict assembly parameters are fixed (95% homology, 30 superposition nucleotides). These parameters avoid 3 to 5% of the clones derived from eukaryotic cells being confused with sequences obtained from the clones derived from *Chlamydia trachomatis*. The eukaryotic sequences are however preserved during the course of this project; the strategy introduced, which is described below, will be designed, inter alia, not to be impeded by these sequences derived from contaminating clones.

Figures 2, 3A, 3B:
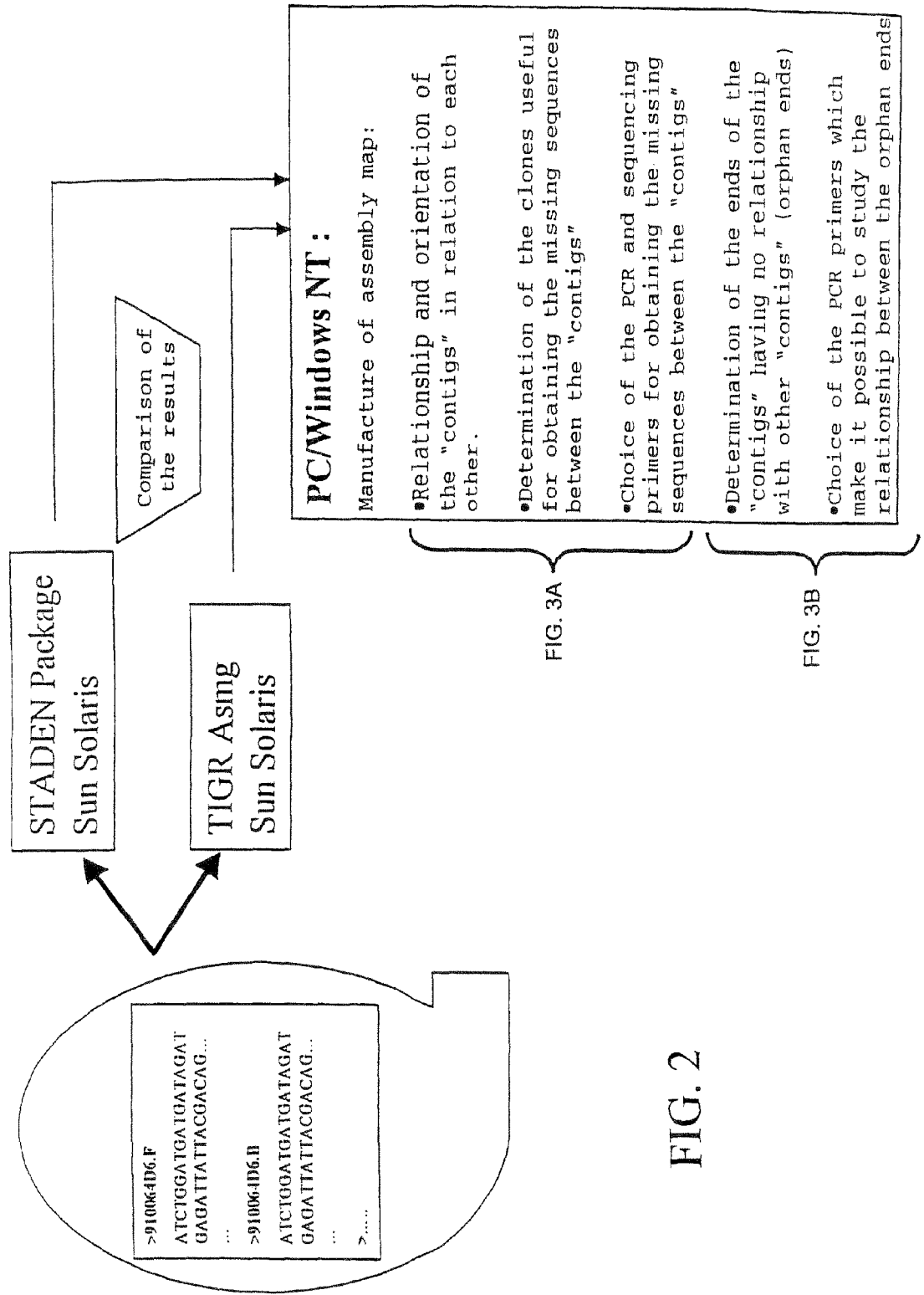
FIG. 2: Anal subjected to a double extraction with phenol-chloroform, two volumes of ethanol are added and the DNA is directly recovered with a Pasteur pipette having one end in the form of a hook. The DNA is dried on the edge of the tube and then resuspended in 500 µl of 2 mM Tris pH 7.5. The DNA is stored at 4° C. for at least 24 hours before being used for the cloning.

The results of these two assemblers are processed in a software developed for this project. This software operates on a Windows NT platform and receives, as data, the results derived from the STADEN software and/or the results derived from the TIGR-Asmg assembler, the software, results, after processing of the data, in the determination of an assembly map which gives the proximity relationship and the orientation of the contigs in relation to one another (FIG. 3a). Using this assembly map, the software determines all the primers necessary for finishing the project. This treatment, which will be detailed below, has the advantage of distinguishing the isolated sequences derived from the contaminations, by the DNA eukaryotic cells, of the small-sized sequences clearly integrated into the project by the relationships which they establish with contigs. In order to allow, without any risk of error, the arrangement and the orientation of the contigs in relation to one another, a statistical evaluation of the accuracy of the names "naming" of sequence is made from the results of "contigation". This evaluation makes it possible to give each of the clone plates, as well as each of the subsets of plates, a weight which is inversely proportional to probable error rate existing in the "naming" of the sequences obtained from this plate or from a subset of this plate. In spite of a low error rate, errors may occur throughout the steps of production of the clones and of the sequences. These steps are numerous, repetitive and although most of them are automated, others, like the deposition in the sequencers, are manual; it is then possible for the operator to make mistakes such as the inversion of two sequences. This type of error has a repercussion on the subsequent processing of the data, by resulting in relationships (between the contigs) which do not exist in reality, then in attempts at directed sequencing between the contigs which will end in failure. It is because of this that the evaluation of the naming errors is of particular importance since it allows the establishment of a probabilistic assembly map from which it becomes possible to determine all the clones which will serve as template to obtain sequences separating two adjacent contigs. Table 2 of parent U.S. Application Ser. No. 60/107,077 filed Nov. 4, 1998, French application 97-15041 filed Nov. 28, 1997 and French application 97-16034 filed Dec. 17, 1997, each of which is incorporated by reference herein in its entirety, gives the clones and the sequences of the primers initially used during the initial operations.

To avoid the step which consists in ordering and then preparing the clones by conventional microbiological means, outer and inner primers oriented towards the regions not yet sequenced are defined by the software. The primers thus determined make it possible to prepare, by PCR, a template covering the nonsequenced region. It is the so-called outer primers (the ones most distant from the region to be sequenced) which are used to prepare this template. The template is then purified and a sequence is obtained on each of the two strands during 2 sequencing reactions which each use one of the 2 inner primers. In order to facilitate the use of this approach, the two outer primers and the two inner primers are prepared and then stored on the same position of 4 different 96-well plates. The two plates containing the outer primers are used to perform the PCRs which serve to prepare the templates. These templates will be purified on purification columns preserving the topography of the plates. Each of the sequences are obtained using primers situated on one and then on the other of the plates containing the inner primers. This distribution allows a very extensive automation of the process and results in a method which is simple to use for finishing the regions not yet sequenced. Table 3 of parent U.S. Application Ser. No. 60/107,077 filed Nov. 4, 1998, French application 97-15041 filed Nov. 28, 1997 and French application 97-16034 filed Dec. 17, 1997, each of which is incorporated by reference herein in its entirety, gives the names and the sequences of the primers used for finishing *Chlamydia trachomatis*.

Finally, a number of contigs exist in a configuration where one of their ends is not linked to any other contig end (FIG. 3b) by a connecting clone relationship (a connecting clone is defined as a clone having one sequence end on a contig and the other end of its sequence on another contig; furthermore, this clone must be derived from a plate or a subset of plates with adequate naming quality). For the *Chlamydia trachomatis* project, this particular case occurred 37 times. Two adjacent PCR primers orienting the synthesis of the DNA towards the end of the consensus sequence are defined for each of the orphan ends of the consensus sequence. The primer which is closest to the end of the sequence is called the inner primer whereas the primer which is more distant from the end of the sequence is called the outer primer. The outer primers are used to explore the mutual relationship between the orphan ends of the different contigs. The presence of a single PCR product and the possibility of amplifying this product unambiguously using the inner primers evokes the probable relationship between the contigs on which the primers which allowed the amplification are situated. This relationship will be confirmed by sequencing and will allow the connection between the orphan ends of the consensus sequences. This strategy has made it possible to obtain a complete map of the *Chlamydia trachomatis* chromosome and then to finish the project.

Quality control. All the bases not determined with certainty in the chromosomal sequence were noted and the density of uncertainties was measured on the entire chromosome. The regions with a high density of uncertainties were noted and the PCR primers spanning these regions were drawn and are represented in Table 4 of parent U.S. Application Ser. No. 60/107,077 filed Nov. 4, 1998, French application 97-15041 filed Nov. 28, 1997 and French application 97-16034 filed Dec. 17, 1997 each of which is incorporated by reference herein in its entirety.

Data banks. Local reorganizations of major public banks were used. The protein bank used consists of the nonredundant fusion of the Genpept bank (automated translation of GenBank, NCBI; Benson et al., 1996).

The entire BLAST software (public domain, Altschul et al., 1990) for searching for homologies between a sequence and protein or nucleic data banks was used. The significance levels used depend on the length and the complexity of the region tested as well as the size of the reference bank. They were adjusted and adapted to each analysis.

The results of the search for homologies between a sequence according to the invention and protein or nucleic data banks are presented and summarized in Table 1 below.

Table 1: List of coding chromosome regions and homologies between these regions and the sequence banks.

Legend to Table 1: Open reading frames are identified with the GenMark software version 2.3A (GenePro), the template used is *Chlamydia trachomatis* of order 4 on a length of 196 nucleotides with a window of 12 nucleotides and a minimum signal of 0.5. These reading frames are numbered in order of appearance on the chromosome, starting with ORF2 (ORF column). The positions of the beginning and of the end are then given in column 2 (position). When the position of the beginning is greater than the position of the end, this means that the region is encoded by the strand complementary to the sequence which was given in the sequence SEQ ID No. 1.

All the putative products were subjected to a search for homology on GENPEPT (release 103 for SEQ ID No. 2 to SEQ ID No. 1076 and release 108 for SEQ ID No. 1077 to SEQ ID No. 1197 with the BLASTp software (Altschul et al. 1990), with, as parameters, the default parameters with the exception of the expected value E set at $10^{-5}$ (for SEQ ID No. 2 to SEQ ID No. 1076) and P value set at $e^{-10}$ (for SEQ ID No. 1077 to SEQ ID No. 1197). Subsequently, only the identities greater than 30% (1% column) were taken into account. The description of the most homologous sequence is given in the Homology column; the identifier for the latter sequence is given in the ID column and the animal species to which this sequence belongs is given in the Species column. The Homology score is evaluated by the sum of the blast scores for each region of homology and reported in the Score column.

Materials and methods: transmembrane domains. The DAS software was used as recommended by the authors (Cserzo et al., 1997).

This method uses, to predict the transmembrane domains, templates derived from a sampling of selected proteins. All the regions for which a "Cutoff" greater than 1.5 was found by the program were taken into account.

Additional ORF Finder Programs. For this analysis, two additional ORF finder programs were used to predict potential open reading frames of a minimum length of 74 amino acids; Glimmer (Salzberg, Delcher, A., Kasif, S., and W. White. 1998. Microbial gene identification using interpolated Markov models. Nucleic Acids Res. 26:544-548.), and an in-house written program. The in-house program used a very simple search algorithm. The analysis required that the genomic DNA sequence text be in the 5' to 3' direction, the genome is circular, and that TAA, TAG, and TGA are stop codons. The search parameters were as follows:

(1) A search for an ORF that started with a GTG codon was performed. If no GTG codons were found, then a search for an ATG codon was performed. However, if a GTG codon was found, then a search downstream for a ATG codon was performed. All start and stop nucleotide positions were recorded.

(2) A search for an ORF that started with a TTG codon was performed. If no TTG codons were found, then a search for a ATG codon was performed. However, if a TTG codon was found, then a search downstream for a ATG codon was performed. All start and stop nucleotide positions were recorded.

(3) The analysis described in steps 1 and 2 were repeated for the opposite strand of DNA sequence.

(4) A search for ORFs that determined all ORF lengths using start and stop positions in the same reading frames was performed.

(5) All ORFs whose DNA length was less than 225 nucleotides were eliminated from the search.

Surface Exposed Protein Search Criteria. Potential cell surface vaccine targets are outer membrane proteins such as porins, lipoproteins, adhesions and other non-integral proteins. In *Chlamydia psittaci*, the major immunogens is a group of putative outer membrane proteins (POMPs) and no homologs have been found in *Chlamydia trachomatis* and *Chlamydia trachomatis* by traditional analysis (Longbottom, D., Russell, M., Dunbar, S. M., Jones, G. E., and A. J. Herring. 1998. Molecular Cloning and Characterization of the Genes Coding for the Highly Immunogenic Cluster of 90-Kilodalton Envelope Proteins from *Chlamydia psittaci* Subtype That Causes Abortion in Sheep. Infect Immun 66:1317-1324.) However, utilizing the criteria described below, several ORFs encoding outer membrane proteins have been identified in *Chlamydia trachomatis*, all of which may represent vaccine candidates. Any ORF which met any one of the criteria described below were considered to encode a surface exposed protein.

Protein homology searches of the translated ORFs were done using the Blastp 2.0 tool (Altschul, S. F., Madden, T. L., Schaffer, A. A., Zhang, J., Zhang, Z., Miller, W., and D. J. Lipman. 1997. Gapped BLAST and PSI-BLAST: a new generation of protein database search programs. Nucleic Acids Res. 25:3389-3402). An ORF was labeled surface exposed if the translated ORF had homology to a known, or hypothetical, or putative surface exposed protein with a P score less than $e^{-10}$.

Most, if not all, proteins that are localized to the membrane of bacteria, via a secretory pathway, contain a signal peptide. The software program SignalP, was used to analyze the amino acid sequence of an ORF for such a signal peptide (Nielsen, H., Engelbrecht. J., Brunak, S., and G. von Heijne. 1997. Identification of prokaryotic and eukaryotic signal peptides and prediction of their cleavage sites. Protein Engineering 10:1-6.) The first 60 N-terminal amino acids of each ORF were analyzed by SignalP using the Gram-negative software database. The output generates four separate values, maximum C, maximum Y, maximum S, and mean S. The S-score, or signal region, is the probability of the position belonging to the signal peptide. The C-score, or cleavage site, is the probability of the position being the first in the mature protein. The Y-score is the geometric average of the C-score and a smoothed derivative of the S-score. A conclusion of either a Yes or No is given next to each score. If all four conclusions are Yes and the C-terminal amino acid is either a phenylalanine (F) or a tyrosine (Y), the ORF was labelled outer membrane (Struyve, M., Moons, M., and J. Tommassen. 1991. Carboxy-terminal Phenylalanine is Essential for the Correct Assembly of a Bacterial Outer Membrane Protein. J. Mol. Biol. 218:141-148.)

The program called Psort was used to determine the localization of a protein based on its signal sequence, recognition of transmembrane segments, and analysis of its amino acid composition (Nakai, K., and M. Kanehisa. 1991. Expert system for predicting protein localization sites in gram-negative bacteria. Proteins 11:95-110.) An ORF is considered to be an outer membrane protein if the output data predicts the ORF encoded protein as outer membrane with a certainty value of 0.5 or better and whose value is at least twice as large as the next predicted localized certainty value.

Finally, ORFs that were not predicted to be outer membrane or surface exposed, based on the above criteria, were further analyzed. The Blastp output data for these ORFs were searched using various general and specific keywords, suggestive of known cell surface exposed proteins. An ORF was labeled surface exposed if the keywords matched had a Blastp hit with a P score less than $e^{-10}$, and there was no better data indicating otherwise. The following is a list of the searched keywords:

| | | |
|---|---|---|
| Adhesion | Adhesin | Invasin |
| Invasion | Extension | Omp |
| Outer Surface | Porin | Outer Membrane |
| Cell Surface | Cell Wall | Pilin |
| Flagellar sheath | Cir | ChuA |
| CopB | ExeD | FadL |
| FecA | FepA | FhuA |
| FmdC | FomA | FrpB |
| GspD | HemR | HgbA |
| Hgp | HmbR | HmuR |
| HMW | HrcC | Hrp |
| InvG | LamB | LbpA |
| LcrQ | Lmp1 | MxiD |
| MOMP | PilE | HpaA |
| NolW | NspA | OpcP |
| OpnP | Opr | OspA |
| PhoE | PldA | Por |
| PscC | PulD | PupA |
| QuiX | RafY | ScrY |
| SepC | ShuA | SomA |
| SpiA | Tbp1 | Yop |
| YscC | mip | Tol |
| Pilus | BtuB | |

Those ORFs that did not meet the minimum requirement for being an outer membrane protein based on the above search criteria but which were homologous to identified outer membrane ORFs in *Chlamydia pneumoniae* were included. The *Chlamydia pneumoniae* genome (French patent application No. 97-14673, filed 21 Nov. 1997) was analyzed using the above search criteria and a number of outer membrane ORFs were identified. These *Chlamydia pneumoniae* ORFs were then tested against the *Chlamydia trachomatis* genome using Blastp. Any *Chlamydia trachomatis* ORF with a Blastp P value less than $e^{-10}$ against a *Chlamydia pneumoniae* outer membrane was included in this section, if there was no better data indicating otherwise. A list of ORFs in the *Chlamydia trachomatis* genome encoding putative surface exposed proteins is set forth above in the specification.

Identification of Putative Lipoproteins in the Genome of *Chlamydia trachomatis*. Lipoproteins are the most abundant post-translationally modified bacterial secretory proteins (Pugsley, A. P. 1993. The complete general secretory pathway in Gram-negative bacteria. Microbiol. Rev. 57:50-108). The characteristic features of lipoproteins are a thiol-linked diacylglyceride and an amine-linked monoacyl group on the cysteine that becomes the amino-terminal residue after signal peptide cleavage by Signal Peptidase II. (Pugsley, A. P. 1993. The complete general secretory pathway in Gram-negative bacteria. Microbiol. Rev. 57:50-108). The identification of putative lipoproteins from the genomic sequencing of *Chlamydia trachomatis* was done by examining the deduced amino acid sequence of identified ORFs for the presence of a signal peptide with a Signal Peptidase II cleavage site analogous to the consensus sequence for prolipoprotein modification and processing reactions (Hayashi, S., and H. C. Wu. 1992. Identification and characterization of lipid-modified proteins in bacteria, p. 261-285. In N. M. Hooper and A. J. Turner (ed.) Lipid modification of proteins: A practical approach. Oxford University Press, New York; Sutcliffe, I. C. and R. R. B. Russell. 1995. Lipoproteins of Gram-positive bacteria. J. Bacteriol. 177:1123-1128).

The deduced amino acid sequences of *Chlamydia trachomatis* ORFs were initially screened for the most basic of lipoprotein characteristics, a cysteine in the first 30 amino acids of the deduced protein. ORFs with a standard start codon (ATG, GTG, or TTG) and having one or more of the following characteristics were selected for direct analysis of their first 30 amino acids:

(a) Significant Signal P value (at least two out-of-the four values are Yes)

(b) PSORT value indicating membrane passage (IM-inner membrane, Peri-periplasm, or OM-outer membrane)

(c) Identification of the word lipoprotein among the ORF Blastp data set.

(d) A Blastp value of $<e^{-10}$ with a putative lipoprotein from *Chlamydia pneumoniae* (French application No. 97-14673 filed 21 Nov. 1997).

The first 30 amino acids encoded by each ORF in this set were analyzed for the characteristics commonly found in lipoprotein signal peptides (Pugsley, A. P. 1993. The complete general secretory pathway in Gram-negative bacteria. Microbiol. Rev. 57:50-108; Hayashi, S., and H. C. Wu. 1992. Identification and characterization of lipid-modified proteins in bacteria, p. 261-285. In N. M. Hooper and A. J. Turner (ed.) Lipid modification of proteins: A practical approach. Oxford University Press, New York; Sutcliffe, I. C. and R. R. B. Russell. 1995. Lipoproteins of Gram-positive bacteria. J. Bacteriol. 177:1123-1128.) Putative lipoprotein signal peptides were required to have a cysteine between amino acid 10 and 30 and reach a minimum score of three based on the following criteria for lipoprotein signal peptides:

(a) Identification of specific amino acids in specific positions around the cysteine which are part of the consensus Signal Peptidase II cleavage site (Hayashi, S., and H. C. Wu. 1992. Identification and characterization of lipid-modified proteins in bacteria, p. 261-285. In N. M. Hooper and A. J. Turner (ed.) Lipid modification of proteins: A practical approach. Oxford University Press, New York); Sutcliffe, I. C. and R. R. B. Russell. 1995. Lipoproteins of Gram-positive bacteria. J. Bacteriol. 177:1123-1128). Since the identification of the cleavage site is the most important factor in identifying putative lipoproteins, each correctly positioned amino acid contributed toward reaching the minimum score of three.

(b) A hydrophobic region rich in alanine and leucine prior to the cleavage site (Pugsley, A. P. 1993. The complete general secretory pathway in Gram-negative bacteria.

Microbiol. Rev. 57:50-108) contributed toward reaching the minimum score of three.

(c) A short stretch of hydrophilic amino acids greater than or equal to 1, usually lysine or arginine, following the N-terminal methionine (Pugsley, A. P. 1993. The complete general secretory pathway in Gram-negative bacteria. Microbiol. Rev. 57:50-108) contributed toward reaching the minimum score of three.

A list of ORFs in the *Chlamydia trachomatis* genome encoding putative lipoproteins is set forth above in the specification.

LPS-Related ORFs of *Chlamydia trachomatis*. Lipopolysaccharide (LPS) is an important major surface antigen of *Chlamydia* cells. Monoclonal antibodies (Mab) directed against LPS of *Chlamydia pneumoniae* have been identified that can neutralize the infectivity of *Chlamydia pneumoniae* both in vitro and in vivo (Peterson et al. 1988). Similar results are expected utilizing monoclonal antibodies against LPS of *Chlamydia trachomatis*. LPS is composed of lipid A and a core oligosaccharide portion and is phenotypically of the rough type (R-LPS) (Lukacova, M., Baumann, M., Brade, L., Mamat, U., Brade, H.1994. Lipopolysaccharide Smooth-Rough Phase Variation in Bacteria of the Genus *Chlamydia*. Infect. Immun. June 62(6):2270-2276.) The lipid A component is composed of fatty acids which serve to anchor LPS in the outer membrane. The core component contains sugars and sugar derivatives such as a trisaccharide of 3-deoxy-D-manno-octulosonic acid (KDO) (Reeves, P. R., Hobbs, M., Valvano, M. A., Skurnik, M., Whitfield, C., Coplin, D., Kido, N., Klena, J., Maskell, D., Raetz, C. R. H., Rick, P. D. 1996. *Bacterial Polysaccharide Synthesis and Gene Nomenclature* pp. 10071-10078, Elsevier Science Ltd.). The KDO gene product is a multifunctional glycosyltransferase and represents a shared epitope among the *Chlamydia*. For a review of LPS biosynthesis see, e.g., Schnaitman, C. A., Klena, J. D. 1993. Genetics of Lipopolysaccharide Biosynthesis in Enteric Bacteria. Microbiol. Rev. 57:655-682.

A text search of the ORF Blastp results identified several genes that are involved in Chlamydial LPS production with a P score less than $e^{-10}$. The following key-terms were used in the text search: KDO, CPS (Capsular Polysaccharide Biosynthesis), capsule, LPS, rfa, rfb, rfc, rfe, rha, rhl, core, epimerase, isomerase, transferase, pyrophosphorylase, phosphatase, aldolase, heptose, manno, glucose, lpxB, fibronectin, fibrinogen, fucosyltransferase, lic, lgt, pgm, tolC, rol, ChoP, phosphorylcholine, waaF, PGL-Tb1. A list of ORFs in the *Chlamydia trachomatis* genome encoding putative polypeptides involved in LPS biosynthesis is set forth above in the specification.

Type III And Other Secreted Products. Type III secretion enables gram-negative bacteria to secrete and inject pathogenicity proteins into the cytosol of eukaryotic host cells (Hueck, C. J., 1998. Type III Protein Secretion Systems in Bacterial Pathogens of Animals and Plants. In Microbiology and Molecular Biology Reviews. 62:379-433.) These secreted factors often resemble eukaryotic signal transduction factors, thus enabling the bacterium to redirect host cell functions (Lee, C. A., 1997. Type III secretion systems: machines to deliver bacterial proteins into eukaryotic cells? Trends Microbiol. 5:148-156.) In an attempt to corrupt normal cellular functions, Chlamydial pathogenicity factors injected into the host cytosol will nonetheless, as cytoplasmic constituents be processed and presented in the context of the Major Histocompatibility Complex (MHC class I). As such, these pathogenicity proteins represent MHC class I antigens and will play an important role in cellular immunity. Also included in this set are secreted non-type III products that may play a role as vaccine components.

A text search of the ORF Blastp results identified genes that are involved in *Chlamydia trachomatis* protein secretion with a P score less than $e^{-10}$. The following key-terms were used in the text search in an effort to identify surface localized or secreted products: Yop, Lcr, Ypk, Exo, Pcr, Pop, Ipa, Vir, Ssp, Spt, Esp, Tir, Hrp, Mxi, hemolysin, toxin, IgA protease, cytolysin, tox, hap, secreted and Mip.

*Chlamydia trachomatis* ORFs that did not meet the above keyword search criteria, but have homologs in *Chlamydia pneumoniae* that do meet the search criteria are included herein. The *Chlamydia pneumoniae* genome (French patent application No. 97-14673, filed 21 Nov. 1997) was analyzed using the above search criteria and a number of ORFs were identified. These *Chlamydia pneumoniae* ORFs were tested against the *Chlamydia trachomatis* genome using Blastp. Any *Chlamydia pneumoniae* ORF with a Blastp P value $<e^{10}$ against a *Chlamydia trachomatis* homolog, identified using the above search criteria, was included. A list of ORFs in the *Chlamydia trachomatis* genome encoding putative secreted proteins is set forth above in the specification.

*Chlamydia trachomatis* RGD Recognition Sequence. Proteins that contain Arg-Gly-Asp (RGD) attachment site, together with integrins that serve as their receptor constitute a major recognition system for cell adhesion. The RGD sequence is the cell attachment site of a large number of adhesive extracellular matrix, blood, and cell surface proteins and nearly half of the known integrins recognize this sequence in their adhesion protein ligands. There are many RGD containing microbial proteins such as the penton protein of adenovirus, the coxsackie virus, the foot and mouth virus and pertactin, a 69 kDa (kilodalton) surface protein of *Bordetella pertussis*, that serve as ligands through which these microbes bind to integrins on the cell surfaces and gain entry into the cell. The following provides evidence supporting the importance of RGD in microbial adhesion:

a) The adenovirus penton base protein has a cell rounding activity and when penton base was expressed in *E. coli*, it caused cell rounding and cells adhered to polystyrene wells coated with the protein. Mutant analysis showed that both these properties required an RGD sequence. Virus mutants with amino acid substitutions in the RGD sequence, showed much less adherence to HeLa S3 cells, and also were delayed in virus reproduction (Bai, M., Harfe, B., and Freimuth, P. 1993. Mutations That Alter an RGD Sequence in the Adenovirus Type 2 Penton Base Protein Abolish Its Cell-Rounding Activity and Delay Virus Reproduction in Flat Cells. J. Virol. 67:5198-5205).

b) It has been shown that attachment and entry of coxsackie virus A9 to GMK cells were dependent on an RGD motif in the capsid protein VP1. VP1 has also been shown to bind $\alpha_v\beta_3$ integrin, which is a vitronectin receptor (Roivainen, M., Piirainen, L., Hovi, T., Virtanen, I., Riikonen, T., Heino, J., and Hyypia, T. 1994. Entry of Coxsackievirus A9 into Host Cells: Specific Interactions with $\alpha_v\beta_3$ Integrin, the Vitronectin Receptor Virology, 203:357-65).

c) During the course of whooping cough, *Bordetella pertussis* interacts with alveolar macrophages and other leukocytes on the respiratory epithelium. Whole bacteria adheres by means of two proteins, filamentous hemagglutinin (FHA) and pertussis toxin. FHA interacts with two classes of molecules on macrophages, galactose containing glycoconjugates and the integrin CR3. The interaction between CR3 and FHA involves recognition of RGD sequence at the positions 1097-1099 in FHA (Relman, D., Tuomanen, E., Falkow, S., Golenbock, D. T., Saukkonen, K., and Wright, S. D. "Recognition of a Bacterial Adhesin by an Integrin: Macrophage CR3 Binds Filamentous Hemagglutinin of *Bordetella Pertussis*." Cell, 61:1375-1382 (1990)).

d) Pertactin, a 69 kDa outer membrane protein of *Bordetella pertussis*, has been shown to promote attachment of Chinese hamster ovary cells (CHO). This attachment is mediated by recognition of RGD sequence in pertactin by integrins on CHO cells and can be inhibited by synthetic RGD containing peptide homologous to the one present in pertactin (Leininger, E., Roberts, M., Kenimer, J. G., Charles, I. G., Fairweather, N., Novotny, P., and Brennan, M. J. 1991. Pertactin, an Arg-Gly-Asp containing *Bordetella pertussis* surface protein that promotes adherence of mammalian cells Proc. Natl. Acad. Sci. USA, 88:345-349).

e) The RGD sequence is highly conserved in the VP1 protein of foot and mouth disease virus (FMDV). Attachment of FMDV to baby hamster kidney cells (BHK) has been shown to be mediated by VP1 protein via the RGD sequence. Antibodies against the RGD sequence of VP1 blocked attachment of virus to BHK cells (Fox, G., Parry, N. R., Barnett, P. V., McGinn, B., Rowland, D. J., and Brown, F. 1989. The Cell Attachment Site on Foot-and-Mouth Disease Virus Includes the Amino Acid Sequence RGD (Arginine-Glycine-Aspartic Acid) J. Gen. Virol., 70:625-637).

It has been demonstrated that bacterial adherence can be based on interaction of a bacterial adhesin RGD sequence with an integrin and that bacterial adhesins can have multiple binding site characteristic of eukaryotic extracellular matrix proteins. RGD recognition is one of the important mechanisms used by microbes to gain entry into eukaryotic cells.

The complete deduced protein sequence of the *Chlamydia trachomatis* genome was searched for the presence of RGD sequence. There were a total of 38 ORFs that had one or more RGD sequences. Not all RGD containing proteins mediate cell attachment. It has been shown that RGD containing peptides that have proline immediately following the RGD sequence are inactive in cell attachment assays (Pierschbacher & Ruoslahti. 1987. Influence of stereochemistry of the sequence Arg-Gly-Asp-Xaa on binding specificity in cell adhesion. J. Biol. Chem. 262:17294-98). ORFs that had RGD, with proline as the amino acid following the RGD sequence were excluded from the list. Also, RGD sequence may not be available at the surface of the protein or may be present in a context that is not compatible with integrin binding. Since not all RGD-containing proteins are involved in cell attachment, several other criteria were used to refine the list of RGD-containing proteins. A list of ORFs in the *Chlamydia trachomatis* genome encoding polypeptides with RGD recognition sequence(s) is set forth above in the specification.

Non-*Chlamydia pneumoniae* ORFs. *Chlamydia trachomatis* ORFs were compared to the ORFs in the *Chlamydia pneumoniae* genome (French patent application No. 97-14673, filed 21 Nov. 1997) using Blastp. Any *Chlamydia trachomatis* ORF with a Blastp "P" value greater than $e^{-10}$ (i.e. $>e^{-10}$) against *Chlamydia pneumoniae* ORFs are included in this section. A list of ORFs in the *Chlamydia trachomatis* genome which are not found in *Chlamydia pneumoniae* is set forth above in the specification.

Cell Wall Anchor Surface ORFs. Many surface proteins are anchored to the cell wall of Gram-positive bacteria via the conserved LPXTG motif (Schneewind, O., Fowler, A., and Faull, K. F. 1995. Structure of the Cell Wall Anchor of Surface Proteins in *Staphylococcus aureus*. Science 268:103-106). A search of the proteins encoded by the *Chlamydia trachomatis* ORFs was done using the motif LPXTG. A list of ORFs in the *Chlamydia trachomatis* genome encoding polypeptides anchored to the cell wall is set forth above in the specification.

ECACC Deposits. Samples of *Chlamydia trachomatis* were deposited with the European Collection of Cell Cultures (ECACC), Salisbury, Wiltshire SP4 OJG, UK on Nov. 26, 1998 and assigned the accession number 98112618. Cells can be grown, harvested and purified, and DNA can be prepared as discussed above. In order to enable recovery of specific fragments of the chromosome, one can run targeted PCR reactions, whose amplification products can then be sequenced and/or cloned into any suitable vector, according to standard procedures known to those skilled in the art.

In addition, a pool of clones covering the *Chlamydia trachomatis* genome was deposited with the ECACC on Nov. 26, 1998 and assigned accession number 98112617. The pool of clones contains a series of clones, which when taken together, cover the whole chromosome, with a redundancy of slightly more than ten. The total number of clones in the sample is 13,572.

Table 4 lists groups of oligonucleotides to be used to amplify each of ORFs 2-1197 according to standard procedures known to those skilled in the art. Such oligonucleotides are listed as SEQ ID Nos. 1198 to 5981. For each ORF, the following is listed: one forward primer positioned 2,000 bp upstream of the beginning of the ORF; one forward primer positioned 200 bp upstream of the beginning of the ORF; one reverse primer positioned 2,000 bp downstream at the end of ORF, which is 2,000 bp upstream of the end site of the ORF on the complementary strand; and one reverse primer 200 bp downstream at the end of ORF, which is 200 bp upstream of the end site of the ORF on the complementary strand. The corresponding SEQ ID Nos. for the primers are listed in Table 4, where Fp is the proximal forward primer; Fd is the distal forward primer; Bp is the proximal reverse primer; and Bd is the distal reverse primer. The positions of the 5' ends of each of these primers on the nucleotide sequence of SEQ ID No. 1 are shown in Table 5.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

TABLE 1

| ORF | begin | stop | Homology | ID | Species | Score | I % |
|---|---|---|---|---|---|---|---|
| ORF2 | 501 | 208 | putative | | | | |
| ORF3 | 3276 | 505 | putative 98 kDa outer membrane protein | U72499 | *Chlamydia psittaci* | 379 | 37 |
| ORF4 | 5068 | 3242 | lipid A disaccharide synthetase (lpxB) | U32786 | *Haemophilus influenzae* | 285 | 40 |
| ORF5 | 6400 | 5126 | poly(A) polymerase | AE000123 | *Escherichia coli* | 552 | 46 |

TABLE 1-continued

| ORF | begin | stop | Homology | ID | Species | Score | I % |
|---|---|---|---|---|---|---|---|
| ORF6 | 7977 | 6619 | D-alanine permease (dagA) | U32770 | Haemophilus influenzae | 265 | 36 |
| ORF7 | 8582 | 8082 | signal peptidase II | X78084 | Staphylococcus carnosus | 174 | 36 |
| ORF8 | 8995 | 8591 | YteA | AF008220 | Bacillus subtilis | 157 | 43 |
| ORF9 | 9440 | 8979 | ORF 168 | D28752 | Synechococcus sp. | 318 | 42 |
| ORF10 | 9828 | 10430 | unknown | Z80108 | Mycobacterium tuberculosis | 324 | 46 |
| ORF11 | 10367 | 11254 | hypothetical protein (SP: P39587) | U67605 | Methanococcus jannaschii | 152 | 38 |
| ORF12 | 11245 | 11916 | rRNA methylase | D90913 | Synechocystis sp. | 209 | 40 |
| ORF13 | 12068 | 13324 | hypothetical | U32691 | Haemophilus influenzae | 367 | 45 |
| ORF14 | 13532 | 14413 | neutral amino acid transporter B0. | U75284 | Oryctolagus cuniculus | 410 | 39 |
| ORF15 | 14807 | 15019 | dihydrolipoamide acetyltransferase | L38646 | Saccharopolyspora erythraea | 324 | 47 |
| ORF16 | 14932 | 15969 | branched chain alpha-keto acid dehydrogenase E2 | M97391 | Bacillus subtilis | 577 | 44 |
| ORF17 | 15995 | 16501 | ORF_o328 | U18997 | Escherichia coli | 223 | 44 |
| ORF18 | 16467 | 16138 | putative | | | | |
| ORF19 | 18190 | 17417 | putative outer membrane protein | U80956 | Borrelia burgdorferi | 86 | 36 |
| ORF20 | 20521 | 18437 | ORF-2 | D11024 | Shigella flexneri | 642 | 37 |
| ORF21 | 22202 | 20814 | dnaK like protein (AA 1-660) | X52175 | Chlamydia trachomatis | 2214 | 99 |
| ORF22 | 22602 | 22153 | ORF, 82 kDa protein | L22180 | Chlamydia trachomatis | 558 | 89 |
| ORF23 | 22804 | 22478 | heat shock protein | M62478 | Chlamydia trachomatis | 503 | 99 |
| ORF24 | 23183 | 22824 | GrpE-like protein | L25105 | Chlamydia trachomatis | 580 | 98 |
| ORF25 | 23394 | 23110 | GrpE-like protein | L25105 | Chlamydia trachomatis | 373 | 87 |
| ORF26 | 24569 | 23394 | has homology to putative heat shock proteins of Bacillus subtilis and Clostridium acetobutylicum; ORFA; putative | L25105 | Chlamydia trachomatis | 1999 | 99 |
| ORF27 | 26383 | 24641 | aminoacyl-tRNA synthetase | L25105 | Chlamydia trachomatis | 3044 | 99 |
| ORF28 | 26640 | 27710 | ORFB; putative | L25105 | Chlamydia trachomatis | 1298 | 99 |
| ORF29 | 28780 | 27725 | putative | | | | |
| ORF30 | 29957 | 28740 | hypothetical protein | D64004 | Synechocystis sp. | 786 | 46 |
| ORF31 | 30721 | 30032 | putative | | | | |
| ORF32 | 31281 | 30520 | putative | | | | |
| ORF33 | 31436 | 31780 | putative | L46591 | Bartonella bacilliformis | 126 | 45 |
| ORF34 | 33356 | 31800 | putative | | | | |
| ORF35 | 33901 | 33314 | putative | | | | |
| ORF36 | 34116 | 35027 | Yer156cp | U18917 | Saccharomyces cerevisiae | 175 | 32 |
| ORF37 | 34988 | 35359 | F21C3.3 | Z71261 | Caenorhabditis elegans | 245 | 44 |
| ORF38 | 35167 | 35919 | putative | | | | |
| ORF39 | 35923 | 36996 | putative | | | | |
| ORF40 | 37810 | 37013 | putative | | | | |
| ORF41 | 38207 | 39085 | DAPH synthase-chorismate mutase | AF008220 | Bacillus subtilis | 529 | 48 |
| ORF42 | 39151 | 39927 | arginine binding protein | X67753 | Escherichia coli | 192 | 44 |
| ORF43 | 39923 | 40756 | putative | | | | |
| ORF44 | 40760 | 42007 | hypothetical protein MTCY154.05c | Z98209 | Mycobacterium tuberculosis | 663 | 43 |
| ORF45 | 42175 | 43116 | phosphoglucoisomerase-like protein | L40822 | Chlamydia trachomatis | 681 | 95 |
| ORF46 | 42999 | 43802 | phosphoglucoisomerase-like protein | L40822 | Chlamydia trachomatis | 959 | 91 |
| ORF47 | 44211 | 45227 | NADP-malate dehydrogenase | L40958 | Flaveria bidentis | 755 | 42 |
| ORF48 | 46072 | 45275 | putative | | | | |
| ORF49 | 46340 | 45975 | putative | | | | |
| ORF50 | 46895 | 46506 | putative | | | | |
| ORF51 | 47955 | 46882 | membrane protein (arcD) | M33223 | Pseudomonas aeruginosa | 892 | 47 |
| ORF52 | 48585 | 48178 | putative | | | | |
| ORF53 | 50072 | 48630 | putative | | | | |
| ORF54 | 50710 | 50099 | putative | | | | |
| ORF55 | 52439 | 50925 | dehydroquinate dehydratase/shikimate dehydrogenase | L32794 | Nicotiana tabacum | 142 | 36 |
| ORF56 | 53484 | 52348 | 3-dehydroquinate synthase | D90911 | Synechocystis sp. | 462 | 39 |
| ORF57 | 54536 | 53466 | chorismate synthase | X67516 | Synechocystis sp. | 801 | 56 |
| ORF58 | 55086 | 54595 | shikimate kinase II | M13045 | Escherichia coli | 154 | 38 |
| ORF59 | 56350 | 55031 | 5-enolpyruvylshikimate 3-phosphate synthase | U67500 | Methanococcus jannaschii | 355 | 37 |
| ORF60 | 55659 | 56084 | putative | | | | |
| ORF61 | 56847 | 58235 | putative | | | | |
| ORF62 | 58423 | 59181 | dihydrodipicolinate reductase | U47017 | Pseudomonas syringae pv. tabaci | 350 | 40 |
| ORF63 | 59185 | 60195 | aspartate-semialdehyde dehydrogenase | U67476 | Methanococcus jannaschii | 590 | 44 |
| ORF64 | 60188 | 61483 | aspartokinase III | U00006 | Escherichia coli | 312 | 41 |
| ORF65 | 61496 | 62353 | dihydrodipicolinate synthetase (dapA) | AE000609 | Helicobacter pylori | 345 | 42 |
| ORF66 | 62500 | 63141 | putative | | | | |
| ORF67 | 63396 | 63983 | hypothetical protein | Y14084 | Bacillus subtilis | 148 | 42 |
| ORF68 | 64628 | 64071 | putative | | | | |
| ORF69 | 64285 | 64656 | putative | | | | |
| ORF70 | 64944 | 64609 | putative | | | | |
| ORF71 | 65347 | 67269 | unknown | D26185 | Bacillus subtilis | 733 | 44 |
| ORF72 | 67656 | 68873 | putative | | | | |
| ORF73 | 68877 | 69233 | KsgA | Z94752 | Mycobacterium tuberculosis | 156 | 38 |
| ORF74 | 69212 | 69721 | high level kasgamycin resistance | D26185 | Bacillus subtilis | 306 | 43 |
| ORF75 | 69958 | 70455 | polypeptide deformylase | Y10305 | Calothrix PCC7601 | 272 | 43 |
| ORF76 | 70701 | 71006 | protein translocation protein, low temperature (secG) | U32727 | Haemophilus influenzae | 90 | 32 |
| ORF77 | 73191 | 71086 | putative | | | | |

TABLE 1-continued

| ORF | begin | stop | Homology | ID | Species | Score | I % |
|---|---|---|---|---|---|---|---|
| ORF78 | 74900 | 73497 | putative | | | | |
| ORF79 | 75463 | 74876 | homologous to unidentified *E. coli* protein | M96343 | *Bacillus subtilis* | 283 | 34 |
| ORF80 | 77124 | 75502 | o530; This 530 aa ORF is 33 pct identical (14 gaps) to 525 residues of an approx. 640 aa protein YHES_HAEIN SW: P44808 | AE000184 | *Escherichia coli* | 1447 | 42 |
| ORF81 | 77000 | 77299 | putative | | | | |
| ORF82 | 78095 | 77145 | integrase-recombinase protein (xerC) | U32750 | *Haemophilus influenzae* | 495 | 38 |
| ORF83 | 79065 | 78154 | hypothetical protein | D64001 | *Synechocystis* sp. | 400 | 40 |
| ORF84 | 81971 | 79878 | LON protease homolog | U88087 | *Arabidopsis thaliana* | 1927 | 48 |
| ORF85 | 82639 | 83271 | putative | | | | |
| ORF86 | 83792 | 84850 | DnaJ | U58360 | *Salmonella typhimurium* | 822 | 42 |
| ORF87 | 84876 | 86921 | putative | | | | |
| ORF88 | 88650 | 87313 | putative | | | | |
| ORF89 | 87440 | 87805 | putative | | | | |
| ORF90 | 88400 | 88747 | putative | | | | |
| ORF91 | 88717 | 89265 | putative | | | | |
| ORF92 | 89355 | 89732 | Hpr protein | X12832 | *Bacillus subtilis* | 128 | 32 |
| ORF93 | 89735 | 91447 | PTS enzyme I | U12340 | *Bacillus stearothermophilus* | 671 | 34 |
| ORF94 | 91749 | 91435 | ORF107 | X17014 | *Bacillus subtilis* | 120 | 35 |
| ORF95 | 92392 | 91745 | putative | | | | |
| ORF96 | 93138 | 92344 | dnaZX-like ORF put. DNA polymerase III | X06803 | *Bacillus subtilis* | 542 | 53 |
| ORF97 | 94134 | 93361 | excinuclease ABC subunit A (uvrA) | AE000583 | *Helicobacter pylori* | 326 | 36 |
| ORF98 | 94637 | 94071 | excinuclease ABC subunit A (uvrA) | AE000583 | *Helicobacter pylori* | 487 | 40 |
| ORF99 | 98299 | 94628 | UvrA | D49911 | *Thermus thermophilus* | 2090 | 44 |
| ORF100 | 98715 | 98113 | excinuclease ABC subunit A (uvrA) | AE000583 | *Helicobacter pylori* | 319 | 42 |
| ORF101 | 100228 | 98741 | pyruvate kinase | U83196 | *Chlamydia trachomatis* | 2411 | 97 |
| ORF102 | 101347 | 100337 | hypothetical protein | D90903 | *Synechocystis* sp. | 494 | 37 |
| ORF103 | 102210 | 101323 | YqiE | D84432 | *Bacillus subtilis* | 471 | 49 |
| ORF104 | 102485 | 102210 | putative | | | | |
| ORF105 | 104315 | 102726 | exonuclease VII, large subunit (xseA) | U32723 | *Haemophilus influenzae* | 634 | 51 |
| ORF106 | 105075 | 104254 | triose phosphate isomerase | L29475 | *Bacillus subtilis* | 558 | 48 |
| ORF107 | 105259 | 105894 | phosphoribosylanthranilate isomerase | U18969 | *Arabidopsis thaliana* | 300 | 38 |
| ORF108 | 107429 | 108460 | putative | | | | |
| ORF109 | 108665 | 108955 | putative | | | | |
| ORF110 | 109459 | 109013 | putative | | | | |
| ORF111 | 110366 | 109704 | putative | | | | |
| ORF112 | 111330 | 112520 | elongation factor Tu | L22216 | *Chlamydia trachomatis* | 2007 | 100 |
| ORF113 | 112915 | 113463 | transcription antitermination protein (nusG) | U32754 | *Haemophilus influenzae* | 313 | 37 |
| ORF114 | 113566 | 113994 | ribosomal protein L11 | D13303 | *Bacillus subtilis* | 443 | 59 |
| ORF115 | 114020 | 114604 | ribosomal protein L1 | Z11839 | *Thermotoga maritima* | 528 | 54 |
| ORF116 | 114720 | 115253 | ribosomal protein L10 | Z11839 | *Thermotoga maritima* | 143 | 38 |
| ORF117 | 115362 | 115676 | rpl12 (AA 1-128) | X53178 | *Synechocystis* PCC6803 | 254 | 62 |
| ORF118 | 116022 | 119795 | DNA-directed RNA polymerase beta chain | X64172 | *Staphylococcus aureus* | 2675 | 61 |
| ORF119 | 119823 | 124010 | DNA-directed RNA polymerase beta' chain (rpoC) | U32733 | *Haemophilus influenzae* | 3486 | 50 |
| ORF120 | 124065 | 124988 | transaldolase | L19437 | *Homo sapiens* | 677 | 50 |
| ORF121 | 124873 | 125106 | transaldolase | U67611 | *Homo sapiens* | 121 | 44 |
| ORF122 | 126261 | 125536 | putative | | | | |
| ORF123 | 126328 | 126930 | putative | | | | |
| ORF124 | 127138 | 127785 | putative | | | | |
| ORF125 | 127924 | 129714 | A1 isoform of vacuolar H+-ATPase subunit A | U22077 | *Gallus gallus* | 1062 | 45 |
| ORF126 | 129720 | 131033 | membrane ATPase | X79516 | *Haloferax volcanii* | 790 | 48 |
| ORF127 | 131018 | 131629 | putative | | | | |
| ORF128 | 131834 | 133156 | Na+-ATPase subunit I | D17462 | *Enterococcus hirae* | 188 | 34 |
| ORF129 | 133075 | 133584 | v-type Na-ATPase | X76913 | *Enterococcus hirae* | 110 | 38 |
| ORF130 | 133625 | 133999 | v-type Na-ATPase | X76913 | *Enterococcus hirae* | 89 | 32 |
| ORF131 | 133861 | 134508 | putative | | | | |
| ORF132 | 134638 | 137454 | valyl-tRNA synthetase | D64006 | *Synechocystis* sp. | 1763 | 51 |
| ORF133 | 137442 | 140276 | PknD | Z95209 | *Mycobacterium tuberculosis* | 452 | 44 |
| ORF134 | 140733 | 140335 | putative | | | | |
| ORF135 | 141799 | 141077 | porphobilinogen deaminase | U22968 | *Yersinia pestis* | 282 | 38 |
| ORF136 | 143240 | 141780 | unknown | D26185 | *Bacillus subtilis* | 1113 | 53 |
| ORF137 | 143829 | 143128 | ORF3 | D64116 | *Bacillus subtilis* | 356 | 39 |
| ORF138 | 143923 | 144393 | putative | | | | |
| ORF139 | 144548 | 146326 | unknown | Z47210 | *Streptococcus pneumoniae* | 741 | 44 |
| ORF140 | 146413 | 147078 | manganese superoxide dismutase precursor | D12984 | *Caenorhabditis elegans* | 625 | 56 |
| ORF141 | 147140 | 148075 | acetyl-CoA carboxylase beta subunit (accD) | AE000604 | *Helicobacter pylori* | 704 | 52 |
| ORF142 | 148115 | 148549 | Dut | Z96072 | *Mycobacterium tuberculosis* | 277 | 53 |
| ORF143 | 148524 | 149027 | enzyme IIANtr | U18997 | *Escherichia coli* | 168 | 44 |
| ORF144 | 149000 | 149305 | putative | | | | |
| ORF145 | 149187 | 149708 | enzyme IIANtr | U18997 | *Escherichia coli* | 169 | 43 |
| ORF146 | 149712 | 150911 | putative | | | | |
| ORF147 | 152044 | 151004 | putative | | | | |
| ORF148 | 152664 | 151999 | putative | | | | |
| ORF149 | 152900 | 153352 | hypothetical | U32702 | *Haemophilus influenzae* | 292 | 47 |
| ORF150 | 153389 | 153997 | hypothetical protein in purB 5' region | AE000213 | *Escherichia coli* | 555 | 49 |
| ORF151 | 155276 | 153984 | ClpC adenosine triphosphatase | U02604 | *Bacillus subtilis* | 986 | 45 |
| ORF152 | 156544 | 155231 | ClpC adenosine triphosphatase | U02604 | *Bacillus subtilis* | 1535 | 53 |

TABLE 1-continued

| ORF | begin | stop | Homology | ID | Species | Score | I % |
|---|---|---|---|---|---|---|---|
| ORF153 | 156806 | 157525 | putative | | | | |
| ORF154 | 157489 | 158955 | Unknown | Y08559 | Bacillus subtilis | 99 | 39 |
| ORF155 | 159104 | 159961 | putative | | | | |
| ORF156 | 159916 | 161220 | putative | | | | |
| ORF157 | 161183 | 161593 | glycine cleavage protein homolog | U12980 | Saccharomyces cerevisiae | 175 | 35 |
| ORF158 | 162354 | 161623 | unidentified protein of Na+-translocating NADH-quinone reductase | D49364 | Vibrio alginolyticus | 524 | 51 |
| ORF159 | 163013 | 162363 | NADH: ubiquinone oxidoreductase | Z37111 | Vibrio alginolyticus | 543 | 55 |
| ORF160 | 163941 | 162994 | NADH:ubiquinone oxidoreductase (GP: Z37111_4) | U32702 | Haemophilus influenzae | 287 | 54 |
| ORF161 | 165505 | 164474 | NADH:ubiquinone oxidoreductase subunit B | Z37111 | Vibrio alginolyticus | 449 | 45 |
| ORF162 | 166686 | 166093 | H. pylori predicted coding region HP1542 | AE000652 | Helicobacter pylori | 111 | 33 |
| ORF163 | 168171 | 166729 | pot. ORF 446 (aa 1-446) | X02369 | Bacillus subtilis | 722 | 42 |
| ORF164 | 169249 | 168848 | putative | | | | |
| ORF165 | 169586 | 170431 | hypothetical protein | D90906 | Synechocystis sp. | 462 | 48 |
| ORF166 | 170780 | 171334 | putative | | | | |
| ORF167 | 171333 | 172376 | penicillin-binding protein 2 | M26645 | Neisseria flavescens | 210 | 47 |
| ORF168 | 172309 | 172722 | penicillin-binding protein 2 | M26645 | Neisseria flavescens | 176 | 44 |
| ORF169 | 173048 | 174496 | murE gene product | Z15056 | Bacillus subtilis | 789 | 43 |
| ORF170 | 174399 | 174968 | N-acetylmuramoyl-L-alanine amidase (amiA) | AE000589 | Helicobacter pylori | 177 | 41 |
| ORF171 | 175267 | 175710 | integration host factor beta subunit | L35259 | Pseudomonas aeruginosa | 110 | 38 |
| ORF172 | 175714 | 177009 | putative | | | | |
| ORF173 | 177423 | 178115 | carboxyltransferase alpha subunit | U59236 | Synechococcus PCC7942 | 558 | 50 |
| ORF174 | 178084 | 180021 | ATP dependent translocator homolog (msbA) | U32691 | Haemophilus influenzae | 453 | 41 |
| ORF175 | 180704 | 180048 | putative | | | | |
| ORF176 | 181398 | 180631 | H. pylori predicted coding region HP0152 | AE000536 | Helicobacter pylori | 256 | 34 |
| ORF177 | 182594 | 181398 | contains similarity to DNA polymerase III, alpha chain (SP: P47277) | AF007270 | Arabidopsis thaliana | 173 | 50 |
| ORF178 | 182895 | 183656 | putative Ptc1 protein | Y13937 | Bacillus subtilis | 371 | 53 |
| ORF179 | 183665 | 184786 | NifS2 | AF008220 | Bacillus subtilis | 452 | 43 |
| ORF180 | 186007 | 184796 | similar to [SwissProt Accession Number P37908] | D90888 | Escherichia coli | 93 | 30 |
| ORF181 | 186848 | 186000 | hypothetical | U32728 | Haemophilus influenzae | 154 | 35 |
| ORF182 | 187270 | 186749 | putative | | | | |
| ORF183 | 187426 | 187809 | regulatory protein for beta-lactamase | D90902 | Synechocystis sp. | 96 | 36 |
| ORF184 | 189481 | 188798 | putative | | | | |
| ORF185 | 189693 | 190352 | prolipoprotein diacylglyceryl transferase | AJ000977 | Rhodobacter sphaeroides | 99 | 38 |
| ORF186 | 190235 | 190510 | putative | | | | |
| ORF187 | 190785 | 191786 | putative | | | | |
| ORF188 | 191790 | 192464 | putative | | | | |
| ORF189 | 192392 | 193183 | 60 kDa inner-membrane protein | AE000645 | Helicobacter pylori | 373 | 40 |
| ORF190 | 193254 | 194630 | DnaA | D89066 | Staphylococcus aureus | 545 | 43 |
| ORF191 | 195046 | 194690 | putative | | | | |
| ORF192 | 195184 | 197031 | glycogen phosphorylase B | U47025 | Homo sapiens | 1758 | 56 |
| ORF193 | 197018 | 197635 | glycogen phosphorylase (AA 1-790) | X16931 | Escherichia coli | 580 | 53 |
| ORF194 | 197762 | 198208 | unknown | X86470 | Saccharomyces cerevisiae | 148 | 42 |
| ORF195 | 198963 | 197668 | F23B12.5 | Z77659 | Caenorhabditis elegans | 795 | 50 |
| ORF196 | 199957 | 198962 | pyruvate dehydrogenase E1 beta subunit | U09137 | Arabidopsis thaliana | 856 | 48 |
| ORF197 | 200327 | 199941 | pyruvate dehydrogenase E1 component, alpha subunit | U38804 | Porphyra purpurea | 170 | 31 |
| ORF198 | 200685 | 200266 | pyruvate dehydrogenase complex E1 alpha subunit | U81808 | Thiobacillus ferrooxidans | 302 | 60 |
| ORF199 | 200962 | 200585 | TPP-dependent acetoin dehydrogenase alpha-subunit | L31844 | Clostridium magnum | 127 | 43 |
| ORF200 | 201169 | 202377 | putative | | | | |
| ORF201 | 203441 | 202380 | UDP-3-O-[3-hydroxymyristoyl]glucosamine N-acyltransferase | U70214 | Escherichia coli | 577 | 38 |
| ORF202 | 203998 | 203471 | putative | | | | |
| ORF203 | 206449 | 204059 | OMP1 precursor | U51683 | Brucella abortus | 83 | 31 |
| ORF204 | 207425 | 206811 | recombination protein | D90916 | Synechocystis sp. | 334 | 40 |
| ORF205 | 207506 | 208528 | beta-ketoacyl-acyl carrier protein synthase III | M77744 | Escherichia coli | 706 | 50 |
| ORF206 | 208545 | 209471 | malonyl-CoA:Acyl carrier protein transacylase | U59433 | Bacillus subtilis | 522 | 48 |
| ORF207 | 209471 | 210214 | 3-ketoacyl-acyl carrier protein reductase | U59433 | Bacillus subtilis | 616 | 51 |
| ORF208 | 210586 | 210816 | acyl carrier protein (acpP) | U32701 | Haemophilus influenzae | 220 | 57 |
| ORF209 | 211332 | 210883 | protein kinase type II regulatory subunit (, EC 2.7.1.37) | J02934 | Rattus norvegicus | 150 | 31 |
| ORF210 | 212978 | 211374 | putative | | | | |
| ORF211 | 214134 | 212875 | unknown | AF017105 | Chlamydia psittaci | 852 | 63 |
| ORF212 | 214710 | 214168 | inclusion membrane protein C | AF017105 | Chlamydia psittaci | 231 | 43 |
| ORF213 | 215143 | 214754 | inclusion membrane protein B | AF017105 | Chlamydia psittaci | 181 | 47 |
| ORF214 | 216705 | 215236 | sodium-dependent transporter | AF017105 | Chlamydia psittaci | 1341 | 70 |
| ORF215 | 217917 | 216892 | amino acid transporter | AF017105 | Chlamydia psittaci | 1027 | 60 |
| ORF216 | 217088 | 217441 | putative | | | | |
| ORF217 | 218364 | 218702 | putative | | | | |
| ORF218 | 218695 | 219009 | putative | | | | |
| ORF219 | 219179 | 219748 | putative | | | | |
| ORF220 | 219891 | 220430 | putative | | | | |

TABLE 1-continued

| ORF | begin | stop | Homology | ID | Species | Score | I% |
|---|---|---|---|---|---|---|---|
| ORF221 | 220499 | 221074 | putative | | | | |
| ORF222 | 221137 | 221541 | putative | | | | |
| ORF223 | 221601 | 222092 | putative | | | | |
| ORF224 | 222472 | 223290 | putative | | | | |
| ORF225 | 223423 | 223818 | LAGLI-DADG endonuclease | U57090 | Chlamydia trachomatis | 619 | 99 |
| ORF226 | 224278 | 225171 | YqfU | D84432 | Bacillus subtilis | 530 | 46 |
| ORF227 | 225749 | 225174 | phenylacrylic acid decarboxylase | U67467 | Methanococcus jannaschii | 334 | 52 |
| ORF228 | 225334 | 225549 | Ydr537cp | U43834 | Saccharomyces cerevisiae | 96 | 42 |
| ORF229 | 226654 | 225749 | 4-hydroxybenzoate octaprenyltransferase | U61168 | Bacillus firmus | 321 | 36 |
| ORF230 | 227299 | 226769 | putative | | | | |
| ORF231 | 227646 | 227161 | stationary-phase survival protein (surE) | AE000602 | Helicobacter pylori | 274 | 48 |
| ORF232 | 228457 | 227750 | f311; This 311 aa ORF is 22 pct identical (13 gaps) to 186 residues of an approx. 488 aa protein YACA_BACSU SW: P37563; pyu1 of D21139 | AE000232 | Escherichia coli | 246 | 36 |
| ORF233 | 230001 | 228607 | GadC | AF005098 | Lactococcus lactis | 740 | 35 |
| ORF234 | 231074 | 230151 | f374; This 374 aa ORF is 30 pct identical (9 gaps) to 102 residues of an approx. 512 aa protein FLIC_SALMU SW: P06177 | AE000299 | Escherichia coli | 985 | 65 |
| ORF235 | 231348 | 233006 | putative | | | | |
| ORF236 | 233059 | 233829 | orf2 | D88555 | Methanobacterium thermoautotrophicum | 351 | 52 |
| ORF237 | 233801 | 234265 | hypothetical protein | D90906 | Synechocystis sp. | 151 | 37 |
| ORF238 | 234282 | 234854 | ORF_o211 | U28377 | Escherichia coli | 105 | 54 |
| ORF239 | 236300 | 235227 | glutamate 1-semialdehyde 2,1aminomutase | X82072 | Pseudomonas aeruginosa | 650 | 52 |
| ORF240 | 236314 | 238209 | leucine tRNA synthetase | AF008220 | Bacillus subtilis | 1836 | 61 |
| ORF241 | 238164 | 238769 | leucine tRNA synthetase | AF008220 | Bacillus subtilis | 410 | 46 |
| ORF242 | 238769 | 240061 | 3-deoxy-D-manno-2-octulosonic acid (Kdo) transferase | Z22659 | Chlamydia trachomatis | 2240 | 100 |
| ORF243 | 242022 | 240313 | pyrophosphate-dependent phosphofructokinase beta subunit | Z32850 | Ricinus communis | 1021 | 43 |
| ORF244 | 242846 | 241941 | putative | | | | |
| ORF245 | 244480 | 242798 | pyrophosphate-dependent phosphofructokinase beta subunit | Z32850 | Ricinus communis | 1017 | 42 |
| ORF246 | 245897 | 244479 | YflS | D86417 | Bacillus subtilis | 951 | 42 |
| ORF247 | 246877 | 245924 | putative | | | | |
| ORF248 | 247731 | 246985 | ATP binding protein | L18760 | Lactococcus lactis | 442 | 47 |
| ORF249 | 248585 | 247743 | sporulation protein | M57689 | Bacillus subtilis | 532 | 38 |
| ORF250 | 249420 | 248569 | sporulation protein | M57689 | Bacillus subtilis | 601 | 38 |
| ORF251 | 250383 | 249766 | sporulation protein | M57689 | Bacillus subtilis | 464 | 47 |
| ORF252 | 251186 | 250545 | oligopeptide permease homolog AII | AF000366 | Borrelia burgdorferi | 119 | 31 |
| ORF253 | 252111 | 251095 | sporulation protein | M57689 | Bacillus subtilis | 317 | 36 |
| ORF254 | 253088 | 252066 | P. haemolytica o-sialoglycoprotein endopeptidase; P36175 (660) transmembrane | D88802 | Bacillus subtilis | 601 | 46 |
| ORF255 | 255153 | 256718 | Mg2+ transporter | D90905 | Synechocystis sp. | 103 | 35 |
| ORF256 | 256762 | 257844 | tRNA guanine transglycosylase | L33777 | Zymomonas mobilis | 482 | 44 |
| ORF257 | 257911 | 258690 | putative | | | | |
| ORF258 | 258780 | 259187 | putative | | | | |
| ORF259 | 259193 | 261604 | subunit B of DNA gyrase | Y07916 | Salmonella typhimurium | 1925 | 58 |
| ORF260 | 261622 | 264129 | DNA gyrase | L47978 | Aeromonas salmonicida | 1963 | 45 |
| ORF261 | 264125 | 264742 | unknown | D26185 | Bacillus subtilis | 307 | 37 |
| ORF262 | 264741 | 265628 | replication protein (dnaX) | U32802 | Haemophilus influenzae | 162 | 35 |
| ORF263 | 266416 | 265631 | putative isozyme of glucose-6-P-dehydrogenase; developmentally regulated gene in heterocyst development | U14553 | Anabaena sp. | 218 | 47 |
| ORF264 | 266938 | 266426 | glucose 6-phosphate dehydrogenase | U83195 | Chlamydia trachomatis | 914 | 99 |
| ORF265 | 267961 | 266942 | glucose 6-phosphate dehydrogenase | U83195 | Chlamydia trachomatis | 1770 | 99 |
| ORF266 | 268320 | 268066 | ORF3 | U15192 | Chlamydia trachomatis | 403 | 100 |
| ORF267 | 268510 | 268205 | ORF3 | U15192 | Chlamydia trachomatis | 320 | 91 |
| ORF268 | 270116 | 268500 | CTP synthetase | U15192 | Chlamydia trachomatis | 2828 | 100 |
| ORF269 | 270892 | 270095 | CMP-2-keto-3-deoxyoctulosonic acid synthetase | U15192 | Chlamydia trachomatis | 1313 | 100 |
| ORF270 | 271191 | 271613 | putative | | | | |
| ORF271 | 272219 | 272932 | nitrate transporter | X61625 | Synechococcus sp. | 300 | 34 |
| ORF272 | 272884 | 273588 | putative | | | | |
| ORF273 | 274816 | 273596 | putative | | | | |
| ORF274 | 274821 | 275666 | putative | | | | |
| ORF275 | 277689 | 276103 | ORF_f535 | U28377 | Escherichia coli | 396 | 38 |
| ORF276 | 278268 | 278816 | putative | | | | |
| ORF277 | 279771 | 279013 | tryptophan synthase alpha subunit | M15826 | Pseudomonas aeruginosa | 357 | 37 |
| ORF278 | 280777 | 279767 | tryptophan synthetase | M91661 | Coprinus cinereus | 1042 | 62 |
| ORF279 | 281603 | 281295 | tryptophan repressor | L26582 | Enterobacter aerogenes | 151 | 35 |
| ORF280 | 282104 | 281787 | putative | | | | |
| ORF281 | 284335 | 282794 | putative | | | | |
| ORF282 | 284460 | 284795 | putative | | | | |
| ORF283 | 284817 | 285674 | putative | | | | |
| ORF284 | 285637 | 286137 | putative | | | | |
| ORF285 | 286357 | 286677 | putative | | | | |

TABLE 1-continued

| ORF | begin | stop | Homology | ID | Species | Score | I % |
|---|---|---|---|---|---|---|---|
| ORF286 | 286681 | 287898 | hypothetical protein | U88070 | Chlamydia psittaci | 99 | 35 |
| ORF287 | 288127 | 289227 | comE ORF1 | D64002 | Synechocystis sp. | 90 | 46 |
| ORF288 | 289744 | 290679 | hypothetical protein | U88070 | Chlamydia psittaci | 246 | 36 |
| ORF289 | 290828 | 291535 | putative | | | | |
| ORF290 | 291514 | 292230 | endonuclease | U09868 | Escherichia coli | 160 | 37 |
| ORF291 | 292326 | 293048 | putative | | | | |
| ORF292 | 293330 | 294853 | putative | | | | |
| ORF293 | 295684 | 295010 | glutamine transport ATP-binding protein Q | U67524 | Methanococcus jannaschii | 407 | 38 |
| ORF294 | 296336 | 295692 | H. influenzae predicted coding region HI1555 | U32830 | Haemophilus influenzae | 134 | 37 |
| ORF295 | 297238 | 296243 | putative | | | | |
| ORF296 | 297791 | 298735 | putative | | | | |
| ORF297 | 298905 | 300458 | similar to putative oxygenase of S. fradiae | U73857 | Escherichia coli | 82 | 40 |
| ORF298 | 302152 | 300527 | putative | | | | |
| ORF299 | 304917 | 302071 | putative | | | | |
| ORF300 | 306157 | 304973 | DNA ligase | M74792 | Thermus aquaticus thermophilus | 745 | 41 |
| ORF301 | 306494 | 306111 | DNA LIGASE (EC 6.5.1.2) (POLYDEOXYRIBONUCLEOTIDE SYNTHASE (NAD+)). | D90870 | Escherichia coli | 197 | 40 |
| ORF302 | 306963 | 306436 | Mycoplasma pneumoniae, DNA ligase; similar to Swiss-Prot Accession Number P15042, from E. coli | AE000047 | Mycoplasma pneumoniae | 292 | 37 |
| ORF303 | 308773 | 306977 | unknown | Z84395 | Mycobacterium tuberculosis | 316 | 52 |
| ORF304 | 309881 | 309276 | putative | | | | |
| ORF305 | 310720 | 309872 | putative | | | | |
| ORF306 | 311570 | 310716 | putative | | | | |
| ORF307 | 312451 | 311972 | Preprotein translocase SecA subunit. | D90832 | Escherichia coli | 123 | 86 |
| ORF308 | 313435 | 314364 | sporulation protein | M57689 | Bacillus subtilis | 202 | 37 |
| ORF309 | 314340 | 314738 | putative | | | | |
| ORF310 | 315526 | 314741 | orfX gene product | X58778 | Klebsiella pneumoniae | 169 | 45 |
| ORF311 | 316507 | 315665 | Similar to Saccharomyces cerevisiae SUA5 protein | Z38002 | Bacillus subtilis | 147 | 41 |
| ORF312 | 317284 | 316529 | serine esterase [Spirulina platensis, C1, Peptide, 207 aa] | S70419 | Spirulina platensis | 167 | 58 |
| ORF313 | 317592 | 317338 | putative | | | | |
| ORF314 | 318470 | 317499 | putative | | | | |
| ORF315 | 317599 | 317874 | putative | | | | |
| ORF316 | 318947 | 318477 | putative | | | | |
| ORF317 | 319342 | 320142 | ORF2 | L35036 | Chlamydia psittaci | 802 | 60 |
| ORF318 | 320544 | 321497 | putative | | | | |
| ORF319 | 321485 | 321937 | putative | | | | |
| ORF320 | 321901 | 322362 | putative | | | | |
| ORF321 | 322301 | 323140 | putative | | | | |
| ORF322 | 323144 | 324913 | putative | | | | |
| ORF323 | 325621 | 324977 | YqiZ | D84432 | Bacillus subtilis | 430 | 43 |
| ORF324 | 326268 | 325621 | integral membrane protein homolog | U97348 | Lactobacillus fermentum | 343 | 44 |
| ORF325 | 326469 | 327203 | adenylate kinase | AB000111 | Synechococcus sp. | 371 | 46 |
| ORF326 | 327281 | 328150 | putative | | | | |
| ORF327 | 328605 | 328204 | RpsI | Z95389 | Mycobacterium tuberculosis | 315 | 55 |
| ORF328 | 329066 | 328734 | 50S ribosomal subunit protein L13 | U18997 | Escherichia coli | 269 | 60 |
| ORF329 | 329663 | 329292 | YqhX | D84432 | Bacillus subtilis | 297 | 56 |
| ORF330 | 330666 | 329608 | biotin carboxylase | L14862 | Anabaena sp. | 1089 | 58 |
| ORF331 | 331161 | 330670 | YqhW | D84432 | Bacillus subtilis | 208 | 52 |
| ORF332 | 331731 | 331177 | elongation factor P | D64001 | Synechocystis sp. | 297 | 33 |
| ORF333 | 332404 | 331721 | putative CfxE protein | Y13937 | Bacillus subtilis | 483 | 55 |
| ORF334 | 332779 | 333021 | putative | | | | |
| ORF335 | 333005 | 333589 | putative | | | | |
| ORF336 | 334357 | 333806 | putative | | | | |
| ORF337 | 334089 | 334361 | putative | | | | |
| ORF338 | 335142 | 334729 | putative | | | | |
| ORF339 | 335195 | 335602 | putative | | | | |
| ORF340 | 335673 | 335194 | putative | | | | |
| ORF341 | 336334 | 335903 | putative | | | | |
| ORF342 | 337378 | 336338 | putative | | | | |
| ORF343 | 339947 | 337347 | ATP-dependent protease binding subunit | M29364 | Escherichia coli | 2005 | 53 |
| ORF344 | 340507 | 341847 | Pz-peptidase | D88209 | Bacillus licheniformis | 508 | 39 |
| ORF345 | 341783 | 342022 | group B oligopeptidase PepB | U49821 | Streptococcus agalactiae | 140 | 48 |
| ORF346 | 342249 | 342470 | hypA protein | M31739 | Chlamydia trachomatis | 361 | 99 |
| ORF347 | 342597 | 343370 | heat shock protein | L12004 | Chlamydia trachomatis | 1271 | 99 |
| ORF348 | 343361 | 344032 | hypB protein | M31739 | Chlamydia trachomatis | 1051 | 100 |
| ORF349 | 343956 | 344225 | hypB protein | M31739 | Chlamydia trachomatis | 344 | 100 |
| ORF350 | 344357 | 345142 | orf 3'of chaperonin homolog hypB [Chlamydia psittaci, pigeon strain P-1041, Peptide Partial, 98 aa] | S40172 | Chlamydia psittaci | 344 | 63 |
| ORF351 | 345934 | 345161 | o247; This 247 aa ORF is 51 pct identical (0 gaps) to 117 residues of an approx. 160 aa protein YPH7_CHRVI SW: P45371 | AE000174 | Escherichia coli | 387 | 41 |
| ORF352 | 347102 | 346080 | mutY homolog | U63329 | Homo sapiens | 492 | 46 |

TABLE 1-continued

| ORF | begin | stop | Homology | ID | Species | Score | I % |
|---|---|---|---|---|---|---|---|
| ORF353 | 347113 | 347940 | hypothetical 36.0 kD protein in rne-rpmF intergenic region | AE000209 | *Escherichia coli* | 397 | 44 |
| ORF354 | 350164 | 348146 | putative | | | | |
| ORF355 | 350423 | 351283 | enoyl-acyl carrier protein reductase [*Brassica napus*, Peptide, 385 aa] | S60064 | *Brassica napus* | 909 | 64 |
| ORF356 | 352207 | 351314 | hypothetical protein | D90914 | *Synechocystis* sp. | 113 | 42 |
| ORF357 | 352727 | 352245 | putative | | | | |
| ORF358 | 353709 | 353305 | FUNCTION UNKNOWN, SIMILAR PRODUCT IN *E. COLI* AND *MYCOPLASMA PNEUMONIAE*. | AB001488 | *Bacillus subtilis* | 213 | 40 |
| ORF359 | 354218 | 353670 | NADPH thioredoxin reductase | Z23108 | *Arabidopsis thaliana* | 577 | 60 |
| ORF360 | 354721 | 354140 | Thioredoxin Reductase (NADPH) | D45049 | *Neurospora crassa* | 417 | 60 |
| ORF361 | 354966 | 356672 | 30S ribosomal protein S1 | D90729 | *Escherichia coli* | 1305 | 44 |
| ORF362 | 356700 | 357377 | NusA | U74759 | *Chlamydia trachomatis* | 948 | 100 |
| ORF363 | 357326 | 358093 | NusA | U74759 | *Chlamydia trachomatis* | 1216 | 100 |
| ORF364 | 358035 | 360743 | | U74759 | *Chlamydia trachomatis* | 3311 | 98 |
| ORF365 | 360753 | 361121 | ORF6 gene product | Z18631 | *Bacillus subtilis* | 116 | 32 |
| ORF366 | 361162 | 361884 | tRNA pseudouridine 55 synthase | D90917 | *Synechocystis* sp. | 362 | 42 |
| ORF367 | 361826 | 362746 | protein X | M35367 | *Pseudomonas fluorescens* | 192 | 49 |
| ORF368 | 363859 | 362816 | hypothetical GTP-binding protein in pth 3' region | AE000219 | *Escherichia coli* | 978 | 52 |
| ORF369 | 364116 | 365195 | cds1 gene product | U88070 | *Chlamydia psittaci* | 1631 | 88 |
| ORF370 | 365198 | 365587 | cds2 gene product | U88070 | *Chlamydia psittaci* | 516 | 93 |
| ORF371 | 365479 | 367320 | cds2 gene product | U88070 | *Chlamydia psittaci* | 2817 | 87 |
| ORF372 | 367341 | 368603 | copN gene product | U88070 | *Chlamydia psittaci* | 585 | 37 |
| ORF373 | 368644 | 369081 | scc1 gene product | U88070 | *Chlamydia psittaci* | 528 | 67 |
| ORF374 | 369088 | 370251 | No definition line found | U88070 | *Chlamydia psittaci* | 1362 | 62 |
| ORF375 | 370769 | 371086 | ribosomal protein L28 (rpL28) | U32776 | *Haemophilus influenzae* | 182 | 46 |
| ORF376 | 371203 | 372816 | hypothetical protein | U88070 | *Chlamydia psittaci* | 1926 | 68 |
| ORF377 | 373119 | 373529 | hypothetical protein | U88070 | *Chlamydia psittaci* | 286 | 49 |
| ORF378 | 373614 | 374204 | hypothetical protein | U88070 | *Chlamydia psittaci* | 379 | 48 |
| ORF379 | 374736 | 374224 | putative | | | | |
| ORF380 | 376391 | 374703 | putative | | | | |
| ORF381 | 377062 | 376748 | corresponds to a 97 amino acid long polypeptide | L40838 | *Chlamydia trachomatis* | 490 | 98 |
| ORF382 | 377853 | 378737 | methylenetetrahydrofolate dehydrogenase | D64000 | *Synechocystis* sp. | 678 | 51 |
| ORF383 | 378626 | 379048 | putative | | | | |
| ORF384 | 379017 | 379403 | hypothetical | U32702 | *Haemophilus influenzae* | 137 | 45 |
| ORF385 | 380009 | 379641 | small protein | D90914 | *Synechocystis* sp. | 216 | 51 |
| ORF386 | 380187 | 381470 | DNA polymerase III beta-subunit (dnaN) | U32780 | *Haemophilus influenzae* | 76 | 39 |
| ORF387 | 381473 | 382567 | recombination protein | D26185 | *Bacillus subtilis* | 477 | 35 |
| ORF388 | 382704 | 383702 | putative | | | | |
| ORF389 | 383945 | 383655 | hypothetical | U70214 | *Escherichia coli* | 134 | 35 |
| ORF390 | 385217 | 383949 | putative | | | | |
| ORF391 | 385507 | 385178 | conserved hypothetical secreted protein | AE000606 | *Helicobacter pylori* | 185 | 45 |
| ORF392 | 386845 | 385706 | hypothetical protein | D64000 | *Synechocystis* sp. | 686 | 41 |
| ORF393 | 386127 | 386627 | putative | | | | |
| ORF394 | 387372 | 386872 | ORF1; putative | M26130 | *Streptococcus parasanguis* | 150 | 35 |
| ORF395 | 387823 | 387338 | ytgD | AF008220 | *Bacillus subtilis* | 168 | 42 |
| ORF396 | 388250 | 387816 | TroR | U55214 | *Treponema pallidum* | 134 | 40 |
| ORF397 | 389169 | 388237 | putative protein of 299 amino acids | U30821 | *Cyanophora paradoxa* | 164 | 31 |
| ORF398 | 389955 | 389173 | TroB | U55214 | *Treponema pallidum* | 592 | 51 |
| ORF399 | 390988 | 389945 | YtgA | AF008220 | *Bacillus subtilis* | 282 | 30 |
| ORF400 | 391514 | 391810 | putative | | | | |
| ORF401 | 392410 | 393996 | adenine nucleotide translocase | Z49227 | *Arabidopsis thaliana* | 1295 | 56 |
| ORF402 | 394170 | 395354 | lepA gene product | X91655 | *Bacillus subtilis* | 1235 | 60 |
| ORF403 | 395309 | 395992 | GTP-binding membrane protein (lepA) | AE000552 | *Helicobacter pylori* | 543 | 54 |
| ORF404 | 396538 | 396059 | phosphogluconate dehydrogenase | U30255 | *Homo sapiens* | 411 | 55 |
| ORF405 | 397507 | 396542 | 6-phosphogluconate dehydrogenase | AB006102 | *Candida albicans* | 908 | 51 |
| ORF406 | 398753 | 397401 | tyrosyl-tRNA synthetase | M13148 | *Bacillus caldotenax* | 844 | 45 |
| ORF407 | 399688 | 398909 | whiG-Stv gene product | X68709 | *Streptoverticillium griseocarneum* | 463 | 41 |
| ORF408 | 400167 | 399778 | FLHA gene product | X63698 | *Bacillus subtilis* | 134 | 35 |
| ORF409 | 401224 | 400034 | flbF | M73782 | *Caulobacter crescentus* | 355 | 39 |
| ORF410 | 401776 | 402021 | ferredoxin IV | M59855 | *Rhodobacter capsulatus* | 98 | 54 |
| ORF411 | 402126 | 403220 | putative | | | | |
| ORF412 | 403348 | 405180 | GcpE | D90908 | *Synechocystis* sp. | 995 | 49 |
| ORF413 | 403788 | 403276 | putative | | | | |
| ORF414 | 405165 | 405920 | YfiH | U50134 | *Escherichia coli* | 166 | 43 |
| ORF415 | 407049 | 405955 | dihydrolipoamide transsuccinylase (odhB; EC 2.3.1.61) | M27141 | *Bacillus subtilis* | 833 | 61 |
| ORF416 | 409773 | 407056 | alpha-ketoglutarate dehydrogenase | U41762 | *Rhodobacter capsulatus* | 1537 | 50 |
| ORF417 | 410532 | 411416 | YqeR | D84432 | *Bacillus subtilis* | 496 | 44 |
| ORF418 | 411707 | 413410 | putative | | | | |
| ORF419 | 413433 | 412606 | putative | | | | |
| ORF420 | 413404 | 413952 | putative | | | | |
| ORF421 | 413841 | 415112 | putative | | | | |

TABLE 1-continued

| ORF | begin | stop | Homology | ID | Species | Score | I % |
|---|---|---|---|---|---|---|---|
| ORF422 | 414379 | 413978 | putative | | | | |
| ORF423 | 416664 | 415177 | putative | | | | |
| ORF424 | 417456 | 416740 | unknown | Z94752 | Mycobacterium tuberculosis | 172 | 36 |
| ORF425 | 418053 | 417721 | putative | | | | |
| ORF426 | 418603 | 418031 | putative | | | | |
| ORF427 | 419531 | 418647 | Hc2 nucleoprotein | L10193 | Chlamydia trachomatis | 1661 | 92 |
| ORF428 | 420190 | 419672 | [karp] gene products | M86605 | Chlamydia trachomatis | 612 | 96 |
| ORF429 | 421171 | 420245 | aminopeptidase | D17450 | Mycoplasma salivarium | 269 | 41 |
| ORF430 | 421988 | 421518 | putative | L39923 | Mycobacterium leprae | 165 | 36 |
| ORF431 | 422486 | 423043 | putative | | | | |
| ORF432 | 423226 | 425079 | glycogen operon protein GlgX | D90908 | Synechocystis sp. | 1229 | 55 |
| ORF433 | 426054 | 425146 | putative | | | | |
| ORF434 | 426985 | 426245 | Holliday junction specific DNA helicase | D83138 | Pseudomonas aeruginosa | 633 | 53 |
| ORF435 | 427248 | 427817 | deoxycytidine triphosphate deaminase (dcd) | AE000554 | Helicobacter pylori | 612 | 63 |
| ORF436 | 429560 | 429886 | putative | | | | |
| ORF437 | 430360 | 429857 | biotin apo-protein ligase | U27182 | Saccharomyces cerevisiae | 173 | 38 |
| ORF438 | 430637 | 430323 | putative | | | | |
| ORF439 | 430933 | 431787 | putative | | | | |
| ORF440 | 431658 | 431987 | putative | | | | |
| ORF441 | 432232 | 434475 | exonuclease V alpha-subunit | U29581 | Escherichia coli | 289 | 53 |
| ORF442 | 436308 | 434620 | methionyl-tRNA synthetase | AB004537 | Schizosaccharomyces pombe | 817 | 54 |
| ORF443 | 436574 | 436272 | putative | | | | |
| ORF444 | 437685 | 436567 | RNAseH II | AF005098 | Lactococcus lactis | 395 | 47 |
| ORF445 | 438262 | 437894 | ribosomal protein L19 | X72627 | Synechocystis sp. | 287 | 47 |
| ORF446 | 439127 | 438285 | tRNA (guanine-N1)-methyltransferase (trmD) | U32705 | Haemophilus influenzae | 374 | 56 |
| ORF447 | 439339 | 438986 | tRNA (guanine-N1)-methyltransferase (trmD) | U32705 | Haemophilus influenzae | 199 | 57 |
| ORF448 | 439705 | 439358 | ribosomal protein S16 (rpS16) | U32705 | Haemophilus influenzae | 168 | 39 |
| ORF449 | 441042 | 439699 | signal recognition particle protein | AE000347 | Escherichia coli | 865 | 40 |
| ORF450 | 441911 | 441042 | product similar to E. coli PRFA2 protein | Z49782 | Bacillus subtilis | 314 | 37 |
| ORF451 | 442593 | 441898 | polypeptide chain release factor 1 (prfA) | U32830 | Haemophilus influenzae | 708 | 62 |
| ORF452 | 444505 | 446388 | leader peptidase I | D90904 | Synechocystis sp. | 268 | 44 |
| ORF453 | 448068 | 446452 | isoleucyl-tRNA synthetase | U04953 | Homo sapiens | 704 | 49 |
| ORF454 | 449575 | 447932 | isoleucyl-tRNA synthetase | U04953 | Homo sapiens | 1687 | 55 |
| ORF455 | 450546 | 451076 | putative | | | | |
| ORF456 | 451623 | 451144 | putative | | | | |
| ORF457 | 452593 | 451517 | putative | | | | |
| ORF458 | 453195 | 452632 | putative | | | | |
| ORF459 | 453567 | 454868 | product similar to E. coli PhoH protein | Z97025 | Bacillus subtilis | 820 | 50 |
| ORF460 | 455430 | 454972 | CydB | Z95554 | Mycobacterium tuberculosis | 105 | 31 |
| ORF461 | 456047 | 455367 | cyanide insensitive terminal oxidase | Y10528 | Pseudomonas aeruginosa | 388 | 38 |
| ORF462 | 457384 | 456047 | cyanide insensitive terminal oxidase | Y10528 | Pseudomonas aeruginosa | 537 | 52 |
| ORF463 | 457659 | 458450 | YbbP | AB002150 | Bacillus subtilis | 324 | 42 |
| ORF464 | 458508 | 459632 | putative | | | | |
| ORF465 | 459839 | 461203 | HtrB protein | X61000 | Escherichia coli | 77 | 31 |
| ORF466 | 461624 | 461196 | unknown | U87792 | Bacillus subtilis | 114 | 38 |
| ORF467 | 461887 | 462621 | hypothetical protein | Z75208 | Bacillus subtilis | 148 | 51 |
| ORF468 | 463758 | 462895 | putative | | | | |
| ORF469 | 464048 | 464629 | putative | | | | |
| ORF470 | 464721 | 465848 | putative | | | | |
| ORF471 | 467420 | 466113 | PET112 | D90913 | Synechocystis sp. | 892 | 48 |
| ORF472 | 468891 | 467419 | amidase | U49269 | Moraxella catarrhalis | 1051 | 46 |
| ORF473 | 469280 | 468906 | putative | | | | |
| ORF474 | 469349 | 469675 | putative | | | | |
| ORF475 | 471226 | 469826 | putative | | | | |
| ORF476 | 471624 | 471106 | putative | | | | |
| ORF477 | 471954 | 473267 | putative 98 kDa outer membrane protein | U72499 | Chlamydia psittaci | 173 | 33 |
| ORF478 | 473252 | 473695 | POMP90A precursor | U65942 | Chlamydia psittaci | 175 | 39 |
| ORF479 | 473982 | 474527 | putative 98 kDa outer membrane protein | U72499 | Chlamydia psittaci | 193 | 38 |
| ORF480 | 475198 | 474602 | putative | | | | |
| ORF481 | 476527 | 475613 | POMP91A | U65942 | Chlamydia psittaci | 100 | 38 |
| ORF482 | 478640 | 476517 | putative 98 kDa outer membrane protein | U72499 | Chlamydia psittaci | 537 | 40 |
| ORF483 | 479084 | 478665 | putative 98 kDa outer membrane protein | U72499 | Chlamydia psittaci | 234 | 35 |
| ORF484 | 479723 | 479088 | putative outer membrane protein | U72499 | Chlamydia psittaci | 313 | 40 |
| ORF485 | 480012 | 479668 | putative | | | | |
| ORF486 | 481466 | 479895 | putative 98 kDa outer membrane protein | U72499 | Chlamydia psittaci | 391 | 38 |
| ORF487 | 481732 | 481496 | putative | | | | |
| ORF488 | 481864 | 483429 | POMP90A precursor | U65942 | Chlamydia psittaci | 114 | 40 |
| ORF489 | 483402 | 484964 | putative 98 kDa outer membrane protein | U72499 | Chlamydia psittaci | 77 | 34 |
| ORF490 | 484898 | 487864 | putative 98 kDa outer membrane protein | U72499 | Chlamydia psittaci | 506 | 39 |
| ORF491 | 485725 | 485222 | putative | | | | |
| ORF492 | 488204 | 489247 | putative | | | | |
| ORF493 | 488571 | 488233 | putative | | | | |
| ORF494 | 489440 | 490456 | putative | | | | |
| ORF495 | 492765 | 490507 | branching enzyme | M31544 | Synechococcus PCC6301 | 1624 | 57 |
| ORF496 | 492357 | 492893 | putative | | | | |
| ORF497 | 493744 | 492737 | putative | | | | |
| ORF498 | 493875 | 494675 | YqkM | D84432 | Bacillus subtilis | 230 | 44 |
| ORF499 | 494573 | 494869 | xprB | M54884 | Escherichia coli | 245 | 48 |

TABLE 1-continued

| ORF | begin | stop | Homology | ID | Species | Score | I % |
|---|---|---|---|---|---|---|---|
| ORF500 | 494835 | 495365 | putative | | | | |
| ORF501 | 495174 | 494872 | putative | | | | |
| ORF502 | 495687 | 496634 | putative | | | | |
| ORF503 | 496295 | 497176 | putative | | | | |
| ORF504 | 497703 | 498515 | putative | | | | |
| ORF505 | 498280 | 499239 | putative | | | | |
| ORF506 | 499215 | 500732 | putative | | | | |
| ORF507 | 501710 | 500790 | penicillin tolerance protein (lytB) | U32781 | *Haemophilus influenzae* | 702 | 50 |
| ORF508 | 502863 | 501808 | putative | | | | |
| ORF509 | 503675 | 502692 | putative | | | | |
| ORF510 | 505002 | 503722 | hypothetical protein | Z96072 | *Mycobacterium tuberculosis* | 102 | 42 |
| ORF511 | 505739 | 506986 | hypothetical protein in pth-prs intergenic region | AE000219 | *Escherichia coli* | 740 | 44 |
| ORF512 | 506999 | 507439 | putative | | | | |
| ORF513 | 508404 | 507649 | fumarate hydratase | AF013216 | *Myxococcus xanthus* | 611 | 54 |
| ORF514 | 508291 | 508590 | putative | | | | |
| ORF515 | 508915 | 508478 | fumarase | D64000 | *Synechocystis* sp. | 386 | 57 |
| ORF516 | 509600 | 510691 | thiamine-repressed protein (nmt1) | U32720 | *Haemophilus influenzae* | 82 | 31 |
| ORF517 | 511039 | 511527 | putative | | | | |
| ORF518 | 511547 | 512185 | hypothetical protein (SP: P46851) | U67608 | *Methanococcus jannaschii* | 208 | 39 |
| ORF519 | 512382 | 513092 | methionine amino peptidase | M15106 | *Escherichia coli* | 384 | 46 |
| ORF520 | 514287 | 513055 | putative | | | | |
| ORF521 | 514789 | 515244 | putative | | | | |
| ORF522 | 514994 | 515269 | putative | | | | |
| ORF523 | 515553 | 515804 | putative | | | | |
| ORF524 | 515808 | 516422 | putative | | | | |
| ORF525 | 516476 | 517171 | putative | | | | |
| ORF526 | 517927 | 517400 | orf150 gene product | X95938 | *Porphyromonas gingivalis* | 340 | 51 |
| ORF527 | 518096 | 518380 | 30S ribosomal protein S15 | D90901 | *Synechocystis* sp. | 245 | 52 |
| ORF528 | 518403 | 518822 | polynucleotide phosphorylase | AF010578 | *Pisum sativum* | 306 | 49 |
| ORF529 | 518923 | 519516 | polyribonucleotide phophorylase | U52048 | *Spinacia oleracea* | 387 | 47 |
| ORF530 | 519577 | 520497 | polynucleotide phosphorylase | U18997 | *Escherichia coli* | 860 | 54 |
| ORF531 | 521986 | 520718 | ATP-binding protein | U01376 | *Escherichia coli* | 970 | 49 |
| ORF532 | 522131 | 521886 | cell division protein (ftsH) | U32812 | *Haemophilus influenzae* | 314 | 76 |
| ORF533 | 523495 | 522143 | putative | | | | |
| ORF534 | 524591 | 523623 | ORF327 gene product | U38804 | *Porphyra purpurea* | 148 | 44 |
| ORF535 | 524652 | 525746 | putative | | | | |
| ORF536 | 525731 | 526078 | putative | | | | |
| ORF537 | 525939 | 526400 | putative | | | | |
| ORF538 | 526301 | 526735 | putative | | | | |
| ORF539 | 528323 | 526851 | putative | | | | |
| ORF540 | 528861 | 528292 | putative | | | | |
| ORF541 | 529723 | 529142 | phenylalanyl-tRNA synthetase alpha subunit | X53057 | *Bacillus subtilis* | 476 | 52 |
| ORF542 | 530166 | 529624 | phenylalany-tRNA synthetase beta subunit | Z75208 | *Bacillus subtilis* | 164 | 40 |
| ORF543 | 530543 | 530223 | ribosomal protein L20 (AA 1-119) | X16188 | *Bacillus stearothermophilus* | 230 | 47 |
| ORF544 | 531378 | 530737 | unknown | Z85982 | *Mycobacterium tuberculosis* | 452 | 50 |
| ORF545 | 532370 | 533272 | UDP-N-acetylenolpyruvylglucosamine reductase | U86147 | *Synechococcus* PCC7942 | 488 | 43 |
| ORF546 | 533849 | 533244 | YtqB | AF008220 | *Bacillus subtilis* | 273 | 38 |
| ORF547 | 534672 | 533944 | hypothetical protein MTCY08D5.03c | Z92669 | *Mycobacterium tuberculosis* | 170 | 35 |
| ORF548 | 535915 | 534878 | ribonucleoside diphosphate reductase, beta subunit (nrdB) | AE000553 | *Helicobacter pylori* | 397 | 33 |
| ORF549 | 539153 | 535956 | ribonucleoside-diphosphate reductase 1 alpha subunit (nrdA) | AE000581 | *Helicobacter pylori* | 1447 | 51 |
| ORF550 | 539731 | 540519 | phosphatidylserine synthase (pssA) | AE000614 | *Helicobacter pylori* | 226 | 49 |
| ORF551 | 540523 | 540969 | putative | | | | |
| ORF552 | 540906 | 541805 | hypothetical 54.7 kD protein in udp 3' region precursor (o475) | AE000459 | *Escherichia coli* | 82 | 39 |
| ORF553 | 543255 | 541825 | Ydr430cp; CAI: 0.15 | U33007 | *Saccharomyces cerevisiae* | 130 | 48 |
| ORF554 | 544133 | 543222 | putative | | | | |
| ORF555 | 544565 | 544179 | hypA gene product | X86493 | *Clostridium perfringens* | 221 | 46 |
| ORF556 | 544762 | 544487 | orf1 gene product | X70951 | *Saccharomyces cerevisiae* | 153 | 38 |
| ORF557 | 546423 | 544951 | serine protease (htrA) | AE000610 | *Helicobacter pylori* | 981 | 46 |
| ORF558 | 547480 | 546584 | succinyl coenzyme A synthetase alpha subunit | U23408 | *Dictyostelium discoideum* | 869 | 63 |
| ORF559 | 546789 | 547382 | putative | | | | |
| ORF560 | 547901 | 547476 | putative succinyl-coA synthetase beta chain | AJ000975 | *Bacillus subtilis* | 388 | 55 |
| ORF561 | 548634 | 547900 | succinate--CoA ligase (ADP-forming) | X54073 | *Thermus aquaticus flavus* | 498 | 46 |
| ORF562 | 548692 | 549459 | cell division protein (ftsY) | AE000588 | *Helicobacter pylori* | 330 | 46 |
| ORF563 | 550385 | 549663 | putative | | | | |
| ORF564 | 551611 | 550421 | Tyrosine-specific transport protein (Tyrosine permease). | D90832 | *Escherichia coli* | 508 | 40 |
| ORF565 | 553041 | 551797 | tyrosine-specific transport protein (tyrP) | U32730 | *Haemophilus influenzae* | 353 | 36 |
| ORF566 | 554946 | 553096 | L-glutamine:D-fructose-6-P amidotransferase precursor | U17352 | *Thermus aquaticus thermophilus* | 1324 | 45 |
| ORF567 | 556300 | 554927 | hypothetical | U32824 | *Haemophilus influenzae* | 1009 | 51 |
| ORF568 | 556524 | 556904 | putative | | | | |
| ORF569 | 558126 | 557314 | putative | | | | |
| ORF570 | 557810 | 558235 | putative | | | | |

TABLE 1-continued

| ORF | begin | stop | Homology | ID | Species | Score | I % |
|---|---|---|---|---|---|---|---|
| ORF571 | 559215 | 558310 | putative | | | | |
| ORF572 | 561349 | 559196 | POMP91A | U65942 | *Chlamydia psittaci* | 245 | 39 |
| ORF573 | 562931 | 561150 | putative 98 kDa outer membrane protein | U72499 | *Chlamydia psittaci* | 130 | 38 |
| ORF574 | 564083 | 563121 | putative PlsX protein | Y13937 | *Bacillus subtilis* | 519 | 45 |
| ORF575 | 563593 | 563943 | putative | | | | |
| ORF576 | 565379 | 566953 | ORF_f495; orfF of ECMRED, uses 2nd start | U18997 | *Escherichia coli* | 874 | 39 |
| ORF577 | 567079 | 567966 | glycerol-3-phosphate acyltransferase | M80571 | *Cucumis sativus* | 594 | 45 |
| ORF578 | 568021 | 570399 | insulin-degrading enzyme | M58465 | *Drosophila melanogaster* | 334 | 42 |
| ORF579 | 571269 | 572021 | putative | | | | |
| ORF580 | 572519 | 572755 | putative | | | | |
| ORF581 | 573519 | 572731 | unknown | Z94752 | *Mycobacterium tuberculosis* | 203 | 35 |
| ORF582 | 572879 | 573427 | putative | | | | |
| ORF583 | 574160 | 573660 | putative heat shock protein ORF; putative | M62820 | *Chlamydia trachomatis* | 315 | 83 |
| ORF584 | 574426 | 574184 | ribosomal protein S18 homolog; putative | M62820 | *Chlamydia trachomatis* | 384 | 99 |
| ORF585 | 574781 | 574446 | ribosomal protein S6 (rps6) | AE000630 | *Helicobacter pylori* | 176 | 39 |
| ORF586 | 575243 | 574923 | peptidyl-tRNA hydrolase | U31570 | *Chlamydia trachomatis* | 358 | 78 |
| ORF587 | 575458 | 575057 | peptidyl-tRNA hydrolase | U31570 | *Chlamydia trachomatis* | 393 | 81 |
| ORF588 | 575849 | 575469 | partial ctc gene product (AA 1-186) | X16518 | *Bacillus subtilis* | 94 | 37 |
| ORF589 | 576545 | 578023 | glycogen (starch) synthase | D90903 | *Synechocystis* sp. | 695 | 48 |
| ORF590 | 578673 | 578017 | phosphatidylglycerophosphate synthase | U87792 | *Bacillus subtilis* | 243 | 48 |
| ORF591 | 579012 | 582104 | glycyl-tRNA synthetase | U20547 | *Chlamydia trachomatis* | 5054 | 99 |
| ORF592 | 582697 | 582206 | putative | | | | |
| ORF593 | 583122 | 582811 | putative | | | | |
| ORF594 | 583514 | 583182 | putative | | | | |
| ORF595 | 583869 | 583438 | putative | | | | |
| ORF596 | 584435 | 583827 | dnaG | AB001896 | *Staphylococcus aureus* | 298 | 41 |
| ORF597 | 584967 | 584299 | DNA primase | U13165 | *Listeria monocytogenes* | 339 | 41 |
| ORF598 | 585297 | 585016 | putative | | | | |
| ORF599 | 585240 | 586610 | DNA mismatch repair protein | D90909 | *Synechocystis* sp. | 673 | 42 |
| ORF600 | 586484 | 587758 | DNA mismatch repair protein | U71154 | *Aquifex pyrophilus* | 845 | 50 |
| ORF601 | 587786 | 589408 | excinuclease ABC subunit C (uvrC) | U32691 | *Haemophilus influenzae* | 719 | 46 |
| ORF602 | 589198 | 589578 | exinuclease ABC subunit C | U29587 | *Rhodobacter sphaeroides* | 156 | 42 |
| ORF603 | 590061 | 589630 | putative | | | | |
| ORF604 | 590739 | 591272 | putative | | | | |
| ORF605 | 592406 | 592765 | homologous to *E. coli* rnpA | X62539 | *Bacillus subtilis* | 117 | 34 |
| ORF606 | 593145 | 592849 | putative | | | | |
| ORF607 | 593900 | 593121 | putative | | | | |
| ORF608 | 594138 | 595637 | cys-tRNA synthetase (cysS) | U32693 | *Haemophilus influenzae* | 991 | 49 |
| ORF609 | 596122 | 595640 | lysyl-tRNA synthetase | D90906 | *Synechocystis* sp. | 375 | 53 |
| ORF610 | 596864 | 596154 | lysine--tRNA ligase | X70708 | *Thermus aquaticus thermophilus* | 571 | 52 |
| ORF611 | 597731 | 597282 | putative | | | | |
| ORF612 | 598524 | 600809 | putative PriA protein | Y13937 | *Bacillus subtilis* | 1097 | 38 |
| ORF613 | 601876 | 600734 | L-alanine - pimelyl CoA ligase | U51868 | *Bacillus subtilis* | 242 | 42 |
| ORF614 | 603523 | 601910 | 2-acylglycerophosphoethanolamine acyltransferase/acyl carrier protein synthetase | L14681 | *Escherichia coli* | 388 | 42 |
| ORF615 | 603794 | 603531 | putative | | | | |
| ORF616 | 604413 | 603757 | putative | | | | |
| ORF617 | 604549 | 605610 | 3'(2'),5-diphosphonucleoside 3'(2') phosphohydrolase | U33283 | *Oryza sativa* | 254 | 45 |
| ORF618 | 606619 | 605582 | leucine dehydrogenase | X79068 | *Thermoactinomyces intermedius* | 638 | 49 |
| ORF619 | 606843 | 607493 | inorganic pyrophosphatase | X57545 | *Arabidopsis thaliana* | 291 | 37 |
| ORF620 | 609068 | 608031 | beta-ketoacyl-ACP synthase | L13242 | *Ricinus communis* | 1069 | 57 |
| ORF621 | 609652 | 609296 | HI0034 homolog | U82598 | *Escherichia coli* | 196 | 36 |
| ORF622 | 611860 | 610109 | putative | | | | |
| ORF623 | 611812 | 612927 | conserved hypothetical protein | AE000579 | *Helicobacter pylori* | 780 | 41 |
| ORF624 | 613597 | 612938 | trna delta(2)-isopentenylpyrophosphate transferase | Z98209 | *Mycobacterium tuberculosis* | 244 | 37 |
| ORF625 | 613952 | 613692 | delta2-isopentenylpyrophosphate tRNA transferase | Z11831 | *Escherichia coli* | 134 | 54 |
| ORF626 | 614315 | 615244 | putative | | | | |
| ORF627 | 615396 | 615683 | unknown | Z74024 | *Mycobacterium tuberculosis* | 93 | 47 |
| ORF628 | 617711 | 615864 | D-alanine:D-alanine ligase | U39788 | *Enterococcus hirae* | 555 | 38 |
| ORF629 | 618313 | 617510 | UDP-N-acetylmuramate-alanine ligase (murC) | U32794 | *Haemophilus influenzae* | 448 | 47 |
| ORF630 | 619338 | 618361 | transferase, peptidoglycan synthesis (murG) | U32793 | *Haemophilus influenzae* | 380 | 39 |
| ORF631 | 620416 | 619247 | spoVE gene product (AA 1-366) | X51419 | *Bacillus subtilis* | 538 | 37 |
| ORF632 | 619863 | 620261 | putative | | | | |
| ORF633 | 621184 | 620420 | hypothetical protein | Y14079 | *Bacillus subtilis* | 313 | 44 |
| ORF634 | 621690 | 621541 | murD gene product (AA 1-438) | X51584 | *Escherichia coli* | 221 | 43 |
| ORF635 | 622399 | 621674 | MurD | Z95388 | *Mycobacterium tuberculosis* | 228 | 41 |
| ORF636 | 623466 | 622414 | ORF-Y (AA 1-360) | X51584 | *Escherichia coli* | 543 | 45 |
| ORF637 | 624178 | 623570 | PROBABLE UDP-N-ACETYLMURAMOYLALANYL-D-GLUTAMYL-2,6-DIAMINOLIGASE (EC 6.3.2.15). | AB001488 | *Bacillus subtilis* | 103 | 43 |

TABLE 1-continued

| ORF | begin | stop | Homology | ID | Species | Score | I % |
|---|---|---|---|---|---|---|---|
| ORF638 | 624918 | 624073 | UDP-N-acetylmuramoylalanyl-D glutamyl-2,6-diaminopimelate--D-alanyl-D-alanine ligase | X62437 | Synechocystis sp. | 243 | 33 |
| ORF639 | 625346 | 626665 | chaperonin 60 | U56021 | Thermoanaerobacter brockii | 136 | 31 |
| ORF640 | 626514 | 626900 | putative | | | | |
| ORF641 | 626954 | 627853 | putative | | | | |
| ORF642 | 627822 | 628124 | putative | | | | |
| ORF643 | 628715 | 628146 | elongation factor P | U14003 | Escherichia coli | 467 | 55 |
| ORF644 | 628932 | 629801 | AMP nucleosidase (EC 3.2.2.4). | D90837 | Escherichia coli | 278 | 47 |
| ORF645 | 630406 | 629804 | transketolase | Z73234 | Bacillus subtilis | 361 | 46 |
| ORF646 | 630960 | 630298 | transketolase | Z73234 | Bacillus subtilis | 460 | 47 |
| ORF647 | 631799 | 630915 | transketolase 1 (TK 1) (tktA) | U32783 | Haemophilus influenzae | 756 | 47 |
| ORF648 | 637488 | 638084 | alanyl-tRNA synthetase | X59956 | Rhizobium leguminosarum | 436 | 56 |
| ORF649 | 638036 | 640207 | alanyl-tRNA synthetase | X95571 | Thiobacillus ferrooxidans | 1121 | 39 |
| ORF650 | 640221 | 643472 | transcription-repair coupling factor (trcF) (mfd) | U32805 | Haemophilus influenzae | 1426 | 46 |
| ORF651 | 640627 | 640220 | putative | | | | |
| ORF652 | 643485 | 644495 | uroporphyrinogen decarboxylase | M97208 | Bacillus subtilis | 416 | 40 |
| ORF653 | 644471 | 645430 | putative oxygen-independent coproporphyrinogen III oxidase | U06779 | Salmonella typhimurium | 638 | 43 |
| ORF654 | 645394 | 645840 | oxygen independent coprophorphyrinogen III oxidase | D90912 | Synechocystis sp. | 283 | 42 |
| ORF655 | 645840 | 647111 | hemY | M97208 | Bacillus subtilis | 133 | 38 |
| ORF656 | 649676 | 647109 | phosphoprotein | L25078 | Chlamydia trachomatis | 2043 | 99 |
| ORF657 | 649970 | 650344 | Hcl | M60902 | Chlamydia trachomatis | 603 | 100 |
| ORF658 | 650418 | 651722 | pCTHom1 gene product | M94254 | Chlamydia trachomatis | 1735 | 100 |
| ORF659 | 651686 | 652171 | putative | | | | |
| ORF660 | 652516 | 652908 | phenolhydroxylase component | U32702 | Haemophilus influenzae | 263 | 41 |
| ORF661 | 652799 | 653593 | phenolhydroxylase component | U32702 | Haemophilus influenzae | 456 | 51 |
| ORF662 | 659884 | 661851 | YtpT | AF008220 | Bacillus subtilis | 709 | 52 |
| ORF663 | 661740 | 662282 | spoIIIEB protein | M17445 | Bacillus subtilis | 330 | 43 |
| ORF664 | 662286 | 663074 | yycJ | D78193 | Bacillus subtilis | 405 | 38 |
| ORF665 | 662951 | 663730 | C41G7.4 | Z81048 | Caenorhabditis elegans | 200 | 36 |
| ORF666 | 664212 | 663745 | hypothetical protein MTCY180.08 | Z97193 | Mycobacterium tuberculosis | 194 | 38 |
| ORF667 | 665619 | 664255 | D-alanine glycine permease (dagA) | AE000603 | Helicobacter pylori | 205 | 34 |
| ORF668 | 666083 | 665727 | putative | | | | |
| ORF669 | 666423 | 665782 | putative | | | | |
| ORF670 | 666831 | 668117 | putative | | | | |
| ORF671 | 668121 | 668375 | putative | | | | |
| ORF672 | 668470 | 668174 | riboflavin synthase beta chain (ribE) | U32810 | Haemophilus influenzae | 192 | 40 |
| ORF673 | 669533 | 668616 | GTP cyclohydrolase II/3,4-dihydroxy-2-butanone-4-phoshate synthase | AJ000053 | Arabidopsis thaliana | 800 | 51 |
| ORF674 | 669892 | 669485 | unnamed protein product | A38767 | Saccharomyces cerevisiae | 288 | 49 |
| ORF675 | 670780 | 669998 | ribG gene product | L09228 | Bacillus subtilis | 191 | 42 |
| ORF676 | 671241 | 670732 | riboflavin-specific deaminase | U27202 | Actinobacillus pleuropneumoniae | 314 | 51 |
| ORF677 | 671182 | 672447 | seryl-tRNA synthetase | X91007 | Haloarcula marismortui | 736 | 49 |
| ORF678 | 672692 | 673231 | putative | | | | |
| ORF679 | 673204 | 674562 | ATPase | L28104 | Transposon Tn5422 | 565 | 41 |
| ORF680 | 674612 | 675232 | unknown | Z74025 | Mycobacterium tuberculosis | 340 | 43 |
| ORF681 | 675327 | 676463 | rod-shape-determining protein | M22857 | Escherichia coli | 442 | 37 |
| ORF682 | 677027 | 676476 | biotin [acetyl-CoA carboxylase] ligase | L02354 | Paracoccus denitrificans | 169 | 49 |
| ORF683 | 678422 | 677700 | ORFX13 | L09228 | Bacillus subtilis | 426 | 43 |
| ORF684 | 678717 | 679508 | 2,3-bisphosphoglycerate | M23068 | Homo sapiens | 494 | 47 |
| ORF685 | 679342 | 680502 | synthesis of [Fe—S] cluster (nifS) | AE000542 | Helicobacter pylori | 150 | 33 |
| ORF686 | 680579 | 681280 | NifU | AF001780 | Cyanothece PCC 8801 | 101 | 31 |
| ORF687 | 681539 | 682558 | putative | | | | |
| ORF688 | 682554 | 683087 | putative | | | | |
| ORF689 | 683164 | 684465 | ORF 4 | M72718 | Bacillus subtilis | 708 | 36 |
| ORF690 | 684774 | 684418 | putative | | | | |
| ORF691 | 684839 | 686203 | AgX-1 antigen [human, infertile patient, testis, Peptide, 505 aa] | S73498 | Homo sapiens | 338 | 37 |
| ORF692 | 686197 | 687204 | L-glycerol 3-phosphate dehydrogenase | U00039 | Escherichia coli | 577 | 38 |
| ORF693 | 687341 | 688360 | putative | | | | |
| ORF694 | 688432 | 688193 | putative | | | | |
| ORF695 | 689616 | 688432 | putative | | | | |
| ORF696 | 689960 | 689631 | putative | | | | |
| ORF697 | 690487 | 689846 | putative | | | | |
| ORF698 | 690717 | 690463 | putative | | | | |
| ORF699 | 691871 | 690672 | putative | | | | |
| ORF700 | 693837 | 692041 | phosphoenolpyruvate carboxykinase | M59372 | Neocallimastix frontalis | 1818 | 59 |
| ORF701 | 694934 | 693837 | MreB protein | M96343 | Bacillus subtilis | 961 | 56 |
| ORF702 | 697263 | 694942 | SNF | X98455 | Bacillus cereus | 1073 | 50 |
| ORF703 | 698084 | 697170 | putative | | | | |
| ORF704 | 698392 | 697979 | putative | | | | |
| ORF705 | 698792 | 700117 | trigger factor (tig) | AE000591 | Helicobacter pylori | 84 | 34 |
| ORF706 | 700269 | 700895 | proteosome major subunit | AF013216 | Myxococcus xanthus | 615 | 59 |
| ORF707 | 700912 | 702165 | ATP-dependent protease ATPase subunit | L18867 | Escherichia coli | 1183 | 55 |

TABLE 1-continued

| ORF | begin | stop | Homology | ID | Species | Score | I % |
|---|---|---|---|---|---|---|---|
| ORF708 | 702183 | 703412 | poly(A) polymerase | L47709 | *Bacillus subtilis* | 362 | 38 |
| ORF709 | 703522 | 705000 | hypothetical protein | D90912 | *Synechocystis* sp. | 809 | 41 |
| ORF710 | 705011 | 705604 | putative | | | | |
| ORF711 | 706159 | 705704 | Preprotein translocase subunit | AF022186 | *Cyanidium caldarium* | 165 | 44 |
| ORF712 | 706521 | 706138 | secA | X99401 | *Bacillus firmus* | 155 | 42 |
| ORF713 | 708103 | 706496 | SecA | U66081 | *Mycobacterium smegmatis* | 1044 | 58 |
| ORF714 | 708398 | 708078 | cp-SecA; chloroplast SecA homolog | U71123 | *Zea mays* | 258 | 69 |
| ORF715 | 708610 | 708248 | SecA | U21192 | *Streptomyces lividans* | 179 | 42 |
| ORF716 | 710278 | 708872 | putative | | | | |
| ORF717 | 711164 | 710262 | phosphatidylserine decarboxylase | U72715 | *Chlamydia trachomatis* | 1548 | 99 |
| ORF718 | 711432 | 712763 | homologous to *E. coli* 50K | X62539 | *Bacillus subtilis* | 713 | 54 |
| ORF719 | 712767 | 713438 | ultraviolet N-glycosylase/AP lyase | U22181 | *Micrococcus luteus* | 273 | 45 |
| ORF720 | 714232 | 713651 | putative | | | | |
| ORF721 | 714632 | 714120 | putative | | | | |
| ORF722 | 715592 | 714834 | putative | | | | |
| ORF723 | 715854 | 715558 | putative | | | | |
| ORF724 | 716937 | 715921 | putative | | | | |
| ORF725 | 718357 | 717149 | 3-phosphoglycerate kinase | U83197 | *Chlamydia trachomatis* | 2049 | 100 |
| ORF726 | 718500 | 718862 | putative | | | | |
| ORF727 | 719797 | 718499 | phosphate permease (YBR296C) | U32834 | *Haemophilus influenzae* | 997 | 42 |
| ORF728 | 720273 | 719782 | putative | | | | |
| ORF729 | 720452 | 720144 | *H. influenzae* predicted coding region HI1603 | U32834 | *Haemophilus influenzae* | 164 | 37 |
| ORF730 | 720613 | 721575 | dciAD | X56678 | *Bacillus subtilis* | 722 | 41 |
| ORF731 | 721559 | 722356 | was dppE | U00039 | *Escherichia coli* | 477 | 44 |
| ORF732 | 723248 | 722397 | chromosome partitioning protein ParB | U87804 | *Caulobacter crescentus* | 388 | 50 |
| ORF733 | 724598 | 723378 | NifS protein. | D90811 | *Escherichia coli* | 805 | 39 |
| ORF734 | 725763 | 724576 | hypothetical protein | D64004 | *Synechocystis* sp. | 154 | 41 |
| ORF735 | 726519 | 725767 | Multidrug resistance protein 1 (P-glycoprotein 1). | D90811 | *Escherichia coli* | 607 | 54 |
| ORF736 | 726819 | 726538 | ABC transporter subunit | D64004 | *Synechocystis* sp. | 266 | 58 |
| ORF737 | 727493 | 726753 | ABC transporter subunit | D64004 | *Synechocystis* sp. | 854 | 71 |
| ORF738 | 727984 | 727469 | ABC transporter subunit | D64004 | *Synechocystis* sp. | 531 | 55 |
| ORF739 | 728778 | 728329 | putative | | | | |
| ORF740 | 729346 | 728759 | antiviral protein | L36940 | *Saccharomyces cerevisiae* | 115 | 33 |
| ORF741 | 732639 | 729442 | penicillin-binding protein 2 (pbp2) | U32688 | *Haemophilus influenzae* | 208 | 43 |
| ORF742 | 733246 | 734427 | major outer membrane protein precursor | M14738 | *Chlamydia trachomatis* | 2045 | 99 |
| ORF743 | 734814 | 735659 | ribosomal protein S2 | U60196 | *Chlamydia trachomatis* | 1269 | 76 |
| ORF744 | 735644 | 736504 | elongation factor Ts | U60196 | *Chlamydia trachomatis* | 1278 | 90 |
| ORF745 | 736520 | 737254 | UMP kinase | U60196 | *Chlamydia trachomatis* | 1153 | 94 |
| ORF746 | 737254 | 737787 | ribosome-releasing factor | U60196 | *Chlamydia trachomatis* | 760 | 92 |
| ORF747 | 737942 | 738679 | putative | | | | |
| ORF748 | 738838 | 739740 | ORF3; putative 39 kDa protein | U40604 | *Listeria monocytogenes* | 116 | 31 |
| ORF749 | 742057 | 740060 | XcpQ | X68594 | *Pseudomonas aeruginosa* | 453 | 37 |
| ORF750 | 742869 | 742045 | putative | | | | |
| ORF751 | 743378 | 742824 | putative | | | | |
| ORF752 | 744298 | 743306 | unknown | Z80233 | *Mycobacterium tuberculosis* | 137 | 40 |
| ORF753 | 744714 | 744430 | putative | M69228 | *Caulobacter crescentus* | 117 | 38 |
| ORF754 | 744985 | 744611 | putative | | | | |
| ORF755 | 745557 | 744958 | putative | | | | |
| ORF756 | 746412 | 745561 | putative | | | | |
| ORF757 | 746772 | 746416 | putative | | | | |
| ORF758 | 748269 | 746944 | PscN | AF010151 | *Pseudomonas aeruginosa* | 1220 | 55 |
| ORF759 | 748966 | 748274 | putative | | | | |
| ORF760 | 749426 | 748965 | putative | | | | |
| ORF761 | 749702 | 749433 | putative | | | | |
| ORF762 | 750029 | 749721 | putative | | | | |
| ORF763 | 752307 | 750007 | putative | | | | |
| ORF764 | 752913 | 752503 | putative | | | | |
| ORF765 | 754659 | 753616 | NAD(P)H:glutamyl-transfer RNA reductase | M57676 | *Bacillus subtilis* | 172 | 40 |
| ORF766 | 755000 | 756814 | DNA gyrase subunit B | U35453 | *Clostridium acetobutylicum* | 970 | 38 |
| ORF767 | 756796 | 758301 | gyrA | X92503 | *Mycobacterium smegmatis* | 409 | 49 |
| ORF768 | 758691 | 758446 | unknown | Z74024 | *Mycobacterium tuberculosis* | 107 | 34 |
| ORF769 | 759787 | 759338 | SfhB | U50134 | *Escherichia coli* | 241 | 48 |
| ORF770 | 760242 | 759871 | putative | | | | |
| ORF771 | 760538 | 760188 | putative | | | | |
| ORF772 | 760966 | 761772 | 3-deoxy-D-manno-octulosonate 8-phosphate synthetase | U72493 | *Chlamydia trachomatis* | 1350 | 99 |
| ORF773 | 761759 | 762142 | unknown | U72493 | *Chlamydia trachomatis* | 536 | 94 |
| ORF774 | 762267 | 762983 | ATP binding protein | U72493 | *Chlamydia trachomatis* | 1197 | 99 |
| ORF775 | 764465 | 763335 | chlanectin coding region | M17875 | *Chlamydia trachomatis* | 239 | 100 |
| ORF776 | 764857 | 764438 | putative | | | | |
| ORF777 | 766068 | 764821 | unknown function | Z32530 | *Chlamydia trachomatis* | 1803 | 99 |
| ORF778 | 766643 | 766065 | unknown function | Z32530 | *Chlamydia trachomatis* | 704 | 100 |
| ORF779 | 768091 | 766934 | RecA | U16739 | *Chlamydia trachomatis* | 1753 | 100 |
| ORF780 | 768785 | 768252 | unknown function | Z32530 | *Chlamydia trachomatis* | 904 | 99 |
| ORF781 | 770092 | 768791 | unknown function | Z32530 | *Chlamydia trachomatis* | 2249 | 100 |
| ORF782 | 770138 | 770470 | putative | | | | |
| ORF783 | 770661 | 770185 | putative | | | | |

TABLE 1-continued

| ORF | begin | stop | Homology | ID | Species | Score | I % |
|---|---|---|---|---|---|---|---|
| ORF784 | 770924 | 770634 | putative | | | | |
| ORF785 | 772010 | 771330 | putative | | | | |
| ORF786 | 772390 | 773391 | unknown | D26185 | Bacillus subtilis | 486 | 35 |
| ORF787 | 774221 | 773427 | ORF_f169 | U18997 | Escherichia coli | 263 | 51 |
| ORF788 | 776035 | 774191 | DNA topoisomerase I | L27797 | Bacillus subtilis | 1357 | 52 |
| ORF789 | 776663 | 777706 | putative | | | | |
| ORF790 | 777195 | 776953 | putative | | | | |
| ORF791 | 779222 | 777732 | ORF_f397 | U29581 | Escherichia coli | 93 | 40 |
| ORF792 | 779321 | 781552 | putative | | | | |
| ORF793 | 781297 | 782442 | putative | | | | |
| ORF794 | 782447 | 785524 | exonuclease V (AA 1-1180) | X04581 | Escherichia coli | 557 | 49 |
| ORF795 | 785532 | 786002 | putative | | | | |
| ORF796 | 786580 | 785546 | MreC protein | M31792 | Escherichia coli | 81 | 64 |
| ORF797 | 787741 | 786611 | aspartate aminotransferase precursor | M12105 | Gallus gallus | 700 | 42 |
| ORF798 | 787620 | 788021 | putative | | | | |
| ORF799 | 790124 | 787920 | GreA | U02878 | Rickettsia prowazekii | 84 | 33 |
| ORF800 | 790160 | 790609 | putative | | | | |
| ORF801 | 790634 | 792016 | NADH:ubiquinone oxidoreductase subunit A | Z37111 | Vibrio alginolyticus | 409 | 37 |
| ORF802 | 793084 | 792059 | delta_aminolevulinic acid dehydratase | L24386 | Bradyrhizobium japonicum | 867 | 52 |
| ORF803 | 793343 | 794056 | putative | | | | |
| ORF804 | 794046 | 794957 | putative | | | | |
| ORF805 | 795401 | 795144 | putative | | | | |
| ORF806 | 795575 | 796255 | ompR gene product | X92405 | Neisseria meningitidis | 103 | 32 |
| ORF807 | 796278 | 797015 | glucose-1-phosphate thymidylyltransferase | U67553 | Methanococcus jannaschii | 216 | 36 |
| ORF808 | 796979 | 797365 | YqiD | D84432 | Bacillus subtilis | 184 | 58 |
| ORF809 | 797260 | 797856 | farnesyl diphosphate synthase | D13293 | Bacillus stearothermophilus | 107 | 37 |
| ORF810 | 797772 | 798086 | putative | | | | |
| ORF811 | 798426 | 797935 | Orf39.9 | X61000 | Escherichia coli | 290 | 51 |
| ORF812 | 798925 | 798416 | This ORF is homologous to a 40.0 kd hypothetical protein in the htrB 3' region from E. coli, Accession Number X61000 | L22217 | Mycoplasma-like organism | 150 | 46 |
| ORF813 | 799301 | 799927 | ribosomal protein S4 (rps4) | AE000633 | Helicobacter pylori | 407 | 46 |
| ORF814 | 800892 | 800029 | apurinic/apyrimidinic endonuclease | U40707 | Caenorhabditis elegans | 397 | 35 |
| ORF815 | 801062 | 802129 | mviB homolog | U50732 | Chlamydia trachomatis | 1716 | 97 |
| ORF816 | 802851 | 802673 | mviB homolog | U50732 | Chlamydia trachomatis | 973 | 97 |
| ORF817 | 802851 | 803246 | lorf2; possible membrane-bound protein | U50732 | Chlamydia trachomatis | 280 | 100 |
| ORF818 | 803105 | 804220 | 76 kDa protein | L23921 | Chlamydia pneumoniae | 775 | 59 |
| ORF819 | 804307 | 805356 | putative | | | | |
| ORF820 | 805290 | 806282 | 76 kDa protein | L23921 | Chlamydia pneumoniae | 125 | 50 |
| ORF821 | 806453 | 808081 | putative | | | | |
| ORF822 | 808026 | 809009 | putative | | | | |
| ORF823 | 810461 | 809079 | putative | | | | |
| ORF824 | 811605 | 810328 | putative | | | | |
| ORF825 | 811725 | 812342 | putative | | | | |
| ORF826 | 812329 | 813522 | putative | | | | |
| ORF827 | 813455 | 813772 | putative | | | | |
| ORF828 | 813732 | 814334 | putative | | | | |
| ORF829 | 815213 | 814314 | putative | | | | |
| ORF830 | 814878 | 814396 | putative | | | | |
| ORF831 | 815733 | 815428 | 30S ribosomal protein S20 | Z67753 | Odontella sinensis | 150 | 38 |
| ORF832 | 816116 | 817456 | KIAA0336 | AB002334 | Homo sapiens | 90 | 32 |
| ORF833 | 817608 | 819320 | RNA polymerase sigma-subunit | J05546 | Chlamydia trachomatis | 2868 | 100 |
| ORF834 | 819324 | 819713 | putative | | | | |
| ORF835 | 819704 | 820402 | dihydropterin pyrophosphokinase/ dihydropteroate synthase | Y08611 | Pisum sativum | 310 | 45 |
| ORF836 | 820375 | 821061 | dihydropteroate synthase | X68068 | Neisseria meningitidis | 100 | 48 |
| ORF837 | 821043 | 821537 | dihydrofolate reductase | Z84379 | Streptococcus pneumoniae | 168 | 45 |
| ORF838 | 821646 | 822239 | M. jannaschii predicted coding region MJ0768 | U67522 | Methanococcus jannaschii | 139 | 41 |
| ORF839 | 822182 | 822931 | putative | | | | |
| ORF840 | 824355 | 823045 | nitrogen metabolism regulator | M58480 | Thiobacillus ferrooxidans | 133 | 58 |
| ORF841 | 825894 | 824359 | helicase | M63176 | Staphylococcus aureus | 893 | 50 |
| ORF842 | 826322 | 825879 | helicase | M63176 | Staphylococcus aureus | 282 | 47 |
| ORF843 | 826340 | 827026 | ipa-57d gene product | X73124 | Bacillus subtilis | 602 | 52 |
| ORF844 | 827014 | 827250 | putative | | | | |
| ORF845 | 827856 | 827230 | hypothetical | U32712 | Haemophilus influenzae | 302 | 45 |
| ORF846 | 828007 | 829275 | 19/20 residue stretch (32-51) identical to N-terminal putative signal sequence of unknown, partly cloned B. subtilis gene.; putative | L19954 | Bacillus subtilis | 442 | 37 |
| ORF847 | 829355 | 830953 | heat shock protein GroEL | U55047 | Bradyrhizobium japonicum | 418 | 36 |
| ORF848 | 831119 | 831748 | bas1 protein | Z34917 | Hordeum vulgare | 516 | 47 |
| ORF849 | 832152 | 831751 | putative | | | | |
| ORF850 | 832744 | 832214 | putative | | | | |
| ORF851 | 833446 | 832805 | putative | | | | |
| ORF852 | 833802 | 833368 | putative | | | | |
| ORF853 | 834679 | 833879 | putative | | | | |
| ORF854 | 835452 | 834661 | putative | | | | |
| ORF855 | 835778 | 835371 | putative | | | | |

TABLE 1-continued

| ORF | begin | stop | Homology | ID | Species | Score | I % |
|---|---|---|---|---|---|---|---|
| ORF856 | 836482 | 835775 | putative | | | | |
| ORF857 | 836602 | 837264 | putative | | | | |
| ORF858 | 837209 | 838699 | putative | | | | |
| ORF859 | 838760 | 839575 | putative | | | | |
| ORF860 | 839942 | 840583 | putative | | | | |
| ORF861 | 840445 | 841713 | putative | | | | |
| ORF862 | 841659 | 842459 | putative | | | | |
| ORF863 | 842523 | 843068 | putative | | | | |
| ORF864 | 843495 | 843031 | putative | | | | |
| ORF865 | 843239 | 846196 | putative | | | | |
| ORF866 | 844137 | 843802 | putative | | | | |
| ORF867 | 848043 | 846217 | putative | | | | |
| ORF868 | 850123 | 848150 | putative | | | | |
| ORF869 | 851645 | 850230 | putative | | | | |
| ORF870 | 853696 | 851669 | putative | | | | |
| ORF871 | 854836 | 853700 | putative | | | | |
| ORF872 | 855525 | 854920 | putative | | | | |
| ORF873 | 856240 | 855437 | putative | | | | |
| ORF874 | 857183 | 856233 | putative | | | | |
| ORF875 | 859439 | 857451 | putative | | | | |
| ORF876 | 859946 | 859587 | putative | | | | |
| ORF877 | 859642 | 860640 | putative | | | | |
| ORF878 | 861599 | 860724 | putative | | | | |
| ORF879 | 862053 | 861580 | putative | | | | |
| ORF880 | 863540 | 862098 | putative | | | | |
| ORF881 | 863930 | 863571 | putative | | | | |
| ORF882 | 864697 | 863996 | putative | | | | |
| ORF883 | 864923 | 866248 | DNA mismatch repair protein (mutL) | U32692 | Haemophilus influenzae | 506 | 47 |
| ORF884 | 866303 | 866605 | putative | | | | |
| ORF885 | 866665 | 867732 | YqhT | D84432 | Bacillus subtilis | 444 | 39 |
| ORF886 | 867810 | 869090 | putative | | | | |
| ORF887 | 869094 | 869357 | putative | | | | |
| ORF888 | 869270 | 871372 | fimbrial assembly protein | L13865 | Pseudomonas aeruginosa | 181 | 40 |
| ORF889 | 871299 | 872582 | xpsE gene product | X59079 | Xanthomonas campestris | 825 | 56 |
| ORF890 | 872429 | 872860 | secretion protein XcpR | Y09102 | Acinetobacter calcoaceticus | 213 | 48 |
| ORF891 | 872773 | 873915 | ORF_o398 | U18997 | Escherichia coli | 271 | 33 |
| ORF892 | 873812 | 873360 | putative | | | | |
| ORF893 | 874028 | 874438 | putative | | | | |
| ORF894 | 874778 | 875386 | putative | | | | |
| ORF895 | 875774 | 876382 | putative | | | | |
| ORF896 | 877872 | 877000 | secretion system apparatus, SsaT | X99944 | Salmonella typhimurium | 174 | 34 |
| ORF897 | 878172 | 877876 | yscS | L25667 | Yersinia pseudotuberculosis | 172 | 44 |
| ORF898 | 879098 | 878172 | pathogenicity protein | M64094 | Xanthomonas campestris | 464 | 46 |
| ORF899 | 878883 | 879161 | putative | | | | |
| ORF900 | 879842 | 879105 | PscL | U56077 | Pseudomonas aeruginosa | 141 | 34 |
| ORF901 | 880885 | 880052 | putative | | | | |
| ORF902 | 881863 | 880889 | HrcJ | U56662 | Erwinia amylovora | 236 | 43 |
| ORF903 | 882904 | 881948 | ORF YOR196c | Z75104 | Saccharomyces cerevisiae | 685 | 44 |
| ORF904 | 883794 | 882901 | dihydrolipoamide dehydrogenase | L31844 | Clostridium magnum | 578 | 38 |
| ORF905 | 884296 | 883661 | YqiV | D84432 | Bacillus subtilis | 437 | 44 |
| ORF906 | 884996 | 884508 | putative | | | | |
| ORF907 | 888777 | 885166 | helicase of the snf2/rad54 family | D90916 | Synechocystis sp. | 824 | 43 |
| ORF908 | 890172 | 888940 | sodium-coupled branched-chain amino acid carrier | D49784 | Clostridium perfringens | 230 | 35 |
| ORF909 | 891164 | 890325 | putative Fmu protein | Y13937 | Bacillus subtilis | 220 | 41 |
| ORF910 | 891463 | 891116 | putative | | | | |
| ORF911 | 893278 | 891968 | DD-carboxypeptidase | M85047 | Bacillus subtilis | 302 | 39 |
| ORF912 | 893356 | 893808 | putative | | | | |
| ORF913 | 893909 | 893643 | putative | | | | |
| ORF914 | 894276 | 893821 | hypothetical protein | D90908 | Synechocystis sp. | 155 | 39 |
| ORF915 | 894778 | 894248 | putative | | | | |
| ORF916 | 895892 | 895050 | putative | | | | |
| ORF917 | 895951 | 896829 | putative | | | | |
| ORF918 | 900783 | 897064 | DNA polymerase III alpha-subunit (dnaE) | AE000646 | Helicobacter pylori | 1974 | 43 |
| ORF919 | 902032 | 900791 | UhpC protein | M17102 | Escherichia coli | 1117 | 52 |
| ORF920 | 902659 | 903876 | histidine--tRNA ligase | Z17214 | Streptococcus equisimilis | 686 | 47 |
| ORF921 | 903731 | 903471 | putative | | | | |
| ORF922 | 903860 | 905605 | aspartyl-tRNA synthetase | D90910 | Synechocystis sp. | 1339 | 51 |
| ORF923 | 905725 | 906474 | mip-like protein | X66126 | Chlamydia trachomatis | 1196 | 98 |
| ORF924 | 906493 | 906945 | spoU | L40369 | Chlamydia trachomatis | 607 | 100 |
| ORF925 | 907306 | 907001 | trxA | L39892 | Chlamydia psittaci | 380 | 76 |
| ORF926 | 908101 | 908742 | putative | | | | |
| ORF927 | 908721 | 909194 | hypothetical protein | D90914 | Synechocystis sp. | 150 | 37 |
| ORF928 | 909198 | 909584 | DNA polymerase III | Z48003 | Staphylococcus aureus | 181 | 40 |
| ORF929 | 909583 | 909951 | putative | | | | |
| ORF930 | 910081 | 910569 | VdlD | U94318 | Helicobacter pylori | 197 | 43 |
| ORF931 | 910615 | 910944 | putative | | | | |
| ORF932 | 910948 | 912261 | acid-inducible gene | L13845 | Sinorhizobium meliloti | 145 | 50 |

TABLE 1-continued

| ORF | begin | stop | Homology | ID | Species | Score | I % |
|---|---|---|---|---|---|---|---|
| ORF933 | 912399 | 912629 | putative | | | | |
| ORF934 | 912595 | 913218 | UDP-3-O-acyl-GlcNAc deacetylase | U67855 | Pseudomonas aeruginosa | 309 | 39 |
| ORF935 | 913203 | 913676 | (3R)-hydroxymyristol acyl carrier protein dehydrase | D90910 | Synechocystis sp. | 302 | 59 |
| ORF936 | 913691 | 914485 | UDP-N-acetylglucosamine acyltransferase | L22690 | Rickettsia rickettsii | 503 | 38 |
| ORF937 | 914516 | 915136 | methionyl-tRNA formyltransferase | X63666 | Escherichia coli | 407 | 42 |
| ORF938 | 915144 | 915467 | putative | | | | |
| ORF939 | 915629 | 916633 | putative | | | | |
| ORF940 | 916051 | 916539 | putative | | | | |
| ORF941 | 916965 | 917627 | ribosomal protein L3 (rpL3) | U32761 | Haemophilus influenzae | 470 | 48 |
| ORF942 | 917612 | 918304 | 50S ribosomal protein L4 | AB000111 | Synechococcus sp. | 210 | 43 |
| ORF943 | 918323 | 918655 | ribosomal protein L23 | Z21677 | Thermotoga maritima | 116 | 47 |
| ORF944 | 918682 | 919533 | rpl2 | M74770 | Mycoplasma-like organism | 800 | 48 |
| ORF945 | 919542 | 919829 | Mycoplasma pneumoniae, ribosomal protein S19; similar to GenBank Accession Number S36895, from M. bovis | AE000061 | Mycoplasma pneumoniae | 315 | 68 |
| ORF946 | 919723 | 920157 | ribosomal protein L22 | Z21677 | Thermotoga maritima | 240 | 49 |
| ORF947 | 920184 | 920840 | ribosomal protein S3 (rpS3) | U32761 | Haemophilus influenzae | 605 | 57 |
| ORF948 | 920866 | 921294 | ribosomal protein L16 | Z21677 | Thermotoga maritima | 434 | 62 |
| ORF949 | 921272 | 921514 | ribosomal protein CtrL29e | M80325 | Chlamydia trachomatis | 343 | 99 |
| ORF950 | 921510 | 921758 | ribosomal protein S17e | M80325 | Chlamydia trachomatis | 419 | 100 |
| ORF951 | 921778 | 922143 | ribosomal protein CtrL14e | M80325 | Chlamydia trachomatis | 618 | 100 |
| ORF952 | 922159 | 922491 | ribosomal protein CtrL24e | M80325 | Chlamydia trachomatis | 568 | 100 |
| ORF953 | 922496 | 923035 | ribosomal protein CtrL5e | M80325 | Chlamydia trachomatis | 793 | 99 |
| ORF954 | 923160 | 923453 | ribosomal protein CtrS8e | M80325 | Chlamydia trachomatis | 487 | 98 |
| ORF955 | 923484 | 924032 | ribosomal protein L6 | M60652 | Chlamydia trachomatis | 927 | 100 |
| ORF956 | 924048 | 924425 | ribosomal protein CtrL18e | M80325 | Chlamydia trachomatis | 605 | 99 |
| ORF957 | 924443 | 924937 | ribosomal protein CtrS5e | M80325 | Chlamydia trachomatis | 814 | 99 |
| ORF958 | 924933 | 925364 | ribosomal protein CtrL15e | M80325 | Chlamydia trachomatis | 740 | 99 |
| ORF959 | 925390 | 926760 | homolog | L25077 | Chlamydia trachomatis | 2254 | 99 |
| ORF960 | 926819 | 927184 | ribosomal protein S13 | L33834 | Chlamydia trachomatis | 604 | 100 |
| ORF961 | 927209 | 927604 | ribosomal protein S11 | L33834 | Chlamydia trachomatis | 646 | 98 |
| ORF962 | 927577 | 928155 | RNA polymerase alpha-subunit | L33834 | Chlamydia trachomatis | 847 | 97 |
| ORF963 | 928100 | 928759 | RNA polymerase alpha-subunit | L33834 | Chlamydia trachomatis | 1040 | 98 |
| ORF964 | 929222 | 930244 | glyceraldehyde-3-phosphate dehydrogenase | U83198 | Chlamydia trachomatis | 1735 | 99 |
| ORF965 | 930222 | 930656 | putative | | | | |
| ORF966 | 930608 | 931078 | putative | | | | |
| ORF967 | 931367 | 931666 | putative | | | | |
| ORF968 | 931549 | 931959 | putative | | | | |
| ORF969 | 932070 | 932579 | crossover junction endodeoxyribonuclease (ruvC) | U32717 | Haemophilus influenzae | 250 | 41 |
| ORF970 | 932602 | 933201 | Holliday junction DNA helicase (ruvA) | U32716 | Haemophilus influenzae | 258 | 38 |
| ORF971 | 933319 | 933621 | nucleoside diphosphate kinase (ndk) | AE000540 | Helicobacter pylori | 264 | 60 |
| ORF972 | 933522 | 933785 | nucleoside 5'-diphosphate phosphotransferase (EC 2.7.4.6) | J05207 | Myxococcus xanthus | 186 | 64 |
| ORF973 | 934546 | 933848 | hypothetical protein (GB: U14003_297) | U39706 | Mycoplasma genitalium | 156 | 36 |
| ORF974 | 936377 | 934539 | homologous to E. coli gidA | X62540 | Pseudomonas putida | 1562 | 51 |
| ORF975 | 938081 | 936666 | replicative DNA helicase | D26185 | Bacillus subtilis | 848 | 41 |
| ORF976 | 938538 | 939098 | phosphatidylglycerophosphate synthase (pgsA) | AE000610 | Helicobacter pylori | 120 | 33 |
| ORF977 | 939329 | 940933 | adenine nucleotide translocase | Z49227 | Arabidopsis thaliana | 668 | 40 |
| ORF978 | 941031 | 942068 | putative protease | AF008220 | Bacillus subtilis | 265 | 36 |
| ORF979 | 942082 | 944685 | DNA polymerase | D12982 | Bacillus caldotenax | 1334 | 42 |
| ORF980 | 944634 | 945287 | T05G5.5 | Z27079 | Caenorhabditis elegans | 198 | 32 |
| ORF981 | 945287 | 946294 | 'The first ATG in the open reading frame was chosen as the initiation codon.' | L27278 | Pseudomonas fluorescens | 882 | 68 |
| ORF982 | 946293 | 946676 | 'The first GTG in the open reading frame was chosen as the initiation codon.' | L27276 | Deinococcus radiodurans | 417 | 65 |
| ORF983 | 947105 | 948454 | ADPglucose pyrophosphorylase | M31616 | Oryza sativa | 755 | 44 |
| ORF984 | 948522 | 949277 | putative | | | | |
| ORF985 | 949277 | 949594 | YlbH protein | Z98682 | Bacillus subtilis | 223 | 41 |
| ORF986 | 949849 | 950676 | putative | | | | |
| ORF987 | 950680 | 951330 | ferrochelatase | M59288 | Mus musculus | 260 | 42 |
| ORF988 | 951281 | 951643 | ferrochelatase | D26106 | Cucumis sativus | 178 | 47 |
| ORF989 | 951788 | 952798 | putative | | | | |
| ORF990 | 953581 | 954264 | putative | | | | |
| ORF991 | 954426 | 955157 | putative | | | | |
| ORF992 | 955754 | 957940 | orf4 gene product | X93084 | Methanosarcina barkeri | 130 | 41 |
| ORF993 | 957837 | 959312 | OppB gene product | X56347 | Bacillus subtilis | 327 | 38 |
| ORF994 | 959299 | 961050 | dipeptide ABC transporter, permease protein (dppC) | AE000548 | Helicobacter pylori | 263 | 39 |
| ORF995 | 961562 | 961053 | methylated DNA protein cysteine methyltransferase | U67593 | Methanococcus jannaschii | 109 | 39 |
| ORF996 | 962575 | 961487 | putative | | | | |
| ORF997 | 961979 | 961584 | putative | | | | |
| ORF998 | 964914 | 962545 | phenylalanyl-tRNA synthetase beta subunit | Z75208 | Bacillus subtilis | 775 | 37 |
| ORF999 | 964941 | 965708 | putative | | | | |
| ORF1000 | 967023 | 966193 | unknown | Z48008 | Saccharomyces cerevisiae | 492 | 44 |

TABLE 1-continued

| ORF | begin | stop | Homology | ID | Species | Score | I % |
|---|---|---|---|---|---|---|---|
| ORF1001 | 967444 | 968061 | putative | | | | |
| ORF1002 | 968903 | 968064 | putative | | | | |
| ORF1003 | 970685 | 969528 | transcriptional activator of pilA | Z12154 | Pseudomonas aeruginosa | 849 | 45 |
| ORF1004 | 971806 | 971024 | sensor protein | L39904 | Myxococcus xanthus | 147 | 30 |
| ORF1005 | 973053 | 972388 | putative | | | | |
| ORF1006 | 974546 | 973746 | unknown | D64126 | Bacillus subtilis | 500 | 50 |
| ORF1007 | 975223 | 974558 | unknown | D26185 | Bacillus subtilis | 141 | 44 |
| ORF1008 | 976193 | 975207 | hypothetical protein in htrA dapD intergenic region | AE000126 | Escherichia coli | 142 | 42 |
| ORF1009 | 976520 | 976254 | unknown | Z49939 | Saccharomyces cerevisiae | 183 | 39 |
| ORF1010 | 976588 | 976899 | putative | | | | |
| ORF1011 | 976886 | 977635 | peptide release factor 2 | X99401 | Bacillus firmus | 534 | 44 |
| ORF1012 | 977661 | 977933 | release factor 2 | AF013188 | Bacillus subtilis | 187 | 52 |
| ORF1013 | 977918 | 978433 | putative | | | | |
| ORF1014 | 978619 | 978984 | spore coat protein CotRC | D50551 | Bacillus subtilis | 355 | 52 |
| ORF1015 | 978933 | 979331 | hypothetical | U32717 | Haemophilus influenzae | 199 | 40 |
| ORF1016 | 981197 | 979389 | putative | | | | |
| ORF1017 | 979711 | 980112 | putative | | | | |
| ORF1018 | 982116 | 981148 | putative | | | | |
| ORF1019 | 982321 | 983598 | UDP-N-acetylglucosamine enolpyruvyl transferase (murZ) | U32788 | Haemophilus influenzae | 593 | 38 |
| ORF1020 | 984488 | 983862 | arginyl-tRNA-synthetase | D64006 | Synechocystis sp. | 347 | 44 |
| ORF1021 | 985381 | 984371 | arginyl-tRNA-synthetase | D64006 | Synechocystis sp. | 782 | 58 |
| ORF1022 | 986103 | 985399 | hypothetical protein | D90915 | Synechocystis sp. | 224 | 35 |
| ORF1023 | 986693 | 986046 | No definition line found | U00021 | Mycobacterium leprae | 286 | 50 |
| ORF1024 | 987607 | 986693 | o298; This 298 aa ORF is 33 pct identical (24 gaps) to 248 residues of an approx. 256 aa protein CDSA_ECOLI SW: P06466 | AE000238 | Escherichia coli | 132 | 46 |
| ORF1025 | 988119 | 987616 | conserved hypothetical protein | AE000627 | Helicobacter pylori | 343 | 49 |
| ORF1026 | 988253 | 987936 | hypothetical protein (HI0920) | U67577 | Methanococcus jannaschii | 110 | 38 |
| ORF1027 | 988831 | 989163 | putative | | | | |
| ORF1028 | 989693 | 993442 | protein-export membrane protein SecD | D64000 | Synechocystis sp. | 447 | 38 |
| ORF1029 | 993408 | 993785 | protein-export membrane protein | U83136 | Rhodobacter sphaeroides | 240 | 43 |
| ORF1030 | 993835 | 993416 | putative | | | | |
| ORF1031 | 993882 | 994262 | putative | | | | |
| ORF1032 | 994226 | 995656 | RecJ recombination protein | U41759 | Chlamydia psittaci | 880 | 66 |
| ORF1033 | 996036 | 996611 | unknown | U41759 | Chlamydia psittaci | 533 | 75 |
| ORF1034 | 996885 | 998267 | glutamyl-tRNA synthetase homolog | U41759 | Chlamydia psittaci | 2018 | 83 |
| ORF1035 | 998962 | 999225 | 9-kDa cysteine-rich outer membrane protein | M35148 | Chlamydia trachomatis | 504 | 100 |
| ORF1036 | 999375 | 1001033 | outer membrane protein 2 | M23001 | Chlamydia trachomatis | 2857 | 100 |
| ORF1037 | 1001211 | 1001516 | 15-kDa serine-rich outer membrane protein | M35148 | Chlamydia trachomatis | 276 | 94 |
| ORF1038 | 1001392 | 1001664 | 15-kDa serine-rich outer membrane protein | M35148 | Chlamydia trachomatis | 438 | 97 |
| ORF1039 | 1003721 | 1001823 | ORF of prc gene (alt.) | D00674 | Escherichia coli | 486 | 42 |
| ORF1040 | 1004459 | 1004845 | StrA | M86701 | Haemophilus influenzae | 454 | 70 |
| ORF1041 | 1004990 | 1005382 | ribosomal protein S7 | Z11567 | Chlamydia trachomatis | 662 | 99 |
| ORF1042 | 1005391 | 1007496 | translation elongation factor EF-G (fusA) | AE000625 | Helicobacter pylori | 2147 | 62 |
| ORF1043 | 1007486 | 1007821 | ribosomal protein S10 | Z21676 | Spirulina platensis | 350 | 68 |
| ORF1044 | 1007802 | 1008698 | NADPH-sulfite reductase flavoprotein component | M23008 | Escherichia coli | 113 | 48 |
| ORF1045 | 1009426 | 1009121 | unknown | Z92774 | Mycobacterium tuberculosis | 102 | 42 |
| ORF1046 | 1010534 | 1012054 | serine hydroxymethyltransferase | Z38002 | Bacillus subtilis | 1021 | 55 |
| ORF1047 | 1012397 | 1011942 | putative | | | | |
| ORF1048 | 1012042 | 1012635 | ATP-dependent Clp protease proteolytic subunit | D90915 | Synechocystis sp. | 365 | 44 |
| ORF1049 | 1012593 | 1012862 | putative | | | | |
| ORF1050 | 1012811 | 1013440 | diaminopimelate epimerase (dapF) | U32759 | Haemophilus influenzae | 108 | 40 |
| ORF1051 | 1013456 | 1014055 | putative | | | | |
| ORF1052 | 1013977 | 1014489 | putative | | | | |
| ORF1053 | 1015224 | 1014529 | hypothetical 28.1 kD protein in udp-rfaH intergenic region | AE000459 | Escherichia coli | 263 | 38 |
| ORF1054 | 1016002 | 1015145 | putative | | | | |
| ORF1055 | 1017120 | 1015939 | conserved hypothetical protein | AE000579 | Helicobacter pylori | 428 | 42 |
| ORF1056 | 1017766 | 1017245 | putative | | | | |
| ORF1057 | 1018911 | 1017916 | putative | | | | |
| ORF1058 | 1019191 | 1018580 | putative | | | | |
| ORF1059 | 1020199 | 1019831 | hemolysin | AE000647 | Helicobacter pylori | 164 | 33 |
| ORF1060 | 1021007 | 1020114 | unknown | Z95208 | Mycobacterium tuberculosis | 201 | 36 |
| ORF1061 | 1021569 | 1021075 | putative | | | | |
| ORF1062 | 1022411 | 1022097 | putative | | | | |
| ORF1063 | 1023344 | 1023667 | 50S ribosomal subunit protein L21 | U18997 | Escherichia coli | 218 | 43 |
| ORF1064 | 1023701 | 1023949 | 50S ribosomal protein L27 | U38804 | Porphyra purpurea | 251 | 64 |
| ORF1065 | 1023976 | 1024776 | ORF_f390 | U18997 | Escherichia coli | 603 | 51 |
| ORF1066 | 1024704 | 1025045 | GTP-binding protein (obg) | U32769 | Haemophilus influenzae | 161 | 37 |
| ORF1067 | 1025881 | 1024967 | hypothetical protein | D90903 | Synechocystis sp. | 439 | 35 |
| ORF1068 | 1026546 | 1025839 | YcdI | AB000617 | Bacillus subtilis | 312 | 40 |
| ORF1069 | 1027379 | 1026546 | adhesion protein | D90903 | Synechocystis sp. | 354 | 35 |
| ORF1070 | 1030604 | 1027929 | putative 98 kDa outer membrane protein | U72499 | Chlamydia psittaci | 95 | 49 |
| ORF1071 | 1033252 | 1030508 | putative 98 kDa outer membrane protein | U72499 | Chlamydia psittaci | 75 | 36 |

TABLE 1-continued

| ORF | begin | stop | Homology | ID | Species | Score | I % |
|---|---|---|---|---|---|---|---|
| ORF1072 | 1031733 | 1032086 | putative | | | | |
| ORF1073 | 1037037 | 1033456 | putative 98 kDa outer membrane protein | U72499 | *Chlamydia psittaci* | 160 | 46 |
| ORF1074 | 1035674 | 1035910 | putative | | | | |
| ORF1075 | 1036175 | 1036507 | putative | | | | |
| ORF1076 | 68 (com) | 1036967 | putative | | | | |
| ORF1077 | 16591 | 16989 | GutQ/KpsF Family Sugar-P Isomerase | AE001313 | *Chlamydia trachomatis* | 658 | 97 |
| ORF1078 | 31779 | 31408 | putative | | | | |
| ORF1079 | 56502 | 56834 | hypothetical protein | AE001309 | *Chlamydia trachomatis* | 284 | 95 |
| ORF1080 | 56686 | 56913 | hypothetical protein | AE001309 | *Chlamydia trachomatis* | 303 | 94 |
| ORF1081 | 64748 | 65074 | hypothetical protein (possible 357R?) | AE001309 | *Chlamydia trachomatis* | 501 | 100 |
| ORF1082 | 73482 | 73195 | Predicted OMP [leader (19) peptide] | AE001308 | *Chlamydia trachomatis* | 476 | 100 |
| ORF1083 | 78482 | 78736 | putative | | | | |
| ORF1084 | 79803 | 79411 | hypothetical protein | AE001307 | *Chlamydia trachomatis* | 583 | 98 |
| ORF1085 | 82333 | 81959 | Lon ATP-dependent protease | AE001307 | *Chlamydia trachomatis* | 607 | 99 |
| ORF1086 | 87313 | 86999 | hypothetical protein | AE001307 | *Chlamydia trachomatis* | 534 | 100 |
| ORF1087 | 109929 | 109456 | hypothetical protein | AE001305 | *Chlamydia trachomatis* | 529 | 98 |
| ORF1088 | 111599 | 111351 | putative | | | | |
| ORF1089 | 112069 | 111734 | putative | | | | |
| ORF1090 | 112666 | 112911 | hypothetical protein | AE001305 | *Chlamydia trachomatis* | 395 | 94 |
| ORF1091 | 114017 | 113715 | putative | | | | |
| ORF1092 | 120757 | 120464 | putative | | | | |
| ORF1093 | 125133 | 125522 | predied ferredoxin | AE001303 | *Chlamydia trachomatis* | 631 | 97 |
| ORF1094 | 131888 | 131604 | putative | | | | |
| ORF1095 | 144164 | 144427 | putative | | | | |
| ORF1096 | 150698 | 150369 | putative | | | | |
| ORF1097 | 164385 | 163948 | NADH (Ubiquinone) Dehydrogenase | AE001300 | *Chlamydia trachomatis* | 755 | 100 |
| ORF1098 | 165690 | 166115 | hypothetical protein | AE001300 | *Chlamydia trachomatis* | 724 | 99 |
| ORF1099 | 168742 | 168425 | hypothetical protein | AE001300 | *Chlamydia trachomatis* | 356 | 96 |
| ORF1100 | 170509 | 170793 | hypothetical protein | AE001300 | *Chlamydia trachomatis* | 489 | 100 |
| ORF1101 | 177145 | 177474 | AcCoA Carboxylase/Transferase Alpha | AE001299 | *Chlamydia trachomatis* | 518 | 99 |
| ORF1102 | 188295 | 188023 | hypothetical protein | AE001298 | *Chlamydia trachomatis* | 451 | 100 |
| ORF1103 | 188791 | 188330 | hypothetical protein | AE001298 | *Chlamydia trachomatis* | 733 | 97 |
| ORF1104 | 190629 | 190336 | putative | | | | |
| ORF1105 | 197313 | 197083 | putative | | | | |
| ORF1106 | 210914 | 211384 | putative | | | | |
| ORF1107 | 235160 | 234852 | Glutamate Aminomutase | AE001295 | *Chlamydia trachomatis* | 507 | 97 |
| ORF1108 | 237227 | 236913 | putative | | | | |
| ORF1109 | 249733 | 249446 | Oligopeptide Permease | AE001293 | *Chlamydia trachomatis* | 512 | 100 |
| ORF1110 | 253493 | 253158 | hypothetical protein | AE001293 | *Chlamydia trachomatis* | 318 | 63 |
| ORF1111 | 253701 | 254789 | hypothetical protein | AE001293 | *Chlamydia trachomatis* | 1860 | 99 |
| ORF1112 | 271633 | 271932 | hypothetical protein | AE001291 | *Chlamydia trachomatis* | 512 | 100 |
| ORF1113 | 275666 | 276070 | Disulfide bond Oxidoreductase | AE001291 | *Chlamydia trachomatis* | 700 | 99 |
| ORF1114 | 277931 | 278218 | putative | | | | |
| ORF1115 | 282741 | 282481 | hypothetical protein | AE001290 | *Chlamydia trachomatis* | 422 | 99 |
| ORF1116 | 293178 | 293489 | Phospholipase D Endonuclease Superfamily | AE001289 | *Chlamydia trachomatis* | 433 | 95 |
| ORF1117 | 303155 | 303469 | putative | | | | |
| ORF1118 | 309297 | 308965 | hypothetical protein | AE001287 | *Chlamydia trachomatis* | 422 | 95 |
| ORF1119 | 312219 | 312536 | putative | | | | |
| ORF1120 | 312853 | 312602 | hypothetical protein | AE001287 | *Chlamydia trachomatis* | 338 | 99 |
| ORF1121 | 313167 | 312772 | hypothetical protein | AE001287 | *Chlamydia trachomatis* | 616 | 98 |
| ORF1122 | 320224 | 320598 | hypothetical protein | AE001286 | *Chlamydia trachomatis* | 628 | 98 |
| ORF1123 | 340249 | 340503 | Oligopeptidase | AE001285 | *Chlamydia trachomatis* | 444 | 100 |
| ORF1124 | 352839 | 353324 | hypothetical protein | AE001284 | *Chlamydia trachomatis* | 751 | 98 |
| ORF1125 | 373475 | 373699 | Phopholipase D Superfamily [leader (33) peptide} | AE001282 | *Chlamydia trachomatis* | 378 | 100 |
| ORF1126 | 377316 | 377756 | hypothetical protein | AE001282 | *Chlamydia trachomatis* | 764 | 99 |
| ORF1127 | 379268 | 379657 | hypothetical protein | AE001282 | *Chlamydia trachomatis* | 535 | 100 |
| ORF1128 | 395098 | 394823 | putative | | | | |
| ORF1129 | 401594 | 401142 | Flagellar Secretion Protein | AE001280 | *Chlamydia trachomatis* | 698 | 100 |
| ORF1130 | 410045 | 410539 | hypothetical protein | AE001279 | *Chlamydia trachomatis* | 767 | 100 |
| ORF1131 | 411425 | 411658 | Coproporphyrinogen III Oxidase | AE001279 | *Chlamydia trachomatis* | 399 | 99 |
| ORF1132 | 414937 | 414416 | putative | | | | |
| ORF1133 | 422889 | 423212 | Glycogen Hydrolase (debranching) | AE001278 | *Chlamydia trachomatis* | 206 | 100 |
| ORF1134 | 427842 | 428183 | hypothetical protein | AE001278 | *Chlamydia trachomatis* | 610 | 100 |
| ORF1135 | 428732 | 429451 | hypothetical protein | AE001278 | *Chlamydia trachomatis* | 1010 | 98 |
| ORF1136 | 442557 | 442799 | hypothetical protein | AE001277 | *Chlamydia trachomatis* | 649 | 94 |
| ORF1137 | 443628 | 444041 | L31 Ribosomal Protein | AE001277 | *Chlamydia trachomatis* | 538 | 96 |
| ORF1138 | 443678 | 443166 | putative | | | | |
| ORF1139 | 445901 | 446155 | putative | | | | |
| ORF1140 | 467981 | 468262 | putative | | | | |
| ORF1141 | 471869 | 472108 | Putative Outer Membrane Protein I | AE001361 | *Chlamydia trachomatis* | 370 | 100 |
| ORF1142 | 488032 | 488337 | Membrane Thiol Protease | AE001360 | *Chlamydia trachomatis* | 483 | 96 |
| ORF1143 | 497179 | 497694 | Low Calcium Response Protein H | AE001359 | *Chlamydia trachomatis* | 864 | 95 |
| ORF1144 | 500474 | 500202 | putative | | | | |
| ORF1145 | 508968 | 509561 | ABC transporter permease | AE001358 | *Chlamydia trachomatis* | 964 | 100 |
| ORF1146 | 510845 | 511264 | hypothetical protein | AE001358 | *Chlamydia trachomatis* | 360 | 89 |
| ORF1147 | 526525 | 526848 | hypothetical protein | AE001356 | *Chlamydia trachomatis* | 242 | 81 |
| ORF1148 | 531318 | 531863 | hypothetical protein | AE001356 | *Chlamydia trachomatis* | 127 | 100 |

TABLE 1-continued

| ORF | begin | stop | Homology | ID | Species | Score | I % |
|---|---|---|---|---|---|---|---|
| ORF1149 | 556826 | 557224 | hypothetical protein | AE001354 | *Chlamydia trachomatis* | 683 | 99 |
| ORF1150 | 564971 | 564537 | hypothetical protein | AE001353 | *Chlamydia trachomatis* | 534 | 100 |
| ORF1151 | 566963 | 567232 | Glycerol-3-P Acyltransferase | AE001353 | *Chlamydia trachomatis* | 220 | 53 |
| ORF1152 | 570351 | 570890 | Insulinase family/Protease III | AE001353 | *Chlamydia trachomatis* | 925 | 100 |
| ORF1153 | 571072 | 571332 | hypothetical protein | AE001353 | *Chlamydia trachomatis* | 441 | 99 |
| ORF1154 | 576025 | 575801 | General Stress Protein | AE001352 | *Chlamydia trachomatis* | 273 | 97 |
| ORF1155 | 590363 | 590650 | hypothetical protein | AE001351 | *Chlamydia trachomatis* | 442 | 100 |
| ORF1156 | 597868 | 598593 | hypothetical protein | AE001350 | *Chlamydia trachomatis* | 1176 | 98 |
| ORF1157 | 606889 | 606626 | putative | | | | |
| ORF1158 | 608031 | 607786 | hydrolase/phosphatase homolog | AE001349 | *Chlamydia trachomatis* | 434 | 99 |
| ORF1159 | 610110 | 610391 | putative | | | | |
| ORF1160 | 632703 | 633353 | putative | | | | |
| ORF1161 | 637213 | 637482 | putative | | | | |
| ORF1162 | 650517 | 649924 | putative | | | | |
| ORF1163 | 652317 | 652562 | Phenolhydrolase/NADH ubiquinone oxidoreductase | AE001345 | *Chlamydia trachomatis* | 324 | 99 |
| ORF1164 | 654753 | 655325 | putative | | | | |
| ORF1165 | 661118 | 660810 | putative | | | | |
| ORF1166 | 677596 | 677057 | hypothetical protein | AE001343 | *Chlamydia trachomatis* | 864 | 98 |
| ORF1167 | 679528 | 679253 | putative | | | | |
| ORF1168 | 732536 | 732210 | putative | | | | |
| ORF1169 | 742069 | 742383 | putative | | | | |
| ORF1170 | 759318 | 758782 | (Pseudouridine Synthase) | AE001336 | *Chlamydia trachomatis* | 909 | 98 |
| ORF1171 | 760282 | 760521 | putative | | | | |
| ORF1172 | 771313 | 770894 | hypothetical protein | AE001335 | *Chlamydia trachomatis* | 661 | 96 |
| ORF1173 | 772115 | 772408 | hypothetical protein | AE001335 | *Chlamydia trachomatis* | 520 | 99 |
| ORF1174 | 788137 | 788457 | putative | | | | |
| ORF1175 | 816302 | 815967 | putative | | | | |
| ORF1176 | 846606 | 846914 | putative | | | | |
| ORF1177 | 867803 | 868054 | putative | | | | |
| ORF1178 | 875386 | 875658 | hypothetical protein | AE001327 | *Chlamydia trachomatis* | 268 | 86 |
| ORF1179 | 876445 | 876915 | hypothetical protein | AE001327 | *Chlamydia trachomatis* | 747 | 99 |
| ORF1180 | 884548 | 884312 | putative | | | | |
| ORF1181 | 891859 | 891467 | hypothetical protein | AE001326 | *Chlamydia trachomatis* | 551 | 95 |
| ORF1182 | 900770 | 900417 | putative | | | | |
| ORF1183 | 902553 | 902269 | putative | | | | |
| ORF1184 | 908046 | 907783 | putative | | | | |
| ORF1185 | 912313 | 912567 | Myristoyl GlcNac Deacetylase | AE001324 | *Chlamydia trachomatis* | 195 | 97 |
| ORF1186 | 935451 | 935741 | putative | | | | |
| ORF1187 | 946961 | 946692 | hypothetical protein | AE001322 | *Chlamydia trachomatis* | 410 | 99 |
| ORF1188 | 953193 | 952783 | hypothetical protein | AE001322 | *Chlamydia trachomatis* | 593 | 100 |
| ORF1189 | 966199 | 965873 | hypothetical protein | AE001321 | *Chlamydia trachomatis* | 542 | 98 |
| ORF1190 | 969298 | 968765 | putative | | | | |
| ORF1191 | 971009 | 970731 | 2-Component Sensor | AE001320 | *Chlamydia trachomatis* | 467 | 97 |
| ORF1192 | 972162 | 972404 | putative | | | | |
| ORF1193 | 973119 | 973508 | Phosphoglycolate Phosphatase | AE001320 | *Chlamydia trachomatis* | 647 | 98 |
| ORF1194 | 998649 | 998404 | putative | | | | |
| ORF1195 | 1004280 | 1003882 | hypothetical protein | AE001317 | *Chlamydia trachomatis* | 571 | 99 |
| ORF1196 | 1010200 | 1009532 | hypothetical protein | AE001317 | *Chlamydia trachomatis* | 1132 | 99 |
| ORF1197 | 1029174 | 1029482 | putative | | | | |

TABLE 2

| SEQ ID NO | begin | stop | preferred start |
|---|---|---|---|
| 2 | 501 | 208 | 501 |
| 3 | 3276 | 505 | 3153 |
| 4 | 5068 | 3242 | 5062 |
| 5 | 6400 | 5126 | 6400 |
| 6 | 7977 | 6619 | 7977 |
| 7 | 8582 | 8082 | 8582 |
| 8 | 8995 | 8591 | 8995 |
| 9 | 9440 | 8979 | 9440 |
| 10 | 9828 | 10430 | 9828 |
| 11 | 10367 | 11254 | 10430 |
| 12 | 11245 | 11916 | 11245 |
| 13 | 12068 | 13324 | 12068 |
| 14 | 13532 | 14413 | 13538 |
| 15 | 14807 | 15019 | 14807 |
| 16 | 14932 | 15969 | 14977 |
| 17 | 15995 | 16501 | 16004 |
| 18 | 16467 | 16138 | 16377 |
| 19 | 18190 | 17417 | 18178 |
| 20 | 20521 | 18437 | 20518 |
| 21 | 22202 | 20814 | 22166 |
| 22 | 22602 | 22153 | 22509 |
| 23 | 22804 | 22478 | 22795 |
| 24 | 23183 | 22824 | 23180 |
| 25 | 23394 | 23110 | 23394 |
| 26 | 24569 | 23394 | 24569 |
| 27 | 26383 | 24641 | 26383 |
| 28 | 26640 | 27710 | 26640 |
| 29 | 28780 | 27725 | 28729 |
| 30 | 29957 | 28740 | 29957 |
| 31 | 30721 | 30032 | 30628 |
| 32 | 31281 | 30520 | 31254 |
| 33 | 31436 | 31780 | 31436 |
| 34 | 33356 | 31800 | 33344 |
| 35 | 33901 | 33314 | 33874 |
| 36 | 34116 | 35027 | 34116 |
| 37 | 34988 | 35359 | 35027 |
| 38 | 35167 | 35919 | 35377 |
| 39 | 35923 | 36996 | 36031 |
| 40 | 37810 | 37013 | 37765 |
| 41 | 38207 | 39085 | 38252 |

TABLE 2-continued

| SEQ ID NO | begin | stop | preferred start |
|---|---|---|---|
| 42 | 39151 | 39927 | 39157 |
| 43 | 39923 | 40756 | 39959 |
| 44 | 40760 | 42007 | 40772 |
| 45 | 42175 | 43116 | 42229 |
| 46 | 42999 | 43802 | 43128 |
| 47 | 44211 | 45227 | 44217 |
| 48 | 46072 | 45275 | 46066 |
| 49 | 46340 | 45975 | 46331 |
| 50 | 46895 | 46506 | 46865 |
| 51 | 47955 | 46882 | 47955 |
| 52 | 48585 | 48178 | 48558 |
| 53 | 50072 | 48630 | 50012 |
| 54 | 50710 | 50099 | 50692 |
| 55 | 52439 | 50925 | 52430 |
| 56 | 53484 | 52348 | 53478 |
| 57 | 54536 | 53466 | 54536 |
| 58 | 55086 | 54595 | 55104 |
| 59 | 56350 | 55031 | 56350 |
| 60 | 55659 | 56084 | 55722 |
| 61 | 56847 | 58235 | 56931 |
| 62 | 58423 | 59181 | 58423 |
| 63 | 59185 | 60195 | 59194 |
| 64 | 60188 | 61483 | 60191 |
| 65 | 61496 | 62353 | 61496 |
| 66 | 62500 | 63141 | 62518 |
| 67 | 63396 | 63983 | 63396 |
| 68 | 64628 | 64071 | 64580 |
| 69 | 64285 | 64656 | 64285 |
| 70 | 64944 | 64609 | 64938 |
| 71 | 65347 | 67269 | 65347 |
| 72 | 67656 | 68873 | 67815 |
| 73 | 68877 | 69233 | 68892 |
| 74 | 69212 | 69721 | 69323 |
| 75 | 69958 | 70455 | 69970 |
| 76 | 70701 | 71006 | 70725 |
| 77 | 73191 | 71086 | 73185 |
| 78 | 74900 | 73497 | 74891 |
| 79 | 75463 | 74876 | 75463 |
| 80 | 77124 | 75502 | 77124 |
| 81 | 77000 | 77299 | 77012 |
| 82 | 78095 | 77145 | 78095 |
| 83 | 79065 | 78154 | 79065 |
| 84 | 81971 | 79878 | 81965 |
| 85 | 82639 | 83271 | 82642 |
| 86 | 83792 | 84850 | 83921 |
| 87 | 84876 | 86921 | 84888 |
| 88 | 88650 | 87313 | 88383 |
| 89 | 87440 | 87805 | 87458 |
| 90 | 88400 | 88747 | 88409 |
| 91 | 88717 | 89265 | 88729 |
| 92 | 89355 | 89732 | 89355 |
| 93 | 89735 | 91447 | 89735 |
| 94 | 91749 | 91435 | 91749 |
| 95 | 92392 | 91745 | 92323 |
| 96 | 93138 | 92344 | 92874 |
| 97 | 94134 | 93361 | 93945 |
| 98 | 94637 | 94071 | 94577 |
| 99 | 98299 | 94628 | 98113 |
| 100 | 98715 | 98113 | 98715 |
| 101 | 100228 | 98741 | 100195 |
| 102 | 101347 | 100337 | 101323 |
| 103 | 102210 | 101323 | 102210 |
| 104 | 102485 | 102210 | 102479 |
| 105 | 104315 | 102726 | 104315 |
| 106 | 105075 | 104254 | 105075 |
| 107 | 105259 | 105894 | 105271 |
| 108 | 107429 | 108460 | 107486 |
| 109 | 108665 | 108955 | 108683 |
| 110 | 109459 | 109013 | 109456 |
| 111 | 110366 | 109704 | 110363 |
| 112 | 111330 | 112520 | 111330 |
| 113 | 112915 | 113463 | 112918 |
| 114 | 113594 | 113994 | 113566 |
| 115 | 114020 | 114604 | 114020 |
| 116 | 114720 | 115253 | 114807 |
| 117 | 115362 | 115676 | 115380 |
| 118 | 116022 | 119795 | 116040 |
| 119 | 119823 | 124010 | 119823 |
| 120 | 124065 | 124988 | 124065 |
| 121 | 124873 | 125106 | 124873 |
| 122 | 126261 | 125536 | 126243 |
| 123 | 126328 | 126930 | 126331 |
| 124 | 127138 | 127785 | 127147 |
| 125 | 127924 | 129714 | 127942 |
| 126 | 129720 | 131033 | 129720 |
| 127 | 131018 | 131629 | 131021 |
| 128 | 131834 | 133156 | 131852 |
| 129 | 133075 | 133584 | 133096 |
| 130 | 133625 | 133999 | 133628 |
| 131 | 133861 | 134508 | 133948 |
| 132 | 134638 | 137454 | 134638 |
| 133 | 137442 | 140276 | 137472 |
| 134 | 140733 | 140335 | 140727 |
| 135 | 141799 | 141077 | 141799 |
| 136 | 143240 | 141780 | 143240 |
| 137 | 143829 | 143128 | 143820 |
| 138 | 143923 | 144393 | 143923 |
| 139 | 144548 | 146326 | 144548 |
| 140 | 146413 | 147078 | 146425 |
| 141 | 147140 | 148075 | 147152 |
| 142 | 148115 | 148549 | 148115 |
| 143 | 148524 | 149027 | 148524 |
| 144 | 149000 | 149305 | 149033 |
| 145 | 149187 | 149708 | 149187 |
| 146 | 149712 | 150911 | 149769 |
| 147 | 152044 | 151004 | 151966 |
| 148 | 152664 | 151999 | 152592 |
| 149 | 152900 | 153352 | 152924 |
| 150 | 153389 | 153997 | 153425 |
| 151 | 155276 | 153984 | 155228 |
| 152 | 156544 | 155231 | 156544 |
| 153 | 156806 | 157525 | 156809 |
| 154 | 157489 | 158955 | 157534 |
| 155 | 159104 | 159961 | 159104 |
| 156 | 159916 | 161220 | 159916 |
| 157 | 161183 | 161593 | 161228 |
| 158 | 162354 | 161623 | 162354 |
| 159 | 163013 | 162363 | 163013 |
| 160 | 163941 | 162994 | 163941 |
| 161 | 165505 | 164474 | 165505 |
| 162 | 166686 | 166093 | 166686 |
| 163 | 168171 | 166729 | 168171 |
| 164 | 169249 | 168848 | 169189 |
| 165 | 169586 | 170431 | 169607 |
| 166 | 170780 | 171334 | 170783 |
| 167 | 171333 | 172376 | 171390 |
| 168 | 172309 | 172722 | 172309 |
| 169 | 173048 | 174496 | 173048 |
| 170 | 174399 | 174968 | 174399 |
| 171 | 175267 | 175710 | 175267 |
| 172 | 175714 | 177009 | 175735 |
| 173 | 177423 | 178115 | 177468 |
| 174 | 178084 | 180021 | 178084 |
| 175 | 180704 | 180048 | 180635 |
| 176 | 181398 | 180631 | 181398 |
| 177 | 182594 | 181398 | 182594 |
| 178 | 182895 | 183656 | 182895 |
| 179 | 183665 | 184786 | 183665 |
| 180 | 186007 | 184796 | 186007 |
| 181 | 186848 | 186000 | 186791 |
| 182 | 187270 | 186749 | 187240 |
| 183 | 187426 | 187809 | 187429 |
| 184 | 189481 | 188798 | 189442 |
| 185 | 189693 | 190352 | 189693 |
| 186 | 190235 | 190510 | 190280 |
| 187 | 190785 | 191786 | 190824 |
| 188 | 191790 | 192464 | 191811 |
| 189 | 192392 | 193183 | 192500 |
| 190 | 193254 | 194630 | 193263 |
| 191 | 195046 | 194690 | 195037 |
| 192 | 195184 | 197031 | 195193 |
| 193 | 197018 | 197635 | 197024 |
| 194 | 197762 | 198208 | 197669 |
| 195 | 198963 | 197668 | 198954 |
| 196 | 199957 | 198962 | 199945 |
| 197 | 200327 | 199941 | 200306 |

TABLE 2-continued

| SEQ ID NO | begin | stop | preferred start |
|---|---|---|---|
| 198 | 200685 | 200266 | 200598 |
| 199 | 200962 | 200585 | 200962 |
| 200 | 201169 | 202377 | 201184 |
| 201 | 203441 | 202380 | 203441 |
| 202 | 203998 | 203471 | 203989 |
| 203 | 206449 | 204059 | 206434 |
| 204 | 207425 | 206811 | 207410 |
| 205 | 207506 | 208528 | 207506 |
| 206 | 208545 | 209471 | 208545 |
| 207 | 209471 | 210214 | 209471 |
| 208 | 210586 | 210816 | 210586 |
| 209 | 211332 | 210883 | 211293 |
| 210 | 212978 | 211374 | 212972 |
| 211 | 214134 | 212875 | 214134 |
| 212 | 214710 | 214168 | 214701 |
| 213 | 215143 | 214754 | 215128 |
| 214 | 216705 | 215236 | 216705 |
| 215 | 217917 | 216892 | 217911 |
| 216 | 217088 | 217441 | 217202 |
| 217 | 218364 | 218702 | 218364 |
| 218 | 218695 | 219009 | 218785 |
| 219 | 219179 | 219748 | 219260 |
| 220 | 219891 | 220430 | 219912 |
| 221 | 220499 | 221074 | 220505 |
| 222 | 221137 | 221541 | 221176 |
| 223 | 221601 | 222092 | 221616 |
| 224 | 222472 | 223290 | 222487 |
| 225 | 223423 | 223818 | 223423 |
| 226 | 224278 | 225171 | 224278 |
| 227 | 225749 | 225174 | 225749 |
| 228 | 225334 | 225549 | 225328 |
| 229 | 226654 | 225749 | 226654 |
| 230 | 227299 | 226769 | 227170 |
| 231 | 227646 | 227161 | 227646 |
| 232 | 228457 | 227750 | 228439 |
| 233 | 230001 | 228607 | 229854 |
| 234 | 231074 | 230151 | 231062 |
| 235 | 231348 | 233006 | 231366 |
| 236 | 233059 | 233829 | 233059 |
| 237 | 233801 | 234265 | 233801 |
| 238 | 234282 | 234854 | 234288 |
| 239 | 236300 | 235227 | 236300 |
| 240 | 236314 | 238209 | 236314 |
| 241 | 238164 | 238769 | 238185 |
| 242 | 238769 | 240061 | 238769 |
| 243 | 242022 | 240313 | 242022 |
| 244 | 242846 | 241941 | 242846 |
| 245 | 244480 | 242798 | 244456 |
| 246 | 245897 | 244479 | 245891 |
| 247 | 246877 | 245924 | 246829 |
| 248 | 247731 | 246985 | 247725 |
| 249 | 248585 | 247743 | 248573 |
| 250 | 249420 | 248569 | 249411 |
| 251 | 250383 | 249766 | 250383 |
| 252 | 251186 | 250545 | 251174 |
| 253 | 252111 | 251095 | 252099 |
| 254 | 253088 | 252066 | 253088 |
| 255 | 255153 | 256718 | 255153 |
| 256 | 256762 | 257844 | 256774 |
| 257 | 257911 | 258690 | 257962 |
| 258 | 258780 | 259187 | 258840 |
| 259 | 259193 | 261604 | 259193 |
| 260 | 261622 | 264129 | 261622 |
| 261 | 264125 | 264742 | 264134 |
| 262 | 264741 | 265628 | 264759 |
| 263 | 266416 | 265631 | 266416 |
| 264 | 266938 | 266426 | 267946 |
| 265 | 267961 | 266942 | 267946 |
| 266 | 268320 | 268066 | 268299 |
| 267 | 268510 | 268205 | 268510 |
| 268 | 270116 | 268500 | 270116 |
| 269 | 270892 | 270095 | 270856 |
| 270 | 271191 | 271613 | 271224 |
| 271 | 272219 | 272932 | 272243 |
| 272 | 272884 | 273588 | 273079 |
| 273 | 274816 | 273596 | 274807 |
| 274 | 274821 | 275666 | 274953 |
| 275 | 277689 | 276103 | 277689 |
| 276 | 278268 | 278816 | 278298 |
| 277 | 279771 | 279013 | 279870 |
| 278 | 280777 | 279767 | 280762 |
| 279 | 281603 | 281295 | 281576 |
| 280 | 282104 | 281787 | 282086 |
| 281 | 284335 | 282794 | 284320 |
| 282 | 284460 | 284795 | 284550 |
| 283 | 284817 | 285674 | 284844 |
| 284 | 285637 | 286137 | 285670 |
| 285 | 286357 | 286677 | 286399 |
| 286 | 286681 | 287898 | 286852 |
| 287 | 288127 | 289227 | 288358 |
| 288 | 289744 | 290679 | 289744 |
| 289 | 290828 | 291535 | 291206 |
| 290 | 291514 | 292230 | 291514 |
| 291 | 292326 | 293048 | 292350 |
| 292 | 293330 | 294853 | 293525 |
| 293 | 295684 | 295010 | 295684 |
| 294 | 296336 | 295692 | 296294 |
| 295 | 297238 | 296243 | 297199 |
| 296 | 297791 | 298735 | 297791 |
| 297 | 298905 | 300458 | 298920 |
| 298 | 302152 | 300527 | 302131 |
| 299 | 304917 | 302071 | 304872 |
| 300 | 306157 | 304973 | 306142 |
| 301 | 306494 | 306111 | 306461 |
| 302 | 306963 | 306436 | 306963 |
| 303 | 308773 | 306977 | 308758 |
| 304 | 309881 | 309276 | 309869 |
| 305 | 310720 | 309872 | 310711 |
| 306 | 311570 | 310716 | 311570 |
| 307 | 312451 | 311972 | 312439 |
| 308 | 313435 | 314364 | 313462 |
| 309 | 314340 | 314738 | 314409 |
| 310 | 315526 | 314741 | 315445 |
| 311 | 316507 | 315665 | 316507 |
| 312 | 317284 | 316529 | 317284 |
| 313 | 317592 | 317338 | 317592 |
| 314 | 318470 | 317499 | 318416 |
| 315 | 317599 | 317874 | 317599 |
| 316 | 318947 | 318477 | 318887 |
| 317 | 319342 | 320142 | 319342 |
| 318 | 320544 | 321497 | 320682 |
| 319 | 321485 | 321937 | 321497 |
| 320 | 321901 | 322362 | 321943 |
| 321 | 322301 | 323140 | 322325 |
| 322 | 323144 | 324913 | 323177 |
| 323 | 325621 | 324977 | 325621 |
| 324 | 326268 | 325621 | 326262 |
| 325 | 326469 | 327203 | 326469 |
| 326 | 327281 | 328150 | 327302 |
| 327 | 328605 | 328204 | 328602 |
| 328 | 329066 | 328734 | 329066 |
| 329 | 329663 | 329292 | 329648 |
| 330 | 330666 | 329608 | 330663 |
| 331 | 331161 | 330670 | 331161 |
| 332 | 331731 | 331177 | 331731 |
| 333 | 332404 | 331721 | 332404 |
| 334 | 332779 | 333021 | 332779 |
| 335 | 333005 | 333589 | 333149 |
| 336 | 334357 | 333806 | 334321 |
| 337 | 334089 | 334361 | 334089 |
| 338 | 335142 | 334729 | 335124 |
| 339 | 335195 | 335602 | 335234 |
| 340 | 335673 | 335194 | 335673 |
| 341 | 336334 | 335903 | 336229 |
| 342 | 337378 | 336338 | 337378 |
| 343 | 339947 | 337347 | 339947 |
| 344 | 340507 | 341847 | 340576 |
| 345 | 341783 | 342022 | 341786 |
| 346 | 342249 | 342470 | 342249 |
| 347 | 342597 | 343370 | 342597 |
| 348 | 343361 | 344032 | 343379 |
| 349 | 343956 | 344225 | 343962 |
| 350 | 344357 | 345142 | 344357 |
| 351 | 345934 | 345161 | 345934 |
| 352 | 347102 | 346080 | 347102 |
| 353 | 347113 | 347940 | 347119 |

TABLE 2-continued

| SEQ ID NO | begin | stop | preferred start |
|---|---|---|---|
| 354 | 350164 | 348146 | 350113 |
| 355 | 350423 | 351283 | 350426 |
| 356 | 352207 | 351314 | 352207 |
| 357 | 352727 | 352245 | 352703 |
| 358 | 353709 | 353305 | 353709 |
| 359 | 354218 | 353670 | 354215 |
| 360 | 354721 | 354140 | 354721 |
| 361 | 354966 | 356672 | 354966 |
| 362 | 356700 | 357377 | 356700 |
| 363 | 357326 | 358093 | 357500 |
| 364 | 358035 | 360743 | 358035 |
| 365 | 360753 | 361121 | 360753 |
| 366 | 361162 | 361884 | 361162 |
| 367 | 361826 | 362746 | 361826 |
| 368 | 363859 | 362816 | 363859 |
| 369 | 364116 | 365195 | 364116 |
| 370 | 365198 | 365587 | 365198 |
| 371 | 365479 | 367320 | 365614 |
| 372 | 367341 | 368603 | 367341 |
| 373 | 368644 | 369081 | 368644 |
| 374 | 369088 | 370251 | 369088 |
| 375 | 370769 | 371086 | 370769 |
| 376 | 371203 | 372816 | 371209 |
| 377 | 373119 | 373529 | 373152 |
| 378 | 373614 | 374204 | 373776 |
| 379 | 374736 | 374224 | 374703 |
| 380 | 376391 | 374703 | 376382 |
| 381 | 377062 | 376748 | 377038 |
| 382 | 377853 | 378737 | 377871 |
| 383 | 378626 | 379048 | 378710 |
| 384 | 379017 | 379403 | 379038 |
| 385 | 380009 | 379641 | 379967 |
| 386 | 380187 | 381470 | 380187 |
| 387 | 381473 | 382567 | 381473 |
| 388 | 382704 | 383702 | 382728 |
| 389 | 383945 | 383655 | 383921 |
| 390 | 385217 | 383949 | 385211 |
| 391 | 385507 | 385178 | 385507 |
| 392 | 386845 | 385706 | 386842 |
| 393 | 386127 | 386627 | 386232 |
| 394 | 387372 | 386872 | 387351 |
| 395 | 387823 | 387338 | 387823 |
| 396 | 388250 | 387816 | 388106 |
| 397 | 389169 | 388237 | 389169 |
| 398 | 389955 | 389173 | 390087 |
| 399 | 390988 | 389945 | 390922 |
| 400 | 391514 | 391810 | 391514 |
| 401 | 392410 | 393996 | 392413 |
| 402 | 394170 | 395354 | 394185 |
| 403 | 395309 | 395992 | 395354 |
| 404 | 396538 | 396059 | 396529 |
| 405 | 397507 | 396542 | 397498 |
| 406 | 398753 | 397401 | 398747 |
| 407 | 399688 | 398909 | 399667 |
| 408 | 400167 | 399778 | 400167 |
| 409 | 401224 | 400034 | 401209 |
| 410 | 401776 | 402021 | 401776 |
| 411 | 402126 | 403220 | 402132 |
| 412 | 403348 | 405180 | 403354 |
| 413 | 403788 | 403276 | 403785 |
| 414 | 405165 | 405920 | 405165 |
| 415 | 407049 | 405955 | 407049 |
| 416 | 409773 | 407056 | 409764 |
| 417 | 410532 | 411416 | 410532 |
| 418 | 411707 | 413410 | 411722 |
| 419 | 413433 | 412606 | 413334 |
| 420 | 413404 | 413952 | 413449 |
| 421 | 413841 | 415112 | 413991 |
| 422 | 414379 | 413978 | 414220 |
| 423 | 416664 | 415177 | 416646 |
| 424 | 417456 | 416740 | 417456 |
| 425 | 418053 | 417721 | 418044 |
| 426 | 418603 | 418031 | 418582 |
| 427 | 419531 | 418647 | 419531 |
| 428 | 420190 | 419672 | 420190 |
| 429 | 421171 | 420245 | 421171 |
| 430 | 421988 | 421518 | 421988 |
| 431 | 422486 | 423043 | 422492 |
| 432 | 423226 | 425079 | 423295 |
| 433 | 426054 | 425146 | 426021 |
| 434 | 426985 | 426245 | 426967 |
| 435 | 427248 | 427817 | 427248 |
| 436 | 429560 | 429886 | 429623 |
| 437 | 430360 | 429857 | 430360 |
| 438 | 430637 | 430323 | 430628 |
| 439 | 430933 | 431787 | 430966 |
| 440 | 431658 | 431987 | 431688 |
| 441 | 432232 | 434475 | 432238 |
| 442 | 436308 | 434620 | 436269 |
| 443 | 436574 | 436272 | 436571 |
| 444 | 437685 | 436567 | 437595 |
| 445 | 438262 | 437894 | 438256 |
| 446 | 439127 | 438285 | 439031 |
| 447 | 439339 | 438986 | 439339 |
| 448 | 439705 | 439358 | 439705 |
| 449 | 441042 | 439699 | 441042 |
| 450 | 441911 | 441042 | 441911 |
| 451 | 442593 | 441898 | 442584 |
| 452 | 444505 | 446388 | 444505 |
| 453 | 448068 | 446452 | 448029 |
| 454 | 449575 | 447932 | 449575 |
| 455 | 450546 | 451076 | 450576 |
| 456 | 451623 | 451144 | 451401 |
| 457 | 452593 | 451517 | 452575 |
| 458 | 453195 | 452632 | 453174 |
| 459 | 453567 | 454868 | 453567 |
| 460 | 455430 | 454972 | 455403 |
| 461 | 456047 | 455367 | 456047 |
| 462 | 457384 | 456047 | 457384 |
| 463 | 457659 | 458450 | 457659 |
| 464 | 458508 | 459632 | 458511 |
| 465 | 459839 | 461203 | 459839 |
| 466 | 461624 | 461196 | 461624 |
| 467 | 461887 | 462621 | 462151 |
| 468 | 463758 | 462895 | 463749 |
| 469 | 464048 | 464629 | 464063 |
| 470 | 464721 | 465848 | 464760 |
| 471 | 467420 | 466113 | 467414 |
| 472 | 468891 | 467419 | 468891 |
| 473 | 469280 | 468906 | 469226 |
| 474 | 469349 | 469675 | 469406 |
| 475 | 471226 | 469826 | 471160 |
| 476 | 471624 | 471106 | 471609 |
| 477 | 471954 | 473267 | 471954 |
| 478 | 473252 | 473695 | 473252 |
| 479 | 473982 | 474527 | 474051 |
| 480 | 475198 | 474602 | 475195 |
| 481 | 476527 | 475613 | 476509 |
| 482 | 478640 | 476517 | 478640 |
| 483 | 479084 | 478665 | 479078 |
| 484 | 479723 | 479088 | 479720 |
| 485 | 480012 | 479668 | 479898 |
| 486 | 481466 | 479895 | 481412 |
| 487 | 481732 | 481496 | 481732 |
| 488 | 481864 | 483429 | 481870 |
| 489 | 483402 | 484964 | 483402 |
| 490 | 484898 | 487864 | 484970 |
| 491 | 485725 | 485222 | 485593 |
| 492 | 488204 | 489247 | 488321 |
| 493 | 488571 | 488233 | 488562 |
| 494 | 489440 | 490456 | 489473 |
| 495 | 492765 | 490507 | 492690 |
| 496 | 492357 | 492893 | 492654 |
| 497 | 493744 | 492737 | 493723 |
| 498 | 493875 | 494675 | 493875 |
| 499 | 494573 | 494869 | 494609 |
| 500 | 494835 | 495365 | 494955 |
| 501 | 495174 | 494872 | 495174 |
| 502 | 495687 | 496634 | 495732 |
| 503 | 496295 | 497176 | 496523 |
| 504 | 497703 | 498515 | 498222 |
| 505 | 498280 | 499239 | 498301 |
| 506 | 499215 | 500732 | 499254 |
| 507 | 501710 | 500790 | 501710 |
| 508 | 502863 | 501808 | 502830 |
| 509 | 503675 | 502692 | 503645 |

TABLE 2-continued

| SEQ ID NO | begin | stop | preferred start |
|---|---|---|---|
| 510 | 505002 | 503722 | 505002 |
| 511 | 505739 | 506986 | 505739 |
| 512 | 506999 | 507439 | 507011 |
| 513 | 508404 | 507649 | 508302 |
| 514 | 508291 | 508590 | 508297 |
| 515 | 508915 | 508478 | 508915 |
| 516 | 509600 | 510691 | 509600 |
| 517 | 511039 | 511527 | 511147 |
| 518 | 511547 | 512185 | 511547 |
| 519 | 512382 | 513092 | 512385 |
| 520 | 514287 | 513055 | 514269 |
| 521 | 514789 | 515244 | 514792 |
| 522 | 514994 | 515269 | 515027 |
| 523 | 515553 | 515804 | 515553 |
| 524 | 515808 | 516422 | 515820 |
| 525 | 516476 | 517171 | 516605 |
| 526 | 517927 | 517400 | 517927 |
| 527 | 518096 | 518380 | 518114 |
| 528 | 518403 | 518822 | 518412 |
| 529 | 518923 | 519516 | 518923 |
| 530 | 519577 | 520497 | 519730 |
| 531 | 521986 | 520718 | 521971 |
| 532 | 522131 | 521886 | 522125 |
| 533 | 523495 | 522143 | 523483 |
| 534 | 524591 | 523623 | 524510 |
| 535 | 524652 | 525746 | 524685 |
| 536 | 525731 | 526078 | 525752 |
| 537 | 525939 | 526400 | 525999 |
| 538 | 526301 | 526735 | 526361 |
| 539 | 528323 | 526851 | 528284 |
| 540 | 528861 | 528292 | 528828 |
| 541 | 529723 | 529142 | 529645 |
| 542 | 530166 | 529624 | 530166 |
| 543 | 530543 | 530223 | 530543 |
| 544 | 531378 | 530737 | 531363 |
| 545 | 532370 | 533272 | 532370 |
| 546 | 533849 | 533244 | 533849 |
| 547 | 534672 | 533944 | 534615 |
| 548 | 535915 | 534878 | 535915 |
| 549 | 539153 | 535956 | 539114 |
| 550 | 539731 | 540519 | 539731 |
| 551 | 540523 | 540969 | 540526 |
| 552 | 540906 | 541805 | 541002 |
| 553 | 543255 | 541825 | 543222 |
| 554 | 544133 | 543222 | 544115 |
| 555 | 544565 | 544179 | 544532 |
| 556 | 544762 | 544487 | 544747 |
| 557 | 546423 | 544951 | 546423 |
| 558 | 547480 | 546584 | 547378 |
| 559 | 546789 | 547382 | 546900 |
| 560 | 547901 | 547476 | 547826 |
| 561 | 548634 | 547900 | 548634 |
| 562 | 548692 | 549459 | 548704 |
| 563 | 550385 | 549663 | 550376 |
| 564 | 551611 | 550421 | 551611 |
| 565 | 553041 | 551797 | 553041 |
| 566 | 554946 | 553096 | 554946 |
| 567 | 556300 | 554927 | 556300 |
| 568 | 556524 | 556904 | 556524 |
| 569 | 558126 | 557314 | 558105 |
| 570 | 557810 | 558235 | 557810 |
| 571 | 559215 | 558310 | 559215 |
| 572 | 561349 | 559196 | 561349 |
| 573 | 562931 | 561150 | 562898 |
| 574 | 564083 | 563121 | 564083 |
| 575 | 563593 | 563943 | 563644 |
| 576 | 565379 | 566953 | 565379 |
| 577 | 567079 | 567966 | 567274 |
| 578 | 568021 | 570399 | 568021 |
| 579 | 571269 | 572021 | 571284 |
| 580 | 572519 | 572755 | 572519 |
| 581 | 573519 | 572731 | 573393 |
| 582 | 572879 | 573427 | 573077 |
| 583 | 574160 | 573660 | 574160 |
| 584 | 574426 | 574184 | 574426 |
| 585 | 574781 | 574446 | 574781 |
| 586 | 575243 | 574923 | 575156 |
| 587 | 575458 | 575057 | 575458 |
| 588 | 575849 | 575469 | 575735 |
| 589 | 576545 | 578023 | 576545 |
| 590 | 578673 | 578017 | 578673 |
| 591 | 579012 | 582104 | 579012 |
| 592 | 582697 | 582206 | 582682 |
| 593 | 583122 | 582811 | 583095 |
| 594 | 583514 | 583182 | 583484 |
| 595 | 583869 | 583438 | 583803 |
| 596 | 584435 | 583827 | 584399 |
| 597 | 584967 | 584299 | 584967 |
| 598 | 585297 | 585016 | 585285 |
| 599 | 585240 | 586610 | 585300 |
| 600 | 586484 | 587758 | 586505 |
| 601 | 587786 | 589408 | 587786 |
| 602 | 589198 | 589578 | 589258 |
| 603 | 590061 | 589630 | 589971 |
| 604 | 590739 | 591272 | 590775 |
| 605 | 592406 | 592765 | 592406 |
| 606 | 593145 | 592849 | 593127 |
| 607 | 593900 | 593121 | 593894 |
| 608 | 594138 | 595637 | 594138 |
| 609 | 596122 | 595640 | 596053 |
| 610 | 596864 | 596154 | 596828 |
| 611 | 597731 | 597282 | 597689 |
| 612 | 598524 | 600809 | 598551 |
| 613 | 601876 | 600734 | 601864 |
| 614 | 603523 | 601910 | 603520 |
| 615 | 603794 | 603531 | 603794 |
| 616 | 604413 | 603757 | 604398 |
| 617 | 604549 | 605610 | 604549 |
| 618 | 606619 | 605582 | 606619 |
| 619 | 606843 | 607493 | 606867 |
| 620 | 609068 | 608031 | 608972 |
| 621 | 609652 | 609296 | 609652 |
| 622 | 611860 | 610109 | 611830 |
| 623 | 611812 | 612927 | 611815 |
| 624 | 613597 | 612938 | 613444 |
| 625 | 613952 | 613692 | 613952 |
| 626 | 614315 | 615244 | 614441 |
| 627 | 615396 | 615683 | 615396 |
| 628 | 617711 | 615864 | 617624 |
| 629 | 618313 | 617510 | 618361 |
| 630 | 619338 | 618361 | 619338 |
| 631 | 620416 | 619247 | 620401 |
| 632 | 619863 | 620261 | 619929 |
| 633 | 621184 | 620420 | 621154 |
| 634 | 621690 | 621154 | 621678 |
| 635 | 622399 | 621674 | 622399 |
| 636 | 623466 | 622414 | 623421 |
| 637 | 624178 | 623570 | 624106 |
| 638 | 624918 | 624073 | 624918 |
| 639 | 625346 | 626665 | 625367 |
| 640 | 626514 | 626900 | 626652 |
| 641 | 626954 | 627853 | 626984 |
| 642 | 627822 | 628124 | 627873 |
| 643 | 628715 | 628146 | 628715 |
| 644 | 628932 | 629801 | 628935 |
| 645 | 630406 | 629804 | 630298 |
| 646 | 630960 | 630298 | 630915 |
| 647 | 631799 | 630915 | 631799 |
| 648 | 637488 | 638084 | 637488 |
| 649 | 638036 | 640207 | 638111 |
| 650 | 640221 | 643472 | 640236 |
| 651 | 640627 | 640220 | 640627 |
| 652 | 643485 | 644495 | 643488 |
| 653 | 644471 | 645430 | 644471 |
| 654 | 645394 | 645840 | 645538 |
| 655 | 645840 | 647111 | 645840 |
| 656 | 649676 | 647109 | 649616 |
| 657 | 649970 | 650344 | 649970 |
| 658 | 650418 | 651722 | 650433 |
| 659 | 651686 | 652171 | 651770 |
| 660 | 652516 | 652908 | 652516 |
| 661 | 652799 | 653593 | 652892 |
| 662 | 659884 | 661851 | 660136 |
| 663 | 661740 | 662282 | 661851 |
| 664 | 662286 | 663074 | 662289 |
| 665 | 662951 | 663730 | 663074 |

TABLE 2-continued

| SEQ ID NO | begin | stop | preferred start |
|---|---|---|---|
| 666 | 664212 | 663745 | 664194 |
| 667 | 665619 | 664255 | 665619 |
| 668 | 666083 | 665727 | 666056 |
| 669 | 666423 | 665782 | 666390 |
| 670 | 666831 | 668117 | 667047 |
| 671 | 668121 | 668375 | 668139 |
| 672 | 668470 | 668174 | 668404 |
| 673 | 669533 | 668616 | 669485 |
| 674 | 669892 | 669485 | 669892 |
| 675 | 670780 | 669998 | 670765 |
| 676 | 671241 | 670732 | 671196 |
| 677 | 671182 | 672447 | 671260 |
| 678 | 672692 | 673231 | 672698 |
| 679 | 673204 | 674562 | 673204 |
| 680 | 674612 | 675232 | 674612 |
| 681 | 675327 | 676463 | 675327 |
| 682 | 677027 | 676476 | 677027 |
| 683 | 678422 | 677700 | 678422 |
| 684 | 678717 | 679508 | 678708 |
| 685 | 679342 | 680502 | 679342 |
| 686 | 680579 | 681280 | 680654 |
| 687 | 681539 | 682558 | 681557 |
| 688 | 682554 | 683087 | 682578 |
| 689 | 683164 | 684465 | 683164 |
| 690 | 684774 | 684418 | 684639 |
| 691 | 684839 | 686203 | 684839 |
| 692 | 686197 | 687204 | 686203 |
| 693 | 687341 | 688360 | 687341 |
| 694 | 688432 | 688193 | 688426 |
| 695 | 689616 | 688432 | 689601 |
| 696 | 689960 | 689631 | 689939 |
| 697 | 690487 | 689846 | 690445 |
| 698 | 690717 | 690463 | 690717 |
| 699 | 691871 | 690672 | 691856 |
| 700 | 693837 | 692041 | 693837 |
| 701 | 694934 | 693837 | 694934 |
| 702 | 697263 | 694942 | 697230 |
| 703 | 698084 | 697170 | 697958 |
| 704 | 698392 | 697979 | 698380 |
| 705 | 698792 | 700117 | 698792 |
| 706 | 700269 | 700895 | 700269 |
| 707 | 700912 | 702165 | 700990 |
| 708 | 702183 | 703412 | 702183 |
| 709 | 703522 | 705000 | 703531 |
| 710 | 705011 | 705604 | 705062 |
| 711 | 706159 | 705704 | 706093 |
| 712 | 706521 | 706138 | 706488 |
| 713 | 708103 | 706496 | 707932 |
| 714 | 708398 | 708078 | 708392 |
| 715 | 708610 | 708248 | 708610 |
| 716 | 710278 | 708872 | 710203 |
| 717 | 711164 | 710262 | 711164 |
| 718 | 711432 | 712763 | 711432 |
| 719 | 712767 | 713438 | 712773 |
| 720 | 714232 | 713651 | 714217 |
| 721 | 714632 | 714120 | 714617 |
| 722 | 715592 | 714834 | 715739 |
| 723 | 715854 | 715558 | 715854 |
| 724 | 716937 | 715921 | 716886 |
| 725 | 718357 | 717149 | 718357 |
| 726 | 718500 | 718862 | 718590 |
| 727 | 719797 | 718499 | 719776 |
| 728 | 720273 | 719782 | 720147 |
| 729 | 720452 | 720144 | 720452 |
| 730 | 720613 | 721575 | 720613 |
| 731 | 721559 | 722356 | 721571 |
| 732 | 723248 | 722397 | 723239 |
| 733 | 724598 | 723378 | 724580 |
| 734 | 725763 | 724576 | 725760 |
| 735 | 726519 | 725767 | 726519 |
| 736 | 726819 | 726538 | 726801 |
| 737 | 727493 | 726753 | 727466 |
| 738 | 727984 | 727469 | 727984 |
| 739 | 728778 | 728329 | 728718 |
| 740 | 729346 | 728759 | 729334 |
| 741 | 732639 | 729442 | 732639 |
| 742 | 733246 | 734427 | 733246 |
| 743 | 734814 | 735659 | 734814 |
| 744 | 735644 | 736504 | 735644 |
| 745 | 736520 | 737254 | 736520 |
| 746 | 737254 | 737787 | 737254 |
| 747 | 737942 | 738679 | 738122 |
| 748 | 738838 | 739740 | 738862 |
| 749 | 742057 | 740060 | 741982 |
| 750 | 742869 | 742045 | 742824 |
| 751 | 743378 | 742824 | 743348 |
| 752 | 744298 | 743306 | 744292 |
| 753 | 744714 | 744430 | 744660 |
| 754 | 744985 | 744611 | 744931 |
| 755 | 745557 | 744958 | 745548 |
| 756 | 746412 | 745561 | 746409 |
| 757 | 746772 | 746416 | 746697 |
| 758 | 748269 | 746944 | 748269 |
| 759 | 748966 | 748274 | 748954 |
| 760 | 749426 | 748965 | 749411 |
| 761 | 749702 | 749433 | 749681 |
| 762 | 750029 | 749721 | 750020 |
| 763 | 752307 | 750007 | 752307 |
| 764 | 752913 | 752503 | 752901 |
| 765 | 754659 | 753616 | 754659 |
| 766 | 755000 | 756814 | 755000 |
| 767 | 756796 | 758301 | 756832 |
| 768 | 758691 | 758446 | 758688 |
| 769 | 759787 | 759338 | 759787 |
| 770 | 760242 | 759871 | 760188 |
| 771 | 760538 | 760188 | 760529 |
| 772 | 760966 | 761772 | 760966 |
| 773 | 761759 | 762142 | 761759 |
| 774 | 762267 | 762983 | 762267 |
| 775 | 764465 | 763335 | 764312 |
| 776 | 764857 | 764438 | 764821 |
| 777 | 766068 | 764821 | 765972 |
| 778 | 766643 | 766065 | 766643 |
| 779 | 768091 | 766934 | 768091 |
| 780 | 768785 | 768252 | 768785 |
| 781 | 770092 | 768791 | 770062 |
| 782 | 770138 | 770470 | 770150 |
| 783 | 770661 | 770185 | 770631 |
| 784 | 770924 | 770634 | 770894 |
| 785 | 772010 | 771330 | 772010 |
| 786 | 772390 | 773391 | 772390 |
| 787 | 774221 | 773427 | 774215 |
| 788 | 776035 | 774191 | 776035 |
| 789 | 776663 | 777706 | 776894 |
| 790 | 777195 | 776953 | 777177 |
| 791 | 779222 | 777732 | 779180 |
| 792 | 779321 | 781552 | 779360 |
| 793 | 781297 | 782442 | 781351 |
| 794 | 782447 | 785524 | 782447 |
| 795 | 785532 | 786002 | 785697 |
| 796 | 786580 | 785546 | 786580 |
| 797 | 787741 | 786611 | 787729 |
| 798 | 787620 | 788021 | 787782 |
| 799 | 790124 | 787920 | 790064 |
| 800 | 790160 | 790609 | 790178 |
| 801 | 790634 | 792016 | 790634 |
| 802 | 793084 | 792059 | 793084 |
| 803 | 793343 | 794056 | 793370 |
| 804 | 794046 | 794957 | 794079 |
| 805 | 795401 | 795144 | 795395 |
| 806 | 795575 | 796255 | 795575 |
| 807 | 796278 | 797015 | 796311 |
| 808 | 796979 | 797365 | 796979 |
| 809 | 797260 | 797856 | 797395 |
| 810 | 797772 | 798086 | 797805 |
| 811 | 798426 | 797935 | 798393 |
| 812 | 798925 | 798416 | 798916 |
| 813 | 799301 | 799927 | 799301 |
| 814 | 800892 | 800029 | 800892 |
| 815 | 801062 | 802129 | 801062 |
| 816 | 802023 | 802673 | 802041 |
| 817 | 802851 | 803246 | 802920 |
| 818 | 803105 | 804220 | 803111 |
| 819 | 804307 | 805356 | 804331 |
| 820 | 805290 | 806282 | 805356 |
| 821 | 806453 | 808081 | 806498 |

TABLE 2-continued

| SEQ ID NO | begin | stop | preferred start |
|---|---|---|---|
| 822 | 808026 | 809009 | 808098 |
| 823 | 810461 | 809079 | 810437 |
| 824 | 811605 | 810328 | 811590 |
| 825 | 811725 | 812342 | 811824 |
| 826 | 812329 | 813522 | 812398 |
| 827 | 813455 | 813772 | 813455 |
| 828 | 813732 | 814334 | 813780 |
| 829 | 815213 | 814314 | 815207 |
| 830 | 814878 | 814396 | 814975 |
| 831 | 815733 | 815428 | 815733 |
| 832 | 816116 | 817456 | 816170 |
| 833 | 817608 | 819320 | 817608 |
| 834 | 819324 | 819713 | 819342 |
| 835 | 819704 | 820402 | 819713 |
| 836 | 820375 | 821061 | 820453 |
| 837 | 821043 | 821537 | 821043 |
| 838 | 821646 | 822239 | 821667 |
| 839 | 822182 | 822931 | 822221 |
| 840 | 824355 | 823045 | 824352 |
| 841 | 825894 | 824359 | 825891 |
| 842 | 826322 | 825879 | 826322 |
| 843 | 826340 | 827026 | 826340 |
| 844 | 827014 | 827250 | 827014 |
| 845 | 827856 | 827230 | 827856 |
| 846 | 828007 | 829275 | 828025 |
| 847 | 829355 | 830953 | 829358 |
| 848 | 831119 | 831748 | 831140 |
| 849 | 832152 | 831751 | 832140 |
| 850 | 832744 | 832214 | 832666 |
| 851 | 833446 | 832805 | 833446 |
| 852 | 833802 | 833368 | 833742 |
| 853 | 834679 | 833879 | 834661 |
| 854 | 835452 | 834661 | 835365 |
| 855 | 835778 | 835371 | 835775 |
| 856 | 836482 | 835775 | 836470 |
| 857 | 836602 | 837264 | 836617 |
| 858 | 837209 | 838699 | 837209 |
| 859 | 838760 | 839575 | 838760 |
| 860 | 839942 | 840583 | 839951 |
| 861 | 840445 | 841713 | 840451 |
| 862 | 841659 | 842459 | 841686 |
| 863 | 842523 | 843068 | 842541 |
| 864 | 843495 | 843031 | 843447 |
| 865 | 843239 | 846196 | 843335 |
| 866 | 844137 | 843802 | 844077 |
| 867 | 848043 | 846217 | 848022 |
| 868 | 850123 | 848150 | 850099 |
| 869 | 851645 | 850230 | 851504 |
| 870 | 853696 | 851669 | 853672 |
| 871 | 854836 | 853700 | 854809 |
| 872 | 855525 | 854920 | 855468 |
| 873 | 856240 | 855437 | 856240 |
| 874 | 857183 | 856233 | 857006 |
| 875 | 859439 | 857451 | 859430 |
| 876 | 859946 | 859587 | 859916 |
| 877 | 859642 | 860640 | 859660 |
| 878 | 861599 | 860724 | 861599 |
| 879 | 862053 | 861580 | 862038 |
| 880 | 863540 | 862098 | 863531 |
| 881 | 863930 | 863571 | 863927 |
| 882 | 864697 | 863996 | 864688 |
| 883 | 864923 | 866248 | 864923 |
| 884 | 866303 | 866605 | 866336 |
| 885 | 866665 | 867732 | 866665 |
| 886 | 867810 | 869090 | 867864 |
| 887 | 869094 | 869357 | 869094 |
| 888 | 869270 | 871372 | 869336 |
| 889 | 871299 | 872582 | 871359 |
| 890 | 872429 | 872860 | 872555 |
| 891 | 872773 | 873915 | 872773 |
| 892 | 873812 | 873360 | 873668 |
| 893 | 874028 | 874438 | 874067 |
| 894 | 874778 | 875386 | 874796 |
| 895 | 875774 | 876382 | 875843 |
| 896 | 877872 | 877000 | 877866 |
| 897 | 878172 | 877876 | 878157 |
| 898 | 879098 | 878172 | 879098 |
| 899 | 878883 | 879161 | 878886 |
| 900 | 879842 | 879105 | 879809 |
| 901 | 880885 | 880052 | 880885 |
| 902 | 881863 | 880889 | 881863 |
| 903 | 882904 | 881948 | 882901 |
| 904 | 883794 | 882901 | 883761 |
| 905 | 884296 | 883661 | 884296 |
| 906 | 884996 | 884508 | 884984 |
| 907 | 888777 | 885166 | 888771 |
| 908 | 890172 | 888940 | 890172 |
| 909 | 891164 | 890325 | 891146 |
| 910 | 891463 | 891116 | 891427 |
| 911 | 893278 | 891968 | 893278 |
| 912 | 893356 | 893808 | 893386 |
| 913 | 893909 | 893643 | 893894 |
| 914 | 894276 | 893821 | 894276 |
| 915 | 894778 | 894248 | 894760 |
| 916 | 895892 | 895050 | 895874 |
| 917 | 895951 | 896829 | 895963 |
| 918 | 900783 | 897064 | 900774 |
| 919 | 902032 | 900791 | 902158 |
| 920 | 902659 | 903876 | 902659 |
| 921 | 903731 | 903471 | 903731 |
| 922 | 903860 | 905605 | 903860 |
| 923 | 905725 | 906474 | 905725 |
| 924 | 906493 | 906945 | 906493 |
| 925 | 907306 | 907001 | 907306 |
| 926 | 908101 | 908742 | 908131 |
| 927 | 908721 | 909194 | 908724 |
| 928 | 909198 | 909584 | 909201 |
| 929 | 909583 | 909951 | 909670 |
| 930 | 910081 | 910569 | 910090 |
| 931 | 910615 | 910944 | 910636 |
| 932 | 910948 | 912261 | 910951 |
| 933 | 912399 | 912629 | 912399 |
| 934 | 912595 | 913218 | 912595 |
| 935 | 913203 | 913676 | 913218 |
| 936 | 913691 | 914485 | 913691 |
| 937 | 914516 | 915136 | 914522 |
| 938 | 915144 | 915467 | 915162 |
| 939 | 915629 | 916633 | 915629 |
| 940 | 916051 | 916539 | 916159 |
| 941 | 916965 | 917627 | 916965 |
| 942 | 917612 | 918304 | 917612 |
| 943 | 918323 | 918655 | 918323 |
| 944 | 918682 | 919533 | 918682 |
| 945 | 919542 | 919829 | 919542 |
| 946 | 919723 | 920157 | 919723 |
| 947 | 920184 | 920840 | 920184 |
| 948 | 920866 | 921294 | 920866 |
| 949 | 921272 | 921514 | 921272 |
| 950 | 921510 | 921758 | 921510 |
| 951 | 921778 | 922143 | 921778 |
| 952 | 922159 | 922491 | 922159 |
| 953 | 922496 | 923035 | 922496 |
| 954 | 923160 | 923453 | 923160 |
| 955 | 923484 | 924032 | 923484 |
| 956 | 924048 | 924425 | 924057 |
| 957 | 924443 | 924937 | 924443 |
| 958 | 924933 | 925364 | 924933 |
| 959 | 925390 | 926760 | 925390 |
| 960 | 926819 | 927184 | 926819 |
| 961 | 927209 | 927604 | 927209 |
| 962 | 927577 | 928155 | 927577 |
| 963 | 928100 | 928759 | 928127 |
| 964 | 929222 | 930244 | 929243 |
| 965 | 930222 | 930656 | 930258 |
| 966 | 930608 | 931078 | 930665 |
| 967 | 931367 | 931666 | 931406 |
| 968 | 931549 | 931959 | 931558 |
| 969 | 932070 | 932579 | 932070 |
| 970 | 932602 | 933201 | 932602 |
| 971 | 933319 | 933621 | 933319 |
| 972 | 933522 | 933785 | 933522 |
| 973 | 934546 | 933848 | 934546 |
| 974 | 936377 | 934539 | 936377 |
| 975 | 938081 | 936666 | 938081 |
| 976 | 938538 | 939098 | 938595 |
| 977 | 939329 | 940933 | 939506 |

TABLE 2-continued

| SEQ ID NO | begin | stop | preferred start |
|---|---|---|---|
| 978 | 941031 | 942068 | 941076 |
| 979 | 942082 | 944685 | 942082 |
| 980 | 944634 | 945287 | 944673 |
| 981 | 945287 | 946294 | 945287 |
| 982 | 946293 | 946676 | 946368 |
| 983 | 947105 | 948454 | 947132 |
| 984 | 948522 | 949277 | 948546 |
| 985 | 949277 | 949594 | 949277 |
| 986 | 949849 | 950676 | 949888 |
| 987 | 950680 | 951330 | 950701 |
| 988 | 951281 | 951643 | 951290 |
| 989 | 951788 | 952798 | 951803 |
| 990 | 953581 | 954264 | 953602 |
| 991 | 954426 | 955157 | 954429 |
| 992 | 955754 | 957940 | 955766 |
| 993 | 957837 | 959312 | 957867 |
| 994 | 959299 | 961050 | 959317 |
| 995 | 961562 | 961053 | 961562 |
| 996 | 962575 | 961487 | 962545 |
| 997 | 961979 | 961584 | 961979 |
| 998 | 964914 | 962545 | 964914 |
| 999 | 964941 | 965708 | 964956 |
| 1000 | 967023 | 966193 | 966984 |
| 1001 | 967444 | 968061 | 967459 |
| 1002 | 968903 | 968064 | 968792 |
| 1003 | 970685 | 969528 | 970685 |
| 1004 | 971806 | 971024 | 971785 |
| 1005 | 973053 | 972388 | 973026 |
| 1006 | 974546 | 973746 | 974546 |
| 1007 | 975223 | 974558 | 975214 |
| 1008 | 976193 | 975207 | 976193 |
| 1009 | 976520 | 976254 | 976511 |
| 1010 | 976588 | 976899 | 976588 |
| 1011 | 976886 | 977635 | 976934 |
| 1012 | 977661 | 977933 | 977682 |
| 1013 | 977918 | 978433 | 977933 |
| 1014 | 978619 | 978984 | 978619 |
| 1015 | 978933 | 979331 | 978987 |
| 1016 | 981197 | 979389 | 981197 |
| 1017 | 979711 | 980112 | 979753 |
| 1018 | 982116 | 981148 | 982107 |
| 1019 | 982321 | 983598 | 982321 |
| 1020 | 984488 | 983862 | 984296 |
| 1021 | 985381 | 984371 | 985381 |
| 1022 | 986103 | 985399 | 986046 |
| 1023 | 986693 | 986046 | 986693 |
| 1024 | 987607 | 986693 | 987607 |
| 1025 | 988119 | 987616 | 987942 |
| 1026 | 988253 | 987936 | 988247 |
| 1027 | 988831 | 989163 | 988834 |
| 1028 | 989693 | 993442 | 989693 |
| 1029 | 993408 | 993785 | 993408 |
| 1030 | 993835 | 993416 | 993754 |
| 1031 | 993882 | 994262 | 993906 |
| 1032 | 994226 | 995656 | 994259 |
| 1033 | 996036 | 996611 | 996036 |
| 1034 | 996885 | 998267 | 996885 |
| 1035 | 998962 | 999225 | 998962 |
| 1036 | 999375 | 1001033 | 999393 |
| 1037 | 1001211 | 1001516 | 1001214 |
| 1038 | 1001392 | 1001664 | 1001443 |
| 1039 | 1003721 | 1001823 | 1003721 |
| 1040 | 1004459 | 1004845 | 1004459 |
| 1041 | 1004990 | 1005382 | 1004990 |
| 1042 | 1005391 | 1007496 | 1005391 |
| 1043 | 1007486 | 1007821 | 1007453 |
| 1044 | 1007802 | 1008698 | 1007841 |
| 1045 | 1009426 | 1009121 | 1009426 |
| 1046 | 1010534 | 1012054 | 1010534 |
| 1047 | 1012397 | 1011942 | 1012241 |
| 1048 | 1012042 | 1012635 | 1012057 |
| 1049 | 1012593 | 1012862 | 1012593 |
| 1050 | 1012811 | 1013440 | 1012829 |
| 1051 | 1013456 | 1014055 | 1013468 |
| 1052 | 1013977 | 1014489 | 1013977 |
| 1053 | 1015224 | 1014529 | 1015206 |
| 1054 | 1016002 | 1015145 | 1015963 |
| 1055 | 1017120 | 1015939 | 1017120 |
| 1056 | 1017766 | 1017245 | 1017658 |
| 1057 | 1018911 | 1017916 | 1018893 |
| 1058 | 1019191 | 1018580 | 1019110 |
| 1059 | 1020199 | 1019831 | 1020196 |
| 1060 | 1021007 | 1020114 | 1020992 |
| 1061 | 1021569 | 1021075 | 1021557 |
| 1062 | 1022411 | 1022097 | 1022402 |
| 1063 | 1023344 | 1023667 | 1023344 |
| 1064 | 1023701 | 1023949 | 1023701 |
| 1065 | 1023976 | 1024776 | 1023976 |
| 1066 | 1024704 | 1025045 | 1024704 |
| 1067 | 1025881 | 1024967 | 1025845 |
| 1068 | 1026546 | 1025839 | 1026546 |
| 1069 | 1027379 | 1026546 | 1027373 |
| 1070 | 1030604 | 1027929 | 1030328 |
| 1071 | 1033252 | 1030508 | 1033249 |
| 1072 | 1031733 | 1032086 | 1031823 |
| 1073 | 1037037 | 1033456 | 1037016 |
| 1074 | 1035674 | 1035910 | 1035674 |
| 1075 | 1036175 | 1036507 | 1036268 |
| 1076 | 68(comp) | 1036967 | 38 |
| 1077 | 16591 | 16989 | 16597 |
| 1078 | 31779 | 31408 | 31764 |
| 1079 | 56502 | 56834 | 56520 |
| 1080 | 56686 | 56913 | 56686 |
| 1081 | 64748 | 65074 | 64790 |
| 1082 | 73482 | 73195 | 73482 |
| 1083 | 78482 | 78736 | 78506 |
| 1084 | 79803 | 79411 | 79773 |
| 1085 | 82333 | 81959 | 82333 |
| 1086 | 87313 | 86999 | 87523 |
| 1087 | 109929 | 109456 | 109716 |
| 1088 | 111599 | 111351 | 111599 |
| 1089 | 112069 | 111734 | 111988 |
| 1090 | 112666 | 112911 | 112666 |
| 1091 | 114017 | 113715 | 113978 |
| 1092 | 120757 | 120464 | 120757 |
| 1093 | 125133 | 125522 | 125133 |
| 1094 | 131888 | 131604 | 131837 |
| 1095 | 144164 | 144427 | 144191 |
| 1096 | 150698 | 150369 | 150635 |
| 1097 | 164385 | 163948 | 164385 |
| 1098 | 165690 | 166115 | 165408 |
| 1099 | 168742 | 168425 | 168742 |
| 1100 | 170509 | 170793 | 170509 |
| 1101 | 177145 | 177474 | 177145 |
| 1102 | 188295 | 188023 | 188295 |
| 1103 | 188791 | 188330 | 188791 |
| 1104 | 190629 | 190336 | 190626 |
| 1105 | 197313 | 197083 | 197307 |
| 1106 | 210914 | 211384 | 210956 |
| 1107 | 235160 | 234852 | 235160 |
| 1108 | 237227 | 236913 | 237188 |
| 1109 | 249733 | 249446 | 249904 |
| 1110 | 253493 | 253158 | 253493 |
| 1111 | 253701 | 254789 | 253701 |
| 1112 | 271633 | 271932 | 271633 |
| 1113 | 275666 | 276070 | 275666 |
| 1114 | 277931 | 278218 | 277976 |
| 1115 | 282741 | 282481 | 282738 |
| 1116 | 293178 | 293489 | 293181 |
| 1117 | 303155 | 303469 | 303185 |
| 1118 | 309297 | 308965 | 309297 |
| 1119 | 312219 | 312536 | 312246 |
| 1120 | 312853 | 312602 | 312844 |
| 1121 | 313167 | 312772 | 313167 |
| 1122 | 320224 | 320598 | 320224 |
| 1123 | 340249 | 340503 | 340249 |
| 1124 | 352839 | 353324 | 352839 |
| 1125 | 373475 | 373699 | 373475 |
| 1126 | 377316 | 377756 | 377316 |
| 1127 | 379268 | 379657 | 379268 |
| 1128 | 395098 | 394823 | 395077 |
| 1129 | 401594 | 401142 | 401594 |
| 1130 | 410045 | 410539 | 410045 |
| 1131 | 411425 | 411658 | 411425 |
| 1132 | 414937 | 414416 | 414937 |
| 1133 | 422889 | 423212 | 422964 |

TABLE 2-continued

| SEQ ID NO | begin | stop | preferred start |
|---|---|---|---|
| 1134 | 427842 | 428183 | 427842 |
| 1135 | 428732 | 429451 | 428732 |
| 1136 | 442557 | 442799 | 442524 |
| 1137 | 443628 | 444041 | 443628 |
| 1138 | 443678 | 443166 | 443678 |
| 1139 | 445901 | 446155 | 445901 |
| 1140 | 467981 | 468262 | 468023 |
| 1141 | 471869 | 472108 | 471869 |
| 1142 | 488032 | 488337 | 488044 |
| 1143 | 497179 | 497694 | 497101 |
| 1144 | 500474 | 500202 | 500471 |
| 1145 | 508968 | 509561 | 508968 |
| 1146 | 510845 | 511264 | 510845 |
| 1147 | 526525 | 526848 | 526525 |
| 1148 | 531318 | 531863 | 531444 |
| 1149 | 556826 | 557224 | 556826 |
| 1150 | 564971 | 564537 | 564971 |
| 1151 | 566963 | 567232 | 566963 |
| 1152 | 570351 | 570890 | 570351 |
| 1153 | 571072 | 571332 | 571072 |
| 1154 | 576025 | 575801 | 576025 |
| 1155 | 590363 | 590650 | 590363 |
| 1156 | 597868 | 598593 | 597868 |
| 1157 | 606889 | 606626 | 606889 |
| 1158 | 608031 | 607786 | 608031 |
| 1159 | 610110 | 610391 | 610143 |
| 1160 | 632703 | 633353 | 632703 |
| 1161 | 637213 | 637482 | 637255 |
| 1162 | 650517 | 649924 | 650517 |
| 1163 | 652317 | 652562 | 652317 |
| 1164 | 654753 | 655325 | 654753 |
| 1165 | 661118 | 660810 | 661118 |
| 1166 | 677596 | 677057 | 677578 |
| 1167 | 679528 | 679253 | 679477 |
| 1168 | 732536 | 732210 | 732536 |
| 1169 | 742069 | 742383 | 742069 |
| 1170 | 759318 | 758782 | 759318 |
| 1171 | 760282 | 760521 | 760282 |
| 1172 | 771313 | 770894 | 771391 |
| 1173 | 772115 | 772408 | 772115 |
| 1174 | 788137 | 788457 | 788137 |
| 1175 | 816302 | 815967 | 816302 |
| 1176 | 846606 | 846914 | 846612 |
| 1177 | 867803 | 868054 | 867806 |
| 1178 | 875386 | 875658 | 875395 |
| 1179 | 876445 | 876915 | 876445 |
| 1180 | 884548 | 884312 | 884548 |
| 1181 | 891859 | 891467 | 891859 |
| 1182 | 900770 | 900417 | 900728 |
| 1183 | 902553 | 902269 | 902529 |
| 1184 | 908046 | 907783 | 908007 |
| 1185 | 912313 | 912567 | 912313 |
| 1186 | 935451 | 935741 | 935451 |
| 1187 | 946961 | 946692 | 946940 |
| 1188 | 953193 | 952783 | 953145 |
| 1189 | 966199 | 965873 | 966184 |
| 1190 | 969298 | 968765 | 969298 |
| 1191 | 971009 | 970731 | 971009 |
| 1192 | 972162 | 972404 | 972165 |
| 1193 | 973119 | 973508 | 973119 |
| 1194 | 998649 | 998404 | 998625 |
| 1195 | 1004280 | 1003882 | 1004280 |
| 1196 | 1010200 | 1009532 | 1010200 |
| 1197 | 1029174 | 1029482 | 1029180 |

TABLE 4

| ORFGenset | ORF-oligosFd | ORFoligosFp | ORFoligosBd | ORF-oligosBp |
|---|---|---|---|---|
| 2 | 1199 | 1198 | 3591 | 3590 |
| 3 | 1201 | 1200 | 3593 | 3592 |
| 4 | 1203 | 1202 | 3595 | 3594 |
| 5 | 1205 | 1204 | 3597 | 3596 |
| 6 | 1207 | 1206 | 3599 | 3598 |
| 7 | 1209 | 1208 | 3601 | 3600 |
| 8 | 1211 | 1210 | 3603 | 3602 |
| 9 | 1213 | 1212 | 3605 | 3604 |
| 10 | 1215 | 1214 | 3607 | 3606 |
| 11 | 1217 | 1216 | 3609 | 3608 |
| 12 | 1219 | 1218 | 3611 | 3610 |
| 13 | 1221 | 1220 | 3613 | 3612 |
| 14 | 1223 | 1222 | 3615 | 3614 |
| 15 | 1225 | 1224 | 3617 | 3616 |
| 16 | 1227 | 1226 | 3619 | 3618 |
| 17 | 1229 | 1228 | 3621 | 3620 |
| 18 | 1231 | 1230 | 3623 | 3622 |
| 19 | 1233 | 1232 | 3625 | 3624 |
| 20 | 1235 | 1234 | 3627 | 3626 |
| 21 | 1237 | 1236 | 3629 | 3628 |
| 22 | 1239 | 1238 | 3631 | 3630 |
| 23 | 1241 | 1240 | 3633 | 3632 |
| 24 | 1243 | 1242 | 3635 | 3634 |
| 25 | 1245 | 1244 | 3637 | 3636 |
| 26 | 1247 | 1246 | 3639 | 3638 |
| 27 | 1249 | 1248 | 3641 | 3640 |
| 28 | 1251 | 1250 | 3643 | 3642 |
| 29 | 1253 | 1252 | 3645 | 3644 |
| 30 | 1255 | 1254 | 3647 | 3646 |
| 31 | 1257 | 1256 | 3649 | 3648 |
| 32 | 1259 | 1258 | 3651 | 3650 |
| 33 | 1261 | 1260 | 3653 | 3652 |
| 34 | 1263 | 1262 | 3655 | 3654 |
| 35 | 1265 | 1264 | 3657 | 3656 |
| 36 | 1267 | 1266 | 3659 | 3658 |
| 37 | 1269 | 1268 | 3661 | 3660 |
| 38 | 1271 | 1270 | 3663 | 3662 |
| 39 | 1273 | 1272 | 3665 | 3664 |
| 40 | 1275 | 1274 | 3667 | 3666 |
| 41 | 1277 | 1276 | 3669 | 3668 |
| 42 | 1279 | 1278 | 3671 | 3670 |
| 43 | 1281 | 1280 | 3673 | 3672 |
| 44 | 1283 | 1282 | 3675 | 3674 |
| 45 | 1285 | 1284 | 3677 | 3676 |
| 46 | 1287 | 1286 | 3679 | 3678 |
| 47 | 1289 | 1288 | 3681 | 3680 |
| 48 | 1291 | 1290 | 3683 | 3682 |
| 49 | 1293 | 1292 | 3685 | 3684 |
| 50 | 1295 | 1294 | 3687 | 3686 |
| 51 | 1297 | 1296 | 3689 | 3688 |
| 52 | 1299 | 1298 | 3691 | 3690 |
| 53 | 1301 | 1300 | 3693 | 3692 |
| 54 | 1303 | 1302 | 3695 | 3694 |
| 55 | 1305 | 1304 | 3697 | 3696 |
| 56 | 1307 | 1306 | 3699 | 3698 |
| 57 | 1309 | 1308 | 3701 | 3700 |
| 58 | 1311 | 1310 | 3703 | 3702 |
| 59 | 1313 | 1312 | 3705 | 3704 |
| 60 | 1315 | 1314 | 3707 | 3706 |
| 61 | 1317 | 1316 | 3709 | 3708 |
| 62 | 1319 | 1318 | 3711 | 3710 |
| 63 | 1321 | 1320 | 3713 | 3712 |
| 64 | 1323 | 1322 | 3715 | 3714 |
| 65 | 1325 | 1324 | 3717 | 3716 |
| 66 | 1327 | 1326 | 3719 | 3718 |
| 67 | 1329 | 1328 | 3721 | 3720 |
| 68 | 1331 | 1330 | 3723 | 3722 |
| 69 | 1333 | 1332 | 3725 | 3724 |
| 70 | 1335 | 1334 | 3727 | 3726 |
| 71 | 1337 | 1336 | 3729 | 3728 |
| 72 | 1339 | 1338 | 3731 | 3730 |
| 73 | 1341 | 1340 | 3733 | 3732 |
| 74 | 1343 | 1342 | 3735 | 3734 |
| 75 | 1345 | 1344 | 3737 | 3736 |
| 76 | 1347 | 1346 | 3739 | 3738 |
| 77 | 1349 | 1348 | 3741 | 3740 |
| 78 | 1351 | 1350 | 3743 | 3742 |
| 79 | 1353 | 1352 | 3745 | 3744 |
| 80 | 1355 | 1354 | 3747 | 3746 |
| 81 | 1357 | 1356 | 3749 | 3748 |
| 82 | 1359 | 1358 | 3751 | 3750 |
| 83 | 1361 | 1360 | 3753 | 3752 |

TABLE 4-continued

| ORFGenset | ORF-oligosFd | ORFoligosFp | ORFoligosBd | ORF-oligosBp | ORFGenset | ORF-oligosFd | ORFoligosFp | ORFoligosBd | ORF-oligosBp |
|---|---|---|---|---|---|---|---|---|---|
| 84 | 1363 | 1362 | 3755 | 3754 | 161 | 1517 | 1516 | 3909 | 3908 |
| 85 | 1365 | 1364 | 3757 | 3756 | 162 | 1519 | 1518 | 3911 | 3910 |
| 86 | 1367 | 1366 | 3759 | 3758 | 163 | 1521 | 1520 | 3913 | 3912 |
| 87 | 1369 | 1368 | 3761 | 3760 | 164 | 1523 | 1522 | 3915 | 3914 |
| 88 | 1371 | 1370 | 3763 | 3762 | 165 | 1525 | 1524 | 3917 | 3916 |
| 89 | 1373 | 1372 | 3765 | 3764 | 166 | 1527 | 1526 | 3919 | 3918 |
| 90 | 1375 | 1374 | 3767 | 3766 | 167 | 1529 | 1528 | 3921 | 3920 |
| 91 | 1377 | 1376 | 3769 | 3768 | 168 | 1531 | 1530 | 3923 | 3922 |
| 92 | 1379 | 1378 | 3771 | 3770 | 169 | 1533 | 1532 | 3925 | 3924 |
| 93 | 1381 | 1380 | 3773 | 3772 | 170 | 1535 | 1534 | 3927 | 3926 |
| 94 | 1383 | 1382 | 3775 | 3774 | 171 | 1537 | 1536 | 3929 | 3928 |
| 95 | 1385 | 1384 | 3777 | 3776 | 172 | 1539 | 1538 | 3931 | 3930 |
| 96 | 1387 | 1386 | 3779 | 3778 | 173 | 1541 | 1540 | 3933 | 3932 |
| 97 | 1389 | 1388 | 3781 | 3780 | 174 | 1543 | 1542 | 3935 | 3934 |
| 98 | 1391 | 1390 | 3783 | 3782 | 175 | 1545 | 1544 | 3937 | 3936 |
| 99 | 1393 | 1392 | 3785 | 3784 | 176 | 1547 | 1546 | 3939 | 3938 |
| 100 | 1395 | 1394 | 3787 | 3786 | 177 | 1549 | 1548 | 3941 | 3940 |
| 101 | 1397 | 1396 | 3789 | 3788 | 178 | 1551 | 1550 | 3943 | 3942 |
| 102 | 1399 | 1398 | 3791 | 3790 | 179 | 1553 | 1552 | 3945 | 3944 |
| 103 | 1401 | 1400 | 3793 | 3792 | 180 | 1555 | 1554 | 3947 | 3946 |
| 104 | 1403 | 1402 | 3795 | 3794 | 181 | 1557 | 1556 | 3949 | 3948 |
| 105 | 1405 | 1404 | 3797 | 3796 | 182 | 1559 | 1558 | 3951 | 3950 |
| 106 | 1407 | 1406 | 3799 | 3798 | 183 | 1561 | 1560 | 3953 | 3952 |
| 107 | 1409 | 1408 | 3801 | 3800 | 184 | 1563 | 1562 | 3955 | 3954 |
| 108 | 1411 | 1410 | 3803 | 3802 | 185 | 1565 | 1564 | 3957 | 3956 |
| 109 | 1413 | 1412 | 3805 | 3804 | 186 | 1567 | 1566 | 3959 | 3958 |
| 110 | 1415 | 1414 | 3807 | 3806 | 187 | 1569 | 1568 | 3961 | 3960 |
| 111 | 1417 | 1416 | 3809 | 3808 | 188 | 1571 | 1570 | 3963 | 3962 |
| 112 | 1419 | 1418 | 3811 | 3810 | 189 | 1573 | 1572 | 3965 | 3964 |
| 113 | 1421 | 1420 | 3813 | 3812 | 190 | 1575 | 1574 | 3967 | 3966 |
| 114 | 1423 | 1422 | 3815 | 3814 | 191 | 1577 | 1576 | 3969 | 3968 |
| 115 | 1425 | 1424 | 3817 | 3816 | 192 | 1579 | 1578 | 3971 | 3970 |
| 116 | 1427 | 1426 | 3819 | 3818 | 193 | 1581 | 1580 | 3973 | 3972 |
| 117 | 1429 | 1428 | 3821 | 3820 | 194 | 1583 | 1582 | 3975 | 3974 |
| 118 | 1431 | 1430 | 3823 | 3822 | 195 | 1585 | 1584 | 3977 | 3976 |
| 119 | 1433 | 1432 | 3825 | 3824 | 196 | 1587 | 1586 | 3979 | 3978 |
| 120 | 1435 | 1434 | 3827 | 3826 | 197 | 1589 | 1588 | 3981 | 3980 |
| 121 | 1437 | 1436 | 3829 | 3828 | 198 | 1591 | 1590 | 3983 | 3982 |
| 122 | 1439 | 1438 | 3831 | 3830 | 199 | 1593 | 1592 | 3985 | 3984 |
| 123 | 1441 | 1440 | 3833 | 3832 | 200 | 1595 | 1594 | 3987 | 3986 |
| 124 | 1443 | 1442 | 3835 | 3834 | 201 | 1597 | 1596 | 3989 | 3988 |
| 125 | 1445 | 1444 | 3837 | 3836 | 202 | 1599 | 1598 | 3991 | 3990 |
| 126 | 1447 | 1446 | 3839 | 3838 | 203 | 1601 | 1600 | 3993 | 3992 |
| 127 | 1449 | 1448 | 3841 | 3840 | 204 | 1603 | 1602 | 3995 | 3994 |
| 128 | 1451 | 1450 | 3843 | 3842 | 205 | 1605 | 1604 | 3997 | 3996 |
| 129 | 1453 | 1452 | 3845 | 3844 | 206 | 1607 | 1606 | 3999 | 3998 |
| 130 | 1455 | 1454 | 3847 | 3846 | 207 | 1609 | 1608 | 4001 | 4000 |
| 131 | 1457 | 1456 | 3849 | 3848 | 208 | 1611 | 1610 | 4003 | 4002 |
| 132 | 1459 | 1458 | 3851 | 3850 | 209 | 1613 | 1612 | 4005 | 4004 |
| 133 | 1461 | 1460 | 3853 | 3852 | 210 | 1615 | 1614 | 4007 | 4006 |
| 134 | 1463 | 1462 | 3855 | 3854 | 211 | 1617 | 1616 | 4009 | 4008 |
| 135 | 1465 | 1464 | 3857 | 3856 | 212 | 1619 | 1618 | 4011 | 4010 |
| 136 | 1467 | 1466 | 3859 | 3858 | 213 | 1621 | 1620 | 4013 | 4012 |
| 137 | 1469 | 1468 | 3861 | 3860 | 214 | 1623 | 1622 | 4015 | 4014 |
| 138 | 1471 | 1470 | 3863 | 3862 | 215 | 1625 | 1624 | 4017 | 4016 |
| 139 | 1473 | 1472 | 3865 | 3864 | 216 | 1627 | 1626 | 4019 | 4018 |
| 140 | 1475 | 1474 | 3867 | 3866 | 217 | 1629 | 1628 | 4021 | 4020 |
| 141 | 1477 | 1476 | 3869 | 3868 | 218 | 1631 | 1630 | 4023 | 4022 |
| 142 | 1479 | 1478 | 3871 | 3870 | 219 | 1633 | 1632 | 4025 | 4024 |
| 143 | 1481 | 1480 | 3873 | 3872 | 220 | 1635 | 1634 | 4027 | 4026 |
| 144 | 1483 | 1482 | 3875 | 3874 | 221 | 1637 | 1636 | 4029 | 4028 |
| 145 | 1485 | 1484 | 3877 | 3876 | 222 | 1639 | 1638 | 4031 | 4030 |
| 146 | 1487 | 1486 | 3879 | 3878 | 223 | 1641 | 1640 | 4033 | 4032 |
| 147 | 1489 | 1488 | 3881 | 3880 | 224 | 1643 | 1642 | 4035 | 4034 |
| 148 | 1491 | 1490 | 3883 | 3882 | 225 | 1645 | 1644 | 4037 | 4036 |
| 149 | 1493 | 1492 | 3885 | 3884 | 226 | 1647 | 1646 | 4039 | 4038 |
| 150 | 1495 | 1494 | 3887 | 3886 | 227 | 1649 | 1648 | 4041 | 4040 |
| 151 | 1497 | 1496 | 3889 | 3888 | 228 | 1651 | 1650 | 4043 | 4042 |
| 152 | 1499 | 1498 | 3891 | 3890 | 229 | 1653 | 1652 | 4045 | 4044 |
| 153 | 1501 | 1500 | 3893 | 3892 | 230 | 1655 | 1654 | 4047 | 4046 |
| 154 | 1503 | 1502 | 3895 | 3894 | 231 | 1657 | 1656 | 4049 | 4048 |
| 155 | 1505 | 1504 | 3897 | 3896 | 232 | 1659 | 1658 | 4051 | 4050 |
| 156 | 1507 | 1506 | 3899 | 3898 | 233 | 1661 | 1660 | 4053 | 4052 |
| 157 | 1509 | 1508 | 3901 | 3900 | 234 | 1663 | 1662 | 4055 | 4054 |
| 158 | 1511 | 1510 | 3903 | 3902 | 235 | 1665 | 1664 | 4057 | 4056 |
| 159 | 1513 | 1512 | 3905 | 3904 | 236 | 1667 | 1666 | 4059 | 4058 |
| 160 | 1515 | 1514 | 3907 | 3906 | 237 | 1669 | 1668 | 4061 | 4060 |

TABLE 4-continued

| ORFGenset | ORFoligosFd | ORFoligosFp | ORFoligosBd | ORFoligosBp |
|---|---|---|---|---|
| 238 | 1671 | 1670 | 4063 | 4062 |
| 239 | 1673 | 1672 | 4065 | 4064 |
| 240 | 1675 | 1674 | 4067 | 4066 |
| 241 | 1677 | 1676 | 4069 | 4068 |
| 242 | 1679 | 1678 | 4071 | 4070 |
| 243 | 1681 | 1680 | 4073 | 4072 |
| 244 | 1683 | 1682 | 4075 | 4074 |
| 245 | 1685 | 1684 | 4077 | 4076 |
| 246 | 1687 | 1686 | 4079 | 4078 |
| 247 | 1689 | 1688 | 4081 | 4080 |
| 248 | 1691 | 1690 | 4083 | 4082 |
| 249 | 1693 | 1692 | 4085 | 4084 |
| 250 | 1695 | 1694 | 4087 | 4086 |
| 251 | 1697 | 1696 | 4089 | 4088 |
| 252 | 1699 | 1698 | 4091 | 4090 |
| 253 | 1701 | 1700 | 4093 | 4092 |
| 254 | 1703 | 1702 | 4095 | 4094 |
| 255 | 1705 | 1704 | 4097 | 4096 |
| 256 | 1707 | 1706 | 4099 | 4098 |
| 257 | 1709 | 1708 | 4101 | 4100 |
| 258 | 1711 | 1710 | 4103 | 4102 |
| 259 | 1713 | 1712 | 4105 | 4104 |
| 260 | 1715 | 1714 | 4107 | 4106 |
| 261 | 1717 | 1716 | 4109 | 4108 |
| 262 | 1719 | 1718 | 4111 | 4110 |
| 263 | 1721 | 1720 | 4113 | 4112 |
| 264 | 1723 | 1722 | 4115 | 4114 |
| 265 | 1725 | 1724 | 4117 | 4116 |
| 266 | 1727 | 1726 | 4119 | 4118 |
| 267 | 1729 | 1728 | 4121 | 4120 |
| 268 | 1731 | 1730 | 4123 | 4122 |
| 269 | 1733 | 1732 | 4125 | 4124 |
| 270 | 1735 | 1734 | 4127 | 4126 |
| 271 | 1737 | 1736 | 4129 | 4128 |
| 272 | 1739 | 1738 | 4131 | 4130 |
| 273 | 1741 | 1740 | 4133 | 4132 |
| 274 | 1743 | 1742 | 4135 | 4134 |
| 275 | 1745 | 1744 | 4137 | 4136 |
| 276 | 1747 | 1746 | 4139 | 4138 |
| 277 | 1749 | 1748 | 4141 | 4140 |
| 278 | 1751 | 1750 | 4143 | 4142 |
| 279 | 1753 | 1752 | 4145 | 4144 |
| 280 | 1755 | 1754 | 4147 | 4146 |
| 281 | 1757 | 1756 | 4149 | 4148 |
| 282 | 1759 | 1758 | 4151 | 4150 |
| 283 | 1761 | 1760 | 4153 | 4152 |
| 284 | 1763 | 1762 | 4155 | 4154 |
| 285 | 1765 | 1764 | 4157 | 4156 |
| 286 | 1767 | 1766 | 4159 | 4158 |
| 287 | 1769 | 1768 | 4161 | 4160 |
| 288 | 1771 | 1770 | 4163 | 4162 |
| 289 | 1773 | 1772 | 4165 | 4164 |
| 290 | 1775 | 1774 | 4167 | 4166 |
| 291 | 1777 | 1776 | 4169 | 4168 |
| 292 | 1779 | 1778 | 4171 | 4170 |
| 293 | 1781 | 1780 | 4173 | 4172 |
| 294 | 1783 | 1782 | 4175 | 4174 |
| 295 | 1785 | 1784 | 4177 | 4176 |
| 296 | 1787 | 1786 | 4179 | 4178 |
| 297 | 1789 | 1788 | 4181 | 4180 |
| 298 | 1791 | 1790 | 4183 | 4182 |
| 299 | 1793 | 1792 | 4185 | 4184 |
| 300 | 1795 | 1794 | 4187 | 4186 |
| 301 | 1797 | 1796 | 4189 | 4188 |
| 302 | 1799 | 1798 | 4191 | 4190 |
| 303 | 1801 | 1800 | 4193 | 4192 |
| 304 | 1803 | 1802 | 4195 | 4194 |
| 305 | 1805 | 1804 | 4197 | 4196 |
| 306 | 1807 | 1806 | 4199 | 4198 |
| 307 | 1809 | 1808 | 4201 | 4200 |
| 308 | 1811 | 1810 | 4203 | 4202 |
| 309 | 1813 | 1812 | 4205 | 4204 |
| 310 | 1815 | 1814 | 4207 | 4206 |
| 311 | 1817 | 1816 | 4209 | 4208 |
| 312 | 1819 | 1818 | 4211 | 4210 |
| 313 | 1821 | 1820 | 4213 | 4212 |
| 314 | 1823 | 1822 | 4215 | 4214 |
| 315 | 1825 | 1824 | 4217 | 4216 |
| 316 | 1827 | 1826 | 4219 | 4218 |
| 317 | 1829 | 1828 | 4221 | 4220 |
| 318 | 1831 | 1830 | 4223 | 4222 |
| 319 | 1833 | 1832 | 4225 | 4224 |
| 320 | 1835 | 1834 | 4227 | 4226 |
| 321 | 1837 | 1836 | 4229 | 4228 |
| 322 | 1839 | 1838 | 4231 | 4230 |
| 323 | 1841 | 1840 | 4233 | 4232 |
| 324 | 1843 | 1842 | 4235 | 4234 |
| 325 | 1845 | 1844 | 4237 | 4236 |
| 326 | 1847 | 1846 | 4239 | 4238 |
| 327 | 1849 | 1848 | 4241 | 4240 |
| 328 | 1851 | 1850 | 4243 | 4242 |
| 329 | 1853 | 1852 | 4245 | 4244 |
| 330 | 1855 | 1854 | 4247 | 4246 |
| 331 | 1857 | 1856 | 4249 | 4248 |
| 332 | 1859 | 1858 | 4251 | 4250 |
| 333 | 1861 | 1860 | 4253 | 4252 |
| 334 | 1863 | 1862 | 4255 | 4254 |
| 335 | 1865 | 1864 | 4257 | 4256 |
| 336 | 1867 | 1866 | 4259 | 4258 |
| 337 | 1869 | 1868 | 4261 | 4260 |
| 338 | 1871 | 1870 | 4263 | 4262 |
| 339 | 1873 | 1872 | 4265 | 4264 |
| 340 | 1875 | 1874 | 4267 | 4266 |
| 341 | 1877 | 1876 | 4269 | 4268 |
| 342 | 1879 | 1878 | 4271 | 4270 |
| 343 | 1881 | 1880 | 4273 | 4272 |
| 344 | 1883 | 1882 | 4275 | 4274 |
| 345 | 1885 | 1884 | 4277 | 4276 |
| 346 | 1887 | 1886 | 4279 | 4278 |
| 347 | 1889 | 1888 | 4281 | 4280 |
| 348 | 1891 | 1890 | 4283 | 4282 |
| 349 | 1893 | 1892 | 4285 | 4284 |
| 350 | 1895 | 1894 | 4287 | 4286 |
| 351 | 1897 | 1896 | 4289 | 4288 |
| 352 | 1899 | 1898 | 4291 | 4290 |
| 353 | 1901 | 1900 | 4293 | 4292 |
| 354 | 1903 | 1902 | 4295 | 4294 |
| 355 | 1905 | 1904 | 4297 | 4296 |
| 356 | 1907 | 1906 | 4299 | 4298 |
| 357 | 1909 | 1908 | 4301 | 4300 |
| 358 | 1911 | 1910 | 4303 | 4302 |
| 359 | 1913 | 1912 | 4305 | 4304 |
| 360 | 1915 | 1914 | 4307 | 4306 |
| 361 | 1917 | 1916 | 4309 | 4308 |
| 362 | 1919 | 1918 | 4311 | 4310 |
| 363 | 1921 | 1920 | 4313 | 4312 |
| 364 | 1923 | 1922 | 4315 | 4314 |
| 365 | 1925 | 1924 | 4317 | 4316 |
| 366 | 1927 | 1926 | 4319 | 4318 |
| 367 | 1929 | 1928 | 4321 | 4320 |
| 368 | 1931 | 1930 | 4323 | 4322 |
| 369 | 1933 | 1932 | 4325 | 4324 |
| 370 | 1935 | 1934 | 4327 | 4326 |
| 371 | 1937 | 1936 | 4329 | 4328 |
| 372 | 1939 | 1938 | 4331 | 4330 |
| 373 | 1941 | 1940 | 4333 | 4332 |
| 374 | 1943 | 1942 | 4335 | 4334 |
| 375 | 1945 | 1944 | 4337 | 4336 |
| 376 | 1947 | 1946 | 4339 | 4338 |
| 377 | 1949 | 1948 | 4341 | 4340 |
| 378 | 1951 | 1950 | 4343 | 4342 |
| 379 | 1953 | 1952 | 4345 | 4344 |
| 380 | 1955 | 1954 | 4347 | 4346 |
| 381 | 1957 | 1956 | 4349 | 4348 |
| 382 | 1959 | 1958 | 4351 | 4350 |
| 383 | 1961 | 1960 | 4353 | 4352 |
| 384 | 1963 | 1962 | 4355 | 4354 |
| 385 | 1965 | 1964 | 4357 | 4356 |
| 386 | 1967 | 1966 | 4359 | 4358 |
| 387 | 1969 | 1968 | 4361 | 4360 |
| 388 | 1971 | 1970 | 4363 | 4362 |
| 389 | 1973 | 1972 | 4365 | 4364 |
| 390 | 1975 | 1974 | 4367 | 4366 |
| 391 | 1977 | 1976 | 4369 | 4368 |

TABLE 4-continued

| ORFGenset | ORFoligosFd | ORFoligosFp | ORFoligosBd | ORFoligosBp |
|---|---|---|---|---|
| 392 | 1979 | 1978 | 4371 | 4370 |
| 393 | 1981 | 1980 | 4373 | 4372 |
| 394 | 1983 | 1982 | 4375 | 4374 |
| 395 | 1985 | 1984 | 4377 | 4376 |
| 396 | 1987 | 1986 | 4379 | 4378 |
| 397 | 1989 | 1988 | 4381 | 4380 |
| 398 | 1991 | 1990 | 4383 | 4382 |
| 399 | 1993 | 1992 | 4385 | 4384 |
| 400 | 1995 | 1994 | 4387 | 4386 |
| 401 | 1997 | 1996 | 4389 | 4388 |
| 402 | 1999 | 1998 | 4391 | 4390 |
| 403 | 2001 | 2000 | 4393 | 4392 |
| 404 | 2003 | 2002 | 4395 | 4394 |
| 405 | 2005 | 2004 | 4397 | 4396 |
| 406 | 2007 | 2006 | 4399 | 4398 |
| 407 | 2009 | 2008 | 4401 | 4400 |
| 408 | 2011 | 2010 | 4403 | 4402 |
| 409 | 2013 | 2012 | 4405 | 4404 |
| 410 | 2015 | 2014 | 4407 | 4406 |
| 411 | 2017 | 2016 | 4409 | 4408 |
| 412 | 2019 | 2018 | 4411 | 4410 |
| 413 | 2021 | 2020 | 4413 | 4412 |
| 414 | 2023 | 2022 | 4415 | 4414 |
| 415 | 2025 | 2024 | 4417 | 4416 |
| 416 | 2027 | 2026 | 4419 | 4418 |
| 417 | 2029 | 2028 | 4421 | 4420 |
| 418 | 2031 | 2030 | 4423 | 4422 |
| 419 | 2033 | 2032 | 4425 | 4424 |
| 420 | 2035 | 2034 | 4427 | 4426 |
| 421 | 2037 | 2036 | 4429 | 4428 |
| 422 | 2039 | 2038 | 4431 | 4430 |
| 423 | 2041 | 2040 | 4433 | 4432 |
| 424 | 2043 | 2042 | 4435 | 4434 |
| 425 | 2045 | 2044 | 4437 | 4436 |
| 426 | 2047 | 2046 | 4439 | 4438 |
| 427 | 2049 | 2048 | 4441 | 4440 |
| 428 | 2051 | 2050 | 4443 | 4442 |
| 429 | 2053 | 2052 | 4445 | 4444 |
| 430 | 2055 | 2054 | 4447 | 4446 |
| 431 | 2057 | 2056 | 4449 | 4448 |
| 432 | 2059 | 2058 | 4451 | 4450 |
| 433 | 2061 | 2060 | 4453 | 4452 |
| 434 | 2063 | 2062 | 4455 | 4454 |
| 435 | 2065 | 2064 | 4457 | 4456 |
| 436 | 2067 | 2066 | 4459 | 4458 |
| 437 | 2069 | 2068 | 4461 | 4460 |
| 438 | 2071 | 2070 | 4463 | 4462 |
| 439 | 2073 | 2072 | 4465 | 4464 |
| 440 | 2075 | 2074 | 4467 | 4466 |
| 441 | 2077 | 2076 | 4469 | 4468 |
| 442 | 2079 | 2078 | 4471 | 4470 |
| 443 | 2081 | 2080 | 4473 | 4472 |
| 444 | 2083 | 2082 | 4475 | 4474 |
| 445 | 2085 | 2084 | 4477 | 4476 |
| 446 | 2087 | 2086 | 4479 | 4478 |
| 447 | 2089 | 2088 | 4481 | 4480 |
| 448 | 2091 | 2090 | 4483 | 4482 |
| 449 | 2093 | 2092 | 4485 | 4484 |
| 450 | 2095 | 2094 | 4487 | 4486 |
| 451 | 2097 | 2096 | 4489 | 4488 |
| 452 | 2099 | 2098 | 4491 | 4490 |
| 453 | 2101 | 2100 | 4493 | 4492 |
| 454 | 2103 | 2102 | 4495 | 4494 |
| 455 | 2105 | 2104 | 4497 | 4496 |
| 456 | 2107 | 2106 | 4499 | 4498 |
| 457 | 2109 | 2108 | 4501 | 4500 |
| 458 | 2111 | 2110 | 4503 | 4502 |
| 459 | 2113 | 2112 | 4505 | 4504 |
| 460 | 2115 | 2114 | 4507 | 4506 |
| 461 | 2117 | 2116 | 4509 | 4508 |
| 462 | 2119 | 2118 | 4511 | 4510 |
| 463 | 2121 | 2120 | 4513 | 4512 |
| 464 | 2123 | 2122 | 4515 | 4514 |
| 465 | 2125 | 2124 | 4517 | 4516 |
| 466 | 2127 | 2126 | 4519 | 4518 |
| 467 | 2129 | 2128 | 4521 | 4520 |
| 468 | 2131 | 2130 | 4523 | 4522 |
| 469 | 2133 | 2132 | 4525 | 4524 |
| 470 | 2135 | 2134 | 4527 | 4526 |
| 471 | 2137 | 2136 | 4529 | 4528 |
| 472 | 2139 | 2138 | 4531 | 4530 |
| 473 | 2141 | 2140 | 4533 | 4532 |
| 474 | 2143 | 2142 | 4535 | 4534 |
| 475 | 2145 | 2144 | 4537 | 4536 |
| 476 | 2147 | 2146 | 4539 | 4538 |
| 477 | 2149 | 2148 | 4541 | 4540 |
| 478 | 2151 | 2150 | 4543 | 4542 |
| 479 | 2153 | 2152 | 4545 | 4544 |
| 480 | 2155 | 2154 | 4547 | 4546 |
| 481 | 2157 | 2156 | 4549 | 4548 |
| 482 | 2159 | 2158 | 4551 | 4550 |
| 483 | 2161 | 2160 | 4553 | 4552 |
| 484 | 2163 | 2162 | 4555 | 4554 |
| 485 | 2165 | 2164 | 4557 | 4556 |
| 486 | 2167 | 2166 | 4559 | 4558 |
| 487 | 2169 | 2168 | 4561 | 4560 |
| 488 | 2171 | 2170 | 4563 | 4562 |
| 489 | 2173 | 2172 | 4565 | 4564 |
| 490 | 2175 | 2174 | 4567 | 4566 |
| 491 | 2177 | 2176 | 4569 | 4568 |
| 492 | 2179 | 2178 | 4571 | 4570 |
| 493 | 2181 | 2180 | 4573 | 4572 |
| 494 | 2183 | 2182 | 4575 | 4574 |
| 495 | 2185 | 2184 | 4577 | 4576 |
| 496 | 2187 | 2186 | 4579 | 4578 |
| 497 | 2189 | 2188 | 4581 | 4580 |
| 498 | 2191 | 2190 | 4583 | 4582 |
| 499 | 2193 | 2192 | 4585 | 4584 |
| 500 | 2195 | 2194 | 4587 | 4586 |
| 501 | 2197 | 2196 | 4589 | 4588 |
| 502 | 2199 | 2198 | 4591 | 4590 |
| 503 | 2201 | 2200 | 4593 | 4592 |
| 504 | 2203 | 2202 | 4595 | 4594 |
| 505 | 2205 | 2204 | 4597 | 4596 |
| 506 | 2207 | 2206 | 4599 | 4598 |
| 507 | 2209 | 2208 | 4601 | 4600 |
| 508 | 2211 | 2210 | 4603 | 4602 |
| 509 | 2213 | 2212 | 4605 | 4604 |
| 510 | 2215 | 2214 | 4607 | 4606 |
| 511 | 2217 | 2216 | 4609 | 4608 |
| 512 | 2219 | 2218 | 4611 | 4610 |
| 513 | 2221 | 2220 | 4613 | 4612 |
| 514 | 2223 | 2222 | 4615 | 4614 |
| 515 | 2225 | 2224 | 4617 | 4616 |
| 516 | 2227 | 2226 | 4619 | 4618 |
| 517 | 2229 | 2228 | 4621 | 4620 |
| 518 | 2231 | 2230 | 4623 | 4622 |
| 519 | 2233 | 2232 | 4625 | 4624 |
| 520 | 2235 | 2234 | 4627 | 4626 |
| 521 | 2237 | 2236 | 4629 | 4628 |
| 522 | 2239 | 2238 | 4631 | 4630 |
| 523 | 2241 | 2240 | 4633 | 4632 |
| 524 | 2243 | 2242 | 4635 | 4634 |
| 525 | 2245 | 2244 | 4637 | 4636 |
| 526 | 2247 | 2246 | 4639 | 4638 |
| 527 | 2249 | 2248 | 4641 | 4640 |
| 528 | 2251 | 2250 | 4643 | 4642 |
| 529 | 2253 | 2252 | 4645 | 4644 |
| 530 | 2255 | 2254 | 4647 | 4646 |
| 531 | 2257 | 2256 | 4649 | 4648 |
| 532 | 2259 | 2258 | 4651 | 4650 |
| 533 | 2261 | 2260 | 4653 | 4652 |
| 534 | 2263 | 2262 | 4655 | 4654 |
| 535 | 2265 | 2264 | 4657 | 4656 |
| 536 | 2267 | 2266 | 4659 | 4658 |
| 537 | 2269 | 2268 | 4661 | 4660 |
| 538 | 2271 | 2270 | 4663 | 4662 |
| 539 | 2273 | 2272 | 4665 | 4664 |
| 540 | 2275 | 2274 | 4667 | 4666 |
| 541 | 2277 | 2276 | 4669 | 4668 |
| 542 | 2279 | 2278 | 4671 | 4670 |
| 543 | 2281 | 2280 | 4673 | 4672 |
| 544 | 2283 | 2282 | 4675 | 4674 |
| 545 | 2285 | 2284 | 4677 | 4676 |

TABLE 4-continued

| ORFGenset | ORF-oligosFd | ORFoligosFp | ORFoligosBd | ORF-oligosBp |
|---|---|---|---|---|
| 546 | 2287 | 2286 | 4679 | 4678 |
| 547 | 2289 | 2288 | 4681 | 4680 |
| 548 | 2291 | 2290 | 4683 | 4682 |
| 549 | 2293 | 2292 | 4685 | 4684 |
| 550 | 2295 | 2294 | 4687 | 4686 |
| 551 | 2297 | 2296 | 4689 | 4688 |
| 552 | 2299 | 2298 | 4691 | 4690 |
| 553 | 2301 | 2300 | 4693 | 4692 |
| 554 | 2303 | 2302 | 4695 | 4694 |
| 555 | 2305 | 2304 | 4697 | 4696 |
| 556 | 2307 | 2306 | 4699 | 4698 |
| 557 | 2309 | 2308 | 4701 | 4700 |
| 558 | 2311 | 2310 | 4703 | 4702 |
| 559 | 2313 | 2312 | 4705 | 4704 |
| 560 | 2315 | 2314 | 4707 | 4706 |
| 561 | 2317 | 2316 | 4709 | 4708 |
| 562 | 2319 | 2318 | 4711 | 4710 |
| 563 | 2321 | 2320 | 4713 | 4712 |
| 564 | 2323 | 2322 | 4715 | 4714 |
| 565 | 2325 | 2324 | 4717 | 4716 |
| 566 | 2327 | 2326 | 4719 | 4718 |
| 567 | 2329 | 2328 | 4721 | 4720 |
| 568 | 2331 | 2330 | 4723 | 4722 |
| 569 | 2333 | 2332 | 4725 | 4724 |
| 570 | 2335 | 2334 | 4727 | 4726 |
| 571 | 2337 | 2336 | 4729 | 4728 |
| 572 | 2339 | 2338 | 4731 | 4730 |
| 573 | 2341 | 2340 | 4733 | 4732 |
| 574 | 2343 | 2342 | 4735 | 4734 |
| 575 | 2345 | 2344 | 4737 | 4736 |
| 576 | 2347 | 2346 | 4739 | 4738 |
| 577 | 2349 | 2348 | 4741 | 4740 |
| 578 | 2351 | 2350 | 4743 | 4742 |
| 579 | 2353 | 2352 | 4745 | 4744 |
| 580 | 2355 | 2354 | 4747 | 4746 |
| 581 | 2357 | 2356 | 4749 | 4748 |
| 582 | 2359 | 2358 | 4751 | 4750 |
| 583 | 2361 | 2360 | 4753 | 4752 |
| 584 | 2363 | 2362 | 4755 | 4754 |
| 585 | 2365 | 2364 | 4757 | 4756 |
| 586 | 2367 | 2366 | 4759 | 4758 |
| 587 | 2369 | 2368 | 4761 | 4760 |
| 588 | 2371 | 2370 | 4763 | 4762 |
| 589 | 2373 | 2372 | 4765 | 4764 |
| 590 | 2375 | 2374 | 4767 | 4766 |
| 591 | 2377 | 2376 | 4769 | 4768 |
| 592 | 2379 | 2378 | 4771 | 4770 |
| 593 | 2381 | 2380 | 4773 | 4772 |
| 594 | 2383 | 2382 | 4775 | 4774 |
| 595 | 2385 | 2384 | 4777 | 4776 |
| 596 | 2387 | 2386 | 4779 | 4778 |
| 597 | 2389 | 2388 | 4781 | 4780 |
| 598 | 2391 | 2390 | 4783 | 4782 |
| 599 | 2393 | 2392 | 4785 | 4784 |
| 600 | 2395 | 2394 | 4787 | 4786 |
| 601 | 2397 | 2396 | 4789 | 4788 |
| 602 | 2399 | 2398 | 4791 | 4790 |
| 603 | 2401 | 2400 | 4793 | 4792 |
| 604 | 2403 | 2402 | 4795 | 4794 |
| 605 | 2405 | 2404 | 4797 | 4796 |
| 606 | 2407 | 2406 | 4799 | 4798 |
| 607 | 2409 | 2408 | 4801 | 4800 |
| 608 | 2411 | 2410 | 4803 | 4802 |
| 609 | 2413 | 2412 | 4805 | 4804 |
| 610 | 2415 | 2414 | 4807 | 4806 |
| 611 | 2417 | 2416 | 4809 | 4808 |
| 612 | 2419 | 2418 | 4811 | 4810 |
| 613 | 2421 | 2420 | 4813 | 4812 |
| 614 | 2423 | 2422 | 4815 | 4814 |
| 615 | 2425 | 2424 | 4817 | 4816 |
| 616 | 2427 | 2426 | 4819 | 4818 |
| 617 | 2429 | 2428 | 4821 | 4820 |
| 618 | 2431 | 2430 | 4823 | 4822 |
| 619 | 2433 | 2432 | 4825 | 4824 |
| 620 | 2435 | 2434 | 4827 | 4826 |
| 621 | 2437 | 2436 | 4829 | 4828 |
| 622 | 2439 | 2438 | 4831 | 4830 |
| 623 | 2441 | 2440 | 4833 | 4832 |
| 624 | 2443 | 2442 | 4835 | 4834 |
| 625 | 2445 | 2444 | 4837 | 4836 |
| 626 | 2447 | 2446 | 4839 | 4838 |
| 627 | 2449 | 2448 | 4841 | 4840 |
| 628 | 2451 | 2450 | 4843 | 4842 |
| 629 | 2453 | 2452 | 4845 | 4844 |
| 630 | 2455 | 2454 | 4847 | 4846 |
| 631 | 2457 | 2456 | 4849 | 4848 |
| 632 | 2459 | 2458 | 4851 | 4850 |
| 633 | 2461 | 2460 | 4853 | 4852 |
| 634 | 2463 | 2462 | 4855 | 4854 |
| 635 | 2465 | 2464 | 4857 | 4856 |
| 636 | 2467 | 2466 | 4859 | 4858 |
| 637 | 2469 | 2468 | 4861 | 4860 |
| 638 | 2471 | 2470 | 4863 | 4862 |
| 639 | 2473 | 2472 | 4865 | 4864 |
| 640 | 2475 | 2474 | 4867 | 4866 |
| 641 | 2477 | 2476 | 4869 | 4868 |
| 642 | 2479 | 2478 | 4871 | 4870 |
| 643 | 2481 | 2480 | 4873 | 4872 |
| 644 | 2483 | 2482 | 4875 | 4874 |
| 645 | 2485 | 2484 | 4877 | 4876 |
| 646 | 2487 | 2486 | 4879 | 4878 |
| 647 | 2489 | 2488 | 4881 | 4880 |
| 648 | 2491 | 2490 | 4883 | 4882 |
| 649 | 2493 | 2492 | 4885 | 4884 |
| 650 | 2495 | 2494 | 4887 | 4886 |
| 651 | 2497 | 2496 | 4889 | 4888 |
| 652 | 2499 | 2498 | 4891 | 4890 |
| 653 | 2501 | 2500 | 4893 | 4892 |
| 654 | 2503 | 2502 | 4895 | 4894 |
| 655 | 2505 | 2504 | 4897 | 4896 |
| 656 | 2507 | 2506 | 4899 | 4898 |
| 657 | 2509 | 2508 | 4901 | 4900 |
| 658 | 2511 | 2510 | 4903 | 4902 |
| 659 | 2513 | 2512 | 4905 | 4904 |
| 660 | 2515 | 2514 | 4907 | 4906 |
| 661 | 2517 | 2516 | 4909 | 4908 |
| 662 | 2519 | 2518 | 4911 | 4910 |
| 663 | 2521 | 2520 | 4913 | 4912 |
| 664 | 2523 | 2522 | 4915 | 4914 |
| 665 | 2525 | 2524 | 4917 | 4916 |
| 666 | 2527 | 2526 | 4919 | 4918 |
| 667 | 2529 | 2528 | 4921 | 4920 |
| 668 | 2531 | 2530 | 4923 | 4922 |
| 669 | 2533 | 2532 | 4925 | 4924 |
| 670 | 2535 | 2534 | 4927 | 4926 |
| 671 | 2537 | 2536 | 4929 | 4928 |
| 672 | 2539 | 2538 | 4931 | 4930 |
| 673 | 2541 | 2540 | 4933 | 4932 |
| 674 | 2543 | 2542 | 4935 | 4934 |
| 675 | 2545 | 2544 | 4937 | 4936 |
| 676 | 2547 | 2546 | 4939 | 4938 |
| 677 | 2549 | 2548 | 4941 | 4940 |
| 678 | 2551 | 2550 | 4943 | 4942 |
| 679 | 2553 | 2552 | 4945 | 4944 |
| 680 | 2555 | 2554 | 4947 | 4946 |
| 681 | 2557 | 2556 | 4949 | 4948 |
| 682 | 2559 | 2558 | 4951 | 4950 |
| 683 | 2561 | 2560 | 4953 | 4952 |
| 684 | 2563 | 2562 | 4955 | 4954 |
| 685 | 2565 | 2564 | 4957 | 4956 |
| 686 | 2567 | 2566 | 4959 | 4958 |
| 687 | 2569 | 2568 | 4961 | 4960 |
| 688 | 2571 | 2570 | 4963 | 4962 |
| 689 | 2573 | 2572 | 4965 | 4964 |
| 690 | 2575 | 2574 | 4967 | 4966 |
| 691 | 2577 | 2576 | 4969 | 4968 |
| 692 | 2579 | 2578 | 4971 | 4970 |
| 693 | 2581 | 2580 | 4973 | 4972 |
| 694 | 2583 | 2582 | 4975 | 4974 |
| 695 | 2585 | 2584 | 4977 | 4976 |
| 696 | 2587 | 2586 | 4979 | 4978 |
| 697 | 2589 | 2588 | 4981 | 4980 |
| 698 | 2591 | 2590 | 4983 | 4982 |
| 699 | 2593 | 2592 | 4985 | 4984 |

TABLE 4-continued

| ORFGenset | ORF-oligosFd | ORFoligosFp | ORFoligosBd | ORF-oligosBp | ORFGenset | ORF-oligosFd | ORFoligosFp | ORFoligosBd | ORF-oligosBp |
|---|---|---|---|---|---|---|---|---|---|
| 700 | 2595 | 2594 | 4987 | 4986 | 777 | 2749 | 2748 | 5141 | 5140 |
| 701 | 2597 | 2596 | 4989 | 4988 | 778 | 2751 | 2750 | 5143 | 5142 |
| 702 | 2599 | 2598 | 4991 | 4990 | 779 | 2753 | 2752 | 5145 | 5144 |
| 703 | 2601 | 2600 | 4993 | 4992 | 780 | 2755 | 2754 | 5147 | 5146 |
| 704 | 2603 | 2602 | 4995 | 4994 | 781 | 2757 | 2756 | 5149 | 5148 |
| 705 | 2605 | 2604 | 4997 | 4996 | 782 | 2759 | 2758 | 5151 | 5150 |
| 706 | 2607 | 2606 | 4999 | 4998 | 783 | 2761 | 2760 | 5153 | 5152 |
| 707 | 2609 | 2608 | 5001 | 5000 | 784 | 2763 | 2762 | 5155 | 5154 |
| 708 | 2611 | 2610 | 5003 | 5002 | 785 | 2765 | 2764 | 5157 | 5156 |
| 709 | 2613 | 2612 | 5005 | 5004 | 786 | 2767 | 2766 | 5159 | 5158 |
| 710 | 2615 | 2614 | 5007 | 5006 | 787 | 2769 | 2768 | 5161 | 5160 |
| 711 | 2617 | 2616 | 5009 | 5008 | 788 | 2771 | 2770 | 5163 | 5162 |
| 712 | 2619 | 2618 | 5011 | 5010 | 789 | 2773 | 2772 | 5165 | 5164 |
| 713 | 2621 | 2620 | 5013 | 5012 | 790 | 2775 | 2774 | 5167 | 5166 |
| 714 | 2623 | 2622 | 5015 | 5014 | 791 | 2777 | 2776 | 5169 | 5168 |
| 715 | 2625 | 2624 | 5017 | 5016 | 792 | 2779 | 2778 | 5171 | 5170 |
| 716 | 2627 | 2626 | 5019 | 5018 | 793 | 2781 | 2780 | 5173 | 5172 |
| 717 | 2629 | 2628 | 5021 | 5020 | 794 | 2783 | 2782 | 5175 | 5174 |
| 718 | 2631 | 2630 | 5023 | 5022 | 795 | 2785 | 2784 | 5177 | 5176 |
| 719 | 2633 | 2632 | 5025 | 5024 | 796 | 2787 | 2786 | 5179 | 5178 |
| 720 | 2635 | 2634 | 5027 | 5026 | 797 | 2789 | 2788 | 5181 | 5180 |
| 721 | 2637 | 2636 | 5029 | 5028 | 798 | 2791 | 2790 | 5183 | 5182 |
| 722 | 2639 | 2638 | 5031 | 5030 | 799 | 2793 | 2792 | 5185 | 5184 |
| 723 | 2641 | 2640 | 5033 | 5032 | 800 | 2795 | 2794 | 5187 | 5186 |
| 724 | 2643 | 2642 | 5035 | 5034 | 801 | 2797 | 2796 | 5189 | 5188 |
| 725 | 2645 | 2644 | 5037 | 5036 | 802 | 2799 | 2798 | 5191 | 5190 |
| 726 | 2647 | 2646 | 5039 | 5038 | 803 | 2801 | 2800 | 5193 | 5192 |
| 727 | 2649 | 2648 | 5041 | 5040 | 804 | 2803 | 2802 | 5195 | 5194 |
| 728 | 2651 | 2650 | 5043 | 5042 | 805 | 2805 | 2804 | 5197 | 5196 |
| 729 | 2653 | 2652 | 5045 | 5044 | 806 | 2807 | 2806 | 5199 | 5198 |
| 730 | 2655 | 2654 | 5047 | 5046 | 807 | 2809 | 2808 | 5201 | 5200 |
| 731 | 2657 | 2656 | 5049 | 5048 | 808 | 2811 | 2810 | 5203 | 5202 |
| 732 | 2659 | 2658 | 5051 | 5050 | 809 | 2813 | 2812 | 5205 | 5204 |
| 733 | 2661 | 2660 | 5053 | 5052 | 810 | 2815 | 2814 | 5207 | 5206 |
| 734 | 2663 | 2662 | 5055 | 5054 | 811 | 2817 | 2816 | 5209 | 5208 |
| 735 | 2665 | 2664 | 5057 | 5056 | 812 | 2819 | 2818 | 5211 | 5210 |
| 736 | 2667 | 2666 | 5059 | 5058 | 813 | 2821 | 2820 | 5213 | 5212 |
| 737 | 2669 | 2668 | 5061 | 5060 | 814 | 2823 | 2822 | 5215 | 5214 |
| 738 | 2671 | 2670 | 5063 | 5062 | 815 | 2825 | 2824 | 5217 | 5216 |
| 739 | 2673 | 2672 | 5065 | 5064 | 816 | 2827 | 2826 | 5219 | 5218 |
| 740 | 2675 | 2674 | 5067 | 5066 | 817 | 2829 | 2828 | 5221 | 5220 |
| 741 | 2677 | 2676 | 5069 | 5068 | 818 | 2831 | 2830 | 5223 | 5222 |
| 742 | 2679 | 2678 | 5071 | 5070 | 819 | 2833 | 2832 | 5225 | 5224 |
| 743 | 2681 | 2680 | 5073 | 5072 | 820 | 2835 | 2834 | 5227 | 5226 |
| 744 | 2683 | 2682 | 5075 | 5074 | 821 | 2837 | 2836 | 5229 | 5228 |
| 745 | 2685 | 2684 | 5077 | 5076 | 822 | 2839 | 2838 | 5231 | 5230 |
| 746 | 2687 | 2686 | 5079 | 5078 | 823 | 2841 | 2840 | 5233 | 5232 |
| 747 | 2689 | 2688 | 5081 | 5080 | 824 | 2843 | 2842 | 5235 | 5234 |
| 748 | 2691 | 2690 | 5083 | 5082 | 825 | 2845 | 2844 | 5237 | 5236 |
| 749 | 2693 | 2692 | 5085 | 5084 | 826 | 2847 | 2846 | 5239 | 5238 |
| 750 | 2695 | 2694 | 5087 | 5086 | 827 | 2849 | 2848 | 5241 | 5240 |
| 751 | 2697 | 2696 | 5089 | 5088 | 828 | 2851 | 2850 | 5243 | 5242 |
| 752 | 2699 | 2698 | 5091 | 5090 | 829 | 2853 | 2852 | 5245 | 5244 |
| 753 | 2701 | 2700 | 5093 | 5092 | 830 | 2855 | 2854 | 5247 | 5246 |
| 754 | 2703 | 2702 | 5095 | 5094 | 831 | 2857 | 2856 | 5249 | 5248 |
| 755 | 2705 | 2704 | 5097 | 5096 | 832 | 2859 | 2858 | 5251 | 5250 |
| 756 | 2707 | 2706 | 5099 | 5098 | 833 | 2861 | 2860 | 5253 | 5252 |
| 757 | 2709 | 2708 | 5101 | 5100 | 834 | 2863 | 2862 | 5255 | 5254 |
| 758 | 2711 | 2710 | 5103 | 5102 | 835 | 2865 | 2864 | 5257 | 5256 |
| 759 | 2713 | 2712 | 5105 | 5104 | 836 | 2867 | 2866 | 5259 | 5258 |
| 760 | 2715 | 2714 | 5107 | 5106 | 837 | 2869 | 2868 | 5261 | 5260 |
| 761 | 2717 | 2716 | 5109 | 5108 | 838 | 2871 | 2870 | 5263 | 5262 |
| 762 | 2719 | 2718 | 5111 | 5110 | 839 | 2873 | 2872 | 5265 | 5264 |
| 763 | 2721 | 2720 | 5113 | 5112 | 840 | 2875 | 2874 | 5267 | 5266 |
| 764 | 2723 | 2722 | 5115 | 5114 | 841 | 2877 | 2876 | 5269 | 5268 |
| 765 | 2725 | 2724 | 5117 | 5116 | 842 | 2879 | 2878 | 5271 | 5270 |
| 766 | 2727 | 2726 | 5119 | 5118 | 843 | 2881 | 2880 | 5273 | 5272 |
| 767 | 2729 | 2728 | 5121 | 5120 | 844 | 2883 | 2882 | 5275 | 5274 |
| 768 | 2731 | 2730 | 5123 | 5122 | 845 | 2885 | 2884 | 5277 | 5276 |
| 769 | 2733 | 2732 | 5125 | 5124 | 846 | 2887 | 2886 | 5279 | 5278 |
| 770 | 2735 | 2734 | 5127 | 5126 | 847 | 2889 | 2888 | 5281 | 5280 |
| 771 | 2737 | 2736 | 5129 | 5128 | 848 | 2891 | 2890 | 5283 | 5282 |
| 772 | 2739 | 2738 | 5131 | 5130 | 849 | 2893 | 2892 | 5285 | 5284 |
| 773 | 2741 | 2740 | 5133 | 5132 | 850 | 2895 | 2894 | 5287 | 5286 |
| 774 | 2743 | 2742 | 5135 | 5134 | 851 | 2897 | 2896 | 5289 | 5288 |
| 775 | 2745 | 2744 | 5137 | 5136 | 852 | 2899 | 2898 | 5291 | 5290 |
| 776 | 2747 | 2746 | 5139 | 5138 | 853 | 2901 | 2900 | 5293 | 5292 |

TABLE 4-continued

| ORFGenset | ORFoligosFd | ORFoligosFp | ORFoligosBd | ORFoligosBp |
|---|---|---|---|---|
| 854 | 2903 | 2902 | 5295 | 5294 |
| 855 | 2905 | 2904 | 5297 | 5296 |
| 856 | 2907 | 2906 | 5299 | 5298 |
| 857 | 2909 | 2908 | 5301 | 5300 |
| 858 | 2911 | 2910 | 5303 | 5302 |
| 859 | 2913 | 2912 | 5305 | 5304 |
| 860 | 2915 | 2914 | 5307 | 5306 |
| 861 | 2917 | 2916 | 5309 | 5308 |
| 862 | 2919 | 2918 | 5311 | 5310 |
| 863 | 2921 | 2920 | 5313 | 5312 |
| 864 | 2923 | 2922 | 5315 | 5314 |
| 865 | 2925 | 2924 | 5317 | 5316 |
| 866 | 2927 | 2926 | 5319 | 5318 |
| 867 | 2929 | 2928 | 5321 | 5320 |
| 868 | 2931 | 2930 | 5323 | 5322 |
| 869 | 2933 | 2932 | 5325 | 5324 |
| 870 | 2935 | 2934 | 5327 | 5326 |
| 871 | 2937 | 2936 | 5329 | 5328 |
| 872 | 2939 | 2938 | 5331 | 5330 |
| 873 | 2941 | 2940 | 5333 | 5332 |
| 874 | 2943 | 2942 | 5335 | 5334 |
| 875 | 2945 | 2944 | 5337 | 5336 |
| 876 | 2947 | 2946 | 5339 | 5338 |
| 877 | 2949 | 2948 | 5341 | 5340 |
| 878 | 2951 | 2950 | 5343 | 5342 |
| 879 | 2953 | 2952 | 5345 | 5344 |
| 880 | 2955 | 2954 | 5347 | 5346 |
| 881 | 2957 | 2956 | 5349 | 5348 |
| 882 | 2959 | 2958 | 5351 | 5350 |
| 883 | 2961 | 2960 | 5353 | 5352 |
| 884 | 2963 | 2962 | 5355 | 5354 |
| 885 | 2965 | 2964 | 5357 | 5356 |
| 886 | 2967 | 2966 | 5359 | 5358 |
| 887 | 2969 | 2968 | 5361 | 5360 |
| 888 | 2971 | 2970 | 5363 | 5362 |
| 889 | 2973 | 2972 | 5365 | 5364 |
| 890 | 2975 | 2974 | 5367 | 5366 |
| 891 | 2977 | 2976 | 5369 | 5368 |
| 892 | 2979 | 2978 | 5371 | 5370 |
| 893 | 2981 | 2980 | 5373 | 5372 |
| 894 | 2983 | 2982 | 5375 | 5374 |
| 895 | 2985 | 2984 | 5377 | 5376 |
| 896 | 2987 | 2986 | 5379 | 5378 |
| 897 | 2989 | 2988 | 5381 | 5380 |
| 898 | 2991 | 2990 | 5383 | 5382 |
| 899 | 2993 | 2992 | 5385 | 5384 |
| 900 | 2995 | 2994 | 5387 | 5386 |
| 901 | 2997 | 2996 | 5389 | 5388 |
| 902 | 2999 | 2998 | 5391 | 5390 |
| 903 | 3001 | 3000 | 5393 | 5392 |
| 904 | 3003 | 3002 | 5395 | 5394 |
| 905 | 3005 | 3004 | 5397 | 5396 |
| 906 | 3007 | 3006 | 5399 | 5398 |
| 907 | 3009 | 3008 | 5401 | 5400 |
| 908 | 3011 | 3010 | 5403 | 5402 |
| 909 | 3013 | 3012 | 5405 | 5404 |
| 910 | 3015 | 3014 | 5407 | 5406 |
| 911 | 3017 | 3016 | 5409 | 5408 |
| 912 | 3019 | 3018 | 5411 | 5410 |
| 913 | 3021 | 3020 | 5413 | 5412 |
| 914 | 3023 | 3022 | 5415 | 5414 |
| 915 | 3025 | 3024 | 5417 | 5416 |
| 916 | 3027 | 3026 | 5419 | 5418 |
| 917 | 3029 | 3028 | 5421 | 5420 |
| 918 | 3031 | 3030 | 5423 | 5422 |
| 919 | 3033 | 3032 | 5425 | 5424 |
| 920 | 3035 | 3034 | 5427 | 5426 |
| 921 | 3037 | 3036 | 5429 | 5428 |
| 922 | 3039 | 3038 | 5431 | 5430 |
| 923 | 3041 | 3040 | 5433 | 5432 |
| 924 | 3043 | 3042 | 5435 | 5434 |
| 925 | 3045 | 3044 | 5437 | 5436 |
| 926 | 3047 | 3046 | 5439 | 5438 |
| 927 | 3049 | 3048 | 5441 | 5440 |
| 928 | 3051 | 3050 | 5443 | 5442 |
| 929 | 3053 | 3052 | 5445 | 5444 |
| 930 | 3055 | 3054 | 5447 | 5446 |
| 931 | 3057 | 3056 | 5449 | 5448 |
| 932 | 3059 | 3058 | 5451 | 5450 |
| 933 | 3061 | 3060 | 5453 | 5452 |
| 934 | 3063 | 3062 | 5455 | 5454 |
| 935 | 3065 | 3064 | 5457 | 5456 |
| 936 | 3067 | 3066 | 5459 | 5458 |
| 937 | 3069 | 3068 | 5461 | 5460 |
| 938 | 3071 | 3070 | 5463 | 5462 |
| 939 | 3073 | 3072 | 5465 | 5464 |
| 940 | 3075 | 3074 | 5467 | 5466 |
| 941 | 3077 | 3076 | 5469 | 5468 |
| 942 | 3079 | 3078 | 5471 | 5470 |
| 943 | 3081 | 3080 | 5473 | 5472 |
| 944 | 3083 | 3082 | 5475 | 5474 |
| 945 | 3085 | 3084 | 5477 | 5476 |
| 946 | 3087 | 3086 | 5479 | 5478 |
| 947 | 3089 | 3088 | 5481 | 5480 |
| 948 | 3091 | 3090 | 5483 | 5482 |
| 949 | 3093 | 3092 | 5485 | 5484 |
| 950 | 3095 | 3094 | 5487 | 5486 |
| 951 | 3097 | 3096 | 5489 | 5488 |
| 952 | 3099 | 3098 | 5491 | 5490 |
| 953 | 3101 | 3100 | 5493 | 5492 |
| 954 | 3103 | 3102 | 5495 | 5494 |
| 955 | 3105 | 3104 | 5497 | 5496 |
| 956 | 3107 | 3106 | 5499 | 5498 |
| 957 | 3109 | 3108 | 5501 | 5500 |
| 958 | 3111 | 3110 | 5503 | 5502 |
| 959 | 3113 | 3112 | 5505 | 5504 |
| 960 | 3115 | 3114 | 5507 | 5506 |
| 961 | 3117 | 3116 | 5509 | 5508 |
| 962 | 3119 | 3118 | 5511 | 5510 |
| 963 | 3121 | 3120 | 5513 | 5512 |
| 964 | 3123 | 3122 | 5515 | 5514 |
| 965 | 3125 | 3124 | 5517 | 5516 |
| 966 | 3127 | 3126 | 5519 | 5518 |
| 967 | 3129 | 3128 | 5521 | 5520 |
| 968 | 3131 | 3130 | 5523 | 5522 |
| 969 | 3133 | 3132 | 5525 | 5524 |
| 970 | 3135 | 3134 | 5527 | 5526 |
| 971 | 3137 | 3136 | 5529 | 5528 |
| 972 | 3139 | 3138 | 5531 | 5530 |
| 973 | 3141 | 3140 | 5533 | 5532 |
| 974 | 3143 | 3142 | 5535 | 5534 |
| 975 | 3145 | 3144 | 5537 | 5536 |
| 976 | 3147 | 3146 | 5539 | 5538 |
| 977 | 3149 | 3148 | 5541 | 5540 |
| 978 | 3151 | 3150 | 5543 | 5542 |
| 979 | 3153 | 3152 | 5545 | 5544 |
| 980 | 3155 | 3154 | 5547 | 5546 |
| 981 | 3157 | 3156 | 5549 | 5548 |
| 982 | 3159 | 3158 | 5551 | 5550 |
| 983 | 3161 | 3160 | 5553 | 5552 |
| 984 | 3163 | 3162 | 5555 | 5554 |
| 985 | 3165 | 3164 | 5557 | 5556 |
| 986 | 3167 | 3166 | 5559 | 5558 |
| 987 | 3169 | 3168 | 5561 | 5560 |
| 988 | 3171 | 3170 | 5563 | 5562 |
| 989 | 3173 | 3172 | 5565 | 5564 |
| 990 | 3175 | 3174 | 5567 | 5566 |
| 991 | 3177 | 3176 | 5569 | 5568 |
| 992 | 3179 | 3178 | 5571 | 5570 |
| 993 | 3181 | 3180 | 5573 | 5572 |
| 994 | 3183 | 3182 | 5575 | 5574 |
| 995 | 3185 | 3184 | 5577 | 5576 |
| 996 | 3187 | 3186 | 5579 | 5578 |
| 997 | 3189 | 3188 | 5581 | 5580 |
| 998 | 3191 | 3190 | 5583 | 5582 |
| 999 | 3193 | 3192 | 5585 | 5584 |
| 1000 | 3195 | 3194 | 5587 | 5586 |
| 1001 | 3197 | 3196 | 5589 | 5588 |
| 1002 | 3199 | 3198 | 5591 | 5590 |
| 1003 | 3201 | 3200 | 5593 | 5592 |
| 1004 | 3203 | 3202 | 5595 | 5594 |
| 1005 | 3205 | 3204 | 5597 | 5596 |
| 1006 | 3207 | 3206 | 5599 | 5598 |
| 1007 | 3209 | 3208 | 5601 | 5600 |

TABLE 4-continued

| ORFGenset | ORF-oligosFd | ORFoligosFp | ORFoligosBd | ORF-oligosBp |
|---|---|---|---|---|
| 1008 | 3211 | 3210 | 5603 | 5602 |
| 1009 | 3213 | 3212 | 5605 | 5604 |
| 1010 | 3215 | 3214 | 5607 | 5606 |
| 1011 | 3217 | 3216 | 5609 | 5608 |
| 1012 | 3219 | 3218 | 5611 | 5610 |
| 1013 | 3221 | 3220 | 5613 | 5612 |
| 1014 | 3223 | 3222 | 5615 | 5614 |
| 1015 | 3225 | 3224 | 5617 | 5616 |
| 1016 | 3227 | 3226 | 5619 | 5618 |
| 1017 | 3229 | 3228 | 5621 | 5620 |
| 1018 | 3231 | 3230 | 5623 | 5622 |
| 1019 | 3233 | 3232 | 5625 | 5624 |
| 1020 | 3235 | 3234 | 5627 | 5626 |
| 1021 | 3237 | 3236 | 5629 | 5628 |
| 1022 | 3239 | 3238 | 5631 | 5630 |
| 1023 | 3241 | 3240 | 5633 | 5632 |
| 1024 | 3243 | 3242 | 5635 | 5634 |
| 1025 | 3245 | 3244 | 5637 | 5636 |
| 1026 | 3247 | 3246 | 5639 | 5638 |
| 1027 | 3249 | 3248 | 5641 | 5640 |
| 1028 | 3251 | 3250 | 5643 | 5642 |
| 1029 | 3253 | 3252 | 5645 | 5644 |
| 1030 | 3255 | 3254 | 5647 | 5646 |
| 1031 | 3257 | 3256 | 5649 | 5648 |
| 1032 | 3259 | 3258 | 5651 | 5650 |
| 1033 | 3261 | 3260 | 5653 | 5652 |
| 1034 | 3263 | 3262 | 5655 | 5654 |
| 1035 | 3265 | 3264 | 5657 | 5656 |
| 1036 | 3267 | 3266 | 5659 | 5658 |
| 1037 | 3269 | 3268 | 5661 | 5660 |
| 1038 | 3271 | 3270 | 5663 | 5662 |
| 1039 | 3273 | 3272 | 5665 | 5664 |
| 1040 | 3275 | 3274 | 5667 | 5666 |
| 1041 | 3277 | 3276 | 5669 | 5668 |
| 1042 | 3279 | 3278 | 5671 | 5670 |
| 1043 | 3281 | 3280 | 5673 | 5672 |
| 1044 | 3283 | 3282 | 5675 | 5674 |
| 1045 | 3285 | 3284 | 5677 | 5676 |
| 1046 | 3287 | 3286 | 5679 | 5678 |
| 1047 | 3289 | 3288 | 5681 | 5680 |
| 1048 | 3291 | 3290 | 5683 | 5682 |
| 1049 | 3293 | 3292 | 5685 | 5684 |
| 1050 | 3295 | 3294 | 5687 | 5686 |
| 1051 | 3297 | 3296 | 5689 | 5688 |
| 1052 | 3299 | 3298 | 5691 | 5690 |
| 1053 | 3301 | 3300 | 5693 | 5692 |
| 1054 | 3303 | 3302 | 5695 | 5694 |
| 1055 | 3305 | 3304 | 5697 | 5696 |
| 1056 | 3307 | 3306 | 5699 | 5698 |
| 1057 | 3309 | 3308 | 5701 | 5700 |
| 1058 | 3311 | 3310 | 5703 | 5702 |
| 1059 | 3313 | 3312 | 5705 | 5704 |
| 1060 | 3315 | 3314 | 5707 | 5706 |
| 1061 | 3317 | 3316 | 5709 | 5708 |
| 1062 | 3319 | 3318 | 5711 | 5710 |
| 1063 | 3321 | 3320 | 5713 | 5712 |
| 1064 | 3323 | 3322 | 5715 | 5714 |
| 1065 | 3325 | 3324 | 5717 | 5716 |
| 1066 | 3327 | 3326 | 5719 | 5718 |
| 1067 | 3329 | 3328 | 5721 | 5720 |
| 1068 | 3331 | 3330 | 5723 | 5722 |
| 1069 | 3333 | 3332 | 5725 | 5724 |
| 1070 | 3335 | 3334 | 5727 | 5726 |
| 1071 | 3337 | 3336 | 5729 | 5728 |
| 1072 | 3339 | 3338 | 5731 | 5730 |
| 1073 | 3341 | 3340 | 5733 | 5732 |
| 1074 | 3343 | 3342 | 5735 | 5734 |
| 1075 | 3345 | 3344 | 5737 | 5736 |
| 1076 | 3347 | 3346 | 5739 | 5738 |
| 1077 | 3349 | 3348 | 5741 | 5740 |
| 1078 | 3351 | 3350 | 5743 | 5742 |
| 1079 | 3353 | 3352 | 5745 | 5744 |
| 1080 | 3355 | 3354 | 5747 | 5746 |
| 1081 | 3357 | 3356 | 5749 | 5748 |
| 1082 | 3359 | 3358 | 5751 | 5750 |
| 1083 | 3361 | 3360 | 5753 | 5752 |
| 1084 | 3363 | 3362 | 5755 | 5754 |
| 1085 | 3365 | 3364 | 5757 | 5756 |
| 1086 | 3367 | 3366 | 5759 | 5758 |
| 1087 | 3369 | 3368 | 5761 | 5760 |
| 1088 | 3371 | 3370 | 5763 | 5762 |
| 1089 | 3373 | 3372 | 5765 | 5764 |
| 1090 | 3375 | 3374 | 5767 | 5766 |
| 1091 | 3377 | 3376 | 5769 | 5768 |
| 1092 | 3379 | 3378 | 5771 | 5770 |
| 1093 | 3381 | 3380 | 5773 | 5772 |
| 1094 | 3383 | 3382 | 5775 | 5774 |
| 1095 | 3385 | 3384 | 5777 | 5776 |
| 1096 | 3387 | 3386 | 5779 | 5778 |
| 1097 | 3389 | 3388 | 5781 | 5780 |
| 1098 | 3391 | 3390 | 5783 | 5782 |
| 1099 | 3393 | 3392 | 5785 | 5784 |
| 1100 | 3395 | 3394 | 5787 | 5786 |
| 1101 | 3397 | 3396 | 5789 | 5788 |
| 1102 | 3399 | 3398 | 5791 | 5790 |
| 1103 | 3401 | 3400 | 5793 | 5792 |
| 1104 | 3403 | 3402 | 5795 | 5794 |
| 1105 | 3405 | 3404 | 5797 | 5796 |
| 1106 | 3407 | 3406 | 5799 | 5798 |
| 1107 | 3409 | 3408 | 5801 | 5800 |
| 1108 | 3411 | 3410 | 5803 | 5802 |
| 1109 | 3413 | 3412 | 5805 | 5804 |
| 1110 | 3415 | 3414 | 5807 | 5806 |
| 1111 | 3417 | 3416 | 5809 | 5808 |
| 1112 | 3419 | 3418 | 5811 | 5810 |
| 1113 | 3421 | 3420 | 5813 | 5812 |
| 1114 | 3423 | 3422 | 5815 | 5814 |
| 1115 | 3425 | 3424 | 5817 | 5816 |
| 1116 | 3427 | 3426 | 5819 | 5818 |
| 1117 | 3429 | 3428 | 5821 | 5820 |
| 1118 | 3431 | 3430 | 5823 | 5822 |
| 1119 | 3433 | 3432 | 5825 | 5824 |
| 1120 | 3435 | 3434 | 5827 | 5826 |
| 1121 | 3437 | 3436 | 5829 | 5828 |
| 1122 | 3439 | 3438 | 5831 | 5830 |
| 1123 | 3441 | 3440 | 5833 | 5832 |
| 1124 | 3443 | 3442 | 5835 | 5834 |
| 1125 | 3445 | 3444 | 5837 | 5836 |
| 1126 | 3447 | 3446 | 5839 | 5838 |
| 1127 | 3449 | 3448 | 5841 | 5840 |
| 1128 | 3451 | 3450 | 5843 | 5842 |
| 1129 | 3453 | 3452 | 5845 | 5844 |
| 1130 | 3455 | 3454 | 5847 | 5846 |
| 1131 | 3457 | 3456 | 5849 | 5848 |
| 1132 | 3459 | 3458 | 5851 | 5850 |
| 1133 | 3461 | 3460 | 5853 | 5852 |
| 1134 | 3463 | 3462 | 5855 | 5854 |
| 1135 | 3465 | 3464 | 5857 | 5856 |
| 1136 | 3467 | 3466 | 5859 | 5858 |
| 1137 | 3469 | 3468 | 5861 | 5860 |
| 1138 | 3471 | 3470 | 5863 | 5862 |
| 1139 | 3473 | 3472 | 5865 | 5864 |
| 1140 | 3475 | 3474 | 5867 | 5866 |
| 1141 | 3477 | 3476 | 5869 | 5868 |
| 1142 | 3479 | 3478 | 5871 | 5870 |
| 1143 | 3481 | 3480 | 5873 | 5872 |
| 1144 | 3483 | 3482 | 5875 | 5874 |
| 1145 | 3485 | 3484 | 5877 | 5876 |
| 1146 | 3487 | 3486 | 5879 | 5878 |
| 1147 | 3489 | 3488 | 5881 | 5880 |
| 1148 | 3491 | 3490 | 5883 | 5882 |
| 1149 | 3493 | 3492 | 5885 | 5884 |
| 1150 | 3495 | 3494 | 5887 | 5886 |
| 1151 | 3497 | 3496 | 5889 | 5888 |
| 1152 | 3499 | 3498 | 5891 | 5890 |
| 1153 | 3501 | 3500 | 5893 | 5892 |
| 1154 | 3503 | 3502 | 5895 | 5894 |
| 1155 | 3505 | 3504 | 5897 | 5896 |
| 1156 | 3507 | 3506 | 5899 | 5898 |
| 1157 | 3509 | 3508 | 5901 | 5900 |
| 1158 | 3511 | 3510 | 5903 | 5902 |
| 1159 | 3513 | 3512 | 5905 | 5904 |
| 1160 | 3515 | 3514 | 5907 | 5906 |
| 1161 | 3517 | 3516 | 5909 | 5908 |

TABLE 4-continued

| ORFGenset | ORF-oligosFd | ORFoligosFp | ORFoligosBd | ORF-oligosBp |
|---|---|---|---|---|
| 1162 | 3519 | 3518 | 5911 | 5910 |
| 1163 | 3521 | 3520 | 5913 | 5912 |
| 1164 | 3523 | 3522 | 5915 | 5914 |
| 1165 | 3525 | 3524 | 5917 | 5916 |
| 1166 | 3527 | 3526 | 5919 | 5918 |
| 1167 | 3529 | 3528 | 5921 | 5920 |
| 1168 | 3531 | 3530 | 5923 | 5922 |
| 1169 | 3533 | 3532 | 5925 | 5924 |
| 1170 | 3535 | 3534 | 5927 | 5926 |
| 1171 | 3537 | 3536 | 5929 | 5928 |
| 1172 | 3539 | 3538 | 5931 | 5930 |
| 1173 | 3541 | 3540 | 5933 | 5932 |
| 1174 | 3543 | 3542 | 5935 | 5934 |
| 1175 | 3545 | 3544 | 5937 | 5936 |
| 1176 | 3547 | 3546 | 5939 | 5938 |
| 1177 | 3549 | 3548 | 5941 | 5940 |
| 1178 | 3551 | 3550 | 5943 | 5942 |
| 1179 | 3553 | 3552 | 5945 | 5944 |
| 1180 | 3555 | 3554 | 5947 | 5946 |
| 1181 | 3557 | 3556 | 5949 | 5948 |
| 1182 | 3559 | 3558 | 5951 | 5950 |
| 1183 | 3561 | 3560 | 5953 | 5952 |
| 1184 | 3563 | 3562 | 5955 | 5954 |
| 1185 | 3565 | 3564 | 5957 | 5956 |
| 1186 | 3567 | 3566 | 5959 | 5958 |
| 1187 | 3569 | 3568 | 5961 | 5960 |
| 1188 | 3571 | 3570 | 5963 | 5962 |
| 1189 | 3573 | 3572 | 5965 | 5964 |
| 1190 | 3575 | 3574 | 5967 | 5966 |
| 1191 | 3577 | 3576 | 5969 | 5968 |
| 1192 | 3579 | 3578 | 5971 | 5970 |
| 1193 | 3581 | 3580 | 5973 | 5972 |
| 1194 | 3583 | 3582 | 5975 | 5974 |
| 1195 | 3585 | 3584 | 5977 | 5976 |
| 1196 | 3587 | 3586 | 5979 | 5978 |
| 1197 | 3589 | 3588 | 5981 | 5980 |

TABLE 5

| SEQ ID | Or. | position |
|---|---|---|
| 1198 | F | 1038449 |
| 1199 | F | 1036517 |
| 1200 | F | 250 |
| 1201 | F | 1036965 |
| 1202 | F | 3011 |
| 1203 | F | 1123 |
| 1204 | F | 4907 |
| 1205 | F | 2996 |
| 1206 | F | 6379 |
| 1207 | F | 4483 |
| 1208 | F | 7837 |
| 1209 | F | 5961 |
| 1210 | F | 8351 |
| 1211 | F | 6467 |
| 1212 | F | 8705 |
| 1213 | F | 6834 |
| 1214 | F | 9598 |
| 1215 | F | 7709 |
| 1216 | F | 10134 |
| 1217 | F | 8248 |
| 1218 | F | 10990 |
| 1219 | F | 9060 |
| 1220 | F | 11823 |
| 1221 | F | 9946 |
| 1222 | F | 13236 |
| 1223 | F | 11410 |
| 1224 | F | 14529 |
| 1225 | F | 12643 |
| 1226 | F | 14668 |
| 1227 | F | 12813 |
| 1228 | F | 15747 |
| 1229 | F | 13844 |
| 1230 | F | 15903 |
| 1231 | F | 14019 |
| 1232 | F | 17198 |
| 1233 | F | 15298 |
| 1234 | F | 18218 |
| 1235 | F | 16263 |
| 1236 | F | 20595 |
| 1237 | F | 18692 |
| 1238 | F | 21932 |
| 1239 | F | 19969 |
| 1240 | F | 22259 |
| 1241 | F | 20338 |
| 1242 | F | 22605 |
| 1243 | F | 20659 |
| 1244 | F | 22890 |
| 1245 | F | 20987 |
| 1246 | F | 23150 |
| 1247 | F | 21244 |
| 1248 | F | 24413 |
| 1249 | F | 22506 |
| 1250 | F | 26379 |
| 1251 | F | 24476 |
| 1252 | F | 27498 |
| 1253 | F | 25602 |
| 1254 | F | 28476 |
| 1255 | F | 26621 |
| 1256 | F | 29785 |
| 1257 | F | 27860 |
| 1258 | F | 30276 |
| 1259 | F | 28363 |
| 1260 | F | 31184 |
| 1261 | F | 29287 |
| 1262 | F | 31574 |
| 1263 | F | 29650 |
| 1264 | F | 33095 |
| 1265 | F | 31184 |
| 1266 | F | 33840 |
| 1267 | F | 31949 |
| 1268 | F | 34769 |
| 1269 | F | 32869 |
| 1270 | F | 34915 |
| 1271 | F | 32961 |
| 1272 | F | 35696 |
| 1273 | F | 33793 |
| 1274 | F | 36794 |
| 1275 | F | 34893 |
| 1276 | F | 37960 |
| 1277 | F | 36085 |
| 1278 | F | 38924 |
| 1279 | F | 37017 |
| 1280 | F | 39704 |
| 1281 | F | 37754 |
| 1282 | F | 40541 |
| 1283 | F | 38615 |
| 1284 | F | 41945 |
| 1285 | F | 40054 |
| 1286 | F | 42779 |
| 1287 | F | 40859 |
| 1288 | F | 43991 |
| 1289 | F | 42061 |
| 1290 | F | 45056 |
| 1291 | F | 43155 |
| 1292 | F | 45755 |
| 1293 | F | 43821 |
| 1294 | F | 46272 |
| 1295 | F | 44382 |
| 1296 | F | 46654 |
| 1297 | F | 44763 |
| 1298 | F | 47926 |
| 1299 | F | 46059 |
| 1300 | F | 48403 |
| 1301 | F | 46485 |
| 1302 | F | 49871 |
| 1303 | F | 47980 |
| 1304 | F | 50706 |
| 1305 | F | 48792 |
| 1306 | F | 52129 |
| 1307 | F | 50199 |
| 1308 | F | 53247 |

TABLE 5-continued

| SEQ ID | Or. | position |
|---|---|---|
| 1309 | F | 51346 |
| 1310 | F | 54376 |
| 1311 | F | 52462 |
| 1312 | F | 54790 |
| 1313 | F | 52890 |
| 1314 | F | 55404 |
| 1315 | F | 53540 |
| 1316 | F | 56602 |
| 1317 | F | 54695 |
| 1318 | F | 58151 |
| 1319 | F | 56284 |
| 1320 | F | 58965 |
| 1321 | F | 57039 |
| 1322 | F | 59955 |
| 1323 | F | 58032 |
| 1324 | F | 61247 |
| 1325 | F | 59364 |
| 1326 | F | 62249 |
| 1327 | F | 60375 |
| 1328 | F | 63117 |
| 1329 | F | 61247 |
| 1330 | F | 63829 |
| 1331 | F | 61908 |
| 1332 | F | 64066 |
| 1333 | F | 62136 |
| 1334 | F | 64369 |
| 1335 | F | 62437 |
| 1336 | F | 65124 |
| 1337 | F | 63225 |
| 1338 | F | 67407 |
| 1339 | F | 65513 |
| 1340 | F | 68652 |
| 1341 | F | 66758 |
| 1342 | F | 68946 |
| 1343 | F | 67080 |
| 1344 | F | 69660 |
| 1345 | F | 67818 |
| 1346 | F | 70432 |
| 1347 | F | 68572 |
| 1348 | F | 70866 |
| 1349 | F | 68946 |
| 1350 | F | 73272 |
| 1351 | F | 71373 |
| 1352 | F | 74657 |
| 1353 | F | 72752 |
| 1354 | F | 75282 |
| 1355 | F | 73383 |
| 1356 | F | 76781 |
| 1357 | F | 74878 |
| 1358 | F | 76925 |
| 1359 | F | 75017 |
| 1360 | F | 77935 |
| 1361 | F | 76028 |
| 1362 | F | 79611 |
| 1363 | F | 77750 |
| 1364 | F | 82371 |
| 1365 | F | 80509 |
| 1366 | F | 83502 |
| 1367 | F | 81655 |
| 1368 | F | 84657 |
| 1369 | F | 82740 |
| 1370 | F | 87093 |
| 1371 | F | 85186 |
| 1372 | F | 87188 |
| 1373 | F | 85320 |
| 1374 | F | 88179 |
| 1375 | F | 86281 |
| 1376 | F | 88486 |
| 1377 | F | 86598 |
| 1378 | F | 89077 |
| 1379 | F | 87236 |
| 1380 | F | 89495 |
| 1381 | F | 87578 |
| 1382 | F | 91202 |
| 1383 | F | 89232 |
| 1384 | F | 91526 |
| 1385 | F | 89598 |
| 1386 | F | 92085 |
| 1387 | F | 90203 |
| 1388 | F | 93104 |
| 1389 | F | 91239 |
| 1390 | F | 93833 |
| 1391 | F | 91938 |
| 1392 | F | 94392 |
| 1393 | F | 92508 |
| 1394 | F | 97894 |
| 1395 | F | 95984 |
| 1396 | F | 98502 |
| 1397 | F | 96620 |
| 1398 | F | 100117 |
| 1399 | F | 98215 |
| 1400 | F | 101104 |
| 1401 | F | 99158 |
| 1402 | F | 101981 |
| 1403 | F | 100080 |
| 1404 | F | 102499 |
| 1405 | F | 100546 |
| 1406 | F | 104014 |
| 1407 | F | 102126 |
| 1408 | F | 105028 |
| 1409 | F | 103092 |
| 1410 | F | 107210 |
| 1411 | F | 105310 |
| 1412 | F | 108446 |
| 1413 | F | 106545 |
| 1414 | F | 108792 |
| 1415 | F | 106853 |
| 1416 | F | 109472 |
| 1417 | F | 107561 |
| 1418 | F | 111060 |
| 1419 | F | 109147 |
| 1420 | F | 112669 |
| 1421 | F | 110796 |
| 1422 | F | 113335 |
| 1423 | F | 111435 |
| 1424 | F | 113733 |
| 1425 | F | 111882 |
| 1426 | F | 114479 |
| 1427 | F | 112580 |
| 1428 | F | 115138 |
| 1429 | F | 113196 |
| 1430 | F | 115765 |
| 1431 | F | 113891 |
| 1432 | F | 119580 |
| 1433 | F | 117660 |
| 1434 | F | 123834 |
| 1435 | F | 121914 |
| 1436 | F | 124649 |
| 1437 | F | 122753 |
| 1438 | F | 125280 |
| 1439 | F | 123416 |
| 1440 | F | 126101 |
| 1441 | F | 124208 |
| 1442 | F | 126871 |
| 1443 | F | 125013 |
| 1444 | F | 127698 |
| 1445 | F | 125787 |
| 1446 | F | 129465 |
| 1447 | F | 127467 |
| 1448 | F | 130799 |
| 1449 | F | 128869 |
| 1450 | F | 131615 |
| 1451 | F | 129711 |
| 1452 | F | 132856 |
| 1453 | F | 130914 |
| 1454 | F | 133401 |
| 1455 | F | 131474 |
| 1456 | F | 133624 |
| 1457 | F | 131706 |
| 1458 | F | 134385 |
| 1459 | F | 132500 |
| 1460 | F | 137183 |
| 1461 | F | 135320 |
| 1462 | F | 140106 |
| 1463 | F | 138215 |
| 1464 | F | 140839 |

TABLE 5-continued

| SEQ ID | Or. | position |
|---|---|---|
| 1465 | F | 138927 |
| 1466 | F | 141535 |
| 1467 | F | 139614 |
| 1468 | F | 142909 |
| 1469 | F | 140952 |
| 1470 | F | 143684 |
| 1471 | F | 141782 |
| 1472 | F | 144309 |
| 1473 | F | 142375 |
| 1474 | F | 146178 |
| 1475 | F | 144294 |
| 1476 | F | 146894 |
| 1477 | F | 144997 |
| 1478 | F | 147858 |
| 1479 | F | 145960 |
| 1480 | F | 148277 |
| 1481 | F | 146347 |
| 1482 | F | 148781 |
| 1483 | F | 146846 |
| 1484 | F | 148947 |
| 1485 | F | 147021 |
| 1486 | F | 149424 |
| 1487 | F | 147592 |
| 1488 | F | 150769 |
| 1489 | F | 148884 |
| 1490 | F | 151743 |
| 1491 | F | 149880 |
| 1492 | F | 152659 |
| 1493 | F | 150769 |
| 1494 | F | 153101 |
| 1495 | F | 151270 |
| 1496 | F | 153719 |
| 1497 | F | 151850 |
| 1498 | F | 155002 |
| 1499 | F | 153096 |
| 1500 | F | 156550 |
| 1501 | F | 154687 |
| 1502 | F | 157206 |
| 1503 | F | 155353 |
| 1504 | F | 158818 |
| 1505 | F | 156924 |
| 1506 | F | 159676 |
| 1507 | F | 157795 |
| 1508 | F | 160957 |
| 1509 | F | 159063 |
| 1510 | F | 161319 |
| 1511 | F | 159504 |
| 1512 | F | 162131 |
| 1513 | F | 160240 |
| 1514 | F | 162775 |
| 1515 | F | 160865 |
| 1516 | F | 164236 |
| 1517 | F | 162345 |
| 1518 | F | 165837 |
| 1519 | F | 163923 |
| 1520 | F | 166508 |
| 1521 | F | 164605 |
| 1522 | F | 168612 |
| 1523 | F | 166683 |
| 1524 | F | 169367 |
| 1525 | F | 167436 |
| 1526 | F | 170556 |
| 1527 | F | 168661 |
| 1528 | F | 171067 |
| 1529 | F | 169173 |
| 1530 | F | 172090 |
| 1531 | F | 170171 |
| 1532 | F | 172797 |
| 1533 | F | 170904 |
| 1534 | F | 174176 |
| 1535 | F | 172236 |
| 1536 | F | 175048 |
| 1537 | F | 173138 |
| 1538 | F | 175476 |
| 1539 | F | 173595 |
| 1540 | F | 177183 |
| 1541 | F | 175275 |
| 1542 | F | 177858 |
| 1543 | F | 175942 |
| 1544 | F | 179819 |
| 1545 | F | 177923 |
| 1546 | F | 180412 |
| 1547 | F | 178455 |
| 1548 | F | 181169 |
| 1549 | F | 179226 |
| 1550 | F | 182628 |
| 1551 | F | 180694 |
| 1552 | F | 183403 |
| 1553 | F | 181494 |
| 1554 | F | 184577 |
| 1555 | F | 182628 |
| 1556 | F | 185763 |
| 1557 | F | 183843 |
| 1558 | F | 186496 |
| 1559 | F | 184614 |
| 1560 | F | 187187 |
| 1561 | F | 185262 |
| 1562 | F | 188542 |
| 1563 | F | 186632 |
| 1564 | F | 189410 |
| 1565 | F | 187514 |
| 1566 | F | 190016 |
| 1567 | F | 188083 |
| 1568 | F | 190545 |
| 1569 | F | 188666 |
| 1570 | F | 191538 |
| 1571 | F | 189595 |
| 1572 | F | 192173 |
| 1573 | F | 190247 |
| 1574 | F | 193015 |
| 1575 | F | 191135 |
| 1576 | F | 194471 |
| 1577 | F | 192522 |
| 1578 | F | 194946 |
| 1579 | F | 193015 |
| 1580 | F | 196798 |
| 1581 | F | 194896 |
| 1582 | F | 197440 |
| 1583 | F | 195550 |
| 1584 | F | 197440 |
| 1585 | F | 195549 |
| 1586 | F | 198736 |
| 1587 | F | 196802 |
| 1588 | F | 199722 |
| 1589 | F | 197822 |
| 1590 | F | 200003 |
| 1591 | F | 198147 |
| 1592 | F | 200361 |
| 1593 | F | 198453 |
| 1594 | F | 200945 |
| 1595 | F | 199009 |
| 1596 | F | 202122 |
| 1597 | F | 200215 |
| 1598 | F | 203251 |
| 1599 | F | 201352 |
| 1600 | F | 203807 |
| 1601 | F | 201903 |
| 1602 | F | 206555 |
| 1603 | F | 204669 |
| 1604 | F | 207269 |
| 1605 | F | 205369 |
| 1606 | F | 208293 |
| 1607 | F | 206395 |
| 1608 | F | 209252 |
| 1609 | F | 207345 |
| 1610 | F | 210330 |
| 1611 | F | 208414 |
| 1612 | F | 210632 |
| 1613 | F | 208694 |
| 1614 | F | 211151 |
| 1615 | F | 209255 |
| 1616 | F | 212650 |
| 1617 | F | 210756 |
| 1618 | F | 213920 |
| 1619 | F | 212036 |
| 1620 | F | 214535 |

TABLE 5-continued

| SEQ ID | Or. | position |
|---|---|---|
| 1621 | F | 212635 |
| 1622 | F | 215003 |
| 1623 | F | 213077 |
| 1624 | F | 216641 |
| 1625 | F | 214772 |
| 1626 | F | 216869 |
| 1627 | F | 214961 |
| 1628 | F | 218145 |
| 1629 | F | 216218 |
| 1630 | F | 218461 |
| 1631 | F | 216576 |
| 1632 | F | 218960 |
| 1633 | F | 217044 |
| 1634 | F | 219646 |
| 1635 | F | 217772 |
| 1636 | F | 220257 |
| 1637 | F | 218379 |
| 1638 | F | 220903 |
| 1639 | F | 218989 |
| 1640 | F | 221314 |
| 1641 | F | 219470 |
| 1642 | F | 222253 |
| 1643 | F | 220338 |
| 1644 | F | 223186 |
| 1645 | F | 221278 |
| 1646 | F | 223994 |
| 1647 | F | 222146 |
| 1648 | F | 224908 |
| 1649 | F | 223014 |
| 1650 | F | 225051 |
| 1651 | F | 223131 |
| 1652 | F | 225510 |
| 1653 | F | 223615 |
| 1654 | F | 226550 |
| 1655 | F | 224609 |
| 1656 | F | 226928 |
| 1657 | F | 225029 |
| 1658 | F | 227528 |
| 1659 | F | 225631 |
| 1660 | F | 228388 |
| 1661 | F | 226475 |
| 1662 | F | 229930 |
| 1663 | F | 228032 |
| 1664 | F | 231129 |
| 1665 | F | 229205 |
| 1666 | F | 232785 |
| 1667 | F | 230915 |
| 1668 | F | 233561 |
| 1669 | F | 231664 |
| 1670 | F | 234013 |
| 1671 | F | 232149 |
| 1672 | F | 234942 |
| 1673 | F | 233061 |
| 1674 | F | 236015 |
| 1675 | F | 234123 |
| 1676 | F | 237945 |
| 1677 | F | 236045 |
| 1678 | F | 238482 |
| 1679 | F | 236599 |
| 1680 | F | 240094 |
| 1681 | F | 238190 |
| 1682 | F | 241713 |
| 1683 | F | 239820 |
| 1684 | F | 242569 |
| 1685 | F | 240653 |
| 1686 | F | 244253 |
| 1687 | F | 242360 |
| 1688 | F | 245693 |
| 1689 | F | 243796 |
| 1690 | F | 246762 |
| 1691 | F | 244825 |
| 1692 | F | 247498 |
| 1693 | F | 245575 |
| 1694 | F | 248343 |
| 1695 | F | 246444 |
| 1696 | F | 249500 |
| 1697 | F | 247625 |
| 1698 | F | 250315 |
| 1699 | F | 248425 |
| 1700 | F | 250832 |
| 1701 | F | 248942 |
| 1702 | F | 251847 |
| 1703 | F | 249939 |
| 1704 | F | 254897 |
| 1705 | F | 252955 |
| 1706 | F | 256543 |
| 1707 | F | 254643 |
| 1708 | F | 257692 |
| 1709 | F | 255790 |
| 1710 | F | 258561 |
| 1711 | F | 256651 |
| 1712 | F | 258927 |
| 1713 | F | 257036 |
| 1714 | F | 261368 |
| 1715 | F | 259469 |
| 1716 | F | 263887 |
| 1717 | F | 262000 |
| 1718 | F | 264503 |
| 1719 | F | 262599 |
| 1720 | F | 265364 |
| 1721 | F | 263512 |
| 1722 | F | 266202 |
| 1723 | F | 264277 |
| 1724 | F | 266709 |
| 1725 | F | 264801 |
| 1726 | F | 267847 |
| 1727 | F | 265947 |
| 1728 | F | 267980 |
| 1729 | F | 266077 |
| 1730 | F | 268271 |
| 1731 | F | 266341 |
| 1732 | F | 269840 |
| 1733 | F | 267913 |
| 1734 | F | 270961 |
| 1735 | F | 269072 |
| 1736 | F | 271883 |
| 1737 | F | 270080 |
| 1738 | F | 272642 |
| 1739 | F | 270748 |
| 1740 | F | 273367 |
| 1741 | F | 271477 |
| 1742 | F | 274562 |
| 1743 | F | 272702 |
| 1744 | F | 275882 |
| 1745 | F | 273984 |
| 1746 | F | 278004 |
| 1747 | F | 276149 |
| 1748 | F | 278747 |
| 1749 | F | 276893 |
| 1750 | F | 279521 |
| 1751 | F | 277632 |
| 1752 | F | 281076 |
| 1753 | F | 279118 |
| 1754 | F | 281551 |
| 1755 | F | 279668 |
| 1756 | F | 282573 |
| 1757 | F | 280663 |
| 1758 | F | 284229 |
| 1759 | F | 282316 |
| 1760 | F | 284598 |
| 1761 | F | 282655 |
| 1762 | F | 285418 |
| 1763 | F | 283518 |
| 1764 | F | 286104 |
| 1765 | F | 284229 |
| 1766 | F | 286456 |
| 1767 | F | 284531 |
| 1768 | F | 287865 |
| 1769 | F | 286008 |
| 1770 | F | 289163 |
| 1771 | F | 287384 |
| 1772 | F | 290609 |
| 1773 | F | 288709 |
| 1774 | F | 291264 |
| 1775 | F | 289389 |
| 1776 | F | 292107 |

TABLE 5-continued

| SEQ ID | Or. | position |
|---|---|---|
| 1777 | F | 290166 |
| 1778 | F | 293099 |
| 1779 | F | 291211 |
| 1780 | F | 294791 |
| 1781 | F | 292883 |
| 1782 | F | 295464 |
| 1783 | F | 293573 |
| 1784 | F | 296018 |
| 1785 | F | 294095 |
| 1786 | F | 297572 |
| 1787 | F | 295664 |
| 1788 | F | 298686 |
| 1789 | F | 296716 |
| 1790 | F | 300305 |
| 1791 | F | 298407 |
| 1792 | F | 301852 |
| 1793 | F | 299946 |
| 1794 | F | 304754 |
| 1795 | F | 302849 |
| 1796 | F | 305854 |
| 1797 | F | 303992 |
| 1798 | F | 306214 |
| 1799 | F | 304303 |
| 1800 | F | 306758 |
| 1801 | F | 304856 |
| 1802 | F | 309057 |
| 1803 | F | 307125 |
| 1804 | F | 309635 |
| 1805 | F | 307750 |
| 1806 | F | 310491 |
| 1807 | F | 308597 |
| 1808 | F | 311753 |
| 1809 | F | 309790 |
| 1810 | F | 313188 |
| 1811 | F | 311292 |
| 1812 | F | 314121 |
| 1813 | F | 312194 |
| 1814 | F | 314489 |
| 1815 | F | 312539 |
| 1816 | F | 315431 |
| 1817 | F | 313526 |
| 1818 | F | 316309 |
| 1819 | F | 314380 |
| 1820 | F | 317102 |
| 1821 | F | 315214 |
| 1822 | F | 317271 |
| 1823 | F | 315343 |
| 1824 | F | 317380 |
| 1825 | F | 315480 |
| 1826 | F | 318256 |
| 1827 | F | 316352 |
| 1828 | F | 319047 |
| 1829 | F | 317181 |
| 1830 | F | 320325 |
| 1831 | F | 318338 |
| 1832 | F | 321228 |
| 1833 | F | 319366 |
| 1834 | F | 321676 |
| 1835 | F | 319782 |
| 1836 | F | 322066 |
| 1837 | F | 320097 |
| 1838 | F | 322910 |
| 1839 | F | 320982 |
| 1840 | F | 324744 |
| 1841 | F | 322849 |
| 1842 | F | 325392 |
| 1843 | F | 323445 |
| 1844 | F | 326217 |
| 1845 | F | 324331 |
| 1846 | F | 327038 |
| 1847 | F | 325162 |
| 1848 | F | 327957 |
| 1849 | F | 326079 |
| 1850 | F | 328458 |
| 1851 | F | 326612 |
| 1852 | F | 329032 |
| 1853 | F | 327173 |
| 1854 | F | 329329 |
| 1855 | F | 327489 |
| 1856 | F | 330446 |
| 1857 | F | 328551 |
| 1858 | F | 330915 |
| 1859 | F | 329032 |
| 1860 | F | 331410 |
| 1861 | F | 329602 |
| 1862 | F | 332534 |
| 1863 | F | 330626 |
| 1864 | F | 332782 |
| 1865 | F | 330879 |
| 1866 | F | 333587 |
| 1867 | F | 331632 |
| 1868 | F | 333870 |
| 1869 | F | 331962 |
| 1870 | F | 334510 |
| 1871 | F | 332594 |
| 1872 | F | 334958 |
| 1873 | F | 333049 |
| 1874 | F | 334958 |
| 1875 | F | 333049 |
| 1876 | F | 335655 |
| 1877 | F | 333766 |
| 1878 | F | 336117 |
| 1879 | F | 334219 |
| 1880 | F | 337108 |
| 1881 | F | 335210 |
| 1882 | F | 340251 |
| 1883 | F | 338372 |
| 1884 | F | 341538 |
| 1885 | F | 339662 |
| 1886 | F | 341953 |
| 1887 | F | 339995 |
| 1888 | F | 342348 |
| 1889 | F | 340450 |
| 1890 | F | 343112 |
| 1891 | F | 341242 |
| 1892 | F | 343736 |
| 1893 | F | 341811 |
| 1894 | F | 344117 |
| 1895 | F | 342207 |
| 1896 | F | 344940 |
| 1897 | F | 343000 |
| 1898 | F | 345837 |
| 1899 | F | 343958 |
| 1900 | F | 346872 |
| 1901 | F | 344994 |
| 1902 | F | 347910 |
| 1903 | F | 345971 |
| 1904 | F | 350124 |
| 1905 | F | 348298 |
| 1906 | F | 351095 |
| 1907 | F | 349167 |
| 1908 | F | 351996 |
| 1909 | F | 350122 |
| 1910 | F | 353051 |
| 1911 | F | 351186 |
| 1912 | F | 353413 |
| 1913 | F | 351481 |
| 1914 | F | 353908 |
| 1915 | F | 351996 |
| 1916 | F | 354723 |
| 1917 | F | 352799 |
| 1918 | F | 356466 |
| 1919 | F | 354569 |
| 1920 | F | 357107 |
| 1921 | F | 355178 |
| 1922 | F | 357767 |
| 1923 | F | 355878 |
| 1924 | F | 360528 |
| 1925 | F | 358628 |
| 1926 | F | 360877 |
| 1927 | F | 358974 |
| 1928 | F | 361573 |
| 1929 | F | 359692 |
| 1930 | F | 362584 |
| 1931 | F | 360681 |
| 1932 | F | 363835 |

TABLE 5-continued

| SEQ ID | Or. | position |
|---|---|---|
| 1933 | F | 361966 |
| 1934 | F | 364960 |
| 1935 | F | 363021 |
| 1936 | F | 365240 |
| 1937 | F | 363360 |
| 1938 | F | 367060 |
| 1939 | F | 365115 |
| 1940 | F | 368383 |
| 1941 | F | 366505 |
| 1942 | F | 368862 |
| 1943 | F | 366963 |
| 1944 | F | 370513 |
| 1945 | F | 368631 |
| 1946 | F | 370974 |
| 1947 | F | 369076 |
| 1948 | F | 372891 |
| 1949 | F | 370980 |
| 1950 | F | 373395 |
| 1951 | F | 371495 |
| 1952 | F | 374005 |
| 1953 | F | 372033 |
| 1954 | F | 374474 |
| 1955 | F | 372572 |
| 1956 | F | 376509 |
| 1957 | F | 374624 |
| 1958 | F | 377630 |
| 1959 | F | 375708 |
| 1960 | F | 378384 |
| 1961 | F | 376507 |
| 1962 | F | 378798 |
| 1963 | F | 376871 |
| 1964 | F | 379413 |
| 1965 | F | 377501 |
| 1966 | F | 379890 |
| 1967 | F | 377989 |
| 1968 | F | 381241 |
| 1969 | F | 379348 |
| 1970 | F | 382485 |
| 1971 | F | 380579 |
| 1972 | F | 383395 |
| 1973 | F | 381536 |
| 1974 | F | 383730 |
| 1975 | F | 381782 |
| 1976 | F | 384948 |
| 1977 | F | 383057 |
| 1978 | F | 385474 |
| 1979 | F | 383532 |
| 1980 | F | 385908 |
| 1981 | F | 384008 |
| 1982 | F | 386643 |
| 1983 | F | 384750 |
| 1984 | F | 387099 |
| 1985 | F | 385204 |
| 1986 | F | 387581 |
| 1987 | F | 385677 |
| 1988 | F | 388009 |
| 1989 | F | 386062 |
| 1990 | F | 388927 |
| 1991 | F | 387033 |
| 1992 | F | 389726 |
| 1993 | F | 387821 |
| 1994 | F | 391295 |
| 1995 | F | 389365 |
| 1996 | F | 392171 |
| 1997 | F | 390291 |
| 1998 | F | 393930 |
| 1999 | F | 392014 |
| 2000 | F | 395085 |
| 2001 | F | 393185 |
| 2002 | F | 395827 |
| 2003 | F | 393940 |
| 2004 | F | 396274 |
| 2005 | F | 394423 |
| 2006 | F | 397156 |
| 2007 | F | 395216 |
| 2008 | F | 398641 |
| 2009 | F | 396790 |
| 2010 | F | 399550 |
| 2011 | F | 397659 |
| 2012 | F | 399797 |
| 2013 | F | 397915 |
| 2014 | F | 401527 |
| 2015 | F | 399623 |
| 2016 | F | 401907 |
| 2017 | F | 399960 |
| 2018 | F | 403017 |
| 2019 | F | 401131 |
| 2020 | F | 403017 |
| 2021 | F | 401131 |
| 2022 | F | 404910 |
| 2023 | F | 403010 |
| 2024 | F | 405728 |
| 2025 | F | 403836 |
| 2026 | F | 406837 |
| 2027 | F | 404932 |
| 2028 | F | 410291 |
| 2029 | F | 408347 |
| 2030 | F | 411488 |
| 2031 | F | 409518 |
| 2032 | F | 412379 |
| 2033 | F | 410487 |
| 2034 | F | 413164 |
| 2035 | F | 411263 |
| 2036 | F | 413606 |
| 2037 | F | 411626 |
| 2038 | F | 413721 |
| 2039 | F | 411859 |
| 2040 | F | 414921 |
| 2041 | F | 413049 |
| 2042 | F | 416517 |
| 2043 | F | 414606 |
| 2044 | F | 417445 |
| 2045 | F | 415557 |
| 2046 | F | 417812 |
| 2047 | F | 415912 |
| 2048 | F | 418381 |
| 2049 | F | 416517 |
| 2050 | F | 419453 |
| 2051 | F | 417447 |
| 2052 | F | 420026 |
| 2053 | F | 418068 |
| 2054 | F | 421270 |
| 2055 | F | 419392 |
| 2056 | F | 422262 |
| 2057 | F | 420364 |
| 2058 | F | 423007 |
| 2059 | F | 421107 |
| 2060 | F | 424834 |
| 2061 | F | 423018 |
| 2062 | F | 426026 |
| 2063 | F | 424110 |
| 2064 | F | 426883 |
| 2065 | F | 425040 |
| 2066 | F | 429303 |
| 2067 | F | 427438 |
| 2068 | F | 429609 |
| 2069 | F | 427737 |
| 2070 | F | 430104 |
| 2071 | F | 428191 |
| 2072 | F | 430622 |
| 2073 | F | 428814 |
| 2074 | F | 431439 |
| 2075 | F | 429537 |
| 2076 | F | 431968 |
| 2077 | F | 430108 |
| 2078 | F | 434401 |
| 2079 | F | 432485 |
| 2080 | F | 436050 |
| 2081 | F | 434134 |
| 2082 | F | 436342 |
| 2083 | F | 434428 |
| 2084 | F | 437672 |
| 2085 | F | 435775 |
| 2086 | F | 438051 |
| 2087 | F | 436165 |
| 2088 | F | 438767 |

TABLE 5-continued

| SEQ ID | Or. | position |
|---|---|---|
| 2089 | F | 436866 |
| 2090 | F | 439139 |
| 2091 | F | 437145 |
| 2092 | F | 439479 |
| 2093 | F | 437574 |
| 2094 | F | 440823 |
| 2095 | F | 438923 |
| 2096 | F | 441668 |
| 2097 | F | 439746 |
| 2098 | F | 444271 |
| 2099 | F | 442371 |
| 2100 | F | 446233 |
| 2101 | F | 444302 |
| 2102 | F | 447687 |
| 2103 | F | 445803 |
| 2104 | F | 450318 |
| 2105 | F | 448399 |
| 2106 | F | 450876 |
| 2107 | F | 449025 |
| 2108 | F | 451274 |
| 2109 | F | 449397 |
| 2110 | F | 452413 |
| 2111 | F | 450513 |
| 2112 | F | 453303 |
| 2113 | F | 451427 |
| 2114 | F | 454713 |
| 2115 | F | 452853 |
| 2116 | F | 455096 |
| 2117 | F | 453248 |
| 2118 | F | 455808 |
| 2119 | F | 453928 |
| 2120 | F | 457440 |
| 2121 | F | 455488 |
| 2122 | F | 458282 |
| 2123 | F | 456354 |
| 2124 | F | 459558 |
| 2125 | F | 457686 |
| 2126 | F | 460960 |
| 2127 | F | 459060 |
| 2128 | F | 461659 |
| 2129 | F | 459758 |
| 2130 | F | 462674 |
| 2131 | F | 460775 |
| 2132 | F | 463788 |
| 2133 | F | 461895 |
| 2134 | F | 464479 |
| 2135 | F | 462602 |
| 2136 | F | 465882 |
| 2137 | F | 463989 |
| 2138 | F | 467200 |
| 2139 | F | 465300 |
| 2140 | F | 468680 |
| 2141 | F | 466787 |
| 2142 | F | 469130 |
| 2143 | F | 467224 |
| 2144 | F | 469572 |
| 2145 | F | 467707 |
| 2146 | F | 470887 |
| 2147 | F | 468984 |
| 2148 | F | 471590 |
| 2149 | F | 469835 |
| 2150 | F | 473033 |
| 2151 | F | 471133 |
| 2152 | F | 473761 |
| 2153 | F | 471861 |
| 2154 | F | 474383 |
| 2155 | F | 472478 |
| 2156 | F | 475333 |
| 2157 | F | 473465 |
| 2158 | F | 476279 |
| 2159 | F | 474390 |
| 2160 | F | 478446 |
| 2161 | F | 476546 |
| 2162 | F | 478869 |
| 2163 | F | 476918 |
| 2164 | F | 479441 |
| 2165 | F | 477548 |
| 2166 | F | 479676 |
| 2167 | F | 477775 |
| 2168 | F | 481277 |
| 2169 | F | 479377 |
| 2170 | F | 481635 |
| 2171 | F | 479745 |
| 2172 | F | 483172 |
| 2173 | F | 481279 |
| 2174 | F | 484659 |
| 2175 | F | 482764 |
| 2176 | F | 485003 |
| 2177 | F | 483097 |
| 2178 | F | 487946 |
| 2179 | F | 486083 |
| 2180 | F | 487946 |
| 2181 | F | 486093 |
| 2182 | F | 489220 |
| 2183 | F | 487274 |
| 2184 | F | 490276 |
| 2185 | F | 488388 |
| 2186 | F | 492138 |
| 2187 | F | 490229 |
| 2188 | F | 492475 |
| 2189 | F | 490618 |
| 2190 | F | 493591 |
| 2191 | F | 491719 |
| 2192 | F | 494297 |
| 2193 | F | 492436 |
| 2194 | F | 494530 |
| 2195 | F | 492679 |
| 2196 | F | 494637 |
| 2197 | F | 492753 |
| 2198 | F | 495467 |
| 2199 | F | 493559 |
| 2200 | F | 496076 |
| 2201 | F | 494126 |
| 2202 | F | 497468 |
| 2203 | F | 495569 |
| 2204 | F | 498050 |
| 2205 | F | 496160 |
| 2206 | F | 498994 |
| 2207 | F | 497096 |
| 2208 | F | 500571 |
| 2209 | F | 498671 |
| 2210 | F | 501547 |
| 2211 | F | 499671 |
| 2212 | F | 502469 |
| 2213 | F | 500572 |
| 2214 | F | 503435 |
| 2215 | F | 501547 |
| 2216 | F | 505469 |
| 2217 | F | 503545 |
| 2218 | F | 506768 |
| 2219 | F | 504880 |
| 2220 | F | 507356 |
| 2221 | F | 505530 |
| 2222 | F | 508015 |
| 2223 | F | 506157 |
| 2224 | F | 508247 |
| 2225 | F | 506351 |
| 2226 | F | 509270 |
| 2227 | F | 507356 |
| 2228 | F | 510759 |
| 2229 | F | 508918 |
| 2230 | F | 511268 |
| 2231 | F | 509359 |
| 2232 | F | 512124 |
| 2233 | F | 510202 |
| 2234 | F | 512836 |
| 2235 | F | 510926 |
| 2236 | F | 514569 |
| 2237 | F | 512663 |
| 2238 | F | 514688 |
| 2239 | F | 512874 |
| 2240 | F | 515334 |
| 2241 | F | 513415 |
| 2242 | F | 515516 |
| 2243 | F | 513670 |
| 2244 | F | 516230 |

TABLE 5-continued

| SEQ ID | Or. | position |
|---|---|---|
| 2245 | F | 514348 |
| 2246 | F | 517181 |
| 2247 | F | 515261 |
| 2248 | F | 517840 |
| 2249 | F | 515977 |
| 2250 | F | 518184 |
| 2251 | F | 516283 |
| 2252 | F | 518704 |
| 2253 | F | 516804 |
| 2254 | F | 519358 |
| 2255 | F | 517404 |
| 2256 | F | 520483 |
| 2257 | F | 518598 |
| 2258 | F | 521632 |
| 2259 | F | 519765 |
| 2260 | F | 521919 |
| 2261 | F | 520024 |
| 2262 | F | 523372 |
| 2263 | F | 521495 |
| 2264 | F | 524404 |
| 2265 | F | 522508 |
| 2266 | F | 525498 |
| 2267 | F | 523600 |
| 2268 | F | 525687 |
| 2269 | F | 523753 |
| 2270 | F | 526036 |
| 2271 | F | 524164 |
| 2272 | F | 526632 |
| 2273 | F | 524732 |
| 2274 | F | 528073 |
| 2275 | F | 526158 |
| 2276 | F | 528835 |
| 2277 | F | 526999 |
| 2278 | F | 529393 |
| 2279 | F | 527504 |
| 2280 | F | 530004 |
| 2281 | F | 528082 |
| 2282 | F | 530518 |
| 2283 | F | 528594 |
| 2284 | F | 532100 |
| 2285 | F | 530224 |
| 2286 | F | 533025 |
| 2287 | F | 531125 |
| 2288 | F | 533710 |
| 2289 | F | 531825 |
| 2290 | F | 534658 |
| 2291 | F | 532758 |
| 2292 | F | 535737 |
| 2293 | F | 533828 |
| 2294 | F | 539456 |
| 2295 | F | 537568 |
| 2296 | F | 540290 |
| 2297 | F | 538375 |
| 2298 | F | 540672 |
| 2299 | F | 538777 |
| 2300 | F | 541573 |
| 2301 | F | 539706 |
| 2302 | F | 542999 |
| 2303 | F | 541102 |
| 2304 | F | 543922 |
| 2305 | F | 542057 |
| 2306 | F | 544268 |
| 2307 | F | 542354 |
| 2308 | F | 544691 |
| 2309 | F | 542785 |
| 2310 | F | 546323 |
| 2311 | F | 544441 |
| 2312 | F | 546467 |
| 2313 | F | 544650 |
| 2314 | F | 547257 |
| 2315 | F | 545357 |
| 2316 | F | 547658 |
| 2317 | F | 545781 |
| 2318 | F | 548406 |
| 2319 | F | 546466 |
| 2320 | F | 549443 |
| 2321 | F | 547527 |
| 2322 | F | 550193 |
| 2323 | F | 548288 |
| 2324 | F | 551554 |
| 2325 | F | 549665 |
| 2326 | F | 552877 |
| 2327 | F | 550963 |
| 2328 | F | 554708 |
| 2329 | F | 552807 |
| 2330 | F | 556293 |
| 2331 | F | 554381 |
| 2332 | F | 557095 |
| 2333 | F | 555164 |
| 2334 | F | 557522 |
| 2335 | F | 555656 |
| 2336 | F | 558021 |
| 2337 | F | 556191 |
| 2338 | F | 558964 |
| 2339 | F | 557076 |
| 2340 | F | 560913 |
| 2341 | F | 559007 |
| 2342 | F | 562832 |
| 2343 | F | 561002 |
| 2344 | F | 563374 |
| 2345 | F | 561474 |
| 2346 | F | 565061 |
| 2347 | F | 563198 |
| 2348 | F | 566840 |
| 2349 | F | 564908 |
| 2350 | F | 567802 |
| 2351 | F | 565896 |
| 2352 | F | 571045 |
| 2353 | F | 569137 |
| 2354 | F | 572300 |
| 2355 | F | 570362 |
| 2356 | F | 572512 |
| 2357 | F | 570612 |
| 2358 | F | 572627 |
| 2359 | F | 570753 |
| 2360 | F | 573416 |
| 2361 | F | 571539 |
| 2362 | F | 573964 |
| 2363 | F | 572065 |
| 2364 | F | 574221 |
| 2365 | F | 572303 |
| 2366 | F | 574704 |
| 2367 | F | 572781 |
| 2368 | F | 574795 |
| 2369 | F | 572936 |
| 2370 | F | 575229 |
| 2371 | F | 573350 |
| 2372 | F | 576318 |
| 2373 | F | 574384 |
| 2374 | F | 577796 |
| 2375 | F | 575893 |
| 2376 | F | 578774 |
| 2377 | F | 576870 |
| 2378 | F | 581976 |
| 2379 | F | 580073 |
| 2380 | F | 582589 |
| 2381 | F | 580679 |
| 2382 | F | 582962 |
| 2383 | F | 581060 |
| 2384 | F | 583210 |
| 2385 | F | 581316 |
| 2386 | F | 583564 |
| 2387 | F | 581697 |
| 2388 | F | 584048 |
| 2389 | F | 582179 |
| 2390 | F | 584797 |
| 2391 | F | 582897 |
| 2392 | F | 584978 |
| 2393 | F | 583031 |
| 2394 | F | 586256 |
| 2395 | F | 584320 |
| 2396 | F | 587527 |
| 2397 | F | 585631 |
| 2398 | F | 588892 |
| 2399 | F | 587052 |
| 2400 | F | 589362 |

TABLE 5-continued

| SEQ ID | Or. | position |
|---|---|---|
| 2401 | F | 587452 |
| 2402 | F | 590516 |
| 2403 | F | 588616 |
| 2404 | F | 592168 |
| 2405 | F | 590235 |
| 2406 | F | 592629 |
| 2407 | F | 590708 |
| 2408 | F | 592901 |
| 2409 | F | 590973 |
| 2410 | F | 593863 |
| 2411 | F | 591990 |
| 2412 | F | 595416 |
| 2413 | F | 593484 |
| 2414 | F | 595935 |
| 2415 | F | 593962 |
| 2416 | F | 597025 |
| 2417 | F | 595158 |
| 2418 | F | 598254 |
| 2419 | F | 596402 |
| 2420 | F | 600515 |
| 2421 | F | 598575 |
| 2422 | F | 601691 |
| 2423 | F | 599745 |
| 2424 | F | 603291 |
| 2425 | F | 601376 |
| 2426 | F | 603538 |
| 2427 | F | 601638 |
| 2428 | F | 604263 |
| 2429 | F | 602388 |
| 2430 | F | 605359 |
| 2431 | F | 603425 |
| 2432 | F | 606622 |
| 2433 | F | 604721 |
| 2434 | F | 607722 |
| 2435 | F | 605908 |
| 2436 | F | 609039 |
| 2437 | F | 607143 |
| 2438 | F | 609842 |
| 2439 | F | 607958 |
| 2440 | F | 611565 |
| 2441 | F | 609657 |
| 2442 | F | 612719 |
| 2443 | F | 610819 |
| 2444 | F | 613473 |
| 2445 | F | 611565 |
| 2446 | F | 614096 |
| 2447 | F | 612172 |
| 2448 | F | 615072 |
| 2449 | F | 613207 |
| 2450 | F | 615645 |
| 2451 | F | 613745 |
| 2452 | F | 617266 |
| 2453 | F | 615347 |
| 2454 | F | 618142 |
| 2455 | F | 616242 |
| 2456 | F | 619019 |
| 2457 | F | 617128 |
| 2458 | F | 619637 |
| 2459 | F | 617695 |
| 2460 | F | 620182 |
| 2461 | F | 618257 |
| 2462 | F | 620929 |
| 2463 | F | 619019 |
| 2464 | F | 621446 |
| 2465 | F | 619529 |
| 2466 | F | 622195 |
| 2467 | F | 620292 |
| 2468 | F | 623244 |
| 2469 | F | 621446 |
| 2470 | F | 623834 |
| 2471 | F | 621954 |
| 2472 | F | 625024 |
| 2473 | F | 623208 |
| 2474 | F | 626291 |
| 2475 | F | 624369 |
| 2476 | F | 626724 |
| 2477 | F | 624821 |
| 2478 | F | 627597 |
| 2479 | F | 625703 |
| 2480 | F | 627927 |
| 2481 | F | 626025 |
| 2482 | F | 628712 |
| 2483 | F | 626787 |
| 2484 | F | 629535 |
| 2485 | F | 627685 |
| 2486 | F | 630055 |
| 2487 | F | 628178 |
| 2488 | F | 630672 |
| 2489 | F | 628789 |
| 2490 | F | 637125 |
| 2491 | F | 635224 |
| 2492 | F | 637807 |
| 2493 | F | 635913 |
| 2494 | F | 639960 |
| 2495 | F | 638102 |
| 2496 | F | 639960 |
| 2497 | F | 638012 |
| 2498 | F | 643252 |
| 2499 | F | 641355 |
| 2500 | F | 644146 |
| 2501 | F | 642204 |
| 2502 | F | 645175 |
| 2503 | F | 643275 |
| 2504 | F | 645519 |
| 2505 | F | 643652 |
| 2506 | F | 646869 |
| 2507 | F | 644983 |
| 2508 | F | 649714 |
| 2509 | F | 647800 |
| 2510 | F | 650199 |
| 2511 | F | 648260 |
| 2512 | F | 651421 |
| 2513 | F | 649536 |
| 2514 | F | 652285 |
| 2515 | F | 650397 |
| 2516 | F | 652562 |
| 2517 | F | 650653 |
| 2518 | F | 659653 |
| 2519 | F | 657741 |
| 2520 | F | 661449 |
| 2521 | F | 659621 |
| 2522 | F | 662058 |
| 2523 | F | 660167 |
| 2524 | F | 662726 |
| 2525 | F | 660831 |
| 2526 | F | 663526 |
| 2527 | F | 661591 |
| 2528 | F | 664035 |
| 2529 | F | 662134 |
| 2530 | F | 665504 |
| 2531 | F | 663591 |
| 2532 | F | 665530 |
| 2533 | F | 663663 |
| 2534 | F | 666606 |
| 2535 | F | 664705 |
| 2536 | F | 667901 |
| 2537 | F | 665987 |
| 2538 | F | 667953 |
| 2539 | F | 666037 |
| 2540 | F | 668397 |
| 2541 | F | 666496 |
| 2542 | F | 669235 |
| 2543 | F | 667366 |
| 2544 | F | 669763 |
| 2545 | F | 667879 |
| 2546 | F | 670513 |
| 2547 | F | 668612 |
| 2548 | F | 670963 |
| 2549 | F | 669058 |
| 2550 | F | 672473 |
| 2551 | F | 670573 |
| 2552 | F | 672985 |
| 2553 | F | 671072 |
| 2554 | F | 674381 |
| 2555 | F | 672493 |
| 2556 | F | 675029 |

TABLE 5-continued

| SEQ ID | Or. | position |
|---|---|---|
| 2557 | F | 673135 |
| 2558 | F | 676254 |
| 2559 | F | 674357 |
| 2560 | F | 677481 |
| 2561 | F | 675559 |
| 2562 | F | 678423 |
| 2563 | F | 676580 |
| 2564 | F | 679049 |
| 2565 | F | 677156 |
| 2566 | F | 680360 |
| 2567 | F | 678423 |
| 2568 | F | 681257 |
| 2569 | F | 679420 |
| 2570 | F | 682281 |
| 2571 | F | 680435 |
| 2572 | F | 682870 |
| 2573 | F | 681012 |
| 2574 | F | 684147 |
| 2575 | F | 682281 |
| 2576 | F | 684582 |
| 2577 | F | 682664 |
| 2578 | F | 685978 |
| 2579 | F | 684033 |
| 2580 | F | 687121 |
| 2581 | F | 685186 |
| 2582 | F | 687974 |
| 2583 | F | 686044 |
| 2584 | F | 688169 |
| 2585 | F | 686313 |
| 2586 | F | 689393 |
| 2587 | F | 687511 |
| 2588 | F | 689580 |
| 2589 | F | 687727 |
| 2590 | F | 690204 |
| 2591 | F | 688342 |
| 2592 | F | 690431 |
| 2593 | F | 688497 |
| 2594 | F | 691790 |
| 2595 | F | 689919 |
| 2596 | F | 693614 |
| 2597 | F | 691704 |
| 2598 | F | 694723 |
| 2599 | F | 692821 |
| 2600 | F | 696922 |
| 2601 | F | 695033 |
| 2602 | F | 697714 |
| 2603 | F | 695816 |
| 2604 | F | 698510 |
| 2605 | F | 696612 |
| 2606 | F | 700037 |
| 2607 | F | 698119 |
| 2608 | F | 700691 |
| 2609 | F | 698783 |
| 2610 | F | 701885 |
| 2611 | F | 699984 |
| 2612 | F | 703303 |
| 2613 | F | 701403 |
| 2614 | F | 704791 |
| 2615 | F | 702877 |
| 2616 | F | 705452 |
| 2617 | F | 703584 |
| 2618 | F | 705918 |
| 2619 | F | 704019 |
| 2620 | F | 706241 |
| 2621 | F | 704322 |
| 2622 | F | 707833 |
| 2623 | F | 705939 |
| 2624 | F | 708029 |
| 2625 | F | 706086 |
| 2626 | F | 708653 |
| 2627 | F | 706753 |
| 2628 | F | 710042 |
| 2629 | F | 708142 |
| 2630 | F | 711185 |
| 2631 | F | 709291 |
| 2632 | F | 712521 |
| 2633 | F | 710641 |
| 2634 | F | 713432 |
| 2635 | F | 711506 |
| 2636 | F | 713901 |
| 2637 | F | 711987 |
| 2638 | F | 714557 |
| 2639 | F | 712708 |
| 2640 | F | 715339 |
| 2641 | F | 713437 |
| 2642 | F | 715702 |
| 2643 | F | 713761 |
| 2644 | F | 716892 |
| 2645 | F | 714970 |
| 2646 | F | 718240 |
| 2647 | F | 716381 |
| 2648 | F | 718240 |
| 2649 | F | 716380 |
| 2650 | F | 719563 |
| 2651 | F | 717658 |
| 2652 | F | 719916 |
| 2653 | F | 718025 |
| 2654 | F | 720346 |
| 2655 | F | 718429 |
| 2656 | F | 721306 |
| 2657 | F | 719440 |
| 2658 | F | 722178 |
| 2659 | F | 720271 |
| 2660 | F | 723159 |
| 2661 | F | 721259 |
| 2662 | F | 724357 |
| 2663 | F | 722451 |
| 2664 | F | 725491 |
| 2665 | F | 723647 |
| 2666 | F | 726312 |
| 2667 | F | 724417 |
| 2668 | F | 726526 |
| 2669 | F | 724590 |
| 2670 | F | 727245 |
| 2671 | F | 725325 |
| 2672 | F | 728081 |
| 2673 | F | 726209 |
| 2674 | F | 728510 |
| 2675 | F | 726618 |
| 2676 | F | 729214 |
| 2677 | F | 727319 |
| 2678 | F | 733006 |
| 2679 | F | 731064 |
| 2680 | F | 734566 |
| 2681 | F | 732618 |
| 2682 | F | 735410 |
| 2683 | F | 733522 |
| 2684 | F | 736226 |
| 2685 | F | 734388 |
| 2686 | F | 736969 |
| 2687 | F | 735092 |
| 2688 | F | 737678 |
| 2689 | F | 735820 |
| 2690 | F | 738618 |
| 2691 | F | 736719 |
| 2692 | F | 739841 |
| 2693 | F | 737941 |
| 2694 | F | 741797 |
| 2695 | F | 739895 |
| 2696 | F | 742583 |
| 2697 | F | 740705 |
| 2698 | F | 743087 |
| 2699 | F | 741169 |
| 2700 | F | 744211 |
| 2701 | F | 742277 |
| 2702 | F | 744391 |
| 2703 | F | 742492 |
| 2704 | F | 744739 |
| 2705 | F | 742813 |
| 2706 | F | 745342 |
| 2707 | F | 743438 |
| 2708 | F | 746197 |
| 2709 | F | 744273 |
| 2710 | F | 746725 |
| 2711 | F | 744784 |
| 2712 | F | 748041 |

TABLE 5-continued

| SEQ ID | Or. | position |
|---|---|---|
| 2713 | F | 746142 |
| 2714 | F | 748723 |
| 2715 | F | 746795 |
| 2716 | F | 749171 |
| 2717 | F | 747310 |
| 2718 | F | 749475 |
| 2719 | F | 747568 |
| 2720 | F | 749761 |
| 2721 | F | 747855 |
| 2722 | F | 752284 |
| 2723 | F | 750384 |
| 2724 | F | 753397 |
| 2725 | F | 751497 |
| 2726 | F | 754693 |
| 2727 | F | 752818 |
| 2728 | F | 756537 |
| 2729 | F | 754648 |
| 2730 | F | 758227 |
| 2731 | F | 756276 |
| 2732 | F | 759119 |
| 2733 | F | 757196 |
| 2734 | F | 759639 |
| 2735 | F | 757745 |
| 2736 | F | 759957 |
| 2737 | F | 758069 |
| 2738 | F | 760675 |
| 2739 | F | 758798 |
| 2740 | F | 761489 |
| 2741 | F | 759589 |
| 2742 | F | 762033 |
| 2743 | F | 760133 |
| 2744 | F | 763116 |
| 2745 | F | 761215 |
| 2746 | F | 764209 |
| 2747 | F | 762315 |
| 2748 | F | 764602 |
| 2749 | F | 762702 |
| 2750 | F | 765834 |
| 2751 | F | 763904 |
| 2752 | F | 766671 |
| 2753 | F | 764806 |
| 2754 | F | 768033 |
| 2755 | F | 766063 |
| 2756 | F | 768572 |
| 2757 | F | 766671 |
| 2758 | F | 769873 |
| 2759 | F | 768006 |
| 2760 | F | 769966 |
| 2761 | F | 768060 |
| 2762 | F | 770411 |
| 2763 | F | 768455 |
| 2764 | F | 771103 |
| 2765 | F | 769211 |
| 2766 | F | 771980 |
| 2767 | F | 770116 |
| 2768 | F | 773176 |
| 2769 | F | 771305 |
| 2770 | F | 773937 |
| 2771 | F | 771980 |
| 2772 | F | 776399 |
| 2773 | F | 774514 |
| 2774 | F | 776672 |
| 2775 | F | 774773 |
| 2776 | F | 777446 |
| 2777 | F | 775596 |
| 2778 | F | 779102 |
| 2779 | F | 777192 |
| 2780 | F | 781078 |
| 2781 | F | 779148 |
| 2782 | F | 782192 |
| 2783 | F | 780236 |
| 2784 | F | 785250 |
| 2785 | F | 783413 |
| 2786 | F | 785324 |
| 2787 | F | 783427 |
| 2788 | F | 786392 |
| 2789 | F | 784488 |
| 2790 | F | 787401 |
| 2791 | F | 785488 |
| 2792 | F | 787693 |
| 2793 | F | 785793 |
| 2794 | F | 789918 |
| 2795 | F | 788039 |
| 2796 | F | 790378 |
| 2797 | F | 788456 |
| 2798 | F | 791834 |
| 2799 | F | 789918 |
| 2800 | F | 793102 |
| 2801 | F | 791176 |
| 2802 | F | 793826 |
| 2803 | F | 791921 |
| 2804 | F | 794911 |
| 2805 | F | 793023 |
| 2806 | F | 795296 |
| 2807 | F | 793427 |
| 2808 | F | 796005 |
| 2809 | F | 794127 |
| 2810 | F | 796729 |
| 2811 | F | 794811 |
| 2812 | F | 797041 |
| 2813 | F | 795065 |
| 2814 | F | 797553 |
| 2815 | F | 795651 |
| 2816 | F | 797716 |
| 2817 | F | 795815 |
| 2818 | F | 798197 |
| 2819 | F | 796285 |
| 2820 | F | 799004 |
| 2821 | F | 797173 |
| 2822 | F | 799785 |
| 2823 | F | 797910 |
| 2824 | F | 800789 |
| 2825 | F | 798866 |
| 2826 | F | 801800 |
| 2827 | F | 799847 |
| 2828 | F | 802561 |
| 2829 | F | 800732 |
| 2830 | F | 802881 |
| 2831 | F | 800926 |
| 2832 | F | 804088 |
| 2833 | F | 802162 |
| 2834 | F | 805071 |
| 2835 | F | 803150 |
| 2836 | F | 806224 |
| 2837 | F | 804333 |
| 2838 | F | 807742 |
| 2839 | F | 805907 |
| 2840 | F | 808860 |
| 2841 | F | 806959 |
| 2842 | F | 810074 |
| 2843 | F | 808209 |
| 2844 | F | 811442 |
| 2845 | F | 809555 |
| 2846 | F | 812088 |
| 2847 | F | 810158 |
| 2848 | F | 813225 |
| 2849 | F | 811336 |
| 2850 | F | 813512 |
| 2851 | F | 811473 |
| 2852 | F | 814095 |
| 2853 | F | 812185 |
| 2854 | F | 814173 |
| 2855 | F | 812276 |
| 2856 | F | 815188 |
| 2857 | F | 813268 |
| 2858 | F | 815897 |
| 2859 | F | 813968 |
| 2860 | F | 817367 |
| 2861 | F | 815456 |
| 2862 | F | 819089 |
| 2863 | F | 817201 |
| 2864 | F | 819482 |
| 2865 | F | 817563 |
| 2866 | F | 820143 |
| 2867 | F | 818252 |
| 2868 | F | 820800 |

TABLE 5-continued

| SEQ ID | Or. | position |
|---|---|---|
| 2869 | F | 818900 |
| 2870 | F | 821426 |
| 2871 | F | 819500 |
| 2872 | F | 821943 |
| 2873 | F | 820003 |
| 2874 | F | 822811 |
| 2875 | F | 820926 |
| 2876 | F | 824117 |
| 2877 | F | 822214 |
| 2878 | F | 825659 |
| 2879 | F | 823747 |
| 2880 | F | 826112 |
| 2881 | F | 824151 |
| 2882 | F | 826773 |
| 2883 | F | 824894 |
| 2884 | F | 826945 |
| 2885 | F | 825061 |
| 2886 | F | 827754 |
| 2887 | F | 825869 |
| 2888 | F | 829117 |
| 2889 | F | 827236 |
| 2890 | F | 830870 |
| 2891 | F | 828917 |
| 2892 | F | 831522 |
| 2893 | F | 829613 |
| 2894 | F | 831995 |
| 2895 | F | 830093 |
| 2896 | F | 832585 |
| 2897 | F | 830686 |
| 2898 | F | 833149 |
| 2899 | F | 831240 |
| 2900 | F | 833660 |
| 2901 | F | 831704 |
| 2902 | F | 834442 |
| 2903 | F | 832539 |
| 2904 | F | 835147 |
| 2905 | F | 833252 |
| 2906 | F | 835536 |
| 2907 | F | 833656 |
| 2908 | F | 836378 |
| 2909 | F | 834480 |
| 2910 | F | 836990 |
| 2911 | F | 835067 |
| 2912 | F | 838512 |
| 2913 | F | 836603 |
| 2914 | F | 839718 |
| 2915 | F | 837811 |
| 2916 | F | 840211 |
| 2917 | F | 838266 |
| 2918 | F | 841434 |
| 2919 | F | 839485 |
| 2920 | F | 842250 |
| 2921 | F | 840377 |
| 2922 | F | 842761 |
| 2923 | F | 840912 |
| 2924 | F | 843000 |
| 2925 | F | 841103 |
| 2926 | F | 843583 |
| 2927 | F | 841683 |
| 2928 | F | 845985 |
| 2929 | F | 844098 |
| 2930 | F | 847919 |
| 2931 | F | 846025 |
| 2932 | F | 850011 |
| 2933 | F | 848109 |
| 2934 | F | 851442 |
| 2935 | F | 849547 |
| 2936 | F | 853479 |
| 2937 | F | 851567 |
| 2938 | F | 854701 |
| 2939 | F | 852801 |
| 2940 | F | 855197 |
| 2941 | F | 853282 |
| 2942 | F | 856012 |
| 2943 | F | 854111 |
| 2944 | F | 857227 |
| 2945 | F | 855326 |
| 2946 | F | 859309 |
| 2947 | F | 857458 |
| 2948 | F | 859418 |
| 2949 | F | 857515 |
| 2950 | F | 860468 |
| 2951 | F | 858583 |
| 2952 | F | 861361 |
| 2953 | F | 859441 |
| 2954 | F | 861872 |
| 2955 | F | 859979 |
| 2956 | F | 863352 |
| 2957 | F | 861444 |
| 2958 | F | 863777 |
| 2959 | F | 861872 |
| 2960 | F | 864636 |
| 2961 | F | 862792 |
| 2962 | F | 866084 |
| 2963 | F | 864184 |
| 2964 | F | 866443 |
| 2965 | F | 864500 |
| 2966 | F | 867576 |
| 2967 | F | 865673 |
| 2968 | F | 868841 |
| 2969 | F | 866960 |
| 2970 | F | 869050 |
| 2971 | F | 867150 |
| 2972 | F | 871062 |
| 2973 | F | 869138 |
| 2974 | F | 872210 |
| 2975 | F | 870310 |
| 2976 | F | 872497 |
| 2977 | F | 870597 |
| 2978 | F | 873141 |
| 2979 | F | 871236 |
| 2980 | F | 873800 |
| 2981 | F | 871909 |
| 2982 | F | 874558 |
| 2983 | F | 872648 |
| 2984 | F | 875521 |
| 2985 | F | 873612 |
| 2986 | F | 876781 |
| 2987 | F | 874848 |
| 2988 | F | 877657 |
| 2989 | F | 875727 |
| 2990 | F | 877935 |
| 2991 | F | 876044 |
| 2992 | F | 878633 |
| 2993 | F | 876695 |
| 2994 | F | 878886 |
| 2995 | F | 876963 |
| 2996 | F | 879824 |
| 2997 | F | 877933 |
| 2998 | F | 880670 |
| 2999 | F | 878769 |
| 3000 | F | 881719 |
| 3001 | F | 879824 |
| 3002 | F | 882682 |
| 3003 | F | 880774 |
| 3004 | F | 883432 |
| 3005 | F | 881540 |
| 3006 | F | 884263 |
| 3007 | F | 882357 |
| 3008 | F | 884947 |
| 3009 | F | 883044 |
| 3010 | F | 888721 |
| 3011 | F | 886762 |
| 3012 | F | 890084 |
| 3013 | F | 888182 |
| 3014 | F | 890897 |
| 3015 | F | 888996 |
| 3016 | F | 891749 |
| 3017 | F | 889830 |
| 3018 | F | 893136 |
| 3019 | F | 891228 |
| 3020 | F | 893415 |
| 3021 | F | 891471 |
| 3022 | F | 893591 |
| 3023 | F | 891684 |
| 3024 | F | 894005 |

TABLE 5-continued

| SEQ ID | Or. | position |
|---|---|---|
| 3025 | F | 892127 |
| 3026 | F | 894827 |
| 3027 | F | 892900 |
| 3028 | F | 895732 |
| 3029 | F | 893790 |
| 3030 | F | 896823 |
| 3031 | F | 894907 |
| 3032 | F | 900571 |
| 3033 | F | 898639 |
| 3034 | F | 902407 |
| 3035 | F | 900507 |
| 3036 | F | 903243 |
| 3037 | F | 901346 |
| 3038 | F | 903616 |
| 3039 | F | 901726 |
| 3040 | F | 905486 |
| 3041 | F | 903589 |
| 3042 | F | 906234 |
| 3043 | F | 904350 |
| 3044 | F | 906774 |
| 3045 | F | 904846 |
| 3046 | F | 907868 |
| 3047 | F | 905924 |
| 3048 | F | 908501 |
| 3049 | F | 906583 |
| 3050 | F | 908975 |
| 3051 | F | 907079 |
| 3052 | F | 909351 |
| 3053 | F | 907456 |
| 3054 | F | 909835 |
| 3055 | F | 907957 |
| 3056 | F | 910382 |
| 3057 | F | 908496 |
| 3058 | F | 910693 |
| 3059 | F | 908829 |
| 3060 | F | 912169 |
| 3061 | F | 910248 |
| 3062 | F | 912376 |
| 3063 | F | 910476 |
| 3064 | F | 912984 |
| 3065 | F | 911084 |
| 3066 | F | 913437 |
| 3067 | F | 911545 |
| 3068 | F | 914282 |
| 3069 | F | 912376 |
| 3070 | F | 914925 |
| 3071 | F | 913023 |
| 3072 | F | 915394 |
| 3073 | F | 913510 |
| 3074 | F | 915827 |
| 3075 | F | 913912 |
| 3076 | F | 916683 |
| 3077 | F | 914788 |
| 3078 | F | 917347 |
| 3079 | F | 915438 |
| 3080 | F | 918089 |
| 3081 | F | 916189 |
| 3082 | F | 918399 |
| 3083 | F | 916506 |
| 3084 | F | 919296 |
| 3085 | F | 917406 |
| 3086 | F | 919457 |
| 3087 | F | 917598 |
| 3088 | F | 919864 |
| 3089 | F | 917963 |
| 3090 | F | 920641 |
| 3091 | F | 918711 |
| 3092 | F | 921029 |
| 3093 | F | 919138 |
| 3094 | F | 921239 |
| 3095 | F | 919366 |
| 3096 | F | 921526 |
| 3097 | F | 919638 |
| 3098 | F | 921930 |
| 3099 | F | 919979 |
| 3100 | F | 922212 |
| 3101 | F | 920325 |
| 3102 | F | 922925 |
| 3103 | F | 921029 |
| 3104 | F | 923258 |
| 3105 | F | 921324 |
| 3106 | F | 923808 |
| 3107 | F | 921929 |
| 3108 | F | 924185 |
| 3109 | F | 922311 |
| 3110 | F | 924680 |
| 3111 | F | 922764 |
| 3112 | F | 925111 |
| 3113 | F | 923258 |
| 3114 | F | 926538 |
| 3115 | F | 924638 |
| 3116 | F | 926972 |
| 3117 | F | 925072 |
| 3118 | F | 927351 |
| 3119 | F | 925415 |
| 3120 | F | 927870 |
| 3121 | F | 925924 |
| 3122 | F | 928974 |
| 3123 | F | 927031 |
| 3124 | F | 930003 |
| 3125 | F | 928103 |
| 3126 | F | 930383 |
| 3127 | F | 928402 |
| 3128 | F | 931084 |
| 3129 | F | 929222 |
| 3130 | F | 931307 |
| 3131 | F | 929397 |
| 3132 | F | 931824 |
| 3133 | F | 929927 |
| 3134 | F | 932352 |
| 3135 | F | 930470 |
| 3136 | F | 933044 |
| 3137 | F | 931084 |
| 3138 | F | 933303 |
| 3139 | F | 931396 |
| 3140 | F | 933626 |
| 3141 | F | 931686 |
| 3142 | F | 934320 |
| 3143 | F | 932412 |
| 3144 | F | 936427 |
| 3145 | F | 934508 |
| 3146 | F | 938309 |
| 3147 | F | 936402 |
| 3148 | F | 939110 |
| 3149 | F | 937204 |
| 3150 | F | 940791 |
| 3151 | F | 938889 |
| 3152 | F | 941806 |
| 3153 | F | 939906 |
| 3154 | F | 944314 |
| 3155 | F | 942412 |
| 3156 | F | 944987 |
| 3157 | F | 943090 |
| 3158 | F | 946072 |
| 3159 | F | 944166 |
| 3160 | F | 946877 |
| 3161 | F | 944986 |
| 3162 | F | 948258 |
| 3163 | F | 946403 |
| 3164 | F | 949037 |
| 3165 | F | 947137 |
| 3166 | F | 949581 |
| 3167 | F | 947671 |
| 3168 | F | 950455 |
| 3169 | F | 948558 |
| 3170 | F | 951058 |
| 3171 | F | 949151 |
| 3172 | F | 951569 |
| 3173 | F | 949653 |
| 3174 | F | 953340 |
| 3175 | F | 951431 |
| 3176 | F | 954174 |
| 3177 | F | 952288 |
| 3178 | F | 955475 |
| 3179 | F | 953604 |
| 3180 | F | 957601 |

TABLE 5-continued

| SEQ ID | Or. | position |
|---|---|---|
| 3181 | F | 955703 |
| 3182 | F | 959053 |
| 3183 | F | 957168 |
| 3184 | F | 960824 |
| 3185 | F | 958932 |
| 3186 | F | 961268 |
| 3187 | F | 959368 |
| 3188 | F | 961365 |
| 3189 | F | 959465 |
| 3190 | F | 962324 |
| 3191 | F | 960423 |
| 3192 | F | 964706 |
| 3193 | F | 962822 |
| 3194 | F | 965974 |
| 3195 | F | 964074 |
| 3196 | F | 967210 |
| 3197 | F | 965307 |
| 3198 | F | 967808 |
| 3199 | F | 965925 |
| 3200 | F | 969286 |
| 3201 | F | 967320 |
| 3202 | F | 970802 |
| 3203 | F | 968888 |
| 3204 | F | 972169 |
| 3205 | F | 970269 |
| 3206 | F | 973487 |
| 3207 | F | 971616 |
| 3208 | F | 974339 |
| 3209 | F | 972408 |
| 3210 | F | 974988 |
| 3211 | F | 973035 |
| 3212 | F | 976035 |
| 3213 | F | 974114 |
| 3214 | F | 976367 |
| 3215 | F | 974411 |
| 3216 | F | 976665 |
| 3217 | F | 974730 |
| 3218 | F | 977439 |
| 3219 | F | 975500 |
| 3220 | F | 977698 |
| 3221 | F | 975799 |
| 3222 | F | 978389 |
| 3223 | F | 976478 |
| 3224 | F | 978665 |
| 3225 | F | 976760 |
| 3226 | F | 979134 |
| 3227 | F | 977270 |
| 3228 | F | 979473 |
| 3229 | F | 977592 |
| 3230 | F | 980915 |
| 3231 | F | 979026 |
| 3232 | F | 982043 |
| 3233 | F | 980178 |
| 3234 | F | 983628 |
| 3235 | F | 981736 |
| 3236 | F | 984149 |
| 3237 | F | 982271 |
| 3238 | F | 985180 |
| 3239 | F | 983280 |
| 3240 | F | 985815 |
| 3241 | F | 983882 |
| 3242 | F | 986458 |
| 3243 | F | 984547 |
| 3244 | F | 987340 |
| 3245 | F | 985462 |
| 3246 | F | 987686 |
| 3247 | F | 985815 |
| 3248 | F | 988559 |
| 3249 | F | 986670 |
| 3250 | F | 989455 |
| 3251 | F | 987558 |
| 3252 | F | 993122 |
| 3253 | F | 991289 |
| 3254 | F | 993186 |
| 3255 | F | 991297 |
| 3256 | F | 993650 |
| 3257 | F | 991727 |
| 3258 | F | 994007 |
| 3259 | F | 992107 |
| 3260 | F | 995743 |
| 3261 | F | 993915 |
| 3262 | F | 996663 |
| 3263 | F | 994763 |
| 3264 | F | 998586 |
| 3265 | F | 996755 |
| 3266 | F | 999153 |
| 3267 | F | 997253 |
| 3268 | F | 1000967 |
| 3269 | F | 999092 |
| 3270 | F | 1001173 |
| 3271 | F | 999246 |
| 3272 | F | 1001604 |
| 3273 | F | 999645 |
| 3274 | F | 1004159 |
| 3275 | F | 1002326 |
| 3276 | F | 1004763 |
| 3277 | F | 1002871 |
| 3278 | F | 1005160 |
| 3279 | F | 1003235 |
| 3280 | F | 1007181 |
| 3281 | F | 1005250 |
| 3282 | F | 1007561 |
| 3283 | F | 1005665 |
| 3284 | F | 1008855 |
| 3285 | F | 1007002 |
| 3286 | F | 1010205 |
| 3287 | F | 1008342 |
| 3288 | F | 1011716 |
| 3289 | F | 1009823 |
| 3290 | F | 1011812 |
| 3291 | F | 1009914 |
| 3292 | F | 1012372 |
| 3293 | F | 1010385 |
| 3294 | F | 1012567 |
| 3295 | F | 1010624 |
| 3296 | F | 1013237 |
| 3297 | F | 1011337 |
| 3298 | F | 1013690 |
| 3299 | F | 1011856 |
| 3300 | F | 1014301 |
| 3301 | F | 1012396 |
| 3302 | F | 1014926 |
| 3303 | F | 1013010 |
| 3304 | F | 1015664 |
| 3305 | F | 1013820 |
| 3306 | F | 1017026 |
| 3307 | F | 1015099 |
| 3308 | F | 1017674 |
| 3309 | F | 1015786 |
| 3310 | F | 1018353 |
| 3311 | F | 1016460 |
| 3312 | F | 1019602 |
| 3313 | F | 1017674 |
| 3314 | F | 1019876 |
| 3315 | F | 1017948 |
| 3316 | F | 1020853 |
| 3317 | F | 1018956 |
| 3318 | F | 1021878 |
| 3319 | F | 1019972 |
| 3320 | F | 1023054 |
| 3321 | F | 1021186 |
| 3322 | F | 1023415 |
| 3323 | F | 1021579 |
| 3324 | F | 1023748 |
| 3325 | F | 1021850 |
| 3326 | F | 1024485 |
| 3327 | F | 1022574 |
| 3328 | F | 1024744 |
| 3329 | F | 1022836 |
| 3330 | F | 1025618 |
| 3331 | F | 1023720 |
| 3332 | F | 1026323 |
| 3333 | F | 1024403 |
| 3334 | F | 1027710 |
| 3335 | F | 1025809 |
| 3336 | F | 1030272 |

TABLE 5-continued

| SEQ ID | Or. | position |
|---|---|---|
| 3337 | F | 1028389 |
| 3338 | F | 1031486 |
| 3339 | F | 1029602 |
| 3340 | F | 1033215 |
| 3341 | F | 1031334 |
| 3342 | F | 1035425 |
| 3343 | F | 1033555 |
| 3344 | F | 1035956 |
| 3345 | F | 1034055 |
| 3346 | F | 1036748 |
| 3347 | F | 1034844 |
| 3348 | F | 16372 |
| 3349 | F | 14463 |
| 3350 | F | 31184 |
| 3351 | F | 29287 |
| 3352 | F | 56283 |
| 3353 | F | 54383 |
| 3354 | F | 56384 |
| 3355 | F | 54538 |
| 3356 | F | 64528 |
| 3357 | F | 62600 |
| 3358 | F | 72965 |
| 3359 | F | 71054 |
| 3360 | F | 78245 |
| 3361 | F | 76347 |
| 3362 | F | 79133 |
| 3363 | F | 77291 |
| 3364 | F | 81740 |
| 3365 | F | 79840 |
| 3366 | F | 86772 |
| 3367 | F | 84880 |
| 3368 | F | 109188 |
| 3369 | F | 107337 |
| 3370 | F | 111132 |
| 3371 | F | 109188 |
| 3372 | F | 111505 |
| 3373 | F | 109597 |
| 3374 | F | 112432 |
| 3375 | F | 110462 |
| 3376 | F | 113446 |
| 3377 | F | 111592 |
| 3378 | F | 120225 |
| 3379 | F | 118303 |
| 3380 | F | 124892 |
| 3381 | F | 123004 |
| 3382 | F | 131327 |
| 3383 | F | 129485 |
| 3384 | F | 143944 |
| 3385 | F | 142043 |
| 3386 | F | 150138 |
| 3387 | F | 148247 |
| 3388 | F | 163715 |
| 3389 | F | 161804 |
| 3390 | F | 165186 |
| 3391 | F | 163274 |
| 3392 | F | 168143 |
| 3393 | F | 166302 |
| 3394 | F | 170287 |
| 3395 | F | 168387 |
| 3396 | F | 176838 |
| 3397 | F | 174996 |
| 3398 | F | 187776 |
| 3399 | F | 185900 |
| 3400 | F | 188083 |
| 3401 | F | 186208 |
| 3402 | F | 190117 |
| 3403 | F | 188168 |
| 3404 | F | 196802 |
| 3405 | F | 194946 |
| 3406 | F | 210685 |
| 3407 | F | 208785 |
| 3408 | F | 234633 |
| 3409 | F | 232727 |
| 3410 | F | 236682 |
| 3411 | F | 234794 |
| 3412 | F | 249227 |
| 3413 | F | 247310 |
| 3414 | F | 252939 |
| 3415 | F | 251036 |
| 3416 | F | 253406 |
| 3417 | F | 251562 |
| 3418 | F | 271365 |
| 3419 | F | 269466 |
| 3420 | F | 275390 |
| 3421 | F | 273489 |
| 3422 | F | 277681 |
| 3423 | F | 275765 |
| 3424 | F | 282260 |
| 3425 | F | 280357 |
| 3426 | F | 292925 |
| 3427 | F | 291054 |
| 3428 | F | 302910 |
| 3429 | F | 301032 |
| 3430 | F | 308746 |
| 3431 | F | 306806 |
| 3432 | F | 311994 |
| 3433 | F | 310073 |
| 3434 | F | 312375 |
| 3435 | F | 310483 |
| 3436 | F | 312531 |
| 3437 | F | 310647 |
| 3438 | F | 319923 |
| 3439 | F | 318009 |
| 3440 | F | 339991 |
| 3441 | F | 338104 |
| 3442 | F | 352535 |
| 3443 | F | 350653 |
| 3444 | F | 373218 |
| 3445 | F | 371320 |
| 3446 | F | 376994 |
| 3447 | F | 375085 |
| 3448 | F | 378954 |
| 3449 | F | 377011 |
| 3450 | F | 394604 |
| 3451 | F | 392704 |
| 3452 | F | 400915 |
| 3453 | F | 398972 |
| 3454 | F | 409744 |
| 3455 | F | 407904 |
| 3456 | F | 411155 |
| 3457 | F | 409253 |
| 3458 | F | 414197 |
| 3459 | F | 412281 |
| 3460 | F | 422638 |
| 3461 | F | 420770 |
| 3462 | F | 427595 |
| 3463 | F | 425701 |
| 3464 | F | 428453 |
| 3465 | F | 426553 |
| 3466 | F | 442272 |
| 3467 | F | 440364 |
| 3468 | F | 443303 |
| 3469 | F | 441380 |
| 3470 | F | 442939 |
| 3471 | F | 441047 |
| 3472 | F | 445572 |
| 3473 | F | 443707 |
| 3474 | F | 467757 |
| 3475 | F | 465801 |
| 3476 | F | 471583 |
| 3477 | F | 469712 |
| 3478 | F | 487813 |
| 3479 | F | 485913 |
| 3480 | F | 496852 |
| 3481 | F | 494952 |
| 3482 | F | 499979 |
| 3483 | F | 498074 |
| 3484 | F | 508715 |
| 3485 | F | 506798 |
| 3486 | F | 510584 |
| 3487 | F | 508632 |
| 3488 | F | 526255 |
| 3489 | F | 524350 |
| 3490 | F | 531098 |
| 3491 | F | 529150 |
| 3492 | F | 556575 |

TABLE 5-continued

| SEQ ID | Or. | position |
|---|---|---|
| 3493 | F | 554706 |
| 3494 | F | 564318 |
| 3495 | F | 562390 |
| 3496 | F | 566692 |
| 3497 | F | 564838 |
| 3498 | F | 570033 |
| 3499 | F | 568150 |
| 3500 | F | 570844 |
| 3501 | F | 568915 |
| 3502 | F | 575571 |
| 3503 | F | 573671 |
| 3504 | F | 590045 |
| 3505 | F | 588196 |
| 3506 | F | 597631 |
| 3507 | F | 595698 |
| 3508 | F | 606387 |
| 3509 | F | 604507 |
| 3510 | F | 607566 |
| 3511 | F | 605637 |
| 3512 | F | 609842 |
| 3513 | F | 607958 |
| 3514 | F | 632472 |
| 3515 | F | 630572 |
| 3516 | F | 636994 |
| 3517 | F | 635071 |
| 3518 | F | 649681 |
| 3519 | F | 647800 |
| 3520 | F | 652059 |
| 3521 | F | 650101 |
| 3522 | F | 654522 |
| 3523 | F | 652562 |
| 3524 | F | 660587 |
| 3525 | F | 658691 |
| 3526 | F | 676785 |
| 3527 | F | 674938 |
| 3528 | F | 679031 |
| 3529 | F | 677133 |
| 3530 | F | 731967 |
| 3531 | F | 730091 |
| 3532 | F | 741797 |
| 3533 | F | 739935 |
| 3534 | F | 758555 |
| 3535 | F | 756641 |
| 3536 | F | 760010 |
| 3537 | F | 758082 |
| 3538 | F | 770670 |
| 3539 | F | 768751 |
| 3540 | F | 771896 |
| 3541 | F | 769996 |
| 3542 | F | 787857 |
| 3543 | F | 785958 |
| 3544 | F | 815714 |
| 3545 | F | 813840 |
| 3546 | F | 846380 |
| 3547 | F | 844470 |
| 3548 | F | 867576 |
| 3549 | F | 865673 |
| 3550 | F | 875167 |
| 3551 | F | 873254 |
| 3552 | F | 876214 |
| 3553 | F | 874314 |
| 3554 | F | 884093 |
| 3555 | F | 882162 |
| 3556 | F | 891248 |
| 3557 | F | 889348 |
| 3558 | F | 900125 |
| 3559 | F | 898298 |
| 3560 | F | 902048 |
| 3561 | F | 900125 |
| 3562 | F | 907563 |
| 3563 | F | 905656 |
| 3564 | F | 912076 |
| 3565 | F | 910133 |
| 3566 | F | 935157 |
| 3567 | F | 933211 |
| 3568 | F | 946473 |
| 3569 | F | 944568 |
| 3570 | F | 952562 |
| 3571 | F | 950664 |
| 3572 | F | 965649 |
| 3573 | F | 963730 |
| 3574 | F | 968519 |
| 3575 | F | 966614 |
| 3576 | F | 970497 |
| 3577 | F | 968601 |
| 3578 | F | 971879 |
| 3579 | F | 970043 |
| 3580 | F | 972888 |
| 3581 | F | 970962 |
| 3582 | F | 998162 |
| 3583 | F | 996241 |
| 3584 | F | 1003657 |
| 3585 | F | 1001756 |
| 3586 | F | 1009313 |
| 3587 | F | 1007413 |
| 3588 | F | 1028954 |
| 3589 | F | 1027039 |
| 3590 | B | 730 |
| 3591 | B | 2645 |
| 3592 | B | 3521 |
| 3593 | B | 5431 |
| 3594 | B | 5295 |
| 3595 | B | 7188 |
| 3596 | B | 6740 |
| 3597 | B | 8652 |
| 3598 | B | 8240 |
| 3599 | B | 10138 |
| 3600 | B | 8959 |
| 3601 | B | 10816 |
| 3602 | B | 9285 |
| 3603 | B | 11160 |
| 3604 | B | 9689 |
| 3605 | B | 11591 |
| 3606 | B | 10679 |
| 3607 | B | 12568 |
| 3608 | B | 11515 |
| 3609 | B | 13376 |
| 3610 | B | 12136 |
| 3611 | B | 14038 |
| 3612 | B | 13565 |
| 3613 | B | 15450 |
| 3614 | B | 14667 |
| 3615 | B | 16535 |
| 3616 | B | 15254 |
| 3617 | B | 17183 |
| 3618 | B | 16189 |
| 3619 | B | 18097 |
| 3620 | B | 16790 |
| 3621 | B | 18621 |
| 3622 | B | 16710 |
| 3623 | B | 18587 |
| 3624 | B | 18458 |
| 3625 | B | 20318 |
| 3626 | B | 20768 |
| 3627 | B | 22647 |
| 3628 | B | 22438 |
| 3629 | B | 24335 |
| 3630 | B | 22892 |
| 3631 | B | 24752 |
| 3632 | B | 23046 |
| 3633 | B | 24924 |
| 3634 | B | 23442 |
| 3635 | B | 25313 |
| 3636 | B | 23623 |
| 3637 | B | 25528 |
| 3638 | B | 24822 |
| 3639 | B | 26708 |
| 3640 | B | 26618 |
| 3641 | B | 28544 |
| 3642 | B | 27972 |
| 3643 | B | 29859 |
| 3644 | B | 29000 |
| 3645 | B | 30908 |
| 3646 | B | 30242 |
| 3647 | B | 32160 |
| 3648 | B | 30966 |

TABLE 5-continued

| SEQ ID | Or. | position |
|---|---|---|
| 3649 | B | 32849 |
| 3650 | B | 31516 |
| 3651 | B | 33401 |
| 3652 | B | 32032 |
| 3653 | B | 33900 |
| 3654 | B | 33576 |
| 3655 | B | 35496 |
| 3656 | B | 34121 |
| 3657 | B | 36052 |
| 3658 | B | 35251 |
| 3659 | B | 37164 |
| 3660 | B | 35588 |
| 3661 | B | 37502 |
| 3662 | B | 36152 |
| 3663 | B | 38041 |
| 3664 | B | 37216 |
| 3665 | B | 39127 |
| 3666 | B | 38041 |
| 3667 | B | 39980 |
| 3668 | B | 39322 |
| 3669 | B | 41205 |
| 3670 | B | 40161 |
| 3671 | B | 42074 |
| 3672 | B | 40985 |
| 3673 | B | 42887 |
| 3674 | B | 42284 |
| 3675 | B | 44180 |
| 3676 | B | 43337 |
| 3677 | B | 45275 |
| 3678 | B | 44022 |
| 3679 | B | 45927 |
| 3680 | B | 45451 |
| 3681 | B | 47375 |
| 3682 | B | 46308 |
| 3683 | B | 48208 |
| 3684 | B | 46560 |
| 3685 | B | 48485 |
| 3686 | B | 47115 |
| 3687 | B | 49053 |
| 3688 | B | 48208 |
| 3689 | B | 50118 |
| 3690 | B | 48806 |
| 3691 | B | 50708 |
| 3692 | B | 50333 |
| 3693 | B | 52220 |
| 3694 | B | 50960 |
| 3695 | B | 52890 |
| 3696 | B | 52660 |
| 3697 | B | 54606 |
| 3698 | B | 53737 |
| 3699 | B | 55645 |
| 3700 | B | 54793 |
| 3701 | B | 56691 |
| 3702 | B | 55329 |
| 3703 | B | 57226 |
| 3704 | B | 56691 |
| 3705 | B | 58566 |
| 3706 | B | 56317 |
| 3707 | B | 58226 |
| 3708 | B | 58469 |
| 3709 | B | 60363 |
| 3710 | B | 59406 |
| 3711 | B | 61301 |
| 3712 | B | 60450 |
| 3713 | B | 62316 |
| 3714 | B | 61722 |
| 3715 | B | 63603 |
| 3716 | B | 62585 |
| 3717 | B | 64473 |
| 3718 | B | 63362 |
| 3719 | B | 65285 |
| 3720 | B | 64203 |
| 3721 | B | 66103 |
| 3722 | B | 64850 |
| 3723 | B | 66749 |
| 3724 | B | 64899 |
| 3725 | B | 66776 |
| 3726 | B | 65164 |
| 3727 | B | 67067 |
| 3728 | B | 67514 |
| 3729 | B | 69390 |
| 3730 | B | 69097 |
| 3731 | B | 71033 |
| 3732 | B | 69470 |
| 3733 | B | 71354 |
| 3734 | B | 69961 |
| 3735 | B | 71898 |
| 3736 | B | 70707 |
| 3737 | B | 72579 |
| 3738 | B | 71249 |
| 3739 | B | 73134 |
| 3740 | B | 73458 |
| 3741 | B | 75376 |
| 3742 | B | 75121 |
| 3743 | B | 77020 |
| 3744 | B | 75741 |
| 3745 | B | 77608 |
| 3746 | B | 77447 |
| 3747 | B | 79300 |
| 3748 | B | 77535 |
| 3749 | B | 79430 |
| 3750 | B | 78333 |
| 3751 | B | 80243 |
| 3752 | B | 79300 |
| 3753 | B | 81197 |
| 3754 | B | 82201 |
| 3755 | B | 84100 |
| 3756 | B | 83493 |
| 3757 | B | 85405 |
| 3758 | B | 85075 |
| 3759 | B | 86973 |
| 3760 | B | 87141 |
| 3761 | B | 89086 |
| 3762 | B | 88903 |
| 3763 | B | 90810 |
| 3764 | B | 88038 |
| 3765 | B | 89946 |
| 3766 | B | 88981 |
| 3767 | B | 90884 |
| 3768 | B | 89485 |
| 3769 | B | 91385 |
| 3770 | B | 89975 |
| 3771 | B | 91855 |
| 3772 | B | 91680 |
| 3773 | B | 93567 |
| 3774 | B | 92008 |
| 3775 | B | 93902 |
| 3776 | B | 92633 |
| 3777 | B | 94569 |
| 3778 | B | 93390 |
| 3779 | B | 95288 |
| 3780 | B | 94354 |
| 3781 | B | 96254 |
| 3782 | B | 94897 |
| 3783 | B | 96772 |
| 3784 | B | 98519 |
| 3785 | B | 100439 |
| 3786 | B | 98962 |
| 3787 | B | 100853 |
| 3788 | B | 100451 |
| 3789 | B | 102387 |
| 3790 | B | 101639 |
| 3791 | B | 103473 |
| 3792 | B | 102457 |
| 3793 | B | 104357 |
| 3794 | B | 102745 |
| 3795 | B | 104666 |
| 3796 | B | 104544 |
| 3797 | B | 106464 |
| 3798 | B | 105338 |
| 3799 | B | 107237 |
| 3800 | B | 106127 |
| 3801 | B | 108014 |
| 3802 | B | 108693 |
| 3803 | B | 110587 |
| 3804 | B | 109189 |

TABLE 5-continued

| SEQ ID | Or. | position |
|---|---|---|
| 3805 | B | 111079 |
| 3806 | B | 109684 |
| 3807 | B | 111580 |
| 3808 | B | 110587 |
| 3809 | B | 112486 |
| 3810 | B | 112740 |
| 3811 | B | 114673 |
| 3812 | B | 113684 |
| 3813 | B | 115653 |
| 3814 | B | 114216 |
| 3815 | B | 116158 |
| 3816 | B | 114836 |
| 3817 | B | 116732 |
| 3818 | B | 115473 |
| 3819 | B | 117380 |
| 3820 | B | 115898 |
| 3821 | B | 117797 |
| 3822 | B | 120031 |
| 3823 | B | 121926 |
| 3824 | B | 124231 |
| 3825 | B | 126158 |
| 3826 | B | 125215 |
| 3827 | B | 127115 |
| 3828 | B | 125352 |
| 3829 | B | 127271 |
| 3830 | B | 126492 |
| 3831 | B | 128390 |
| 3832 | B | 127150 |
| 3833 | B | 129050 |
| 3834 | B | 128010 |
| 3835 | B | 129905 |
| 3836 | B | 129947 |
| 3837 | B | 131873 |
| 3838 | B | 131255 |
| 3839 | B | 133205 |
| 3840 | B | 131873 |
| 3841 | B | 133749 |
| 3842 | B | 133381 |
| 3843 | B | 135305 |
| 3844 | B | 133804 |
| 3845 | B | 135704 |
| 3846 | B | 134219 |
| 3847 | B | 136133 |
| 3848 | B | 134729 |
| 3849 | B | 136633 |
| 3850 | B | 137694 |
| 3851 | B | 139583 |
| 3852 | B | 140496 |
| 3853 | B | 142396 |
| 3854 | B | 140953 |
| 3855 | B | 142856 |
| 3856 | B | 142031 |
| 3857 | B | 143950 |
| 3858 | B | 143520 |
| 3859 | B | 145425 |
| 3860 | B | 144066 |
| 3861 | B | 145967 |
| 3862 | B | 144629 |
| 3863 | B | 146519 |
| 3864 | B | 146547 |
| 3865 | B | 148446 |
| 3866 | B | 147304 |
| 3867 | B | 149227 |
| 3868 | B | 148296 |
| 3869 | B | 150255 |
| 3870 | B | 148769 |
| 3871 | B | 150670 |
| 3872 | B | 149320 |
| 3873 | B | 151168 |
| 3874 | B | 149532 |
| 3875 | B | 151470 |
| 3876 | B | 149934 |
| 3877 | B | 151845 |
| 3878 | B | 151168 |
| 3879 | B | 153047 |
| 3880 | B | 152275 |
| 3881 | B | 154165 |
| 3882 | B | 152887 |
| 3883 | B | 154804 |
| 3884 | B | 153600 |
| 3885 | B | 155482 |
| 3886 | B | 154217 |
| 3887 | B | 156157 |
| 3888 | B | 155523 |
| 3889 | B | 157396 |
| 3890 | B | 156823 |
| 3891 | B | 158731 |
| 3892 | B | 157745 |
| 3893 | B | 159645 |
| 3894 | B | 159207 |
| 3895 | B | 161084 |
| 3896 | B | 160216 |
| 3897 | B | 162127 |
| 3898 | B | 161451 |
| 3899 | B | 163350 |
| 3900 | B | 161818 |
| 3901 | B | 163726 |
| 3902 | B | 162601 |
| 3903 | B | 164501 |
| 3904 | B | 163282 |
| 3905 | B | 165205 |
| 3906 | B | 164171 |
| 3907 | B | 166082 |
| 3908 | B | 165812 |
| 3909 | B | 167672 |
| 3910 | B | 166939 |
| 3911 | B | 168861 |
| 3912 | B | 168421 |
| 3913 | B | 170322 |
| 3914 | B | 169503 |
| 3915 | B | 171369 |
| 3916 | B | 170715 |
| 3917 | B | 172587 |
| 3918 | B | 171554 |
| 3919 | B | 173512 |
| 3920 | B | 172596 |
| 3921 | B | 174496 |
| 3922 | B | 173021 |
| 3923 | B | 174847 |
| 3924 | B | 174716 |
| 3925 | B | 176619 |
| 3926 | B | 175205 |
| 3927 | B | 177143 |
| 3928 | B | 175943 |
| 3929 | B | 177830 |
| 3930 | B | 177244 |
| 3931 | B | 179180 |
| 3932 | B | 178337 |
| 3933 | B | 180239 |
| 3934 | B | 180274 |
| 3935 | B | 182181 |
| 3936 | B | 180972 |
| 3937 | B | 182864 |
| 3938 | B | 181659 |
| 3939 | B | 183572 |
| 3940 | B | 182864 |
| 3941 | B | 184750 |
| 3942 | B | 183876 |
| 3943 | B | 185778 |
| 3944 | B | 185007 |
| 3945 | B | 186910 |
| 3946 | B | 186246 |
| 3947 | B | 188160 |
| 3948 | B | 187080 |
| 3949 | B | 189016 |
| 3950 | B | 187490 |
| 3951 | B | 189421 |
| 3952 | B | 188044 |
| 3953 | B | 189929 |
| 3954 | B | 189711 |
| 3955 | B | 191656 |
| 3956 | B | 190594 |
| 3957 | B | 192533 |
| 3958 | B | 190731 |
| 3959 | B | 192679 |
| 3960 | B | 192027 |

TABLE 5-continued

| SEQ ID | Or. | position |
|---|---|---|
| 3961 | B | 193906 |
| 3962 | B | 192684 |
| 3963 | B | 194643 |
| 3964 | B | 193419 |
| 3965 | B | 195348 |
| 3966 | B | 194878 |
| 3967 | B | 196750 |
| 3968 | B | 195270 |
| 3969 | B | 197166 |
| 3970 | B | 197255 |
| 3971 | B | 199165 |
| 3972 | B | 197859 |
| 3973 | B | 199756 |
| 3974 | B | 198443 |
| 3975 | B | 200328 |
| 3976 | B | 199202 |
| 3977 | B | 201084 |
| 3978 | B | 200198 |
| 3979 | B | 202084 |
| 3980 | B | 200547 |
| 3981 | B | 202447 |
| 3982 | B | 200934 |
| 3983 | B | 202806 |
| 3984 | B | 201224 |
| 3985 | B | 203115 |
| 3986 | B | 202606 |
| 3987 | B | 204583 |
| 3988 | B | 203735 |
| 3989 | B | 205603 |
| 3990 | B | 204218 |
| 3991 | B | 206147 |
| 3992 | B | 206686 |
| 3993 | B | 208569 |
| 3994 | B | 207672 |
| 3995 | B | 209558 |
| 3996 | B | 208799 |
| 3997 | B | 210648 |
| 3998 | B | 209701 |
| 3999 | B | 211599 |
| 4000 | B | 210500 |
| 4001 | B | 212364 |
| 4002 | B | 211064 |
| 4003 | B | 212957 |
| 4004 | B | 211557 |
| 4005 | B | 213453 |
| 4006 | B | 213248 |
| 4007 | B | 215101 |
| 4008 | B | 214372 |
| 4009 | B | 216286 |
| 4010 | B | 214931 |
| 4011 | B | 216887 |
| 4012 | B | 215375 |
| 4013 | B | 217268 |
| 4014 | B | 216928 |
| 4015 | B | 218828 |
| 4016 | B | 218137 |
| 4017 | B | 220037 |
| 4018 | B | 217661 |
| 4019 | B | 219561 |
| 4020 | B | 218937 |
| 4021 | B | 220822 |
| 4022 | B | 219229 |
| 4023 | B | 221130 |
| 4024 | B | 220005 |
| 4025 | B | 221868 |
| 4026 | B | 220654 |
| 4027 | B | 222560 |
| 4028 | B | 221294 |
| 4029 | B | 223195 |
| 4030 | B | 221762 |
| 4031 | B | 223673 |
| 4032 | B | 222338 |
| 4033 | B | 224212 |
| 4034 | B | 223510 |
| 4035 | B | 225417 |
| 4036 | B | 224094 |
| 4037 | B | 226033 |
| 4038 | B | 225417 |
| 4039 | B | 227291 |
| 4040 | B | 226033 |
| 4041 | B | 227907 |
| 4042 | B | 225811 |
| 4043 | B | 227671 |
| 4044 | B | 226947 |
| 4045 | B | 228871 |
| 4046 | B | 227523 |
| 4047 | B | 229432 |
| 4048 | B | 227907 |
| 4049 | B | 229784 |
| 4050 | B | 228692 |
| 4051 | B | 230578 |
| 4052 | B | 230253 |
| 4053 | B | 232157 |
| 4054 | B | 231299 |
| 4055 | B | 233194 |
| 4056 | B | 233226 |
| 4057 | B | 235130 |
| 4058 | B | 234073 |
| 4059 | B | 235950 |
| 4060 | B | 234510 |
| 4061 | B | 236399 |
| 4062 | B | 235094 |
| 4063 | B | 236993 |
| 4064 | B | 236552 |
| 4065 | B | 238440 |
| 4066 | B | 238440 |
| 4067 | B | 240381 |
| 4068 | B | 238989 |
| 4069 | B | 240917 |
| 4070 | B | 240294 |
| 4071 | B | 242181 |
| 4072 | B | 242260 |
| 4073 | B | 244157 |
| 4074 | B | 243066 |
| 4075 | B | 245029 |
| 4076 | B | 244703 |
| 4077 | B | 246603 |
| 4078 | B | 246151 |
| 4079 | B | 248017 |
| 4080 | B | 247104 |
| 4081 | B | 248997 |
| 4082 | B | 248001 |
| 4083 | B | 249872 |
| 4084 | B | 248835 |
| 4085 | B | 250713 |
| 4086 | B | 249697 |
| 4087 | B | 251574 |
| 4088 | B | 250643 |
| 4089 | B | 252560 |
| 4090 | B | 251439 |
| 4091 | B | 253306 |
| 4092 | B | 252401 |
| 4093 | B | 254231 |
| 4094 | B | 253312 |
| 4095 | B | 255224 |
| 4096 | B | 256969 |
| 4097 | B | 258840 |
| 4098 | B | 258065 |
| 4099 | B | 259964 |
| 4100 | B | 258945 |
| 4101 | B | 260826 |
| 4102 | B | 259428 |
| 4103 | B | 261313 |
| 4104 | B | 261845 |
| 4105 | B | 263746 |
| 4106 | B | 264350 |
| 4107 | B | 266263 |
| 4108 | B | 264963 |
| 4109 | B | 266887 |
| 4110 | B | 265848 |
| 4111 | B | 267749 |
| 4112 | B | 266644 |
| 4113 | B | 268546 |
| 4114 | B | 268188 |
| 4115 | B | 270091 |
| 4116 | B | 268188 |

TABLE 5-continued

| SEQ ID | Or. | position |
|---|---|---|
| 4117 | B | 270091 |
| 4118 | B | 268546 |
| 4119 | B | 270440 |
| 4120 | B | 268785 |
| 4121 | B | 270697 |
| 4122 | B | 270439 |
| 4123 | B | 272288 |
| 4124 | B | 271181 |
| 4125 | B | 273043 |
| 4126 | B | 271833 |
| 4127 | B | 273738 |
| 4128 | B | 273188 |
| 4129 | B | 275062 |
| 4130 | B | 273817 |
| 4131 | B | 275718 |
| 4132 | B | 275062 |
| 4133 | B | 277005 |
| 4134 | B | 275886 |
| 4135 | B | 277857 |
| 4136 | B | 277923 |
| 4137 | B | 279868 |
| 4138 | B | 279043 |
| 4139 | B | 281004 |
| 4140 | B | 280126 |
| 4141 | B | 282004 |
| 4142 | B | 281004 |
| 4143 | B | 282911 |
| 4144 | B | 281825 |
| 4145 | B | 283746 |
| 4146 | B | 282335 |
| 4147 | B | 284236 |
| 4148 | B | 284583 |
| 4149 | B | 286455 |
| 4150 | B | 285055 |
| 4151 | B | 286921 |
| 4152 | B | 285894 |
| 4153 | B | 287794 |
| 4154 | B | 286441 |
| 4155 | B | 288315 |
| 4156 | B | 286921 |
| 4157 | B | 288811 |
| 4158 | B | 288145 |
| 4159 | B | 290018 |
| 4160 | B | 289448 |
| 4161 | B | 291407 |
| 4162 | B | 290899 |
| 4163 | B | 292805 |
| 4164 | B | 291814 |
| 4165 | B | 293655 |
| 4166 | B | 292489 |
| 4167 | B | 294373 |
| 4168 | B | 293317 |
| 4169 | B | 295183 |
| 4170 | B | 295073 |
| 4171 | B | 297037 |
| 4172 | B | 295932 |
| 4173 | B | 297846 |
| 4174 | B | 296556 |
| 4175 | B | 298475 |
| 4176 | B | 297474 |
| 4177 | B | 299413 |
| 4178 | B | 298970 |
| 4179 | B | 300855 |
| 4180 | B | 300679 |
| 4181 | B | 302595 |
| 4182 | B | 302372 |
| 4183 | B | 304272 |
| 4184 | B | 305137 |
| 4185 | B | 307039 |
| 4186 | B | 306377 |
| 4187 | B | 308287 |
| 4188 | B | 306730 |
| 4189 | B | 308614 |
| 4190 | B | 307199 |
| 4191 | B | 309120 |
| 4192 | B | 309018 |
| 4193 | B | 310903 |
| 4194 | B | 310128 |
| 4195 | B | 312001 |
| 4196 | B | 310966 |
| 4197 | B | 312899 |
| 4198 | B | 311790 |
| 4199 | B | 313705 |
| 4200 | B | 312671 |
| 4201 | B | 314590 |
| 4202 | B | 314590 |
| 4203 | B | 316484 |
| 4204 | B | 314977 |
| 4205 | B | 316880 |
| 4206 | B | 315775 |
| 4207 | B | 317646 |
| 4208 | B | 316760 |
| 4209 | B | 318627 |
| 4210 | B | 317541 |
| 4211 | B | 319422 |
| 4212 | B | 317829 |
| 4213 | B | 319763 |
| 4214 | B | 318703 |
| 4215 | B | 320628 |
| 4216 | B | 318094 |
| 4217 | B | 320048 |
| 4218 | B | 319182 |
| 4219 | B | 321067 |
| 4220 | B | 320404 |
| 4221 | B | 322278 |
| 4222 | B | 321720 |
| 4223 | B | 323625 |
| 4224 | B | 322158 |
| 4225 | B | 324071 |
| 4226 | B | 322582 |
| 4227 | B | 324500 |
| 4228 | B | 323371 |
| 4229 | B | 325260 |
| 4230 | B | 325173 |
| 4231 | B | 327057 |
| 4232 | B | 325882 |
| 4233 | B | 327770 |
| 4234 | B | 326509 |
| 4235 | B | 328388 |
| 4236 | B | 327463 |
| 4237 | B | 329330 |
| 4238 | B | 328374 |
| 4239 | B | 330270 |
| 4240 | B | 328850 |
| 4241 | B | 330751 |
| 4242 | B | 329330 |
| 4243 | B | 331210 |
| 4244 | B | 329883 |
| 4245 | B | 331822 |
| 4246 | B | 330886 |
| 4247 | B | 332797 |
| 4248 | B | 331395 |
| 4249 | B | 333375 |
| 4250 | B | 331990 |
| 4251 | B | 333884 |
| 4252 | B | 332669 |
| 4253 | B | 334575 |
| 4254 | B | 333375 |
| 4255 | B | 335166 |
| 4256 | B | 333811 |
| 4257 | B | 335709 |
| 4258 | B | 334579 |
| 4259 | B | 336497 |
| 4260 | B | 334590 |
| 4261 | B | 336497 |
| 4262 | B | 335362 |
| 4263 | B | 337262 |
| 4264 | B | 335863 |
| 4265 | B | 337723 |
| 4266 | B | 335939 |
| 4267 | B | 337848 |
| 4268 | B | 336558 |
| 4269 | B | 338461 |
| 4270 | B | 337647 |
| 4271 | B | 339503 |
| 4272 | B | 340181 |

TABLE 5-continued

| SEQ ID | Or. | position |
|---|---|---|
| 4273 | B | 342110 |
| 4274 | B | 342069 |
| 4275 | B | 343977 |
| 4276 | B | 342269 |
| 4277 | B | 344168 |
| 4278 | B | 342694 |
| 4279 | B | 344593 |
| 4280 | B | 343594 |
| 4281 | B | 345503 |
| 4282 | B | 344269 |
| 4283 | B | 346199 |
| 4284 | B | 344452 |
| 4285 | B | 346382 |
| 4286 | B | 345362 |
| 4287 | B | 347262 |
| 4288 | B | 346199 |
| 4289 | B | 348069 |
| 4290 | B | 347326 |
| 4291 | B | 349228 |
| 4292 | B | 348165 |
| 4293 | B | 350060 |
| 4294 | B | 350399 |
| 4295 | B | 352288 |
| 4296 | B | 351503 |
| 4297 | B | 353403 |
| 4298 | B | 352460 |
| 4299 | B | 354356 |
| 4300 | B | 352948 |
| 4301 | B | 354901 |
| 4302 | B | 353959 |
| 4303 | B | 355890 |
| 4304 | B | 354438 |
| 4305 | B | 356378 |
| 4306 | B | 354997 |
| 4307 | B | 356866 |
| 4308 | B | 356897 |
| 4309 | B | 358793 |
| 4310 | B | 357643 |
| 4311 | B | 359499 |
| 4312 | B | 358323 |
| 4313 | B | 360222 |
| 4314 | B | 360972 |
| 4315 | B | 362863 |
| 4316 | B | 361348 |
| 4317 | B | 363263 |
| 4318 | B | 362109 |
| 4319 | B | 364008 |
| 4320 | B | 362983 |
| 4321 | B | 364867 |
| 4322 | B | 364110 |
| 4323 | B | 366002 |
| 4324 | B | 365415 |
| 4325 | B | 367338 |
| 4326 | B | 365807 |
| 4327 | B | 367733 |
| 4328 | B | 367607 |
| 4329 | B | 369440 |
| 4330 | B | 368881 |
| 4331 | B | 370788 |
| 4332 | B | 369317 |
| 4333 | B | 371209 |
| 4334 | B | 370522 |
| 4335 | B | 372440 |
| 4336 | B | 371311 |
| 4337 | B | 373206 |
| 4338 | B | 373097 |
| 4339 | B | 374941 |
| 4340 | B | 373753 |
| 4341 | B | 375649 |
| 4342 | B | 374424 |
| 4343 | B | 376324 |
| 4344 | B | 374956 |
| 4345 | B | 376888 |
| 4346 | B | 376611 |
| 4347 | B | 378511 |
| 4348 | B | 377297 |
| 4349 | B | 379209 |
| 4350 | B | 378960 |
| 4351 | B | 380880 |
| 4352 | B | 379309 |
| 4353 | B | 381180 |
| 4354 | B | 379667 |
| 4355 | B | 381553 |
| 4356 | B | 380238 |
| 4357 | B | 382152 |
| 4358 | B | 381699 |
| 4359 | B | 383615 |
| 4360 | B | 382790 |
| 4361 | B | 384687 |
| 4362 | B | 383935 |
| 4363 | B | 385837 |
| 4364 | B | 384167 |
| 4365 | B | 386065 |
| 4366 | B | 385479 |
| 4367 | B | 387365 |
| 4368 | B | 385730 |
| 4369 | B | 387635 |
| 4370 | B | 387115 |
| 4371 | B | 389019 |
| 4372 | B | 386903 |
| 4373 | B | 388753 |
| 4374 | B | 387595 |
| 4375 | B | 389504 |
| 4376 | B | 388133 |
| 4377 | B | 390055 |
| 4378 | B | 388524 |
| 4379 | B | 390455 |
| 4380 | B | 389428 |
| 4381 | B | 391321 |
| 4382 | B | 390313 |
| 4383 | B | 392241 |
| 4384 | B | 391321 |
| 4385 | B | 393147 |
| 4386 | B | 392032 |
| 4387 | B | 393943 |
| 4388 | B | 394245 |
| 4389 | B | 396116 |
| 4390 | B | 395604 |
| 4391 | B | 397475 |
| 4392 | B | 396249 |
| 4393 | B | 398133 |
| 4394 | B | 396759 |
| 4395 | B | 398660 |
| 4396 | B | 397746 |
| 4397 | B | 399639 |
| 4398 | B | 398973 |
| 4399 | B | 400878 |
| 4400 | B | 399921 |
| 4401 | B | 401846 |
| 4402 | B | 400393 |
| 4403 | B | 402287 |
| 4404 | B | 401444 |
| 4405 | B | 403344 |
| 4406 | B | 402258 |
| 4407 | B | 404150 |
| 4408 | B | 403461 |
| 4409 | B | 405340 |
| 4410 | B | 405400 |
| 4411 | B | 407325 |
| 4412 | B | 404027 |
| 4413 | B | 405941 |
| 4414 | B | 406141 |
| 4415 | B | 408055 |
| 4416 | B | 407325 |
| 4417 | B | 409172 |
| 4418 | B | 409999 |
| 4419 | B | 411893 |
| 4420 | B | 411645 |
| 4421 | B | 413542 |
| 4422 | B | 413693 |
| 4423 | B | 415530 |
| 4424 | B | 413693 |
| 4425 | B | 415559 |
| 4426 | B | 414172 |
| 4427 | B | 416072 |
| 4428 | B | 415337 |

TABLE 5-continued

| SEQ ID | Or. | position |
|---|---|---|
| 4429 | B | 417275 |
| 4430 | B | 414599 |
| 4431 | B | 416499 |
| 4432 | B | 416887 |
| 4433 | B | 418821 |
| 4434 | B | 417700 |
| 4435 | B | 419585 |
| 4436 | B | 418274 |
| 4437 | B | 420173 |
| 4438 | B | 418823 |
| 4439 | B | 420732 |
| 4440 | B | 419778 |
| 4441 | B | 421678 |
| 4442 | B | 420461 |
| 4443 | B | 422361 |
| 4444 | B | 421460 |
| 4445 | B | 423336 |
| 4446 | B | 422265 |
| 4447 | B | 424120 |
| 4448 | B | 423263 |
| 4449 | B | 425182 |
| 4450 | B | 425302 |
| 4451 | B | 427252 |
| 4452 | B | 426283 |
| 4453 | B | 428210 |
| 4454 | B | 427252 |
| 4455 | B | 429129 |
| 4456 | B | 428040 |
| 4457 | B | 429940 |
| 4458 | B | 430106 |
| 4459 | B | 432063 |
| 4460 | B | 430580 |
| 4461 | B | 432480 |
| 4462 | B | 430860 |
| 4463 | B | 432776 |
| 4464 | B | 432063 |
| 4465 | B | 433919 |
| 4466 | B | 432263 |
| 4467 | B | 434137 |
| 4468 | B | 434730 |
| 4469 | B | 436671 |
| 4470 | B | 436671 |
| 4471 | B | 438495 |
| 4472 | B | 436803 |
| 4473 | B | 438696 |
| 4474 | B | 437953 |
| 4475 | B | 439850 |
| 4476 | B | 438490 |
| 4477 | B | 440383 |
| 4478 | B | 439374 |
| 4479 | B | 441289 |
| 4480 | B | 439562 |
| 4481 | B | 441466 |
| 4482 | B | 439976 |
| 4483 | B | 441847 |
| 4484 | B | 441301 |
| 4485 | B | 443216 |
| 4486 | B | 442161 |
| 4487 | B | 444066 |
| 4488 | B | 442834 |
| 4489 | B | 444713 |
| 4490 | B | 446608 |
| 4491 | B | 448508 |
| 4492 | B | 448288 |
| 4493 | B | 450225 |
| 4494 | B | 449798 |
| 4495 | B | 451705 |
| 4496 | B | 451345 |
| 4497 | B | 453199 |
| 4498 | B | 451891 |
| 4499 | B | 453768 |
| 4500 | B | 452813 |
| 4501 | B | 454720 |
| 4502 | B | 453439 |
| 4503 | B | 455315 |
| 4504 | B | 455088 |
| 4505 | B | 456988 |
| 4506 | B | 455682 |
| 4507 | B | 457551 |
| 4508 | B | 456302 |
| 4509 | B | 458221 |
| 4510 | B | 457645 |
| 4511 | B | 459519 |
| 4512 | B | 458699 |
| 4513 | B | 460570 |
| 4514 | B | 459867 |
| 4515 | B | 461758 |
| 4516 | B | 461464 |
| 4517 | B | 463337 |
| 4518 | B | 461887 |
| 4519 | B | 463795 |
| 4520 | B | 462842 |
| 4521 | B | 464780 |
| 4522 | B | 464031 |
| 4523 | B | 465946 |
| 4524 | B | 464849 |
| 4525 | B | 466801 |
| 4526 | B | 466078 |
| 4527 | B | 467968 |
| 4528 | B | 467670 |
| 4529 | B | 469540 |
| 4530 | B | 469208 |
| 4531 | B | 471075 |
| 4532 | B | 469520 |
| 4533 | B | 471400 |
| 4534 | B | 469895 |
| 4535 | B | 471798 |
| 4536 | B | 471533 |
| 4537 | B | 473363 |
| 4538 | B | 471867 |
| 4539 | B | 473744 |
| 4540 | B | 473542 |
| 4541 | B | 475387 |
| 4542 | B | 473919 |
| 4543 | B | 475824 |
| 4544 | B | 474747 |
| 4545 | B | 476666 |
| 4546 | B | 475493 |
| 4547 | B | 477373 |
| 4548 | B | 476747 |
| 4549 | B | 478682 |
| 4550 | B | 478861 |
| 4551 | B | 480821 |
| 4552 | B | 479311 |
| 4553 | B | 481243 |
| 4554 | B | 479943 |
| 4555 | B | 481858 |
| 4556 | B | 480257 |
| 4557 | B | 482146 |
| 4558 | B | 481708 |
| 4559 | B | 483633 |
| 4560 | B | 481969 |
| 4561 | B | 483871 |
| 4562 | B | 483668 |
| 4563 | B | 485559 |
| 4564 | B | 485198 |
| 4565 | B | 487094 |
| 4566 | B | 488084 |
| 4567 | B | 489985 |
| 4568 | B | 485945 |
| 4569 | B | 487859 |
| 4570 | B | 489498 |
| 4571 | B | 491367 |
| 4572 | B | 488799 |
| 4573 | B | 490691 |
| 4574 | B | 490677 |
| 4575 | B | 492589 |
| 4576 | B | 492994 |
| 4577 | B | 494929 |
| 4578 | B | 493113 |
| 4579 | B | 495035 |
| 4580 | B | 493985 |
| 4581 | B | 495864 |
| 4582 | B | 494929 |
| 4583 | B | 496801 |
| 4584 | B | 495090 |

TABLE 5-continued

| SEQ ID | Or. | position |
|---|---|---|
| 4585 | B | 496989 |
| 4586 | B | 495585 |
| 4587 | B | 497485 |
| 4588 | B | 495436 |
| 4589 | B | 497304 |
| 4590 | B | 496854 |
| 4591 | B | 498754 |
| 4592 | B | 497396 |
| 4593 | B | 499316 |
| 4594 | B | 498735 |
| 4595 | B | 500635 |
| 4596 | B | 499484 |
| 4597 | B | 501409 |
| 4598 | B | 501005 |
| 4599 | B | 502852 |
| 4600 | B | 501937 |
| 4601 | B | 503853 |
| 4602 | B | 503083 |
| 4603 | B | 505003 |
| 4604 | B | 503895 |
| 4605 | B | 505846 |
| 4606 | B | 505263 |
| 4607 | B | 507137 |
| 4608 | B | 507214 |
| 4609 | B | 509106 |
| 4610 | B | 507687 |
| 4611 | B | 509559 |
| 4612 | B | 508632 |
| 4613 | B | 510534 |
| 4614 | B | 508863 |
| 4615 | B | 510730 |
| 4616 | B | 509202 |
| 4617 | B | 511062 |
| 4618 | B | 510940 |
| 4619 | B | 512832 |
| 4620 | B | 511747 |
| 4621 | B | 513649 |
| 4622 | B | 512446 |
| 4623 | B | 514305 |
| 4624 | B | 513313 |
| 4625 | B | 515212 |
| 4626 | B | 514529 |
| 4627 | B | 516410 |
| 4628 | B | 515466 |
| 4629 | B | 517364 |
| 4630 | B | 515496 |
| 4631 | B | 517389 |
| 4632 | B | 516069 |
| 4633 | B | 517978 |
| 4634 | B | 516642 |
| 4635 | B | 518551 |
| 4636 | B | 517420 |
| 4637 | B | 519349 |
| 4638 | B | 518187 |
| 4639 | B | 520053 |
| 4640 | B | 518617 |
| 4641 | B | 520500 |
| 4642 | B | 519078 |
| 4643 | B | 520963 |
| 4644 | B | 519736 |
| 4645 | B | 521636 |
| 4646 | B | 520719 |
| 4647 | B | 522655 |
| 4648 | B | 522221 |
| 4649 | B | 524115 |
| 4650 | B | 522354 |
| 4651 | B | 524287 |
| 4652 | B | 523763 |
| 4653 | B | 525689 |
| 4654 | B | 524854 |
| 4655 | B | 526756 |
| 4656 | B | 525970 |
| 4657 | B | 527866 |
| 4658 | B | 526312 |
| 4659 | B | 528202 |
| 4660 | B | 526640 |
| 4661 | B | 528553 |
| 4662 | B | 526991 |
| 4663 | B | 528855 |
| 4664 | B | 528553 |
| 4665 | B | 530443 |
| 4666 | B | 529081 |
| 4667 | B | 530988 |
| 4668 | B | 529943 |
| 4669 | B | 531844 |
| 4670 | B | 530424 |
| 4671 | B | 532301 |
| 4672 | B | 530799 |
| 4673 | B | 532675 |
| 4674 | B | 531670 |
| 4675 | B | 533594 |
| 4676 | B | 533498 |
| 4677 | B | 535393 |
| 4678 | B | 534147 |
| 4679 | B | 535997 |
| 4680 | B | 534892 |
| 4681 | B | 536813 |
| 4682 | B | 536191 |
| 4683 | B | 538068 |
| 4684 | B | 539438 |
| 4685 | B | 541306 |
| 4686 | B | 540771 |
| 4687 | B | 542639 |
| 4688 | B | 541223 |
| 4689 | B | 543141 |
| 4690 | B | 542025 |
| 4691 | B | 543927 |
| 4692 | B | 543495 |
| 4693 | B | 545375 |
| 4694 | B | 544367 |
| 4695 | B | 546253 |
| 4696 | B | 544790 |
| 4697 | B | 546697 |
| 4698 | B | 544982 |
| 4699 | B | 546890 |
| 4700 | B | 546655 |
| 4701 | B | 548555 |
| 4702 | B | 547701 |
| 4703 | B | 549667 |
| 4704 | B | 547609 |
| 4705 | B | 549533 |
| 4706 | B | 548121 |
| 4707 | B | 550040 |
| 4708 | B | 548878 |
| 4709 | B | 550836 |
| 4710 | B | 549681 |
| 4711 | B | 551602 |
| 4712 | B | 550605 |
| 4713 | B | 552527 |
| 4714 | B | 551849 |
| 4715 | B | 553750 |
| 4716 | B | 553261 |
| 4717 | B | 555165 |
| 4718 | B | 555176 |
| 4719 | B | 557075 |
| 4720 | B | 556590 |
| 4721 | B | 558489 |
| 4722 | B | 557130 |
| 4723 | B | 559024 |
| 4724 | B | 558346 |
| 4725 | B | 560246 |
| 4726 | B | 558455 |
| 4727 | B | 560376 |
| 4728 | B | 559450 |
| 4729 | B | 561362 |
| 4730 | B | 561581 |
| 4731 | B | 563478 |
| 4732 | B | 563153 |
| 4733 | B | 565073 |
| 4734 | B | 564319 |
| 4735 | B | 566220 |
| 4736 | B | 564201 |
| 4737 | B | 566078 |
| 4738 | B | 567243 |
| 4739 | B | 569143 |
| 4740 | B | 568192 |

TABLE 5-continued

| SEQ ID | Or. | position |
|---|---|---|
| 4741 | B | 570133 |
| 4742 | B | 570619 |
| 4743 | B | 572532 |
| 4744 | B | 572241 |
| 4745 | B | 574208 |
| 4746 | B | 572994 |
| 4747 | B | 574916 |
| 4748 | B | 573744 |
| 4749 | B | 575640 |
| 4750 | B | 573679 |
| 4751 | B | 575571 |
| 4752 | B | 574398 |
| 4753 | B | 576288 |
| 4754 | B | 574677 |
| 4755 | B | 576633 |
| 4756 | B | 575033 |
| 4757 | B | 576922 |
| 4758 | B | 575482 |
| 4759 | B | 577363 |
| 4760 | B | 575699 |
| 4761 | B | 577606 |
| 4762 | B | 576078 |
| 4763 | B | 577993 |
| 4764 | B | 578265 |
| 4765 | B | 580143 |
| 4766 | B | 578948 |
| 4767 | B | 580848 |
| 4768 | B | 582336 |
| 4769 | B | 584225 |
| 4770 | B | 582917 |
| 4771 | B | 584817 |
| 4772 | B | 583359 |
| 4773 | B | 585252 |
| 4774 | B | 583734 |
| 4775 | B | 585634 |
| 4776 | B | 584122 |
| 4777 | B | 585990 |
| 4778 | B | 584665 |
| 4779 | B | 586598 |
| 4780 | B | 585213 |
| 4781 | B | 587123 |
| 4782 | B | 585517 |
| 4783 | B | 587434 |
| 4784 | B | 586850 |
| 4785 | B | 588730 |
| 4786 | B | 588017 |
| 4787 | B | 589878 |
| 4788 | B | 589628 |
| 4789 | B | 591543 |
| 4790 | B | 589798 |
| 4791 | B | 591723 |
| 4792 | B | 590323 |
| 4793 | B | 592211 |
| 4794 | B | 591492 |
| 4795 | B | 593419 |
| 4796 | B | 593002 |
| 4797 | B | 594885 |
| 4798 | B | 593367 |
| 4799 | B | 595321 |
| 4800 | B | 594166 |
| 4801 | B | 596020 |
| 4802 | B | 595942 |
| 4803 | B | 597826 |
| 4804 | B | 596354 |
| 4805 | B | 598255 |
| 4806 | B | 597147 |
| 4807 | B | 598998 |
| 4808 | B | 597960 |
| 4809 | B | 599851 |
| 4810 | B | 601068 |
| 4811 | B | 602929 |
| 4812 | B | 602096 |
| 4813 | B | 603996 |
| 4814 | B | 603761 |
| 4815 | B | 605643 |
| 4816 | B | 604014 |
| 4817 | B | 605920 |
| 4818 | B | 604634 |
| 4819 | B | 606548 |
| 4820 | B | 605864 |
| 4821 | B | 607736 |
| 4822 | B | 606903 |
| 4823 | B | 608742 |
| 4824 | B | 607722 |
| 4825 | B | 609674 |
| 4826 | B | 609329 |
| 4827 | B | 611215 |
| 4828 | B | 609916 |
| 4829 | B | 611866 |
| 4830 | B | 612090 |
| 4831 | B | 613998 |
| 4832 | B | 613166 |
| 4833 | B | 615091 |
| 4834 | B | 613838 |
| 4835 | B | 615761 |
| 4836 | B | 614217 |
| 4837 | B | 616094 |
| 4838 | B | 615464 |
| 4839 | B | 617391 |
| 4840 | B | 615913 |
| 4841 | B | 617803 |
| 4842 | B | 617932 |
| 4843 | B | 619837 |
| 4844 | B | 618598 |
| 4845 | B | 620532 |
| 4846 | B | 619591 |
| 4847 | B | 621465 |
| 4848 | B | 620636 |
| 4849 | B | 622536 |
| 4850 | B | 620532 |
| 4851 | B | 622381 |
| 4852 | B | 621404 |
| 4853 | B | 623307 |
| 4854 | B | 621932 |
| 4855 | B | 623834 |
| 4856 | B | 622666 |
| 4857 | B | 624588 |
| 4858 | B | 623689 |
| 4859 | B | 625605 |
| 4860 | B | 624435 |
| 4861 | B | 626298 |
| 4862 | B | 625204 |
| 4863 | B | 627128 |
| 4864 | B | 626885 |
| 4865 | B | 628790 |
| 4866 | B | 627128 |
| 4867 | B | 629026 |
| 4868 | B | 628073 |
| 4869 | B | 629983 |
| 4870 | B | 628359 |
| 4871 | B | 630267 |
| 4872 | B | 628976 |
| 4873 | B | 630850 |
| 4874 | B | 630023 |
| 4875 | B | 631988 |
| 4876 | B | 630642 |
| 4877 | B | 632526 |
| 4878 | B | 631205 |
| 4879 | B | 633081 |
| 4880 | B | 632046 |
| 4881 | B | 633969 |
| 4882 | B | 638311 |
| 4883 | B | 640204 |
| 4884 | B | 640448 |
| 4885 | B | 642328 |
| 4886 | B | 643695 |
| 4887 | B | 645639 |
| 4888 | B | 640847 |
| 4889 | B | 642769 |
| 4890 | B | 644745 |
| 4891 | B | 646615 |
| 4892 | B | 645686 |
| 4893 | B | 647558 |
| 4894 | B | 646060 |
| 4895 | B | 647972 |
| 4896 | B | 647331 |

TABLE 5-continued

| SEQ ID | Or. | position |
|---|---|---|
| 4897 | B | 649231 |
| 4898 | B | 649987 |
| 4899 | B | 651829 |
| 4900 | B | 650580 |
| 4901 | B | 652484 |
| 4902 | B | 651942 |
| 4903 | B | 653852 |
| 4904 | B | 652395 |
| 4905 | B | 654310 |
| 4906 | B | 653132 |
| 4907 | B | 655028 |
| 4908 | B | 653827 |
| 4909 | B | 655713 |
| 4910 | B | 662071 |
| 4911 | B | 664023 |
| 4912 | B | 662543 |
| 4913 | B | 664403 |
| 4914 | B | 663295 |
| 4915 | B | 665205 |
| 4916 | B | 663972 |
| 4917 | B | 665850 |
| 4918 | B | 664432 |
| 4919 | B | 666332 |
| 4920 | B | 665860 |
| 4921 | B | 667789 |
| 4922 | B | 666312 |
| 4923 | B | 668233 |
| 4924 | B | 666652 |
| 4925 | B | 668550 |
| 4926 | B | 668338 |
| 4927 | B | 670238 |
| 4928 | B | 668605 |
| 4929 | B | 670495 |
| 4930 | B | 668690 |
| 4931 | B | 670590 |
| 4932 | B | 669766 |
| 4933 | B | 671653 |
| 4934 | B | 670160 |
| 4935 | B | 672109 |
| 4936 | B | 671000 |
| 4937 | B | 672900 |
| 4938 | B | 671470 |
| 4939 | B | 673412 |
| 4940 | B | 672685 |
| 4941 | B | 674567 |
| 4942 | B | 673461 |
| 4943 | B | 675365 |
| 4944 | B | 674786 |
| 4945 | B | 676682 |
| 4946 | B | 675456 |
| 4947 | B | 677375 |
| 4948 | B | 676683 |
| 4949 | B | 678594 |
| 4950 | B | 677334 |
| 4951 | B | 679183 |
| 4952 | B | 678726 |
| 4953 | B | 680596 |
| 4954 | B | 679729 |
| 4955 | B | 681628 |
| 4956 | B | 680747 |
| 4957 | B | 682668 |
| 4958 | B | 681500 |
| 4959 | B | 683406 |
| 4960 | B | 682779 |
| 4961 | B | 684716 |
| 4962 | B | 683320 |
| 4963 | B | 685249 |
| 4964 | B | 684716 |
| 4965 | B | 686585 |
| 4966 | B | 685010 |
| 4967 | B | 686897 |
| 4968 | B | 686423 |
| 4969 | B | 688323 |
| 4970 | B | 687426 |
| 4971 | B | 689324 |
| 4972 | B | 688619 |
| 4973 | B | 690482 |
| 4974 | B | 688653 |
| 4975 | B | 690563 |
| 4976 | B | 689836 |
| 4977 | B | 691775 |
| 4978 | B | 690186 |
| 4979 | B | 692088 |
| 4980 | B | 690715 |
| 4981 | B | 692616 |
| 4982 | B | 690937 |
| 4983 | B | 692837 |
| 4984 | B | 692091 |
| 4985 | B | 693991 |
| 4986 | B | 694171 |
| 4987 | B | 696078 |
| 4988 | B | 695197 |
| 4989 | B | 697093 |
| 4990 | B | 697486 |
| 4991 | B | 699428 |
| 4992 | B | 698313 |
| 4993 | B | 700238 |
| 4994 | B | 698646 |
| 4995 | B | 700515 |
| 4996 | B | 700337 |
| 4997 | B | 702249 |
| 4998 | B | 701115 |
| 4999 | B | 703015 |
| 5000 | B | 702385 |
| 5001 | B | 704285 |
| 5002 | B | 703636 |
| 5003 | B | 705561 |
| 5004 | B | 705271 |
| 5005 | B | 707136 |
| 5006 | B | 705875 |
| 5007 | B | 707725 |
| 5008 | B | 706444 |
| 5009 | B | 708279 |
| 5010 | B | 706741 |
| 5011 | B | 708673 |
| 5012 | B | 708324 |
| 5013 | B | 710226 |
| 5014 | B | 708673 |
| 5015 | B | 710518 |
| 5016 | B | 708876 |
| 5017 | B | 710791 |
| 5018 | B | 710498 |
| 5019 | B | 712447 |
| 5020 | B | 711435 |
| 5021 | B | 713354 |
| 5022 | B | 712993 |
| 5023 | B | 714887 |
| 5024 | B | 713686 |
| 5025 | B | 715574 |
| 5026 | B | 714474 |
| 5027 | B | 716354 |
| 5028 | B | 714867 |
| 5029 | B | 716760 |
| 5030 | B | 716047 |
| 5031 | B | 717877 |
| 5032 | B | 716086 |
| 5033 | B | 717976 |
| 5034 | B | 717189 |
| 5035 | B | 719068 |
| 5036 | B | 718624 |
| 5037 | B | 720503 |
| 5038 | B | 719083 |
| 5039 | B | 720983 |
| 5040 | B | 720047 |
| 5041 | B | 722004 |
| 5042 | B | 720503 |
| 5043 | B | 722393 |
| 5044 | B | 720753 |
| 5045 | B | 722653 |
| 5046 | B | 721798 |
| 5047 | B | 723724 |
| 5048 | B | 722631 |
| 5049 | B | 724493 |
| 5050 | B | 723468 |
| 5051 | B | 725376 |
| 5052 | B | 724852 |

TABLE 5-continued

| SEQ ID | Or. | position |
|---|---|---|
| 5053 | B | 726743 |
| 5054 | B | 726005 |
| 5055 | B | 727903 |
| 5056 | B | 726779 |
| 5057 | B | 728691 |
| 5058 | B | 727058 |
| 5059 | B | 728947 |
| 5060 | B | 727727 |
| 5061 | B | 729613 |
| 5062 | B | 728224 |
| 5063 | B | 730116 |
| 5064 | B | 729048 |
| 5065 | B | 730907 |
| 5066 | B | 729566 |
| 5067 | B | 731468 |
| 5068 | B | 732909 |
| 5069 | B | 734770 |
| 5070 | B | 734663 |
| 5071 | B | 736569 |
| 5072 | B | 735879 |
| 5073 | B | 737785 |
| 5074 | B | 736724 |
| 5075 | B | 738632 |
| 5076 | B | 737474 |
| 5077 | B | 739421 |
| 5078 | B | 738007 |
| 5079 | B | 739907 |
| 5080 | B | 738911 |
| 5081 | B | 740799 |
| 5082 | B | 739960 |
| 5083 | B | 741908 |
| 5084 | B | 742277 |
| 5085 | B | 744187 |
| 5086 | B | 743089 |
| 5087 | B | 744989 |
| 5088 | B | 743603 |
| 5089 | B | 745539 |
| 5090 | B | 744565 |
| 5091 | B | 746432 |
| 5092 | B | 744977 |
| 5093 | B | 746867 |
| 5094 | B | 745249 |
| 5095 | B | 747138 |
| 5096 | B | 745777 |
| 5097 | B | 747677 |
| 5098 | B | 746632 |
| 5099 | B | 748532 |
| 5100 | B | 747054 |
| 5101 | B | 748893 |
| 5102 | B | 748519 |
| 5103 | B | 750396 |
| 5104 | B | 749186 |
| 5105 | B | 751108 |
| 5106 | B | 749646 |
| 5107 | B | 751546 |
| 5108 | B | 749922 |
| 5109 | B | 751824 |
| 5110 | B | 750260 |
| 5111 | B | 752151 |
| 5112 | B | 752527 |
| 5113 | B | 754427 |
| 5114 | B | 753169 |
| 5115 | B | 755064 |
| 5116 | B | 755004 |
| 5117 | B | 756843 |
| 5118 | B | 757034 |
| 5119 | B | 758991 |
| 5120 | B | 758532 |
| 5121 | B | 760452 |
| 5122 | B | 758911 |
| 5123 | B | 760841 |
| 5124 | B | 760015 |
| 5125 | B | 761913 |
| 5126 | B | 760463 |
| 5127 | B | 762363 |
| 5128 | B | 760782 |
| 5129 | B | 762671 |
| 5130 | B | 762053 |

TABLE 5-continued

| SEQ ID | Or. | position |
|---|---|---|
| 5131 | B | 763911 |
| 5132 | B | 762363 |
| 5133 | B | 764264 |
| 5134 | B | 763203 |
| 5135 | B | 765107 |
| 5136 | B | 764690 |
| 5137 | B | 766595 |
| 5138 | B | 765107 |
| 5139 | B | 766977 |
| 5140 | B | 766327 |
| 5141 | B | 768221 |
| 5142 | B | 766932 |
| 5143 | B | 768851 |
| 5144 | B | 768314 |
| 5145 | B | 770221 |
| 5146 | B | 769045 |
| 5147 | B | 770945 |
| 5148 | B | 770315 |
| 5149 | B | 772234 |
| 5150 | B | 770705 |
| 5151 | B | 772598 |
| 5152 | B | 770882 |
| 5153 | B | 772781 |
| 5154 | B | 771156 |
| 5155 | B | 773044 |
| 5156 | B | 772234 |
| 5157 | B | 774148 |
| 5158 | B | 773611 |
| 5159 | B | 775511 |
| 5160 | B | 774513 |
| 5161 | B | 776404 |
| 5162 | B | 776333 |
| 5163 | B | 778191 |
| 5164 | B | 777926 |
| 5165 | B | 779832 |
| 5166 | B | 777455 |
| 5167 | B | 779380 |
| 5168 | B | 779476 |
| 5169 | B | 781342 |
| 5170 | B | 781774 |
| 5171 | B | 783686 |
| 5172 | B | 782667 |
| 5173 | B | 784562 |
| 5174 | B | 785748 |
| 5175 | B | 787658 |
| 5176 | B | 786222 |
| 5177 | B | 788126 |
| 5178 | B | 786803 |
| 5179 | B | 788703 |
| 5180 | B | 787998 |
| 5181 | B | 789876 |
| 5182 | B | 788279 |
| 5183 | B | 790255 |
| 5184 | B | 790369 |
| 5185 | B | 792247 |
| 5186 | B | 790862 |
| 5187 | B | 792787 |
| 5188 | B | 792247 |
| 5189 | B | 794137 |
| 5190 | B | 793352 |
| 5191 | B | 795215 |
| 5192 | B | 794276 |
| 5193 | B | 796196 |
| 5194 | B | 795215 |
| 5195 | B | 797077 |
| 5196 | B | 795667 |
| 5197 | B | 797571 |
| 5198 | B | 796515 |
| 5199 | B | 798382 |
| 5200 | B | 797235 |
| 5201 | B | 799168 |
| 5202 | B | 797585 |
| 5203 | B | 799553 |
| 5204 | B | 798102 |
| 5205 | B | 799976 |
| 5206 | B | 798306 |
| 5207 | B | 800214 |
| 5208 | B | 798662 |

TABLE 5-continued

| SEQ ID | Or. | position |
|---|---|---|
| 5209 | B | 800546 |
| 5210 | B | 799168 |
| 5211 | B | 801074 |
| 5212 | B | 800159 |
| 5213 | B | 802054 |
| 5214 | B | 801153 |
| 5215 | B | 803031 |
| 5216 | B | 802363 |
| 5217 | B | 804257 |
| 5218 | B | 802893 |
| 5219 | B | 804802 |
| 5220 | B | 803466 |
| 5221 | B | 805366 |
| 5222 | B | 804440 |
| 5223 | B | 806374 |
| 5224 | B | 805576 |
| 5225 | B | 807523 |
| 5226 | B | 806511 |
| 5227 | B | 808410 |
| 5228 | B | 808305 |
| 5229 | B | 810207 |
| 5230 | B | 809229 |
| 5231 | B | 811164 |
| 5232 | B | 810700 |
| 5233 | B | 812581 |
| 5234 | B | 811825 |
| 5235 | B | 813787 |
| 5236 | B | 812574 |
| 5237 | B | 814467 |
| 5238 | B | 813787 |
| 5239 | B | 815676 |
| 5240 | B | 814082 |
| 5241 | B | 815892 |
| 5242 | B | 814571 |
| 5243 | B | 816454 |
| 5244 | B | 815441 |
| 5245 | B | 817347 |
| 5246 | B | 815101 |
| 5247 | B | 817025 |
| 5248 | B | 815953 |
| 5249 | B | 817887 |
| 5250 | B | 817709 |
| 5251 | B | 819618 |
| 5252 | B | 819559 |
| 5253 | B | 821442 |
| 5254 | B | 819933 |
| 5255 | B | 821846 |
| 5256 | B | 820622 |
| 5257 | B | 822548 |
| 5258 | B | 821281 |
| 5259 | B | 823181 |
| 5260 | B | 821778 |
| 5261 | B | 823666 |
| 5262 | B | 822494 |
| 5263 | B | 824387 |
| 5264 | B | 823155 |
| 5265 | B | 825057 |
| 5266 | B | 824589 |
| 5267 | B | 826509 |
| 5268 | B | 826122 |
| 5269 | B | 828041 |
| 5270 | B | 826572 |
| 5271 | B | 828500 |
| 5272 | B | 827246 |
| 5273 | B | 829208 |
| 5274 | B | 827489 |
| 5275 | B | 829407 |
| 5276 | B | 828274 |
| 5277 | B | 830176 |
| 5278 | B | 829495 |
| 5279 | B | 831395 |
| 5280 | B | 831192 |
| 5281 | B | 833082 |
| 5282 | B | 832005 |
| 5283 | B | 833870 |
| 5284 | B | 832373 |
| 5285 | B | 834280 |
| 5286 | B | 832964 |
| 5287 | B | 834864 |
| 5288 | B | 833672 |
| 5289 | B | 835604 |
| 5290 | B | 834022 |
| 5291 | B | 835945 |
| 5292 | B | 834907 |
| 5293 | B | 836803 |
| 5294 | B | 835683 |
| 5295 | B | 837593 |
| 5296 | B | 836018 |
| 5297 | B | 837902 |
| 5298 | B | 836714 |
| 5299 | B | 838602 |
| 5300 | B | 837484 |
| 5301 | B | 839424 |
| 5302 | B | 838950 |
| 5303 | B | 840832 |
| 5304 | B | 839800 |
| 5305 | B | 841700 |
| 5306 | B | 840808 |
| 5307 | B | 842715 |
| 5308 | B | 841975 |
| 5309 | B | 843834 |
| 5310 | B | 842679 |
| 5311 | B | 844614 |
| 5312 | B | 843342 |
| 5313 | B | 845247 |
| 5314 | B | 843736 |
| 5315 | B | 845626 |
| 5316 | B | 846423 |
| 5317 | B | 848330 |
| 5318 | B | 844423 |
| 5319 | B | 846258 |
| 5320 | B | 848265 |
| 5321 | B | 850174 |
| 5322 | B | 850343 |
| 5323 | B | 852246 |
| 5324 | B | 851875 |
| 5325 | B | 853765 |
| 5326 | B | 853944 |
| 5327 | B | 855822 |
| 5328 | B | 855056 |
| 5329 | B | 856964 |
| 5330 | B | 855750 |
| 5331 | B | 857714 |
| 5332 | B | 856488 |
| 5333 | B | 858370 |
| 5334 | B | 857403 |
| 5335 | B | 859303 |
| 5336 | B | 859659 |
| 5337 | B | 861570 |
| 5338 | B | 860166 |
| 5339 | B | 862082 |
| 5340 | B | 860879 |
| 5341 | B | 862767 |
| 5342 | B | 861861 |
| 5343 | B | 863727 |
| 5344 | B | 862284 |
| 5345 | B | 864173 |
| 5346 | B | 863792 |
| 5347 | B | 865660 |
| 5348 | B | 864164 |
| 5349 | B | 866050 |
| 5350 | B | 864925 |
| 5351 | B | 866860 |
| 5352 | B | 866468 |
| 5353 | B | 868368 |
| 5354 | B | 866860 |
| 5355 | B | 868734 |
| 5356 | B | 867952 |
| 5357 | B | 869878 |
| 5358 | B | 869311 |
| 5359 | B | 871226 |
| 5360 | B | 869582 |
| 5361 | B | 871517 |
| 5362 | B | 871614 |
| 5363 | B | 873536 |
| 5364 | B | 872804 |

TABLE 5-continued

| SEQ ID | Or. | position |
|---|---|---|
| 5365 | B | 874702 |
| 5366 | B | 873093 |
| 5367 | B | 874980 |
| 5368 | B | 874158 |
| 5369 | B | 876056 |
| 5370 | B | 874033 |
| 5371 | B | 875932 |
| 5372 | B | 874670 |
| 5373 | B | 876580 |
| 5374 | B | 875606 |
| 5375 | B | 877506 |
| 5376 | B | 876619 |
| 5377 | B | 878519 |
| 5378 | B | 878160 |
| 5379 | B | 880034 |
| 5380 | B | 878429 |
| 5381 | B | 880292 |
| 5382 | B | 879336 |
| 5383 | B | 881230 |
| 5384 | B | 879393 |
| 5385 | B | 881281 |
| 5386 | B | 880089 |
| 5387 | B | 881994 |
| 5388 | B | 881108 |
| 5389 | B | 883062 |
| 5390 | B | 882094 |
| 5391 | B | 884013 |
| 5392 | B | 883124 |
| 5393 | B | 885027 |
| 5394 | B | 884014 |
| 5395 | B | 885924 |
| 5396 | B | 884530 |
| 5397 | B | 886432 |
| 5398 | B | 885226 |
| 5399 | B | 887139 |
| 5400 | B | 889010 |
| 5401 | B | 890900 |
| 5402 | B | 890421 |
| 5403 | B | 892310 |
| 5404 | B | 891438 |
| 5405 | B | 893287 |
| 5406 | B | 891703 |
| 5407 | B | 893606 |
| 5408 | B | 893606 |
| 5409 | B | 895490 |
| 5410 | B | 894049 |
| 5411 | B | 896024 |
| 5412 | B | 894139 |
| 5413 | B | 896074 |
| 5414 | B | 894545 |
| 5415 | B | 896413 |
| 5416 | B | 894999 |
| 5417 | B | 896912 |
| 5418 | B | 896127 |
| 5419 | B | 898012 |
| 5420 | B | 897049 |
| 5421 | B | 898949 |
| 5422 | B | 901018 |
| 5423 | B | 902955 |
| 5424 | B | 902393 |
| 5425 | B | 904301 |
| 5426 | B | 904098 |
| 5427 | B | 906002 |
| 5428 | B | 903951 |
| 5429 | B | 905851 |
| 5430 | B | 905825 |
| 5431 | B | 907725 |
| 5432 | B | 906700 |
| 5433 | B | 908669 |
| 5434 | B | 907174 |
| 5435 | B | 909066 |
| 5436 | B | 907579 |
| 5437 | B | 909480 |
| 5438 | B | 908962 |
| 5439 | B | 910922 |
| 5440 | B | 909415 |
| 5441 | B | 911315 |
| 5442 | B | 909804 |
| 5443 | B | 911704 |
| 5444 | B | 910218 |
| 5445 | B | 912075 |
| 5446 | B | 910834 |
| 5447 | B | 912689 |
| 5448 | B | 911225 |
| 5449 | B | 913064 |
| 5450 | B | 912492 |
| 5451 | B | 914381 |
| 5452 | B | 912852 |
| 5453 | B | 914763 |
| 5454 | B | 913438 |
| 5455 | B | 915340 |
| 5456 | B | 913901 |
| 5457 | B | 915814 |
| 5458 | B | 914730 |
| 5459 | B | 916694 |
| 5460 | B | 915356 |
| 5461 | B | 917256 |
| 5462 | B | 915717 |
| 5463 | B | 917608 |
| 5464 | B | 916854 |
| 5465 | B | 918761 |
| 5466 | B | 916762 |
| 5467 | B | 918712 |
| 5468 | B | 917848 |
| 5469 | B | 919756 |
| 5470 | B | 918588 |
| 5471 | B | 920424 |
| 5472 | B | 918875 |
| 5473 | B | 920796 |
| 5474 | B | 919756 |
| 5475 | B | 921710 |
| 5476 | B | 920055 |
| 5477 | B | 921949 |
| 5478 | B | 920389 |
| 5479 | B | 922328 |
| 5480 | B | 921130 |
| 5481 | B | 922978 |
| 5482 | B | 921517 |
| 5483 | B | 923414 |
| 5484 | B | 921740 |
| 5485 | B | 923646 |
| 5486 | B | 921979 |
| 5487 | B | 923926 |
| 5488 | B | 922396 |
| 5489 | B | 924327 |
| 5490 | B | 922729 |
| 5491 | B | 924611 |
| 5492 | B | 923256 |
| 5493 | B | 925216 |
| 5494 | B | 923673 |
| 5495 | B | 925589 |
| 5496 | B | 924297 |
| 5497 | B | 926176 |
| 5498 | B | 924645 |
| 5499 | B | 926555 |
| 5500 | B | 925216 |
| 5501 | B | 927117 |
| 5502 | B | 925589 |
| 5503 | B | 927489 |
| 5504 | B | 926980 |
| 5505 | B | 928903 |
| 5506 | B | 927408 |
| 5507 | B | 929331 |
| 5508 | B | 927824 |
| 5509 | B | 929727 |
| 5510 | B | 928418 |
| 5511 | B | 930287 |
| 5512 | B | 928979 |
| 5513 | B | 930879 |
| 5514 | B | 930474 |
| 5515 | B | 932367 |
| 5516 | B | 930879 |
| 5517 | B | 932776 |
| 5518 | B | 931298 |
| 5519 | B | 933223 |
| 5520 | B | 931886 |

TABLE 5-continued

| SEQ ID | Or. | position |
|---|---|---|
| 5521 | B | 933812 |
| 5522 | B | 932187 |
| 5523 | B | 934117 |
| 5524 | B | 932803 |
| 5525 | B | 934733 |
| 5526 | B | 933421 |
| 5527 | B | 935352 |
| 5528 | B | 933841 |
| 5529 | B | 935758 |
| 5530 | B | 934062 |
| 5531 | B | 935933 |
| 5532 | B | 934794 |
| 5533 | B | 936682 |
| 5534 | B | 936606 |
| 5535 | B | 938521 |
| 5536 | B | 938373 |
| 5537 | B | 940324 |
| 5538 | B | 939321 |
| 5539 | B | 941229 |
| 5540 | B | 941153 |
| 5541 | B | 943053 |
| 5542 | B | 942291 |
| 5543 | B | 944212 |
| 5544 | B | 944964 |
| 5545 | B | 946809 |
| 5546 | B | 945527 |
| 5547 | B | 947426 |
| 5548 | B | 946546 |
| 5549 | B | 948430 |
| 5550 | B | 946896 |
| 5551 | B | 948823 |
| 5552 | B | 948677 |
| 5553 | B | 950581 |
| 5554 | B | 949505 |
| 5555 | B | 951398 |
| 5556 | B | 949834 |
| 5557 | B | 951743 |
| 5558 | B | 950897 |
| 5559 | B | 952796 |
| 5560 | B | 951550 |
| 5561 | B | 953534 |
| 5562 | B | 951870 |
| 5563 | B | 953763 |
| 5564 | B | 953037 |
| 5565 | B | 954930 |
| 5566 | B | 954509 |
| 5567 | B | 956384 |
| 5568 | B | 955397 |
| 5569 | B | 957278 |
| 5570 | B | 958191 |
| 5571 | B | 960060 |
| 5572 | B | 959570 |
| 5573 | B | 961432 |
| 5574 | B | 961273 |
| 5575 | B | 963183 |
| 5576 | B | 961837 |
| 5577 | B | 963749 |
| 5578 | B | 962823 |
| 5579 | B | 964695 |
| 5580 | B | 962199 |
| 5581 | B | 964099 |
| 5582 | B | 965286 |
| 5583 | B | 967118 |
| 5584 | B | 965928 |
| 5585 | B | 967828 |
| 5586 | B | 967261 |
| 5587 | B | 969179 |
| 5588 | B | 968345 |
| 5589 | B | 970181 |
| 5590 | B | 969123 |
| 5591 | B | 971023 |
| 5592 | B | 970973 |
| 5593 | B | 972849 |
| 5594 | B | 972081 |
| 5595 | B | 973933 |
| 5596 | B | 973279 |
| 5597 | B | 975173 |
| 5598 | B | 974803 |

TABLE 5-continued

| SEQ ID | Or. | position |
|---|---|---|
| 5599 | B | 976683 |
| 5600 | B | 975459 |
| 5601 | B | 977346 |
| 5602 | B | 976431 |
| 5603 | B | 978335 |
| 5604 | B | 976740 |
| 5605 | B | 978640 |
| 5606 | B | 977175 |
| 5607 | B | 979042 |
| 5608 | B | 977855 |
| 5609 | B | 979768 |
| 5610 | B | 978153 |
| 5611 | B | 980060 |
| 5612 | B | 978655 |
| 5613 | B | 980553 |
| 5614 | B | 979204 |
| 5615 | B | 981104 |
| 5616 | B | 979554 |
| 5617 | B | 981465 |
| 5618 | B | 981423 |
| 5619 | B | 983319 |
| 5620 | B | 980363 |
| 5621 | B | 982289 |
| 5622 | B | 982361 |
| 5623 | B | 984236 |
| 5624 | B | 983818 |
| 5625 | B | 985718 |
| 5626 | B | 984720 |
| 5627 | B | 986608 |
| 5628 | B | 985607 |
| 5629 | B | 987553 |
| 5630 | B | 986323 |
| 5631 | B | 988223 |
| 5632 | B | 986925 |
| 5633 | B | 988825 |
| 5634 | B | 987850 |
| 5635 | B | 989749 |
| 5636 | B | 988354 |
| 5637 | B | 990252 |
| 5638 | B | 988474 |
| 5639 | B | 990393 |
| 5640 | B | 989437 |
| 5641 | B | 991305 |
| 5642 | B | 993662 |
| 5643 | B | 995596 |
| 5644 | B | 994015 |
| 5645 | B | 995906 |
| 5646 | B | 994084 |
| 5647 | B | 995955 |
| 5648 | B | 994523 |
| 5649 | B | 996382 |
| 5650 | B | 995903 |
| 5651 | B | 997791 |
| 5652 | B | 996831 |
| 5653 | B | 998764 |
| 5654 | B | 998505 |
| 5655 | B | 1000417 |
| 5656 | B | 999445 |
| 5657 | B | 1001345 |
| 5658 | B | 1001253 |
| 5659 | B | 1003169 |
| 5660 | B | 1001751 |
| 5661 | B | 1003637 |
| 5662 | B | 1001954 |
| 5663 | B | 1003786 |
| 5664 | B | 1004003 |
| 5665 | B | 1005872 |
| 5666 | B | 1005114 |
| 5667 | B | 1006999 |
| 5668 | B | 1005620 |
| 5669 | B | 1007561 |
| 5670 | B | 1007761 |
| 5671 | B | 1009618 |
| 5672 | B | 1008052 |
| 5673 | B | 1009941 |
| 5674 | B | 1008954 |
| 5675 | B | 1010818 |
| 5676 | B | 1009679 |

TABLE 5-continued

| SEQ ID | Or. | position |
|---|---|---|
| 5677 | B | 1011621 |
| 5678 | B | 1012274 |
| 5679 | B | 1014193 |
| 5680 | B | 1012682 |
| 5681 | B | 1014550 |
| 5682 | B | 1012855 |
| 5683 | B | 1014755 |
| 5684 | B | 1013104 |
| 5685 | B | 1014996 |
| 5686 | B | 1013698 |
| 5687 | B | 1015571 |
| 5688 | B | 1014289 |
| 5689 | B | 1016181 |
| 5690 | B | 1014730 |
| 5691 | B | 1016653 |
| 5692 | B | 1015459 |
| 5693 | B | 1017377 |
| 5694 | B | 1016272 |
| 5695 | B | 1018122 |
| 5696 | B | 1017377 |
| 5697 | B | 1019285 |
| 5698 | B | 1018043 |
| 5699 | B | 1019888 |
| 5700 | B | 1019146 |
| 5701 | B | 1021064 |
| 5702 | B | 1019421 |
| 5703 | B | 1021323 |
| 5704 | B | 1020440 |
| 5705 | B | 1022319 |
| 5706 | B | 1021269 |
| 5707 | B | 1023161 |
| 5708 | B | 1021789 |
| 5709 | B | 1023722 |
| 5710 | B | 1022638 |
| 5711 | B | 1024535 |
| 5712 | B | 1023900 |
| 5713 | B | 1025787 |
| 5714 | B | 1024169 |
| 5715 | B | 1026083 |
| 5716 | B | 1024996 |
| 5717 | B | 1026938 |
| 5718 | B | 1025295 |
| 5719 | B | 1027165 |
| 5720 | B | 1026136 |
| 5721 | B | 1028031 |
| 5722 | B | 1026823 |
| 5723 | B | 1028699 |
| 5724 | B | 1027642 |
| 5725 | B | 1029524 |
| 5726 | B | 1030824 |
| 5727 | B | 1032737 |
| 5728 | B | 1033510 |
| 5729 | B | 1035372 |
| 5730 | B | 1032306 |
| 5731 | B | 1034209 |
| 5732 | B | 1037275 |
| 5733 | B | 1162 |
| 5734 | B | 1036130 |
| 5735 | B | 1038037 |
| 5736 | B | 1036727 |
| 5737 | B | 149 |
| 5738 | B | 225 |
| 5739 | B | 2104 |
| 5740 | B | 17209 |
| 5741 | B | 19109 |
| 5742 | B | 32032 |
| 5743 | B | 33899 |
| 5744 | B | 57057 |
| 5745 | B | 58954 |
| 5746 | B | 57141 |
| 5747 | B | 59033 |
| 5748 | B | 65406 |
| 5749 | B | 67210 |
| 5750 | B | 73871 |
| 5751 | B | 75741 |
| 5752 | B | 78956 |
| 5753 | B | 80903 |
| 5754 | B | 80042 |
| 5755 | B | 81944 |
| 5756 | B | 82642 |
| 5757 | B | 84491 |
| 5758 | B | 87820 |
| 5759 | B | 89658 |
| 5760 | B | 110184 |
| 5761 | B | 112086 |
| 5762 | B | 111873 |
| 5763 | B | 113837 |
| 5764 | B | 112302 |
| 5765 | B | 114206 |
| 5766 | B | 113165 |
| 5767 | B | 115093 |
| 5768 | B | 114270 |
| 5769 | B | 116158 |
| 5770 | B | 121039 |
| 5771 | B | 122904 |
| 5772 | B | 125742 |
| 5773 | B | 127643 |
| 5774 | B | 132170 |
| 5775 | B | 134028 |
| 5776 | B | 144647 |
| 5777 | B | 146547 |
| 5778 | B | 150960 |
| 5779 | B | 152837 |
| 5780 | B | 164761 |
| 5781 | B | 166686 |
| 5782 | B | 166362 |
| 5783 | B | 168305 |
| 5784 | B | 168970 |
| 5785 | B | 170889 |
| 5786 | B | 171056 |
| 5787 | B | 173021 |
| 5788 | B | 177747 |
| 5789 | B | 179629 |
| 5790 | B | 188605 |
| 5791 | B | 190552 |
| 5792 | B | 189016 |
| 5793 | B | 190924 |
| 5794 | B | 190871 |
| 5795 | B | 192749 |
| 5796 | B | 197533 |
| 5797 | B | 199449 |
| 5798 | B | 211604 |
| 5799 | B | 213554 |
| 5800 | B | 235455 |
| 5801 | B | 237385 |
| 5802 | B | 237448 |
| 5803 | B | 239387 |
| 5804 | B | 250266 |
| 5805 | B | 252155 |
| 5806 | B | 253731 |
| 5807 | B | 255663 |
| 5808 | B | 255115 |
| 5809 | B | 256969 |
| 5810 | B | 272158 |
| 5811 | B | 274093 |
| 5812 | B | 276317 |
| 5813 | B | 278190 |
| 5814 | B | 278470 |
| 5815 | B | 280366 |
| 5816 | B | 283005 |
| 5817 | B | 284873 |
| 5818 | B | 293718 |
| 5819 | B | 295643 |
| 5820 | B | 303690 |
| 5821 | B | 305624 |
| 5822 | B | 309538 |
| 5823 | B | 311476 |
| 5824 | B | 312791 |
| 5825 | B | 314685 |
| 5826 | B | 313073 |
| 5827 | B | 314977 |
| 5828 | B | 313506 |
| 5829 | B | 315343 |
| 5830 | B | 320823 |
| 5831 | B | 322730 |
| 5832 | B | 340723 |

TABLE 5-continued

| SEQ ID | Or. | position |
|---|---|---|
| 5833 | B | 342638 |
| 5834 | B | 353562 |
| 5835 | B | 355444 |
| 5836 | B | 373944 |
| 5837 | B | 375838 |
| 5838 | B | 377997 |
| 5839 | B | 379877 |
| 5840 | B | 379877 |
| 5841 | B | 381778 |
| 5842 | B | 395318 |
| 5843 | B | 397228 |
| 5844 | B | 401846 |
| 5845 | B | 403782 |
| 5846 | B | 410759 |
| 5847 | B | 412677 |
| 5848 | B | 411878 |
| 5849 | B | 413779 |
| 5850 | B | 415199 |
| 5851 | B | 417099 |
| 5852 | B | 423479 |
| 5853 | B | 425332 |
| 5854 | B | 428421 |
| 5855 | B | 430332 |
| 5856 | B | 429678 |
| 5857 | B | 431571 |
| 5858 | B | 443036 |
| 5859 | B | 444947 |
| 5860 | B | 444280 |
| 5861 | B | 446161 |
| 5862 | B | 443964 |
| 5863 | B | 445811 |
| 5864 | B | 446392 |
| 5865 | B | 448276 |
| 5866 | B | 468498 |
| 5867 | B | 470382 |
| 5868 | B | 472328 |
| 5869 | B | 474285 |
| 5870 | B | 488594 |
| 5871 | B | 490459 |
| 5872 | B | 497914 |
| 5873 | B | 499837 |
| 5874 | B | 500718 |
| 5875 | B | 502596 |
| 5876 | B | 509811 |
| 5877 | B | 511702 |
| 5878 | B | 511485 |
| 5879 | B | 513385 |
| 5880 | B | 527090 |
| 5881 | B | 529014 |
| 5882 | B | 532083 |
| 5883 | B | 533999 |
| 5884 | B | 557487 |
| 5885 | B | 559357 |
| 5886 | B | 565191 |
| 5887 | B | 567099 |
| 5888 | B | 567452 |
| 5889 | B | 569355 |
| 5890 | B | 571110 |
| 5891 | B | 573047 |
| 5892 | B | 571557 |
| 5893 | B | 573461 |
| 5894 | B | 576288 |
| 5895 | B | 578181 |
| 5896 | B | 590890 |
| 5897 | B | 592770 |
| 5898 | B | 598813 |
| 5899 | B | 600714 |
| 5900 | B | 607146 |
| 5901 | B | 609012 |
| 5902 | B | 608260 |
| 5903 | B | 610162 |
| 5904 | B | 610621 |
| 5905 | B | 612514 |
| 5906 | B | 633573 |
| 5907 | B | 635473 |
| 5908 | B | 637702 |
| 5909 | B | 639603 |
| 5910 | B | 650757 |
| 5911 | B | 652667 |
| 5912 | B | 652808 |
| 5913 | B | 654682 |
| 5914 | B | 655545 |
| 5915 | B | 657446 |
| 5916 | B | 661392 |
| 5917 | B | 663292 |
| 5918 | B | 677837 |
| 5919 | B | 679716 |
| 5920 | B | 679748 |
| 5921 | B | 681674 |
| 5922 | B | 732909 |
| 5923 | B | 734756 |
| 5924 | B | 742639 |
| 5925 | B | 744503 |
| 5926 | B | 759613 |
| 5927 | B | 761510 |
| 5928 | B | 760782 |
| 5929 | B | 762671 |
| 5930 | B | 771617 |
| 5931 | B | 773519 |
| 5932 | B | 772628 |
| 5933 | B | 774528 |
| 5934 | B | 788703 |
| 5935 | B | 790577 |
| 5936 | B | 816591 |
| 5937 | B | 818443 |
| 5938 | B | 847145 |
| 5939 | B | 849042 |
| 5940 | B | 868276 |
| 5941 | B | 870177 |
| 5942 | B | 875887 |
| 5943 | B | 877779 |
| 5944 | B | 877137 |
| 5945 | B | 879035 |
| 5946 | B | 884780 |
| 5947 | B | 886680 |
| 5948 | B | 892172 |
| 5949 | B | 894073 |
| 5950 | B | 900990 |
| 5951 | B | 902955 |
| 5952 | B | 902780 |
| 5953 | B | 904687 |
| 5954 | B | 908266 |
| 5955 | B | 910218 |
| 5956 | B | 912811 |
| 5957 | B | 914730 |
| 5958 | B | 935988 |
| 5959 | B | 937863 |
| 5960 | B | 947227 |
| 5961 | B | 949089 |
| 5962 | B | 953426 |
| 5963 | B | 955397 |
| 5964 | B | 966421 |
| 5965 | B | 968345 |
| 5966 | B | 969548 |
| 5967 | B | 971477 |
| 5968 | B | 971390 |
| 5969 | B | 973279 |
| 5970 | B | 972661 |
| 5971 | B | 974581 |
| 5972 | B | 973730 |
| 5973 | B | 975665 |
| 5974 | B | 998885 |
| 5975 | B | 1000774 |
| 5976 | B | 1004572 |
| 5977 | B | 1006449 |
| 5978 | B | 1010507 |
| 5979 | B | 1012353 |
| 5980 | B | 1029707 |
| 5981 | B | 1031628 |

Publications Cited in the Specification

Adames et al., 1985, Nature, 318:533-538.
Altschul et al., 1993, Nature Genetics, 3:266-272.

Altschul et al., 1997, Nucl. Acids Res., 25:3389-3402.
Altschul, S. F. et al., 1990, J. Mol. Biol., 215:403-410.
Ansubel et al., 1989, Current Protocols in Molecular Biology, Green Publishing Associates and Wiley Interscience, NY.
Arlinghaus, H. F. et al., 1997, Anal. Biochem., 69, 18, 3747-53.
Bai, M. Et al., 1993, J. Virol., 67:5198-5205.
Barany, F., 1911, Proc. Natl. Acad. Sci. USA, 88:189-193.
Beattie, K. et al., 1993, Clin. Chem., 39(4):719-721.
Bernoist and Chambon, 1981, Nature, 290:304-310.
Borman, S., 1996, Chem. Eng. News, 74(50):42-43.
Brinster et al., 1982, Nature, 296:39-42.
Buckholz, R. G., 1993, Curr. Op. Biotechnology, 4:538-542.
Burg, J. L. et al., 1996, Mol. and Cell. Probes, 10:257-271.
Casas-Ciria J. et al., 1996
Chatelier, R. C. et al., 1995, Anal. Biochem., 229, 1, 112-118.
Chee, M. et al., 1996, Science, 274:610-613.
Chu, B. C. F. et al., 1986, Nucleic Acids Research, 14:5591-5603.
Cole et al., 1985, in Monoclonal Antibodies and Cancer Therapy, Alan R. Liss, Inc., pp. 77-96.
Cote et al., 1983, PNAS USA, 80:2026-2030.
Cserzo, M., Wallin, E., Simon, I. von Heijne G and Elofsson, A., 1997, Prot. Eng., 10:673-676.
DeBoer et al., 1980, Scientific American, 242:74-94.
DeBoer et al., 1983, PNAS USA, 80:21-25.
Derisi, J. et al., 1996, Nature Genet., 14:457-460.
Duck, P. et al., 1990, Biotechniques, 9:142-147.
Edwards, C. P., and Aruffo, A., 1993, Curr. Op. Biotechnology 4:558-563.
Erlich, H. A., 1989, In PCR Technology. Principles and Applications for DNA Amplification. New York: Stockton Press.
Fanger and Drakeman, 1995, Drug News and Perspectives, 8:133-137.
Felgner, et al., 1987, Proc. Natl. Acad. Sci. USA, 84:7413.
Fodor, S. P. A. et al., 1991, Science, 251:767-771.
Fox, G. Et al., 1989, J. Gen. Virol., 70:625-637.
Fraley et al., 1980, J. Biol. Chem., 255:10431.
Gardner et al., 1981, Nucl. Acids Res. 9:2871.
Gonnet et al., Science, 256:1443-1445.
Grosschedl et al., 1984, Cell, 38:647-658.
Guateli, J. C. et al., 1990, Proc. Natl. Acad. Sci. USA, 87:1874-1878.
Hackstadt T., Trends Microbiol. 1996 5:288-293.
Hammer et al., 1987, Science, 235:53-58.
Hanahan, 1985, Nature, 315:115-122.
Hayashi, S, and Wu, H. C., 1992, in N. M. Hooper and A. J. Turner (ed.) Lipid Modification of Proteins: A Practical Approach. Oxford University Press, New York, pp. 261-285.
Heinkoff and Heinkoff, 1993, Proteins, 17:49-61.
Herrera-Estrella et al., 1983, Nature, 303:209-213.
Herrera-Estrella, 1984, Nature, 310:115-120.
Higgins et al., 1996, Meth. Enzymol., 266:383-402.
Houbenweyl, 1974, in Meuthode der Organischen Chemie, E. Wunsch Ed., Volume 15-I et 15-II, Thieme, Stuttgart.
Hsia, R. et al., 1997, Molecular Micorbiology, 25:351-359.
Hueck, C. J., 1998, Molec. Biology Rev., 62:379-433.
Huovinen, P. et al., 1989 Ann., Intern Med 110:612-616.
Huse et al., 1989, Science, 246:1275-1281.
Huygen, K. et al., 1996, Nature Medicine, 2(8):893-898.
Innis, M. A. et al. 1990, in PCR Protocols. A guide to Methods and Applications. San Diego: Academic Press.
Inoue et al., 1987, Nucl. Acids Res., 15:6131-6148.
Inoue et al., 1987, FEBS Lett. 215:327-330.
Kabat E. Et al., 1983, Sequences of Proteins of Immunological Interest, U.S. Dept. Of Health and Human Services.
Kaneda, et al., 1989, Science, 243:375.
Karlin and Altschul, 1990, Proc. Natl. Acad. Sci. USA, 87:2267-2268.
Kelsey et al., 1987, Genes and Devel., 1:161-171.
Kievitis, T. et al., 1991, J. Virol. Methods, 35:273-286.
Kohler, G. et al., 1975, Nature, 256(5517):495-497.
Kollias et al., 1986, Cell, 46:89-94.
Kozbor et al., 1983, Immunol. Today, 4:72.
Krumlauf et al., 1985, Mol. Cell. Biol., 5:1639-1648.
Krone, J. R. et al., 1997, Anal. Biochem., 244, 1, 124-132.
Kwoh, D. Y. et al., 1989, Proc. Natl. Acad. Sci. USA, 86:1173-1177.
Leder et al., 1986, Cell, 45:485-495.
Lee, C. A., 1997, Trends Microbiol., 5:148-156.
Leininger, E. et al., 1991, PNAS USA, 88:345-349.
Lipshutz, R. J. et al., 1995, Biotechniques, 19(3):442-447.
Livache, T. et al., 1994, Nucleic Acids Research, 22(15): 2915-2921.
Lockhart, D. J. et al., 1996, Nature Biotechnol., 14:1675-1680.
Longbottom et al., 1998, Infect Immunol., 66:1317-1324.
Luckow, V. A., 1993, Curr. Op. Biotechnology, 4:564-572.
Lukacova, M. Et al., 1994, Infect. Immunol. June, 62(6): 2270-2276.
Mason et al., 1986, Science, 234:1372-1378.
Matson, R. S. et al., 1994, Anal. Biochem., 217:306-310.
Matthews, J. A. et al., 1988, Anal. Biochem., 169:1-25.
Mérel, P., 1994, Biofutur, 139:58.
Merrifield, R. D., 1966, J. Am. Chem. Soc., 88(21):5051-5052.
Midoux, 1993, Nucleic Acids Research, 21:871-878.
Miele, E. A. et al., 1983, J. Mol. Biol., 171:281-295.
Mogram et al., 1985, Nature, 315:338-340.
Morrison et al., 1984, PNAS USA, 81:6851-6855.
Morrison, R. P. et al., 1995. Gene Knockout Mice Establish a Primary Protective Role for Major Histocompatibility Complex Class II-Restricted Responses in *Chlamydia trachomatis*. Infect. Immun. 63:4661-4668.
Nakai, K. and Kanehisa, M., 1991, Proteins, 11:95-110.
Nielsen, H. et al., 1997, Protein Engin., 10:1-6.
Neuberger et al., 1984, Nature, 312:604-608.
O'Donell-Maloney, M. J., 1996, Trends Biotechnol., 14:401-407.
Olins, P. O., and Lee, S. C., 1993, Recent advances in heterologous gene expression in *E. coli*. Curr. Op. Biotechnology 4:520-525.
Ornitz et al., 1986, Cold Spring Harbor Symp. Quant. Biol., 50: 399-409.
Pagano et al., 1967, J. Virol., 1:891.
Pearson and Lipman, 1988, PNAS USA, 85(8):2444-2448.
Peterson, E. et al., 1988. Protective Role of Magnesium in the Neutralization by Antibodies of *Chlamydia trachomatis* Infectivity.
Pierschbacher and Ruoslahti, 1987, J. Biol. Chem., 262: 17294-17298.
Pinkert et al., 1987, Genes and Devel., 1:268-276.
Pugsley, A. P., 1993, Microbiol. Rev., 57:50-108.
Raulston J E., Mol Microbiol 1995 15:607-616.
Rank, R. G. et al., 1988. Susceptibility to reinfection after a primary chlamydial genital infection. Infect. Immun. 56:2243-2249.
Readhead et al., 1987, Cell, 48:703-712.
Reeves, P. R. et al., 1996, in Bacterial Polysaccharide Synthesis and Gene Nomenclature, Elsevier Science Ltd., pp. 10071-10078.

Relman, D. et al., 1990, Cell, 61:1375-1382.
Roivainen, M. Et al., 1994, Virology, 203:357-365.
Rolfs, A. et al., 1991, In PCR Topics. Usage of Polymerase Chain reaction in Genetic and Infectious Disease. Berlin: Springer-Verlag.
Sambrook, J. et al., 1989, In Molecular cloning: A Laboratory Manual. Cold Spring Harbor, N.Y.: Cold Spring Harbor Laboratory Press.
Sanchez-Pescador, R., 1988, J. Clin. Microbiol., 26(10): 1934-1938.
Salzberg et al., 1998, Nucl. Acids Res., 26:544-548.
Sani, 1985, Nature, 314:283-286.
Sarver et al., 1990, Science, 247:1222-1225.
Schachter, J. 1980. Chlamydiae, p. 357-365. In E. H. Lennette (ed.), Manual of clinical microbiology, 3rd ed. American Society for Microbiology, Washington, D.C.
Schnaitman, C. A. and Klena, J. D., 1993, Microbiol. Rev., 57:655-682.
Schneewind, O. Et al., 1995, Science, 268:103-106.
Schwartz and Dayhoff, eds., 1978, Matrices for Detecting Distance Relationships Atlas of Protein Sequence and Structure, Washington: National Biomedical Research Foundation.
Segev D., 1992, in Non-radioactive Labeling and Detection of Biomolecules, Kessler C. Springer Verlag, Berlin, New York: 197-205.
Sheldon, E. L., 1993, Clin. Chem., 39(4):718-719.
Shiver, J. W., 1995, in Vaccines, eds Chanock, R. M. Brown, F. Ginsberg, H. S. & Norrby, E., pp. 95-98, Cold Spring Harbor Laboratory Press, Cold Spring Harbor, N.Y.
Shoemaker, D. D. et al., 1996, Nature Genet., 14:450-456.
Sosnowsky et al., 1997, Proc. Natl. Acad. Sci. USA, 94, 1119-1123.
Struyve, M. et al., 1991, J. Mol. Biol., 218:141-148.
Sundelof, et al., 1993, Scand. J. Infec. Dis., 25:259-261.
Sutcliffe, I. C. and Russell, R. R. B., 1995, J. Bacteriol. 177:1123-1128.
Swift et al., 1984, Cell, 38:639-646.
Takeda et al., 1985, Nature, 314:452-454.
Tascon, R. E et al., 1996, Nature Medicine, 2(8):888-892.
Thompson et al., 1994, Nucl. Acids Res., 22(2):4673-4680.
Urdea, M. S., 1988, Nucleic Acids Research, 11:4937-4957.
Villa-Kamaroff et al., 1978, PNAS USA, 75:3727-3731.
Wagner et al., 1981, PNAS USA, 78:1441-1445.
Walker, G. T. et al., 1992, Nucleic Acids Research, 20:1691-1696.
Walker, G. T. et al., 1992, Proc. Natl. Acad. Sci. USA, 89:392-396.
White, B. A. et al., 1997, Methods in Molecular Biology, 67, Humana Press, Towota.
Yamamoto et al., 1980, Cell, 22:787-797.
Yershov, G. et al., 1996, Proc. Natl. Acad. Sci. USA, 93:4913-4918.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08143024B2). An electronic copy of the "Sequence Listing" will also be available from the USPTO upon request and payment of the fee set forth in 37 CFR 1.19(b)(3).

We claim:

1. An isolated polynucleotide encoding an open reading frame (ORF) of a *Chlamydia trachomatis* genome, said ORF comprising SEQ ID NO: 52 (ORF 52), SEQ ID NO: 347 (ORF 347) or SEQ ID NO: 508 (ORF 508).

2. The isolated polynucleotide according to claim 1, wherein said polynucleotide encodes SEQ ID NO: 52 (ORF 52).

3. The isolated polynucleotide according to claim 1, wherein SEQ ID NO: 52 is encoded by a polynucleotide fully complementary to nucleotides 48585 to 48178 of SEQ ID NO: 1.

4. The isolated polynucleotide according to claim 1, wherein said polynucleotide encodes SEQ ID NO: 347 (ORF 347).

5. The isolated polynucleotide according to claim 1, wherein SEQ ID NO: 347 is encoded by nucleotides 342597 to 343370 of SEQ ID NO: 1.

6. The isolated polynucleotide according to claim 1, wherein said polynucleotide encodes SEQ ID NO: 508 (ORF 508).

7. The isolated polynucleotide according to claim 1, wherein SEQ ID NO: 508 is encoded by a polynucleotide fully complementary to nucleotides 502863 to 501808 of SEQ ID NO: 1.

8. An isolated vector comprising a polynucleotide encoding an open reading frame (ORF) of a *Chlamydia trachomatis* genome, said ORF comprising SEQ ID NO: 52 (ORF 52), SEQ ID NO: 347 (ORF 347) or SEQ ID NO: 508 (ORF 508).

9. The isolated vector according to claim 8, wherein said polynucleotide encodes SEQ ID NO: 52 (ORF 52).

10. The isolated vector according to claim 8, wherein SEQ ID NO: 52 is encoded by a polynucleotide fully complementary to nucleotides 48585 to 48178 of SEQ ID NO 1.

11. The isolated vector according to claim 8, wherein said polynucleotide encodes SEQ ID NO: 347 (ORF 347).

12. The isolated vector according to claim 8, wherein SEQ ID NO: 347 is encoded by nucleotides 342597 to 343370 of SEQ ID NO: 1.

13. The isolated vector according to claim 8, wherein said polynucleotide encodes SEQ ID NO: 508 (ORF 508).

14. The isolated vector according to claim 8, wherein SEQ ID NO: 508 is encoded by a polynucleotide fully complementary to nucleotides 502863 to 501808 of SEQ ID NO: 1.

15. An isolated genetically engineered host cell comprising a polynucleotide encoding an open reading frame (ORF) of a *Chlamydia trachomatis* genome, said ORF comprising SEQ ID NO: 52 (ORF 52), SEQ ID NO: 347 (ORF 347) or SEQ ID NO: 508 (ORF 508).

16. The host cell according to claim 15, wherein said polynucleotide encodes SEQ ID NO: 52 (ORF 52).

17. The host cell according to claim 15, wherein SEQ ID NO: 52 is encoded by nucleotides 48585 to 48178 of SEQ ID NO: 1.

18. The host cell according to claim 15, wherein said polynucleotide encodes SEQ ID NO: 347 (ORF 347).

19. The host cell according to claim 15, wherein SEQ ID NO: 347 is encoded by nucleotides 342597 to 343370 of SEQ ID NO: 1.

20. The host cell according to claim 15, wherein said polynucleotide encodes SEQ ID NO: 508 (ORF 508).

21. The host cell according to claim 15, wherein SEQ ID NO: 508 is encoded by a polynucleotide fully complementary to nucleotides 502863 to 501808 of SEQ ID NO: 1.

22. A method for producing a polypeptide, comprising:
(a) culturing a genetically engineered host cell according to claim 15 under conditions suitable to produce a polypeptide; and
(b) recovering the polypeptide from the culture.

23. The method according to claim 22, wherein said genetically engineered host cell comprises a polynucleotide that encodes SEQ ID NO: 52 (ORF 52).

24. The method according to claim 22, wherein SEQ ID NO: 52 is encoded by nucleotides 48585 to 48178 of SEQ ID NO: 1.

25. The method according to claim 22, wherein said polynucleotide encodes SEQ ID NO: 347 (ORF 347).

26. The method according to claim 22, wherein SEQ ID NO: 347 is encoded by nucleotides 342597 to 343370 of SEQ ID NO: 1.

27. The method according to claim 22, wherein said polynucleotide encodes SEQ ID NO: 508 (ORF 508).

28. The method according to claim 22, wherein SEQ ID NO: 508 is encoded by a polynucleotide fully complementary to nucleotides 502863 to 501808 of SEQ ID NO: 1.

* * * * *

UNITED STATES PATENT AND TRADEMARK OFFICE
CERTIFICATE OF CORRECTION

PATENT NO. : 8,143,024 B2
APPLICATION NO. : 13/036310
DATED : March 27, 2012
INVENTOR(S) : Rémy Griffais et al.

It is certified that error appears in the above-identified patent and that said Letters Patent is hereby corrected as shown below:

Column 8,
Line 49, "Biol. 2/5:" should read --Biol. 215:--.

Column 14,
Line 53, "normatural" should read --nonnatural--.

Column 17,
Line 49, "normatural" should read --nonnatural--.
Line 53, "normatural" should read --nonnatural--.

Column 20,
Line 55, "ORF1253;" should read --ORF253;--.

Column 21,
Line 27, "ORF51;" should read --ORF511;--.

Column 23,
Line 8, "have Cysteine-rich" should read --have. Cysteine-rich--.

Column 24,
Line 62, "0182" should read --ORF82--.

Column 27,
Line 7, "ORF1101;" should read --ORF110;--.

Column 28,
Line 10, "SEQ ID No. 1;" should read --SEQ ID No. 11;--.

Signed and Sealed this
Third Day of July, 2012

David J. Kappos
*Director of the United States Patent and Trademark Office*

Column 34,
Line 64, "SEQ ID No. 110," should read --SEQ ID No. 1110,--.

Column 39,
Line 56, "SEQ ID No. 016;" should read --SEQ ID No. 1016;--.

Column 46,
Line 27, "(VIIIa-Kamaroff," should read --(Villa-Kamaroff,--.

Column 49,
Line 5, "(Bemoist" should read --(Bernoist--.
Lines 16-17, "a 2'-β-methylribonucleotide" should read --a 2'-0- methylribonucleotide--.

Column 53,
Line 54, "Fe receptors" should read --Fc receptors--.

Column 55,
Line 65, "BLAcore-type" should read --BIAcore-type--.

Column 61,
Line 11, "nucleo-tide" should read --nucleotide--.
Line 45, "Skoultehi," should read --Skoultchi,--.

Column 72,
Line 1, "(Salzberg, Delcher" should read --(Salzberg, S.L., Delcher--.

Column 76,
Line 16, "value $<e^{10}$" should read --value $< e^{-10}$--.